(12) United States Patent
Banister et al.

(10) Patent No.: US 12,415,804 B2
(45) Date of Patent: Sep. 16, 2025

(54) COMPOUNDS FOR ACTIVATING A SEROTONIN RECEPTOR

(71) Applicant: PSYLO PTY LTD, Sydney (AU)

(72) Inventors: Samuel Banister, Sydney (AU);
William Jorgensen, Sydney (AU);
Jinlong Tan, Sydney (AU); Lachlan Whish, Sydney (AU)

(73) Assignee: PSYLO PTY LTD, Sydney (AU)

( * ) Notice: Subject to any disclaimer, the term of this patent is extended or adjusted under 35 U.S.C. 154(b) by 0 days.

(21) Appl. No.: 19/002,520

(22) Filed: Dec. 26, 2024

(65) Prior Publication Data

US 2025/0206739 A1 Jun. 26, 2025

Related U.S. Application Data

(63) Continuation of application No. PCT/AU2024/050706, filed on Jun. 28, 2024.

(30) Foreign Application Priority Data

Jun. 28, 2023 (AU) ................. 2023902053

(51) Int. Cl.
*C07D 471/04* (2006.01)
*A61K 31/437* (2006.01)
*A61K 31/4545* (2006.01)
*A61K 31/5377* (2006.01)

(52) U.S. Cl.
CPC .......... *C07D 471/04* (2013.01); *A61K 31/437* (2013.01); *A61K 31/4545* (2013.01); *A61K 31/5377* (2013.01)

(58) Field of Classification Search
CPC .................................................. C07D 471/04
USPC ...................................................... 514/234.5
See application file for complete search history.

(56) References Cited

U.S. PATENT DOCUMENTS

| 5,364,866 | A | 11/1994 | Strupczewski et al. |
| 11,000,534 | B1 | 5/2021 | Sippy |
| 2010/0029629 | A1 | 2/2010 | Conticello et al. |

FOREIGN PATENT DOCUMENTS

| EP | 0737685 B1 | 7/2000 |
| EP | 0870768 B1 | 5/2002 |
| WO | WO 1995/010513 A1 | 4/1995 |
| WO | 2008004117 A1 | 1/2008 |
| WO | WO 2008/003736 A1 | 1/2008 |
| WO | 2009102805 A1 | 8/2009 |
| WO | 2010011546 A1 | 1/2010 |
| WO | 2013063492 A1 | 5/2013 |
| WO | WO 2018/106907 A1 | 6/2018 |
| WO | WO 2021/041539 A2 | 3/2021 |
| WO | 2021076572 A1 | 4/2021 |
| WO | 2021155468 A1 | 8/2021 |
| WO | 2021155470 A1 | 8/2021 |
| WO | 2021168082 A1 | 8/2021 |
| WO | 2021179091 A1 | 9/2021 |
| WO | 2021226416 A1 | 11/2021 |
| WO | WO 2022/120181 A1 | 6/2022 |
| WO | 2023018864 A1 | 2/2023 |
| WO | WO 2023/115165 A1 | 6/2023 |
| WO | WO 2024/026359 A1 | 2/2024 |
| WO | WO-2025000051 A1 * | 1/2025 ............ A61P 25/00 |

OTHER PUBLICATIONS

Berge et al.; "Pharmaceuticals Salts"; Journal of Pharmaceutical Sciences; vol. 66 No. 1; Jan. 1977; 19 pages.
Whelligan et al.; "Two-Step Synthesis of Aza- and Diazaindoles from Chloroamino-N-heterocycles Using Ethoxyvinylborolane"; The Journal of Organic Chemistry; vol. 75; 2010; p. 11-15.
CAS Registry No. 784079-60-3; dated Nov. 18, 2024; 1 page.
CAS Registry No. 1337205-20-5; dated Oct. 18, 2011; 1 page.
CAS Registry No. 2172589-79-4; dated Feb. 1, 2018; 1 page.
CAS Registry No. 2025497-87-2; dated Nov. 6, 2016; 1 page.
Blache et al.; "Application of the mercuric acetate-edetic acid oxidation method to the synthesis of 11-aza-1, 2, 3, 4, 5, 6, 7, 12b-octahydroindolo [2, 3-a] quinolizines"; Heterocycles; vol. 45 No. 1; 1997; p. 57-69.
Fukuya et al.; "Practical Synthesis of 7-Azaserotonin and 7-Azamelatonin"; Synlett; vol. 33; 2022; p. 2033-2037.
Bertaccini et al., The relative potency of 5-hydroxytryptamine like substances, Arch Int Pharmacodyn Ther., 133:138-56, 1961.
Communication pursuant to Rule 114(2) EPC, Third Party Observations Regarding European Application No. 22908927.1, mailed Mar. 21, 2025, 27 pages.
Klein et al., Toward selective drug development for the human 5-hydroxytryptamine 1E receptor: a comparison of 5-hydroxytryptamine 1E and 1F receptor structure-affinity relationships, Journal of Pharmacology and Experimental Therapeutics, 337(3), 860-867, 2011.
Pigini et al., Analogs with a 1,2-benzisoxazole nucleus of biologically active indole derivatives. IV. 5-Hydroxytryptamine isosteres, Eur J Med Chem, 10:33-6, 1975.
Rao et al., Synthesis and radioprotective activity of beta-(3-indazolyl)-ethylamine derivatives , Yao Xue Xue Bao 22 (6): 426-432, 1987.

* cited by examiner

*Primary Examiner* — Niloofar Rahmani
(74) *Attorney, Agent, or Firm* — BakerHostetler

(57) ABSTRACT

The present disclosure relates generally to compounds, their methods of synthesis, and their use in the treatment of mental illness or central nervous system disorders.

1 Claim, 6 Drawing Sheets

COMPOUNDS FOR ACTIVATING A SEROTONIN RECEPTOR

This application is a continuation of PCT/AU2024/050706 filed 28 Jun. 2024, which claims priority to Australian provisional application no. 2023902053 (filed on 28 Jun. 2023), the entire contents of which are incorporated herein by reference.

FIELD OF THE INVENTION

The present disclosure relates generally to novel compounds, their methods of synthesis, and their use in the treatment of mental illness or central nervous system disorders.

BACKGROUND OF THE INVENTION

Mental illness covers many neuropsychiatric disorders which cause enormous burden to the lives of their sufferers. Diagnoses such as treatment resistant depression, major depressive disorder, eating disorders, substance abuse disorders, post-traumatic stress disorder, obsessive compulsive disorder, attention deficit disorders, schizophrenia, and others can cause such devastating symptoms that many sufferers lose the capability of leading a normal life.

A variety of serotonergic drugs such as antidepressants, serotonin reuptake inhibitors, monoamine oxidase inhibitors, selective serotonin reuptake inhibitors, and others are commercially available to treat mental illnesses. Unfortunately, in many indications, these therapeutics provide limited benefit when compared to a placebo. Additionally, these therapeutics can result in a wide range of side effects including loss of libido, insomnia, fatigue, weight gain, and others. In spite of their limited efficacy, these drugs continue to be used to treat neuropsychiatric conditions as well as a broad range of auxiliary medical indications. There have been limited advances in new treatment options since many of these drugs were released, and the pharmaceutical industry has come under increased financial pressure to de-emphasize neuroscience programmes entirely. The unmet need for more efficacious mental health treatment is on the rise, and the global COVID-19 pandemic is likely to increase disease burden around the world.

In the 1950s and 1960s, the use of psychedelic drugs to treat various mental illnesses was extensively explored, and these substances showed promise as treatments for many diseases of the central nervous system (CNS). Following decades of prohibition, scientific research into the application of psychedelics as treatments for mental illnesses has been gaining momentum. The serotonergic psychedelic agent psilocybin has been designated a Breakthrough Therapy by the FDA for the treatment of major depressive disorder (2019) and treatment-resistant depression (2018). Psilocybin is the prodrug compound produced by many species of mushrooms known collectively as psilocybin mushrooms or "magic mushrooms". Psilocybin is rapidly metabolized to the bioactive compound psilocin, which produces a state of altered consciousness including changes in perception, visual hallucinations, and distorted sense of space, time, and self. Many patients report spiritual or "mystical" experiences which have profound and lasting impact on the patients' mood and behaviour. Psilocybin has shown promise in more than 50 clinical trials for neuropsychiatric indications, including numerous anxiety disorders, obsessive-compulsive disorder, anorexia nervosa, alcohol dependence, and tobacco addiction. Psilocybin and other psychedelic compounds such as N,N-dimethyltryptamine (DMT) and 5-methoxy-N,N-dimethyltryptamine (5-MeO-DMT) have both immediate and persistent effects on mental state, with the latter extending far beyond the duration of action, possibly as a result of their ability to incite increased neuroplasticity, promote neural outgrowth, and increase spine density of the synaptic neurons in the brain.

To date, psilocybin remains classified as a controlled substance and/or drug of abuse in most countries under national drug laws. However, clinical investigations have recently led to increased awareness of the potential for psychedelic drugs as breakthrough therapies to treat CNS diseases of enormous unmet medical need.

Despite its therapeutic potential, psilocybin and other psychedelics remain scheduled drugs of abuse in most countries and the commercial path to market for these drugs as medicines is uncertain. As an adjunct to psychotherapy, the long duration of action of psilocybin and LSD make treatment sessions costly and impractical for broad implementation. In spite of a long history of safe human use, several adverse events have been reported in clinical trials, and it is possible that these may be attributed to signalling bias at 5-HT2A (the primary target) or off-target activity at, for example, 5-HT2B receptors (a cardiac liability antitarget) or 5-HT1A (an anxiolytic target) or 5-HT2C receptors (a disease-relevant target for obesity and some genetic epilepsies, for example). Naturally-occurring psychedelics provide important lead structures for a new generation of neurotherapeutic agents with novel mechanisms of action and/or superior clinical efficacy to currently available neuropsychiatric medications.

In view of the foregoing there is an ongoing need to develop new compounds which may be useful in the treatment of mental illness or central nervous system disorders.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

Compounds possessing potential efficacy in treating mental illness or central nervous system disorders are described in international application no. PCT/AU2022/051591. The compounds described herein are surprisingly highly active at the $5HT_{2A}$ serotonin receptor. Preferred compounds may also be surprisingly selective for the $5HT_{2A}$ over the $5HT_{2B}$ and/or the $5HT_{2C}$ serotonin receptors. Preferred compounds may also be surprisingly selective for the $5HT_{2A}$ over both the $5HT_{2B}$ and $5HT_{2C}$ serotonin receptors. Also, the compounds described herein may surprisingly possess enhanced metabolic stability while retaining desirable activity. Accordingly, the compounds described herein may also be useful for treating mental illness or central nervous system disorders.

In one aspect, the present disclosure provides a compound of formula (I):

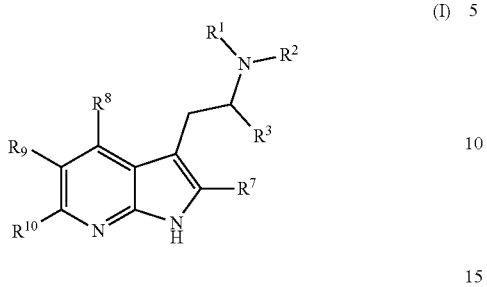

or a pharmaceutically acceptable salt, solvate, tautomer, N-oxide, stereoisomer, metabolite, polymorph or prodrug thereof,
wherein
$R^1$ and $R^2$ are each independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl,
said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$,
said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;
alternatively $R^1$ and $R^2$ together with the nitrogen atom to which they are attached form a $C_{3-8}$ heterocycloalkyl including 0, 1 or 2 additional ring heteromoieties selected from O, S, S(O), $SO_2$, N and $NR^4$,
said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;
$R^3$ is selected from hydrogen, $C_{1-6}$ alkyl, $C_{3-8}$ cycloalkyl, or $C_{4-14}$ alkylenecycloalkyl;
alternatively $R^3$ and one of $R^1$ and $R^2$ together the atoms to which they are attached to form a $C_{3-12}$ heterocycloalkyl,
said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;
each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$,
said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$,
said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;
each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl,
said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;
$R^7$, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_2$-$C_6$ alkenyl, $C_{2-6}$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2, $S(O)R^{13}$, $S(O)N(R^{13})_2$, $SO_2R^{13}$, $N(R^{13})_2$, $N(R^{13})$ $C(O)R^{13}$, $N(R^{13})C(O)OR^{13}$, $N(R^{13})$ $C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{6-10}$ heteroaryl, $C_{4-16}$ alkyleneheteroaryl,
said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $X^2$ is $CR^7$, $R^7$ and one of $R^1$, $R^2$, or $R^3$ are combined with the atoms to which they are attached to form a $C_{5-8}$ heterocycloalkyl, said $C_{5-8}$ heterocyclyalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

alternatively, when $X^1$ is $NR^6$ and $X^2$ is $CR^7$, $R^6$ and $R^7$ are combined with the atoms to which they are each attached to form a $C_{4-10}$ heterocycloalkyl or a $C_{5-10}$ heteroaryl, said $C_{4-10}$ heterocycloalkyl and $C_{5-10}$ heteroaryl each being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In embodiments of the compound of formula (I):

$R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituent independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the atoms to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

one or more substituents $R^7$, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)$(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

one or more substituents.

Any compound of formula (I) may be provided in the form of a pharmaceutically acceptable salt, solvate, tautomer, N-oxide, stereoisomer, metabolite, polymorph or prodrug.

In embodiments, the compound of formula (I) is not one of the following:
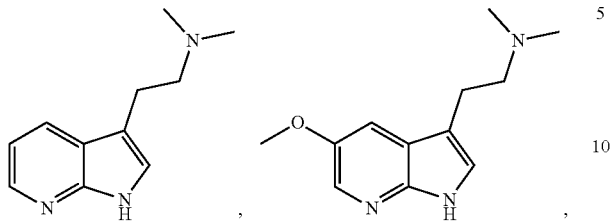
,
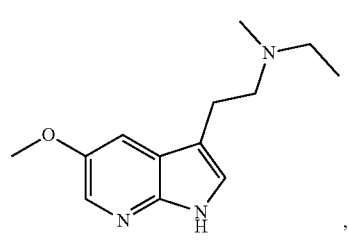
,
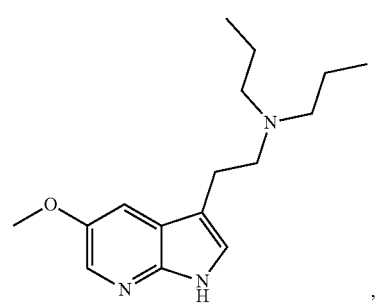
,
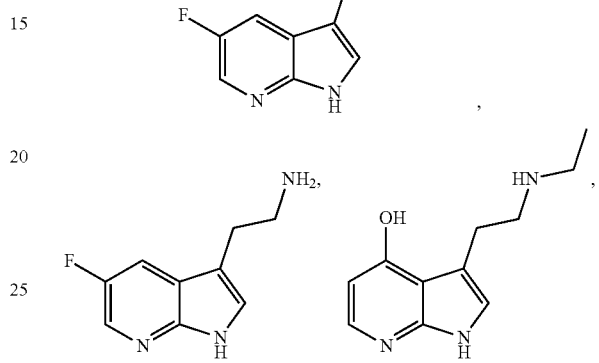
,
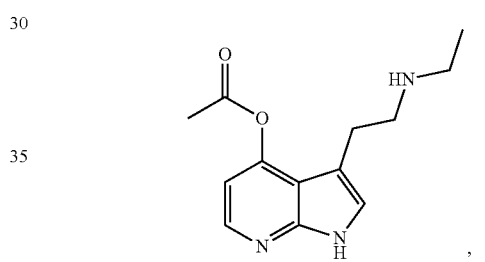
,
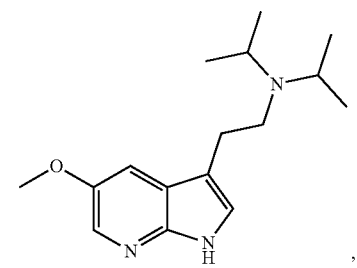
,
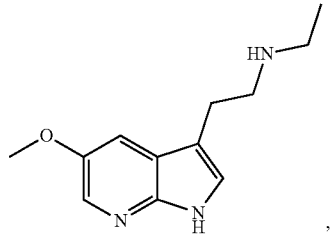
,
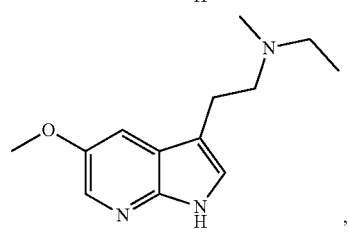
,
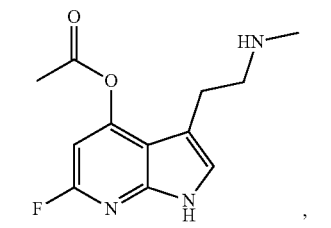
,
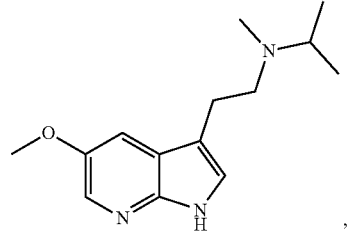
,
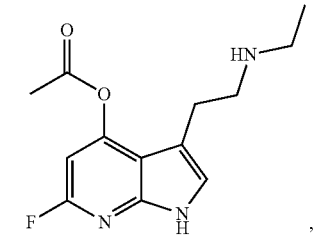
,

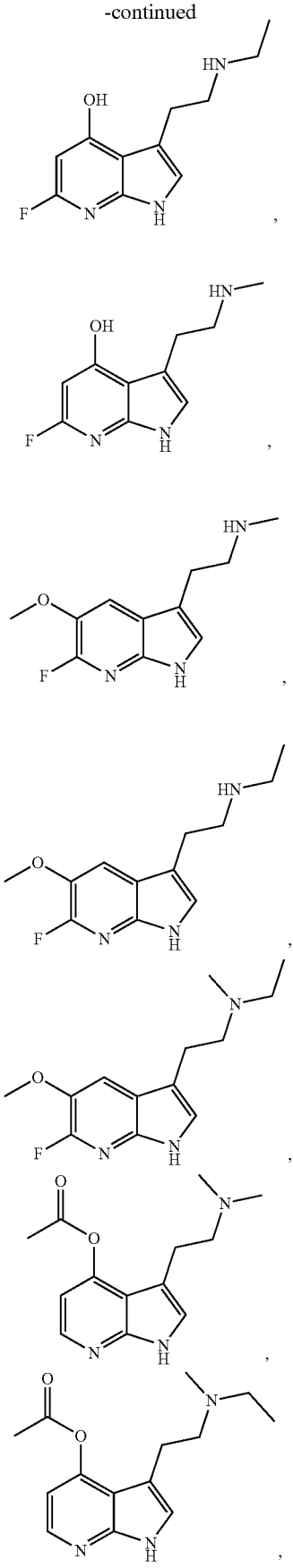
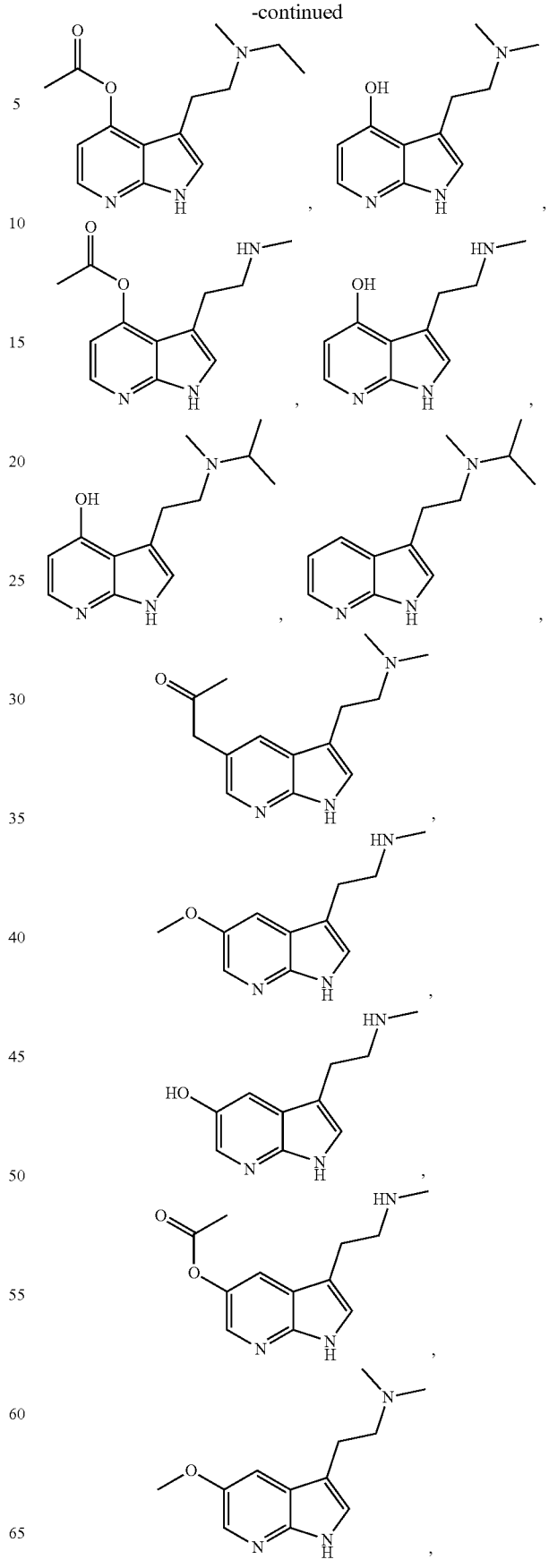

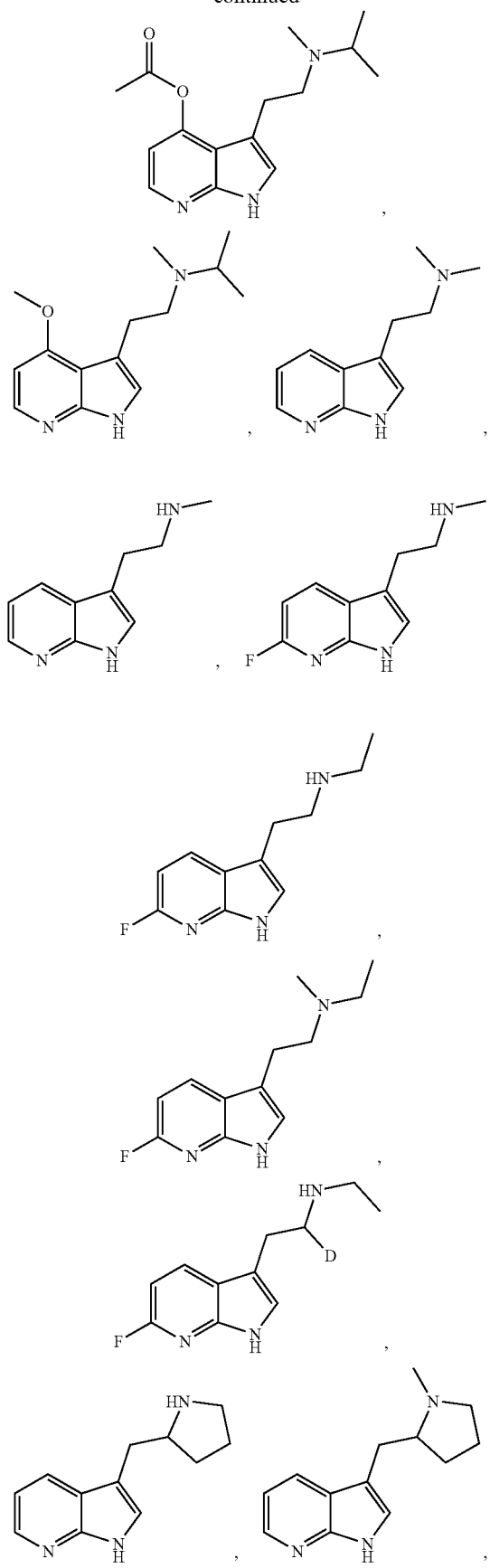
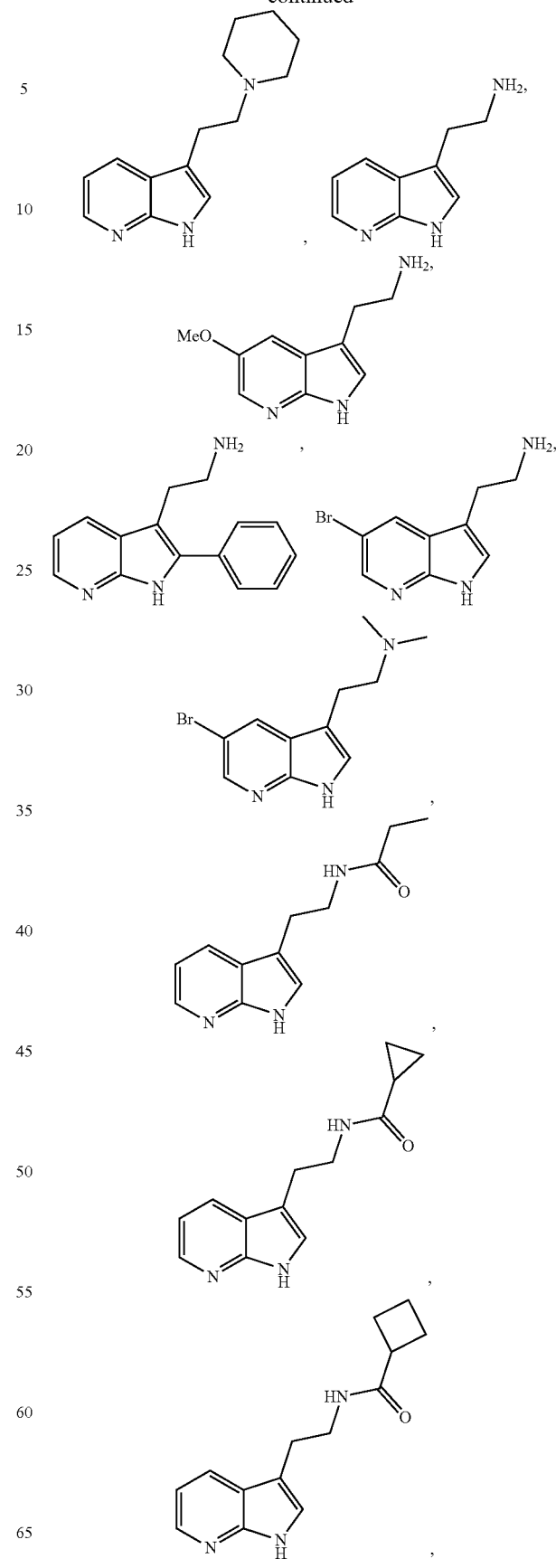

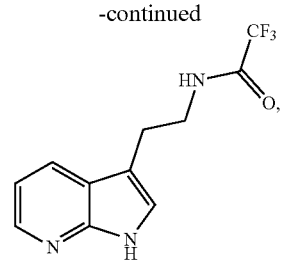
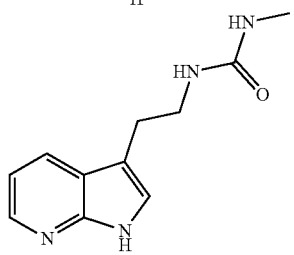
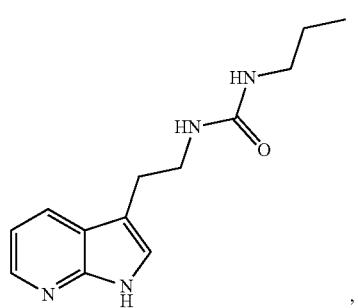
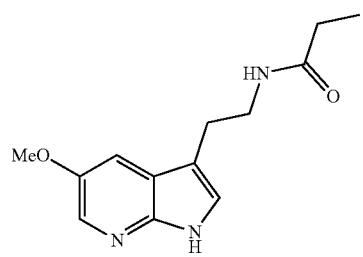
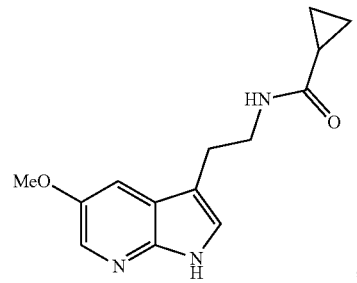
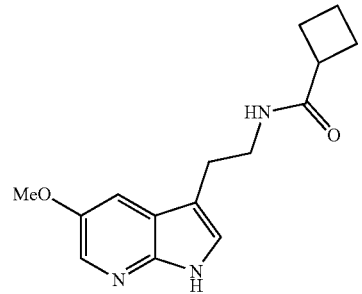
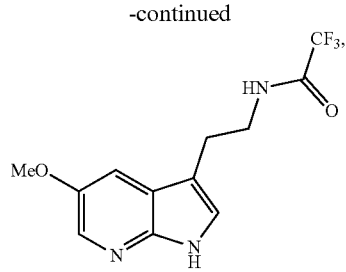
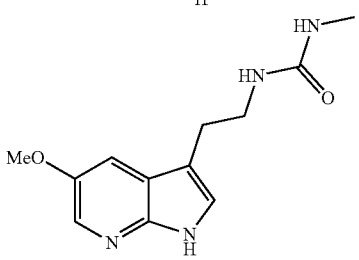
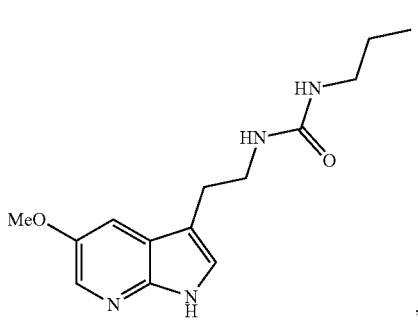
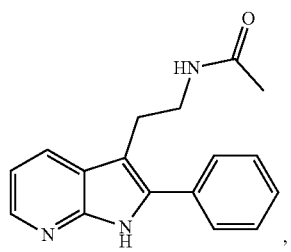
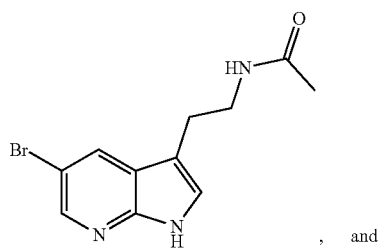
, and
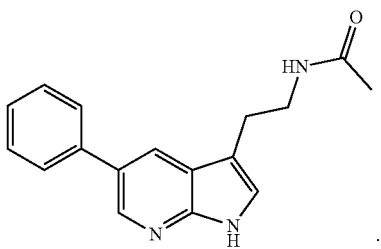

In embodiments, the compound of formula (I) is not one of the following:

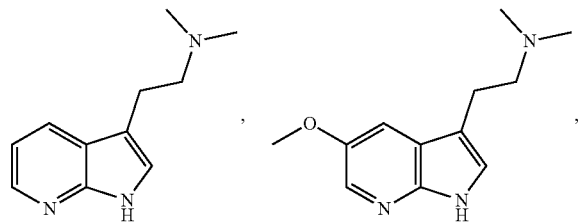

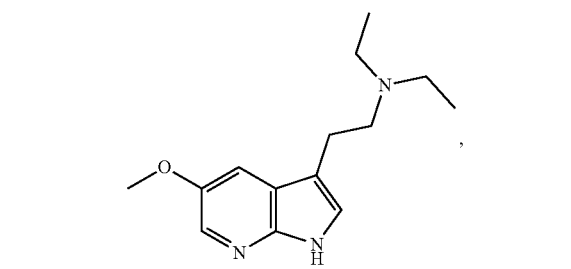

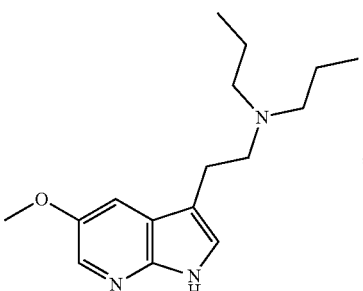

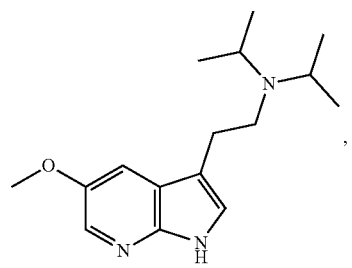

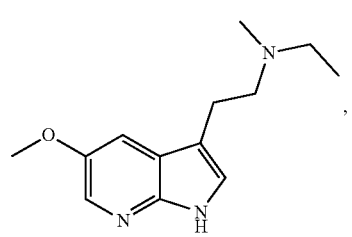

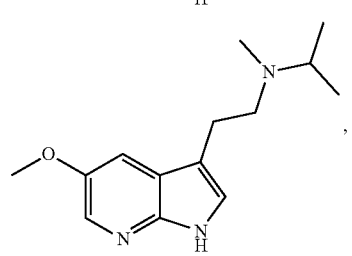

, and

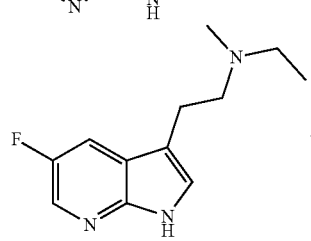

In another aspect the present disclosure provides a medicament comprising a compound according to any one of the herein disclosed embodiments, or a pharmaceutically acceptable salt, solvate, tautomer, N-oxide, stereoisomer, metabolite, polymorph or prodrug thereof.

In another aspect the present disclosure provides a pharmaceutical composition comprising a compound according to any one of the herein disclosed embodiments, or a pharmaceutically acceptable salt, solvate, tautomer, N-oxide, stereoisomer, metabolite, polymorph or prodrug thereof, and a pharmaceutically acceptable excipient.

In another aspect the present disclosure provides a pharmaceutical composition comprising a compound according to any one of the herein disclosed embodiments, or a pharmaceutically acceptable salt, solvate, tautomer, N-oxide, stereoisomer, metabolite, polymorph or prodrug thereof, an additional therapeutic agent, and a pharmaceutically acceptable excipient.

In another aspect the present disclosure provides a method of treating a disease, disorder or condition by activation of a serotonin receptor, the method comprising administering to a subject in need thereof a compound of formula (I) or a pharmaceutically acceptable salt, solvate, tautomer, N-oxide, stereoisomer, metabolite, polymorph or prodrug thereof.

In another aspect the present disclosure provides a method of treating a disease, disorder or condition by activation of a serotonin receptor, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof, in combination with another known agent useful for treatment of a disease, disorder or condition by activation of a serotonin receptor.

In another aspect the present disclosure provides a method of treating a mental illness, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof.

In some embodiments, the mental illness is selected from anxiety disorders; depression; mood disorders; psychotic disorders; impulse control and addiction disorders; drug addiction; obsessive-compulsive disorder (OCD); post-traumatic stress disorder (PTSD); stress response syndromes; dissociative disorders; depersonalization disorder; factitious disorders; sexual and gender disorders; somatic symptom disorders; hallucinations; delusions; psychosis; and combinations thereof.

In another aspect the present disclosure provides a method for treating a central nervous system (CNS) disease, disorder or condition and/or a neurological disease, disorder or condition, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof.

In some embodiments, the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neurootological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa and bulimia nervosa; binge eating disorder, trichotillomania, dermotillomania, nail biting; migraine; fibromyalgia; and peripheral neuropathy of any etiology, and combinations thereof.

In another aspect the present disclosure provides a method for increasing neuronal plasticity and/or increasing dendritic spine density, the method comprising contacting a neuronal cell with a compound of formula (I) as defined in any one of the herein disclosed embodiments, or a pharmaceutically acceptable salt, solvate, tautomer, N-oxide, stereoisomer, metabolite, polymorph or prodrug thereof, in an amount sufficient to increase neuronal plasticity and/or increase dendritic spine density of the neuronal cell.

In another aspect the present disclosure provides methods of treating weight, comprising administering an effective amount of a compound of the invention to a subject in need thereof. Treatment of weight may include treating weight gain; weight loss; metabolic disorder; weight gain associated with pharmaceutical intervention; weight gain associated with a mental illness (including those described herein); eating disorders such as anorexia, bulimia, cachexia, etc.; eating behaviour; obesity; diabetes; insulin resistance; pre-diabetes; glucose intolerance; hyperlipidemia; and cardiovascular disease.

In another aspect the present disclosure provides a method for activating a serotonin receptor in a cell, either in a biological sample or in a patient, comprising administering a compound of formula (I) as defined in any one of the herein disclosed embodiments to the cell.

In any aspect or embodiments, the compound of the invention may be any one of compounds S1 to S42.

Any embodiment herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
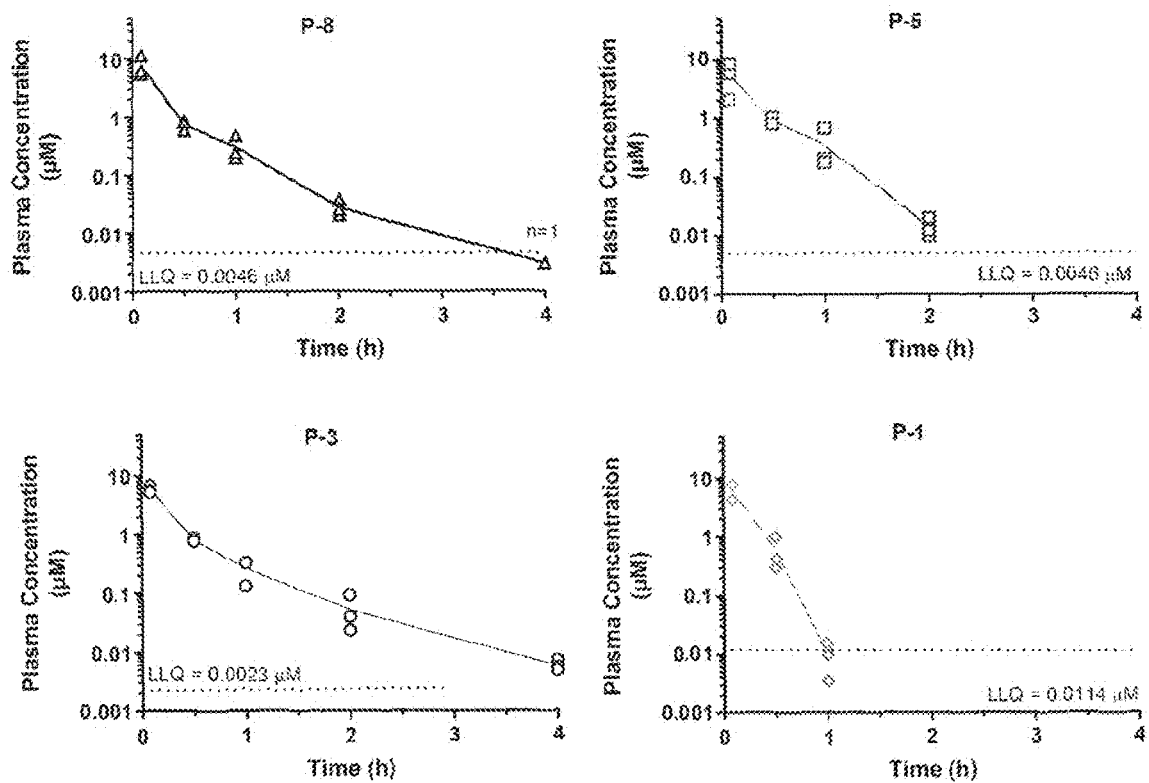
FIG. 1: Plasma concentrations of a subset of exemplar compounds P-8, P-5, P-3, and P-1 in male C57BL/6 mice following IP administration at 10 mg/kg described in Example 76.
Figure 2:
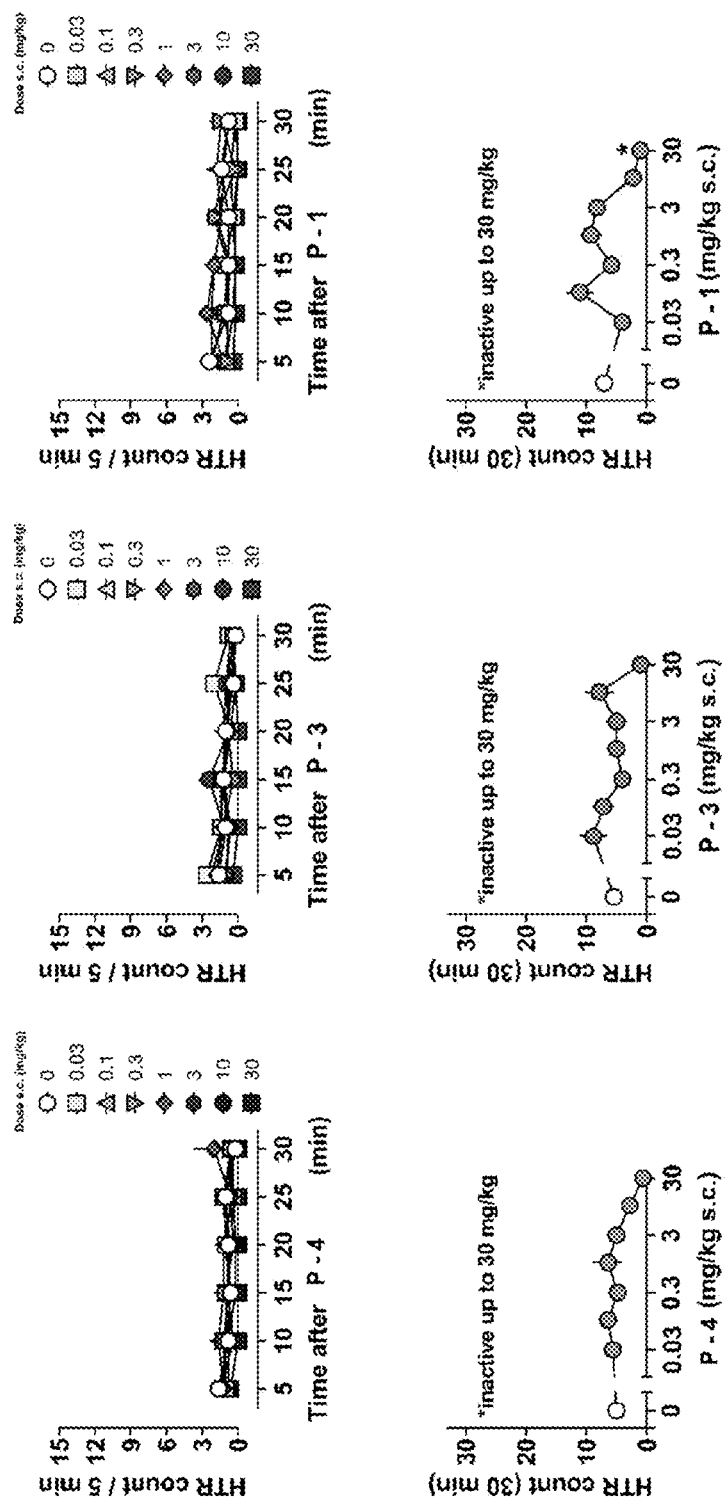
FIG. 2: Time binned and mean±SD (n=3) HTR counts of a subset of exemplar compounds P-4, P-3, and P-1 in male C57BL/6 mice following SC administration over several doses as described in Example 77.
Figure 3:
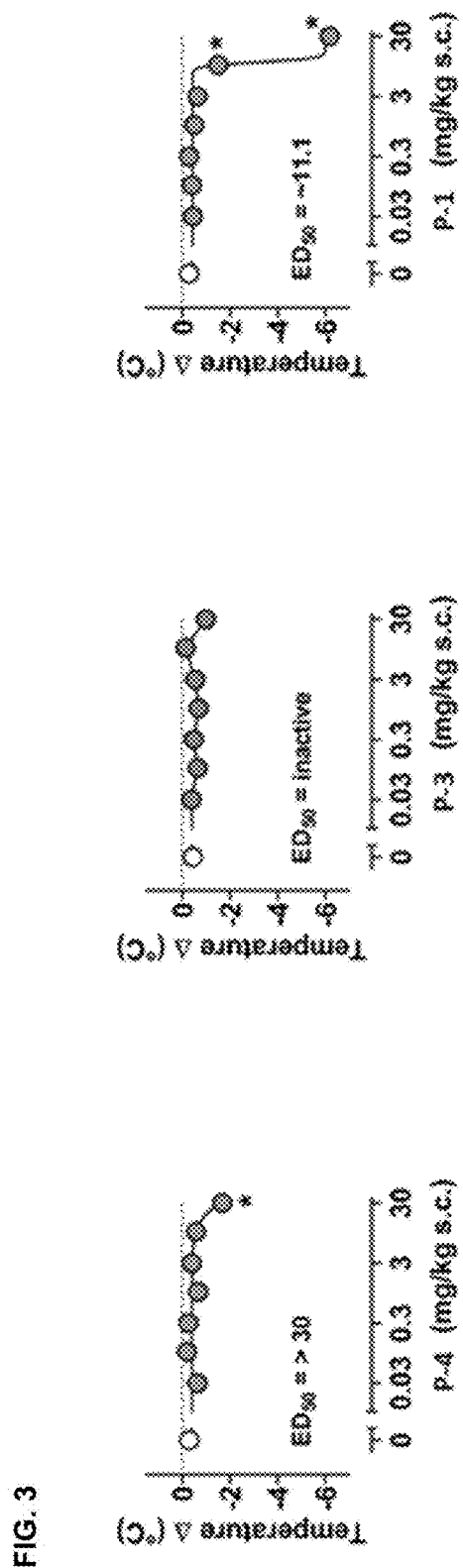
FIG. 3: Temperature results displayed as mean±SD (n=3) Y of a subset of exemplar compounds P-4, P-3, and P-1 in male C57BL/6 mice following SC administration over several doses as described in Example 77.
Figure 4:
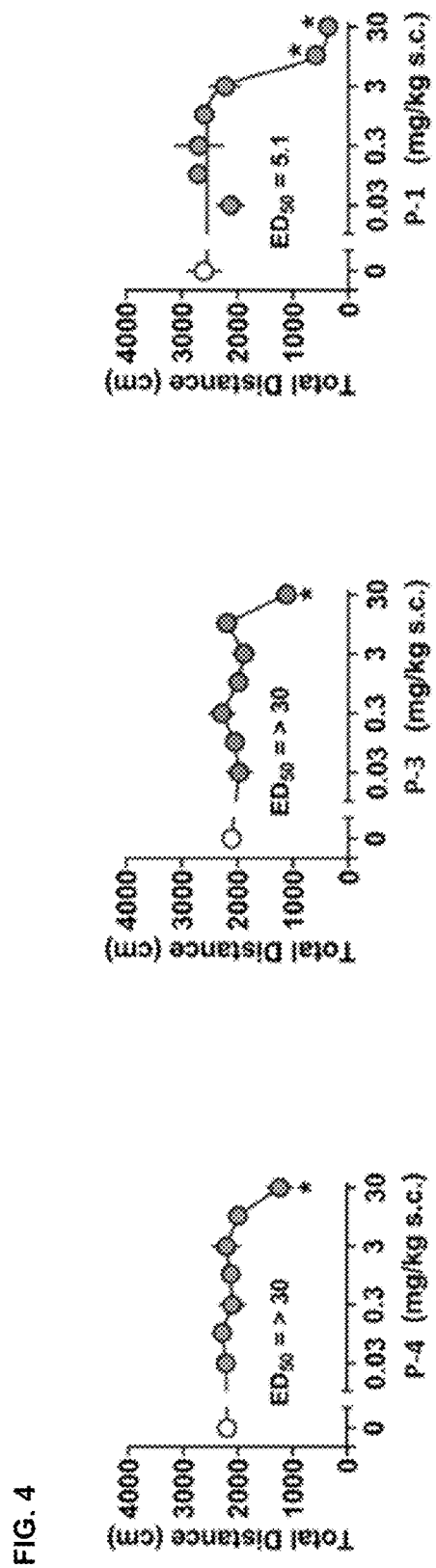
FIG. 4: Locomotor results (total distance) displayed as mean±SD (n=3) HTR counts of a subset of exemplar compounds P-4, P-3, and P-1 in male C57BL/6 mice following SC administration over several doses as described in Example 77.
Figure 5:
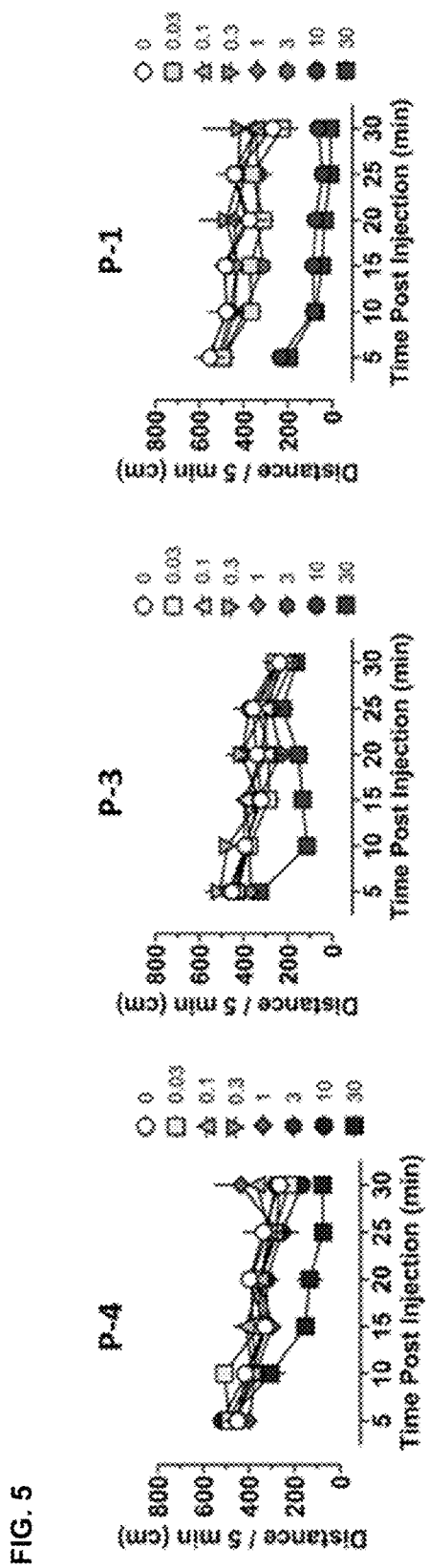
FIG. 5: Locomotor results (distance/time) displayed as mean±SD (n=3) HTR counts of a subset of exemplar compounds P-4, P-3, and P-1 in male C57BL/6 mice following SC administration over several doses as described in Example 77.

It will be understood that the invention disclosed and defined in this specification extends to all alternative combinations of two or more of the individual features mentioned or evident from the text or drawings. All of these different combinations constitute various alternative aspects of the invention.

Definitions

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps.

The terms "treatment" or "treating" of a subject includes delaying, slowing, stabilizing, curing, healing, alleviating, relieving, altering, remedying, less worsening, ameliorating, improving, or affecting the disease or condition, the sign or symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of signs or symptoms or making the injury, pathology or condition more tolerable to the individual; slowing in the rate of degeneration or decline; making the final point of degeneration less debilitating.

In particularly preferred embodiments, the methods of the present invention can be to prevent or reduce the severity, or inhibit or minimise progression, of a sign or symptom of a disease or condition as described herein. As such, the methods of the present invention have utility as treatments as well as prophylaxes.

As used herein, "preventing" or "prevention" is intended to refer to at least the reduction of likelihood of the risk of (or susceptibility to) acquiring a disease or disorder (i.e., causing at least one of the clinical signs or symptoms of the disease not to develop in an individual that may be exposed to or predisposed to the disease but does not yet experience or display signs or symptoms of the disease). Biological and physiological parameters for identifying such patients are provided herein and are also well known by physicians.

Herein, the term "subject" or "patient" can be used interchangeably with each other. The term "individual" or "patient" refers to an animal that is treatable by the compound and/or method, respectively, including but not limited to, for example, dogs, cats, horses, sheep, pigs, cows, and the like, as well as human, non-human primates. Unless otherwise specified, the "subject" or "patient" may include both male and female genders. Further, it also includes a subject or patient, preferably a human, suitable for receiving treatment with a pharmaceutical composition and/or method of the present invention.

The term "selective" means a greater activity against a first target (e.g., a 5-HT receptor subtype) relative to a second target (e.g., a second 5-HT receptor subtype). In some embodiments a compound has a selectivity of at least 1.25-fold, at least 1.5 fold, at least 2-fold, at least 3-fold, at least 4-fold, at least 5-fold, at least 6-fold, at least 10-fold or at least 100-fold greater towards a first target relative to a second target. In some embodiments, a compound described herein is selective towards the 5-HT$_{2A}$ receptor relative to one or more other 5-HT receptor subtypes such as 5-HT$_{2B}$ and/or 5-HT$_{2C}$, preferably 5-HT$_{2B}$. In some embodiments, a compound described herein is selective towards the 5-HT$_{2C}$ receptor relative to one or more other 5-HT receptor subtypes such as 5-HT$_{2A}$ and/or 5-HT$_{2B}$, preferably 5-HT$_{2B}$.

"About" as used herein when referring to a measurable value such as an amount, a temporal duration, and the like, is meant to encompass variations of ±20% or ±10%, in some instances ±5%, in some instances ±1%, and in some instances ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein the term "alkyl" refers to a straight or branched chain hydrocarbon radical having from one to twelve carbon atoms, or any range between, i.e. it contains 1, 2, 3, 4, 5, 6, 7, 8, 9, 10, 11 or 12 carbon atoms. The alkyl group is optionally substituted with substituents. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "C$_1$-C$_2$ alkyl", "C$_1$-C$_3$ alkyl" and "C$_1$-C$_6$ alkyl" refer to an alkyl group, as defined herein, containing at least 1, and at most 2, 3 or 6 carbon atoms respectively, or any range in between (eg alkyl groups containing 2-5 carbon atoms are also within the range of C$_1$-C$_6$).

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

The term "alkenyl" whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "C$_{n1-n2}$". For example, the term C$_{2-6}$ alkylene means an alkylene group having 2, 3, 4, 5 or 6 carbon atoms. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "C$_{n1-n2}$". For example, the term C$_{2-6}$ alkynyl means an alkynyl group having 2, 3, 4, 5 or 6 carbon atoms. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

The term "cycloalkyl" is intended to include mono-, bi- or tricyclic alkyl groups. The number of carbon atoms that are possible in the referenced cycloalkyl group are indicated by the prefix "C$_{n1-n2}$". For example, the term C$_{3-8}$ cycloalkyl means an cycloalkyl group having 3, 4, 5, 6, 7 or 8 carbon atoms. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi- and tricyclic ring systems include bridged, spiro, and fused cycloalkyl ring systems. Examples of bi- and tricyclic ring cycloalkyl systems include, but are not limited to, bicyclo

[3.1.0]hexanyl, bicyclo[2.1.1]hexanyl, bicyclo[2.2.1]heptanyl, adamantyl, and decalinyl.

The term "alkylenecycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined herein. The numerical range from x to y in "$C_{x-y}$ alkylenecycloalkyl" relates to the total number of alkyl carbons and cycloalkyl ring atoms. Exemplary alkylenecycloalkyl groups include, but are not limited to, methylenecyclopropyl, methylenecyclobutyl, methylenecyclopentyl and methylenecyclohexyl.

The term "aryl" refers to an aromatic ring system having any suitable number of ring atoms and any suitable number of rings. The number of carbon atoms that are possible in the referenced aryl group are indicated by the prefix "$C_{n1-n2}$". For example, the term $C_{6-12}$ aryl means an aryl group having 6, 7, 8, 9, 10, 11 or 12 carbon atoms. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

The term "alkylenearyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. The numerical range from x to y in "$C_{x-y}$ alkylenearyl" relates to the total number of alkyl carbons and aryl ring atoms. Examples of alkylenearyl groups include, but are not limited to, benzyl and ethylenephenyl.

As used herein, the term "alkoxy" refers to an alkyl group as defined herein covalently bound via an O linkage. The alkoxy group is optionally substituted with substituents. Examples of "alkoxy" as used herein include, but are not limited to methoxy, ethoxy, propoxy, isoproxy, butoxy, isobutoxy, tert-butoxy and pentoxy.

As used herein, the terms "$C_1$-$C_2$ alkoxy", "$C_1$-$C_3$ alkoxy" and "$C_1$-$C_6$ alkoxy" refer to an alkoxy group, as defined herein, containing at least 1, and at most 2, 3 or 6 carbon atoms respectively, or any range in between (eg alkoxy groups containing 2-5 carbon atoms are also within the range of $C_1$-$C_6$).

As used herein, the term "alkylamine" refers to an alkyl group as defined herein having one or more amino groups. The amino groups can be primary, secondary or tertiary. The alkyl amine can be further substituted with a hydroxy group to form an amino-hydroxy group. Examples of alkylamines include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the terms "$C_1$-$C_2$ alkylamine", "$C_1$-$C_3$ alkylamine" and "$C_1$-$C_6$ alkylamine" refer to an alkylamine group, as defined herein, containing at least 1, and at most 2, 3 or 6 carbon atoms respectively, or any range in between (e.g., alkylamine groups containing 2-5 carbon atoms are also within the range of $C_1$-$C_6$).

As used herein, the term "alkylsulfonyl" refers to an alkyl group as defined herein having one or more sulfonyl groups. The sulfonyl group can link the alkylsulfonyl to the point of attachment with the rest of the compound, be at the omega position of the alkyl group, or link together at least two carbon atoms of the alkyl group.

As used herein, the terms "$C_1$-$C_2$ alkylsulfonyl", "$C_1$-$C_3$ alkylsulfonyl" and "$C_1$-$C_6$ alkylsulfonyl" refer to an alkylsulfonyl group, as defined herein, containing at least 1, and at most 2, 3 or 6 carbon atoms respectively, or any range in between (e.g., alkylsulfonyl groups containing 2-5 carbon atoms are also within the range of $C_1$-$C_6$).

The term "heteroatom" as used herein means an atom of any element other than carbon or hydrogen. Examples of heteroatoms include nitrogen, oxygen, sulfur and phosphorus. Preferred heteroatoms include N, O and S, preferably N and O.

The term "heteromoiety" as used herein means a chemical group comprising a heteroatom. Examples of heteromoieties include O, S, S(O), $SO_2$, N and NH.

A "substituent" as used herein, refers to a molecular moiety that is covalently bonded to an atom within a molecule of interest. Reference to "a substituent" may include a single substituent or to one or more substituents from the specified list. In some embodiments, a substituted moiety may include 1, 2, 3, 4, 5 or 6 substituents, preferably 1, 2, 3 or 4, more preferably 1, 2 or 3, 1 or 2 or only 1 substituent. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, ie, a compound that can be isolated, characterized and tested for biological activity.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art.

Examples of substituents include but are not limited to $C_1$-$C_6$ alkyl, $C_1$-$C_6$ haloalkyl, $C_1$-$C_6$ haloalkoxy, $C_1$-$C_6$ hydroxyalkyl, $C_3$-$C_7$ heterocyclyl, $C_3$-$C_7$ cycloalkyl, $C_1$-$C_6$ alkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_1$-$C_6$ perfluoroalkyl. Preferably the substituents include amino, halo, $C_1$-$C_6$ alkyl, amido, hydroxyl.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I). Preferably, 'halo' is fluoro or chloro.

As used herein, the term "haloalkyl" refers to an alkyl group as defined herein in which one or more (up to all) of the available hydrogen atoms have been replaced with a halogen. In some instances, the term "perfluoro" can be used to define a compound or radical where all the hydrogens are replaced with fluorine. For example, perfluoromethyl refers to 1,1,1-trifluoromethyl.

As used herein, the terms "$C_1$-$C_2$ haloalkyl", "$C_1$-$C_3$ haloalkyl" and "$C_1$-$C_6$ haloalkyl" refer to a haloalkyl group, as defined herein, containing at least 1, and at most 2, 3 or 6 carbon atoms respectively, or any range in between (e.g. haloalkyl groups containing 2-5 carbon atoms are also within the range of $C_1$-$C_6$).

For example, a C1 haloalkyl group could be, but is not limited to, fluoromethyl, or difluoromethyl, or trifluoromethyl.

As used herein, the term "haloalkenyl" refers to an alkenyl group as defined above in which one or more of the available hydrogen atoms have been replaced with a halogen.

Thus, for example, "$C_{1-6}$ haloalkenyl" (or "$C_1$-$C_6$ haloalkenyl") refers to a $C_1$ to $C_6$ linear or branched alkenyl group as defined above with one or more halogen substituents.

As used herein, the term "haloalkynyl" refers to an alkynyl group as defined above in which one or more of the available hydrogen atoms have been replaced with a halogen. Thus, for example, "$C_{1-6}$ haloalkynyl" (or "$C_1$-$C_6$ haloalkynyl") refers to a $C_1$ to $C_6$ linear or branched alkynyl group as defined above with one or more halogen substituents.

As used herein the term haloalkoxy refers to an alkoxy group as defined herein substituted with at least one halogen.

The term "amino" or "amine" refers to the group-$NH_2$.

The term "substituted amino" or "secondary amino" refers to an amino group having a hydrogen replaced with, for example a $C_1$-$C_6$ alkyl group ("$C_1$-$C_6$ alkylamino"), an aryl or aralkyl group ("arylamino", "aralkylamino") and so on. $C_1$-$C_3$ alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_1$-$C_6$alkyl group, which may be the same or different ("dialkylamino"), an aryl and alkyl group ("aryl (alkyl)amino") and so on. Di($C_1$-$C_3$alkyl)amino groups are preferred, such as for example, dimethylamino ($NMe_2$), diethylamino ($NEt_2$), dipropylamino ($NPr_2$) and variations thereof (eg N(Me)(Et) and so on).

The term "nitro" refers to the group —$NO_2$.

The term "cyano" and "nitrile" refer to the group —CN.

The term "amido" or "amide" refers to the group —C(O)$NH_2$.

The term "substituted amido" or "substituted amide" refers to an amido group having a hydrogen replaced with, for example a $C_1$-$C_6$ alkyl group ("$C_1$-$C_6$ alkylamido" or "$C_1$-$C_6$ alkylamide"), an aryl ("arylamido"), aralkyl group ("aralkylamido") and so on. $C_1$-$C_3$ alkylamide groups are preferred, such as for example, methylamide (—C(O) NHMe), ethylamide (—C(O)NHEt) and propylamide (—C(O)NHPr) and includes reverse amides thereof (eg NHMeC(O)—, —NHEtC(O)— and —NHPrC(O)—).

The term "disubstituted amido" or "disubstituted amide" refers to an amido group having the two hydrogens replaced with, for example a $C_1$-$C_6$alkyl group ("di($C_1$-$C_6$ alkyl) amido" or "di($C_1$-$C_6$ alkyl)amide"), an aralkyl and alkyl group ("alkyl(aralkyl)amido") and so on. Di($C_1$-$C_3$ alkyl) amide groups are preferred, such as for example, dimethylamide (—C(O)$NMe_2$), diethylamide (—C(O)$NEt_2$) and dipropylamide ((—C(O)$NPr_2$) and variations thereof (eg C(O)N(Me)Et and so on) and includes reverse amides thereof.

The term "sulfonyl" refers to the group —$SO_2H$.

The term "substituted sulfonyl" refers to a sulfonyl group having the hydrogen replaced with, for example a $C_1$-$C_6$ alkyl group ("sulfonyl$C_1$-$C_6$ alkyl"), an aryl ("arylsulfonyl"), an aralkyl ("aralkylsulfonyl") and so on. Sulfonyl $C_1$-$C_3$ alkyl groups are preferred, such as for example, —$SO_2Me$, —$SO_2Et$ and —$SO_2Pr$.

The term "sulfonylamido" or "sulfonamide" refers to the group —$SO_2NH_2$.

The term "substituted sulfonamido" or "substituted sulphonamide" refers to an sulfonylamido group having a hydrogen replaced with, for example a $C_1$-$C_6$ alkyl group ("sulfonylamido$C_1$-$C_6$ alkyl"), an aryl ("arylsulfonamide"), aralkyl ("aralkylsulfonamide") and so on. Sulfonylamido$C_1$-$C_3$ alkyl groups are preferred, such as for example, $SO_2NHMe$, $SO_2NHEt$ and —$SO_2NHPr$ and includes reverse sulfonamides thereof (e.g. —$NHSO_2Me$, $NHSO_2Et$ and —$NHSO_2Pr$).

The term "disubstituted sulfonamido" or "disubstituted sulphonamide" refers to an sulfonylamido group having the two hydrogens replaced with, for example a $C_1$-$C_6$ alkyl group, which may be the same or different ("sulfonylamidodi($C_1$-$C_6$ alkyl)"), an aralkyl and alkyl group ("sulfonamido(aralkyl)alkyl") and so on. Sulfonylamidodi($C_1$-$C_3$ alkyl) groups are preferred, such as for example, —$SO_2NMe_2$, —$SO_2NEt_2$ and —$SO_2NPr_2$ and variations thereof (eg $SO_2N$(Me)Et and so on) and includes reserve sulfonamides thereof (eg —N(Me)$SO_2Me$ and so on).

The term "sulfate" refers to the group $OS(O)_2OH$ and includes groups having the hydrogen replaced with, for example a $C_1$-$C_6$ alkyl group ("alkylsulfates"), an aryl ("arylsulfate"), an aralkyl ("aralkylsulfate") and so on. $C_1$-$C_3$ alkylsulfates are preferred, such as for example, $OS(O)_2OMe$, $OS(O)_2OEt$ and $OS(O)_2OPr$.

The term "sulfonate" refers to the group $SO_3H$ and includes groups having the hydrogen replaced with, for example a $C_1$-$C_6$ alkyl group ("alkylsulfonate"), an aryl ("arylsulfonate"), an aralkyl ("aralkylsulfonate") and so on. $C_1$-$C_3$ alkylsulfonates are preferred, such as for example, $SO_3Me$, $SO_3Et$ and $SO_3Pr$.

The term "amino acid" as herein defined refers to a moiety containing an amino group and a carboxyl group linked by at least one carbon. An amino acid may refer a natural or non-natural amino acid, preferably a natural amino acid such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, preferably the amino acid is arginine, lysine or histidine, most preferably lysine.

The term "carboxylate" or "carboxyl" refers to the group —COO— or —COOH.

The term "carbamate" or "carbomyl" refers to the group —OC(O)$NH_2$. The carbamate may be substituted, or may be disubstituted, for example with an alkyl group such as but not limited to $C_1$-$C_6$ alkyl.

The term "carbonate" refers to the group —OC(O)O— or —OC(O)OH.

The term "alkylcarbonate" as herein defined refers to a carbonate group having the hydrogen replaced with, for example a $C_1$-$C_6$ alkyl group, an aryl or aralkyl group ("arylcarbonate" or "aralkylcarbonate") and so on. $CO_3C_1$-$C_3$alkyl groups are preferred, such as for example, methylcarbonate ($CO_3Me$), ethylcarbonate ($CO_3Et$) and propylcarbonate ($CO_3Pr$).

The term "ester" refers to a carboxyl group having the hydrogen replaced with, for example a $C_1$-$C_6$ alkyl group ("carboxyl$C_1$-$C_6$ alkyl" or "alkylester"), an aryl or aralkyl group ("arylester" or "aralkylester") and so on. $CO_2C_1$-$C_3$ alkyl groups are preferred, such as for example, methylester ($CO_2Me$), ethylester ($CO_2Et$) and propylester ($CO_2Pr$) and includes reverse esters thereof (eg —OC(O)Me, —OC(O)Et and —OC(O)Pr).

The term "heterocyclyl" refers to a moiety obtained by removing a hydrogen atom from a ring atom of a heterocyclic compound which moiety has from 3 to 12 ring atoms (unless otherwise specified), of which 1, 2, 3, 4 or more are ring heteroatoms, for example independently selected from O, S and N, or ring heteromoieties, for example independently selected from O, S, S(O), $SO_2$, N and NH. When a heterocyclyl group contains the prefix $C_{n1-n2}$ or "n1 to n2" this prefix indicates the number of carbon atoms in the corresponding carbocyclic group, in which one or more, suitably 1, 2, 3, 4 or more, of the ring atoms is replaced with a heteroatom or heteromoiety.

In this context, the prefixes 3-, 4-, 5-, 6-, 7-, 8-, 9- and 10-membered denote the number of ring atoms, or range of ring atoms, whether carbon atoms or heteroatoms. For example, the term "$C_{3-10}$ heterocyclyl" or "3-10 membered heterocyclyl", as used herein, pertains to a heterocyclyl group having 3, 4, 5, 6, 7, 8, 9 or 10 ring atoms. Examples of heterocyclyl groups include 5-6-membered monocyclic heterocyclyls and 6-10 membered bicyclic heterocyclyls (including fused, bridged and spirocyclic ring systems).

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (eg 3-pyrroline, 2,5-dihydropyrrole), 2Hpyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6 membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass heteroaryl (aromatic heterocyclyls) and heterocycloalkyl (non-aromatic heterocyclyls). Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O. The aromatic heterocyclyl groups may comprise 1, 2, 3, 4 or more ring heteroatoms. When a heteroaryl group contains the prefix $C_{n1-n2}$ or "n1 to n2" this prefix indicates the number of carbon atoms in the corresponding aryl group, in which one or more, suitably 1, 2, 3, 4 or more, of the ring atoms is replaced with a heteroatom. In the case of fused aromatic heterocyclyl groups, only one of the rings may contain a heteroatom and not all rings must be aromatic.

"Heteroaryl" is used herein to denote a heterocyclic group having aromatic character and embraces aromatic monocyclic ring systems and polycyclic (eg bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6 membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoine, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "heterocycloalkyl" or "non-aromatic heterocyclyl" encompasses optionally substituted saturated and unsaturated rings which contain at least one heteroatom such as N, S and O, or a heteromoiety such as O, S, S(O), $SO_2$, N and NH. The ring may contain 1, 2, 3, 4 or more heteroatoms or heteromoieties. When a heterocycloalkyl group contains the prefix $C_{n1-n2}$ or "n1 to n2" this prefix indicates the number of carbon atoms in the corresponding carbocyclic group, in which one or more, suitably 1, 2, 3, 4 or more, of the ring atoms is replaced with a heteroatom or heteromoiety. The ring may be a monocyclic ring or part of a polycyclic ring system. Polycyclic ring systems include fused and/or bridged rings and spirocycles. Not every ring in a non-aromatic heterocyclic polycyclic ring system must contain a heteroatom, provided at least one ring contains one or more heteroatoms.

Non-aromatic heterocyclyls may be 3-8 membered monocyclic rings.

Examples of 5-membered non-aromatic heterocyclyl rings include 2H-pyrrolyl, 1pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5trioxalanyl, 1,3,5-trithianyl, 1,4-morpholinyl, thiomorpholinyl, 1,4-oxathianyl, triazinyl, 1,4thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7 membered heterocyclyls fused to carbocyclic aromatic rings include indolinyl, benzodiazepinyl, benzazepinyl, dihydrobenzofuranyl and the like.

The term "alkyleneheteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined herein. The numerical range from x to y in "$C_{x-y}$ alkylenecycloalkyl" relates to the total number of alkyl carbons and heteroaryl ring atoms (carbon and heteroatoms together).

The term "alkyleneheterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined herein. The numerical range from x to y in "$C_{x-y}$ alkyleneheterocycloalkyl" relates to the total number of alkyl carbons and heterocycloalkyl ring atoms (carbon and heteroatoms together).

As used herein, the term solvate refers to a complex of the compound and either stoichiometric or non-stoichiometric amounts of a solvent. Solvates are often formed during the process of crystallization with pharmaceutically acceptable solvents such as water, ethanol, and the like. Hydrates are formed when the solvent is water, or alcoholates are formed when the solvent is alcohol.

As used herein, the term polymorph refers to the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

As used herein, the term "metabolite" refers to a derivative of a compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. Metabolites of the compounds disclosed herein are optionally identified either by administration of compounds to a host and analysis of tissue samples from the host, or by incubation of compounds with hepatic cells in vitro and analysis of the resulting compounds.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. The term "stereoisomers" refers to compounds which have identical chemical constitution, but differ with regard to the arrangement of the atoms or groups in space. As used herein, the term "stereoisomer" includes but is not limited to diastereomers, enantiomers and atropisomers, as well as mixtures thereof such as racemic mixtures.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Compounds

The present disclosure provides compounds of formula (I):

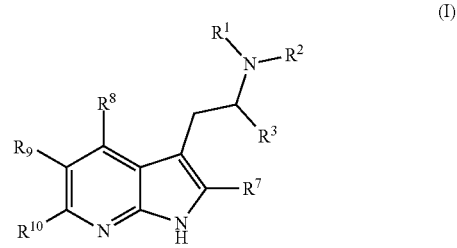

(I)

or a pharmaceutically acceptable salt, solvate, tautomer, N-oxide, stereoisomer, metabolite, polymorph or prodrug thereof, wherein $R^1$ and $R^2$ are each independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the nitrogen atom to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ together the atoms to which they are attached to form a $C_{3-12}$ heterocycloalkyl, said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

$R^7$, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)$(OR^{13})_2$, $S(O)R^{13}$, $S(O)N(R^{13})_2$, $SO_2R^{13}$, $N(R^{13})_2$, $N(R^{13})$ $C(O)R^{13}$, $N(R^{13})C(O)OR^{13}$, $N(R^{13})$ $C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $X^2$ is $CR^7$, $R^7$ and one of $R^1$, $R^2$, or $R^3$ are combined with the atoms to which they are attached to form a $C_{5-8}$ heterocycloalkyl, said $C_{5-8}$ heterocyclyalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

alternatively, when $X^1$ is $NR^6$ and $X^2$ is $CR^7$, $R^6$ and $R^7$ are combined with the atoms to which they are each attached to form a $C_{4-10}$ heterocycloalkyl or a $C_{5-10}$ heteroaryl, said $C_{4-10}$ heterocycloalkyl and $C_{5-10}$ heteroaryl each being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, one of $R^8$ and $R^9$ (if present) is selected from halogen, $OR^{13}$, $N(R^{13})_2$, $SR^{13}$, $C_{1-6}$ alkyl and $C_{1-6}$ haloalkyl, the other (if present) being hydrogen.

In some embodiments, $R^8$ (if present) is selected from halogen, $OR^{13}$, $N(R^{13})_2$, $SR^{13}$, $C_{1-6}$ alkyl and $C_{1-6}$ haloalkyl, and $R^9$ (if present) is hydrogen.

In some embodiments, $R^9$ (if present) is selected from halogen, $OR^{13}$, $N(R^{13})_2$, $SR^{13}$, $C_{1-6}$ alkyl and $C_{1-6}$ haloalkyl, and $R^8$ (if present) is hydrogen.

In some embodiments, $R^8$ (if present) is selected from halogen, $OR^{13}$ and $C_{1-6}$ alkyl, and $R^9$ (if present) is hydrogen.

In some embodiments, $R^9$ (if present) is selected from halogen, $OR^{13}$ and $C_{1-6}$ alkyl, and $R^8$ (if present) is hydrogen.

In some embodiments, one of $R^8$ and $R^9$ is $OR^{13}$.

In some embodiments, each $R^{13}$ (if present) is independently selected from hydrogen and $C_{1-6}$ alkyl.

In some embodiments, each $R^{13}$ (if present) is H.

In some embodiments, each $R^{13}$ (if present) is $C_{1-6}$alkyl, preferably $C_{1-4}$alkyl, more preferably methyl.

In some embodiments, $R^7$ (if present) is hydrogen.
In some embodiments, $R^8$ (if present) is hydrogen.
In some embodiments, $R^9$ (if present) is hydrogen.
In some embodiments, $R^{10}$ (if present) is hydrogen.
In some embodiments, $R^7$ and $R^8$ (if present) are hydrogen.
In some embodiments, $R^7$ and $R^{10}$ (if present) are hydrogen.
In some embodiments, $R^8$ and $R^{10}$ (if present) are hydrogen.
In some embodiments, $R^7$, $R^8$ and $R^{10}$ (if present) are hydrogen.

In some embodiments, only one of $R^8$, $R^9$, and $R^{10}$ is other than hydrogen. In some embodiments, only $R^8$ of $R^8$, $R^9$, and $R^{10}$ is other than hydrogen. In some embodiments, only $R^9$ of $R^8$, $R^9$, and $R^{10}$ is other than hydrogen. In some embodiments, only $R^{10}$ of $R^8$, $R^9$, and $R^{10}$ is other than hydrogen.

In some embodiments, at least one of $R^1$ and $R^2$ is not methyl. In some embodiments, both of $R^1$ and $R^2$ are not methyl.

In some embodiments, $R^1$ and $R^2$ are each independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

$R^7$ is selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)$(OR^{13})_2$, $S(O)R^{13}$, $S(O)N(R^{13})_2$, $SO_2R^{13}$, $N(R^{13})_2$, $N(R^{13})$ $C(O)R^{13}$, $N(R^{13})C(O)OR^{13}$, $N(R^{13})$ $C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively $R^7$ and one of $R^1$, $R^2$, or $R^3$ are combined with the atoms to which they are attached to form a $C_{5-8}$ heterocycloalkyl, said $C_{5-8}$ heterocyclyalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

$R^8$, $R^9$ and $R^{10}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)$(OR^{13})_2$, $S(O)R^{13}$, $S(O)N(R^{13})_2$, $SO_2R^{13}$, $N(R^{13})_2$, $N(R^{13})$ $C(O)R^{13}$, $N(R^{13})C(O)OR^{13}$, $N(R^{13})$ $C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), SO$_2$, N, and NR$^{13}$;

each R$^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO$_2$, N, NH and NCH$_3$;

alternatively, R$^8$ and R$^9$ or R$^9$ and R$^{10}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents selected from halogen, (O), CN, $C_{1-8}$ alkoxy, $C_{1-8}$ alkylamino, $C_{1-8}$ alkylsulfonyl, CO$_2$R$^{14}$, C(O)N(R$^{14}$)$_2$, OR$^{14}$, N(R$^{14}$)$_2$, NO$_2$, SR$^{14}$, SO$_2$R$^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO$_2$ and NR$^{14}$;

each R$^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NO$_2$, NHCH$_3$, SH, SCH$_3$, SO$_2$CH$_3$, SOCH$_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{3-6}$ heterocycloalkyl including 1 or 2 ring heteromoieties selected from O, S, S(O), SO$_2$, N, NH and NCH$_3$.

In some embodiments, R$^1$ and R$^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, R$^1$ and R$^2$ are each independently selected from $C_{1-4}$ alkyl.

In some embodiments, R$^1$ and R$^2$, together with the nitrogen to which they are attached, form any one of the following:

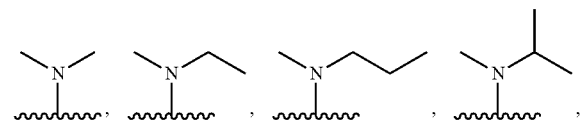

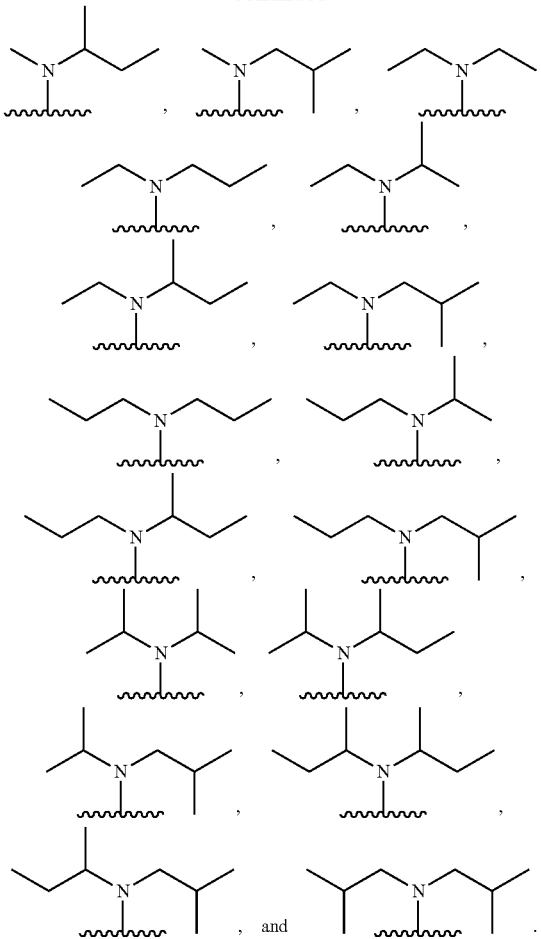

In some embodiments, R$^1$ and R$^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, CO$_2$R$^4$, C(O)N(R$^4$)$_2$, OR$^4$, N(R$^4$)$_2$, NO$_2$, SR$^4$ and SO$_2$R$^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO$_2$ and NR$^4$, wherein R$^4$ is defined as in any one of the foregoing paragraphs.

In some embodiments R$^3$ is hydrogen.

In some embodiments, R$^3$ and one of R$^1$ and R$^2$ are combined with the atoms to which they are attached to form a $C_{3-8}$ heterocycloalkyl, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, CO$_2$R$^4$, C(O)N(R$^4$)$_2$, OR$^4$, N(R$^4$)$_2$, NO$_2$, SR$^4$, SO$_2$R$^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO$_2$ and NR$^4$, wherein R$^4$ is defined as in any one of the foregoing paragraphs.

In some embodiments, R$^7$, R$^8$, R$^9$ and R$^{10}$ are each independently selected from hydrogen, halogen, CN, OR$^{13}$, N(R$^{13}$)$_2$, SR$^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, CO$_2$R$^{13}$, C(O)R$^{13}$, C(O)N(R$^{13}$)$_2$, C(O)C(O)N(R$^{13}$)$_2$, OC(O)R$^{13}$, OC(O)OR$^{13}$, OC(O)N(R$^{13}$)$_2$, OS(O)R$^{13}$, OS(O)N(R$^{13}$)$_2$, OSO$_2$R$^{13}$, OP(O)(OR$^{13}$)$_2$, OC$_{1-6}$alkyleneP(O)(OR$^{13}$)$_2$, S(O)R$^{13}$, S(O)N(R$^{13}$)$_2$, SO$_2$R$^{13}$, N(R$^{13}$)$_2$, N(R$^{13}$) C(O)R$^{13}$, N(R$^{13}$)C(O)OR$^{13}$, N(R$^{13}$) C(O)N(R$^{13}$)$_2$, NO$_2$, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, C$_{4-16}$ alkyleneheteroaryl, said C$_{1-6}$ alkyl, C$_{1-6}$ haloalkyl, C$_{2-6}$ alkenyl, C$_2$-C$_6$ haloalkenyl, C$_{2-6}$ alkynyl, C$_{2-6}$ haloalkynyl, C$_{1-6}$ alkylamine, C$_{1-6}$ alkoxy, C$_{1-6}$ haloalkoxy, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{4-16}$ alkyleneheteroaryl being optionally substituted with one or more substituents independently selected from halogen, CN, C$_{1-8}$ alkoxy, C$_{1-8}$ alkylamino, C$_{1-8}$ alkylsulfonyl, CO$_2$R$^{13}$, C(O)N(R$^{13}$)$_2$, OR$^{13}$, N(R$^{13}$)$_2$, NO$_2$, SR$^{13}$ and SO$_2$R$^{13}$, said C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{4-16}$ alkyleneheteroaryl each being further optionally substituted with one or more substituents selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$cycloalkyl and C$_{3-6}$ heterocycloalkyl including 1 or 2 ring heteromoieties selected from O, S, S(O), SO$_2$, N, and NR$^{13}$;

wherein R$^{13}$ is as defined in any one of the foregoing paragraphs.

In some embodiments, R$^7$, R$^8$, R$^9$ and R$^{10}$ are each independently selected from hydrogen, halogen, CN, OR$^{13}$, N(R$^{13}$)$_2$, SR$^{13}$, C$_{1-6}$ alkyl, C$_{1-6}$ haloalkyl, C$_{2-6}$ alkenyl, C$_2$-C$_6$ haloalkenyl, C$_{2-6}$ alkynyl, C$_{2-6}$ haloalkynyl, C$_{1-6}$ alkylamine, C$_{1-6}$ alkoxy, C$_{1-6}$ haloalkoxy, CO$_2$R$^{13}$, C(O)N (R$^{13}$)$_2$, OC(O)R$^{13}$, OSO$_2$R$^{13}$, OP(O)(OR$^{13}$)$_2$, OC$_{1-6}$alkyleneP(O)(OR$^{13}$)$_2$, S(O)R$^{13}$, SO$_2$R$^{13}$, N(R$^{13}$)$_2$, NO$_2$, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, C$_{4-16}$ alkyleneheteroaryl, said C$_{1-6}$ alkyl, C$_{1-6}$ haloalkyl, C$_{2-6}$ alkenyl, C$_2$-C$_6$ haloalkenyl, C$_{2-6}$ alkynyl, C$_{2-6}$ haloalkynyl, C$_{1-6}$ alkylamine, C$_{1-6}$ alkoxy, C$_{1-6}$ haloalkoxy, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{4-16}$ alkyleneheteroaryl being optionally substituted with one or more substituents independently selected from halogen, CN, C$_{1-8}$ alkoxy, C$_{1-8}$ alkylamino, C$_{1-8}$ alkylsulfonyl, CO$_2$H, CO$_2$CH$_3$, C(O)NH$_2$, C(O)N(CH$_3$)$_2$, C(O) NHCH$_3$, OH, NH$_2$, N(CH$_3$)$_2$, NO$_2$, NHCH$_3$, SH, SCH$_3$, SO$_2$CH$_3$, and SOCH$_3$, said C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{4-16}$ alkyleneheteroaryl each being further optionally substituted with one or more substituents selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$cycloalkyl and C$_{3-6}$ heterocycloalkyl including 1 or 2 ring heteromoieties selected from O, S, S(O), SO$_2$, N, NH and NCH$_3$;

wherein R$^{13}$ is as defined as in any one of the foregoing paragraphs.

In some embodiments, 1 or 2 of R$^7$, R$^8$, R$^9$ and R$^{10}$ are each independently selected from halogen, C$_{1-6}$ alkyl, C$_{1-6}$ haloalkyl and OR$^{13}$ wherein R$^{13}$ is selected from C$_{1-6}$ alkyl and C$_{1-6}$ haloalkyl, and the other of R$^7$, R$^8$, R$^9$ and R$^{10}$ are each hydrogen.

FURTHER EMBODIMENTS

In embodiments, the compound of the invention is a compound of formula (I):

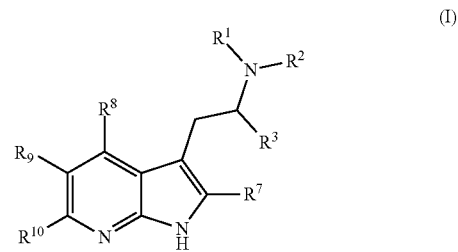

(I)

wherein:

R$^1$ is independently selected from hydrogen, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl, said C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$ and SO$_2$R$^4$, said C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being further optionally substituted with one or more substituent independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, N, S(O), SO$_2$ and NR$^4$;

R$^2$ is independently selected from hydrogen, C$_{1-6}$haloalkyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl, said C$_{1-6}$haloalkyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$ and SO$_2$R$^4$, said C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the atoms to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

one or more substituents $R^7$, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In embodiments, the compound of formula (I) is not one of the following:

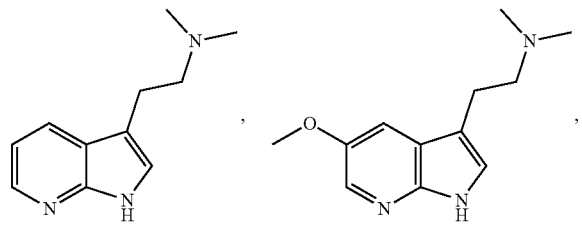,

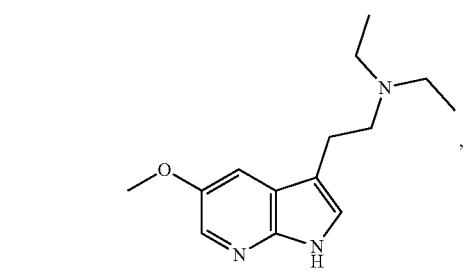,

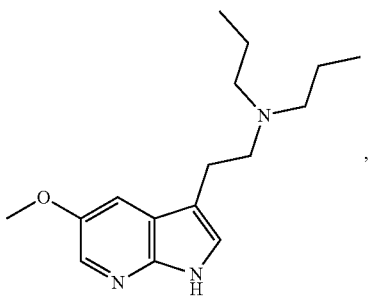,

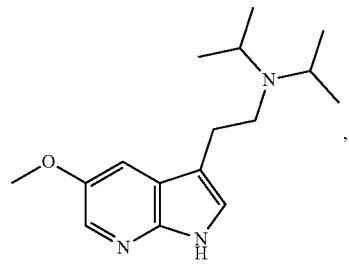,

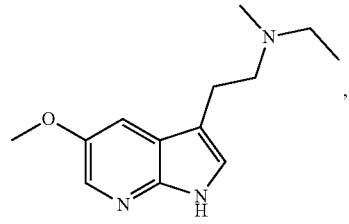,

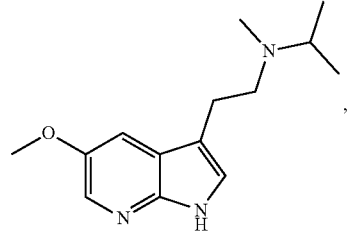,

, and

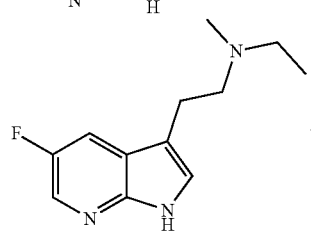

In some embodiments, $R^7$ is H, $R^8$ is H and $R^{10}$ is H. In these embodiments, the compound may be provided by formula (II):

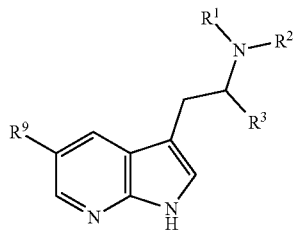

(II)

wherein $R^1$, $R^2$, $R^3$ and $R^9$ are as defined for any aspect or embodiment herein.

$R^1$, $R^2$ and $R^3$

In embodiments, $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituent independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the atoms to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

In embodiments, $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$.

In embodiments, $R^1$ is independently selected from hydrogen, $C_{1-6}$ alkyl, $C_{1-6}$ haloalkyl, said $C_{1-6}$ alkyl, $C_{1-6}$ haloalkyl, each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$.

In embodiments, $R^2$ is independently selected from $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$.

In embodiments, at least one of $R^1$ and $R^2$ is not hydrogen.

In embodiments, both of $R^1$ and $R^2$ are not hydrogen. In embodiments, neither of $R^1$ and $R^2$ are hydrogen.

In embodiments, $R^1$ and $R^2$ together with the atoms to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$.

In embodiments, $R^1$ and $R^2$ together with the nitrogen atom to which they are attached form a $C_{4-8}$ heterocycloalkyl including 0 or 1 additional ring heteromoieties selected from O, S, S(O), $SO_2$, N and $NR^4$, wherein the $C_{4-8}$heterocycloalkyl is optionally substituted with one or more substituents selected from halogen, $C_{1-8}$ alkoxy, $C_{1-6}$ alkyl, $C_{1-6}$ haloalkyl, $C_{3-6}$ cycloalkyl and $C_{3-6}$ heterocycloalkyl including 1 or 2 ring heteromoieties selected from O, S, N, S(O), $SO_2$ and $NR^4$.

In embodiments, $R^1$ and $R^2$ together with $R^1$ and $R^2$ together with the nitrogen atom to which they are attached form an optionally substituted $C_{4-8}$ heterocycloalkyl. In these embodiments, the compound of formula (I) may be provided as a compound of formula (III):

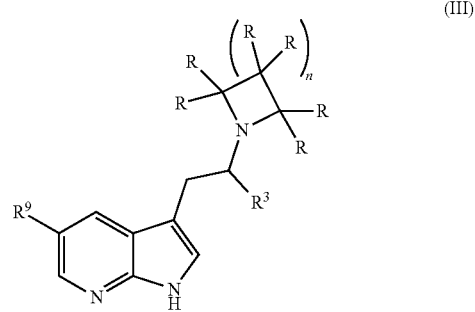

(III)

wherein:

R³ and R⁹ are as defined for any aspect or embodiment herein;

n is an integer from 1 to 5, preferably 1, 2 or 3; and each R may be the same or different and is independently selected from hydrogen, halogen, $C_{1-8}$ alkoxy, $C_{1-6}$ alkyl, $C_{1-6}$ haloalkyl, $C_{3-6}$ cycloalkyl and $C_{3-6}$ heterocycloalkyl, or two Rs together with the atoms to which they are attached form an optionally substituted $C_{4-12}$ cycloalkyl or an optionally substituted 4-12 membered heterocycloalkyl ring, which may thus form a fused-, spiro- or bridged-cyclic system. In embodiments, 2 Rs bonded to the same ring carbon atom form an optionally substituted $C_{4-12}$ cycloalkyl or an optionally substituted 4-12 membered heterocycloalkyl ring such that it forms a spirocyclic ring system. Preferably 2 Rs bonded to the same ring carbon atom form an optionally substituted $C_{4-6}$ cycloalkyl or an optionally substituted 4-6 membered heterocycloalkyl ring such that it forms a spirocyclic ring system.

In embodiments, R¹ and R² together with the nitrogen atom to which they are attached form a $C_{4-8}$ heterocycloalkyl that does not include additional ring heteromoieties.

In embodiments, R¹ and R² together with the nitrogen atom to which they are attached form a $C_{4-8}$ heterocycloalkyl that is monocyclic or fused bicyclic.

In embodiments, R¹ and R² together with the nitrogen atom to which they are attached form a monocyclic $C_{6-8}$ heterocycloalkyl.

In embodiments, R¹ and R² together with the nitrogen atom to which they are attached form a bicyclic $C_{6-8}$ heterocycloalkyl.

In embodiments, R¹ and R² together with the nitrogen atom to which they are attached form a $C_{4-8}$ heterocycloalkyl that is fused.

In embodiments, R¹ and R² together with the nitrogen atom to which they are attached form a $C_{4-8}$ heterocycloalkyl that is unsubstituted.

In embodiments, R¹ and R² together with the nitrogen atom to which they are attached form a $C_{4-8}$ heterocycloalkyl that is unsubstituted and monocyclic or fused bicyclic.

In embodiments, R¹ and R² together with the nitrogen atom to which they are attached form a $C_{4-8}$ heterocycloalkyl that is unsubstituted and monocyclic.

In embodiments, R¹ and R² together with the nitrogen atom to which they are attached form a $C_{4-8}$ heterocycloalkyl that is unsubstituted and fused bicyclic.

In embodiments, R¹ is independently selected from hydrogen, optionally substituted $C_{1-6}$ alkyl, optionally substituted $C_{1-6}$ haloalkyl, optionally substituted $C_{3-8}$ cycloalkyl, optionally substituted $C_{4-14}$ alkylenecycloalkyl, optionally substituted $C_{3}$-$C_{8}$ heterocycloalkyl, optionally substituted $C_{4}$-$C_{14}$ alkyleneheterocycloalkyl, optionally substituted $C_{6-12}$ aryl, optionally substituted $C_{7-18}$ alkylenearyl, optionally substituted $C_{5-10}$ heteroaryl, and optionally substituted $C_{6-16}$ alkyleneheteroaryl, and R² is independently selected from optionally substituted $C_{3-8}$ cycloalkyl, optionally substituted $C_{4-14}$ alkylenecycloalkyl, optionally substituted $C_{3}$-$C_{8}$ heterocycloalkyl, optionally substituted $C_{4}$-$C_{14}$ alkyleneheterocycloalkyl, optionally substituted $C_{6-12}$ aryl, optionally substituted $C_{7-18}$ alkylenearyl, optionally substituted $C_{5-10}$ heteroaryl, and optionally substituted $C_{6-16}$ alkyleneheteroaryl, or alternatively R¹ and R² together with the atoms to which they are attached form an optionally substituted $C_{3-8}$ heterocycloalkyl including 0, 1 or 2 additional ring heteromoieties selected from O, S, S(O), SO₂, N and NR⁴.

In embodiments, R² is an optionally substituted $C_{1-6}$haloalkyl.

In embodiments, R¹ is independently selected from hydrogen, methyl, ethyl, iso-propyl, and cyclopropyl.

In embodiments, R² is selected from hydrogen, trifluoroisopropyl, cyclopropyl, difluorocyclopropyl, cyclobutyl, methylenecyclopropyl, 1-cyclopropyl-ethyl, benzyl, methoxybenzyl and fluorobenzyl.

In embodiments, R¹ and R², together with the nitrogen to which they are attached, form any one of the following:

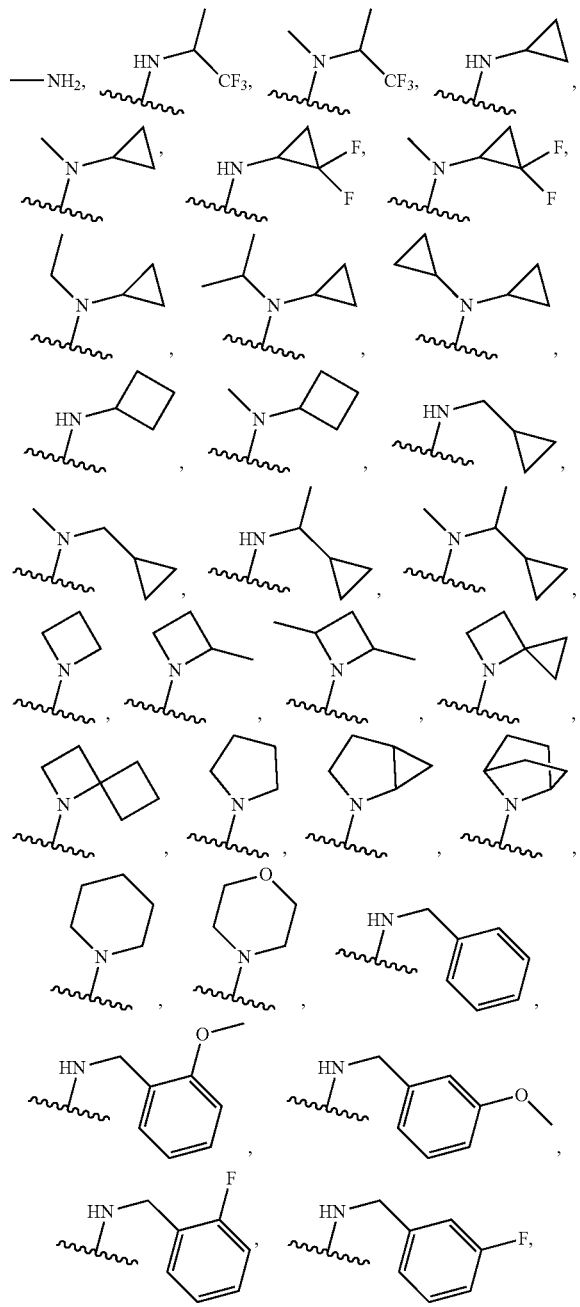

-continued

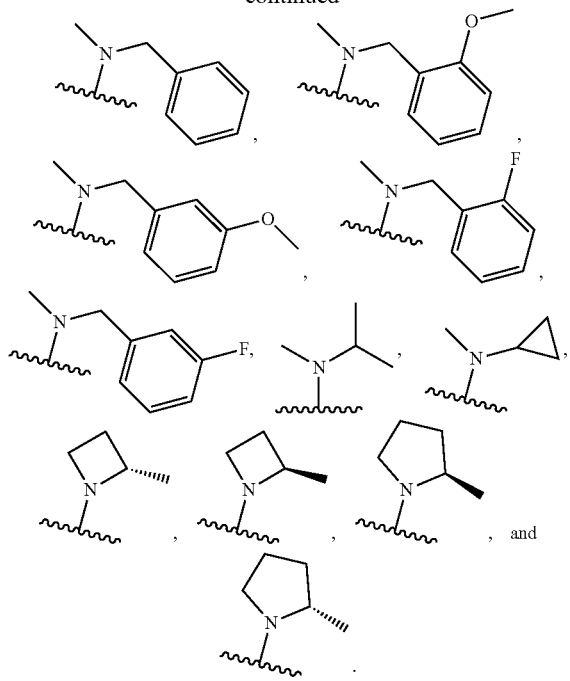

In embodiments, $R^1$ and $R^2$, together with the nitrogen to which they are attached, form any one of the following:

-continued

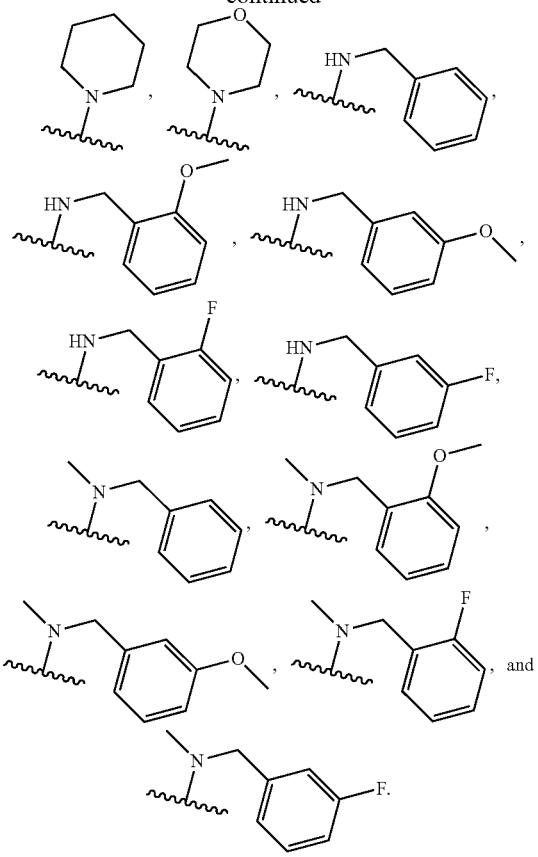

In some embodiments, $R^1$ and $R^2$, together with the nitrogen to which they are attached, form any one of the following:

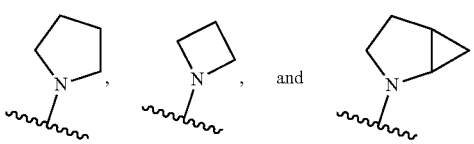

In embodiments, $R^3$ is independently selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

In embodiments, $R^3$ is independently selected from hydrogen and optionally substituted $C_{1-6}$ alkyl;

alternatively $R^3$ and one of $R^1$ and $R^2$ are combined with the atoms to which they are attached to form an optionally substituted $C_{3-12}$ heterocycloalkyl.

In some embodiments, $R^3$ is hydrogen.

In some embodiments, $R^3$ is optionally substituted $C_{1-6}$ alkyl.

In some embodiments, $R^1$ is H, $R^2$ is H and $R^3$ is optionally substituted $C_{1-6}$ alkyl. In some embodiments, $R^1$ is H, $R^2$ is H and $R^3$ is optionally substituted $C_{1-4}$ alkyl. In some embodiments, $R^1$ is H, $R^2$ is H and $R^3$ is optionally substituted $C_{1-3}$ alkyl.

In embodiments, $R^3$ and $R^2$ are combined with the atoms to which they are attached to form an optionally substituted $C_{3-12}$ heterocycloalkyl. In these embodiments, the compound of formula (I) may be provided as a compound of formula (IV):

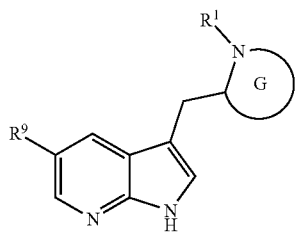

(IV)

wherein:
$R^1$ and $R^9$ are as defined for any embodiment or aspect herein, and
G is an optionally substituted $C_{3-12}$ heterocycloalkyl, preferably a $C_{4-6}$ heterocycloalkyl. The reference to "$C_{x-y}$" for the heterocycloalkyl moiety includes the depicted nitrogen atom within the atom count. Accordingly, G may alternatively be defined as a 3-12 membered heterocycloalkyl including the nitrogen atom as drawn and optionally 1 or 2 additional ring heteromoieties selected from O, S, S(O), $SO_2$, N, NH and $NCH_3$, with the remainder of ring atoms being carbon atoms.

$R^9$

In embodiments, $R^9$ is independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13}) C(O)R^{13}$, $N(R^{13})C(O)OR^{13}$, $N(R^{13}) C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

In embodiments, $R^9$ is independently selected from halogen, CN, $OR^{13}$, $N(R^{13})_2$, $SR^{13}$, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})$ $C(O)R^{13}$, $N(R^{13})C(O)OR^{13}$, $N(R^{13})$ $C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

In embodiments, $R^9$ is independently selected from halogen, CN, —OH, $C_{1-6}$ haloalkyl, $C_{1-6}$ alkoxy, and $C_{1-6}$ haloalkoxy, said $C_{1-6}$ haloalkyl, $C_{1-6}$ alkoxy, $C_{1-6}$ haloalkoxy, is optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$.

In embodiments, $R^9$ is independently selected from halogen, —OH, $C_{1-6}$ haloalkyl, $C_{1-6}$ alkoxy, and $C_{1-6}$ haloalkoxy, said $C_{1-6}$ haloalkyl, $C_{1-6}$ alkoxy, $C_{1-6}$ haloalkoxy, is optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$.

In embodiments, $R^9$ is selected from halo, CN, —OH, $C_{1-4}$alkoxy, $C_{1-4}$haloalkoxy and $C_{1-4}$haloalkyl.

In embodiments, $R^9$ is selected from halo, —OH, $C_{1-4}$alkoxy, $C_{1-4}$haloalkoxy and $C_{1-4}$haloalkyl.

In embodiments, $R^9$ is selected from fluoro, chloro, bromo, CN, —OH, methoxy, trifluoromethoxy and trifluoromethyl.

In embodiments, $R^9$ is selected from fluoro, chloro, —OH, methoxy, trifluoromethoxy and trifluoromethyl.

In embodiments, $R^9$ is fluoro.

In embodiments, $R^9$ is fluoro; and $R^1$ and $R^2$ together with the nitrogen atom to which they are attached form a $C_{4-8}$ heterocycloalkyl that does not include additional ring heteromoieties.

In embodiments, $R^9$ is fluoro; and $R^1$ and $R^2$ together with the nitrogen atom to which they are attached form a $C_{4-8}$ heterocycloalkyl that is monocyclic or fused.

In embodiments, $R^9$ is fluoro; and $R^1$ and $R^2$ together with the nitrogen atom to which they are attached form a $C_{4-8}$ heterocycloalkyl that is monocyclic.

In embodiments, $R^9$ is fluoro; and $R^1$ and $R^2$ together with the nitrogen atom to which they are attached form a $C_{4-8}$ heterocycloalkyl that is unsubstituted and monocyclic or fused.

In embodiments, $R^9$ is fluoro; and $R^1$ and $R^2$ together with the nitrogen atom to which they are attached form a $C_{4-8}$ heterocycloalkyl that is unsubstituted and monocyclic.

In embodiments, $R^9$ is chloro.
In embodiments, $R^9$ is bromo.
In embodiments, $R^9$ is CN.
In embodiments, $R^9$ is methoxy.
In embodiments, $R^9$ is trifluoromethoxy.

$R^8$ and $R^{10}$

In embodiments, $R^8$ is hydrogen.
In embodiments, $R^{10}$ is hydrogen.
In embodiments, $R^8$ and $R^{10}$ are hydrogen.
In embodiments, $R^8$ and $R^{10}$ are hydrogen and $R^9$ is not hydrogen.
In embodiments, $R^8$ and $R^{10}$ are hydrogen and $R^9$ is selected from fluoro, chloro, bromo, CN, —OH, methoxy, trifluoromethoxy and trifluoromethyl.
In embodiments, $R^8$ and $R^{10}$ are hydrogen and $R^9$ is fluoro.

Further Formulas of the Compound

In embodiments, the compound of Formula (I) is selected from S1-S75, or a pharmaceutically acceptable salt, solvate, tautomer, N-oxide, stereoisomer, metabolite, polymorph or prodrug thereof.

In embodiments, the compound of Formula (I) is selected from S1-S42, or a pharmaceutically acceptable salt, solvate, tautomer, N-oxide, stereoisomer, metabolite, polymorph or prodrug thereof.

In embodiments, the compound of Formula (I) is selected from S1-S28 and S30-S75, or a pharmaceutically acceptable salt, solvate, tautomer, N-oxide, stereoisomer, metabolite, polymorph or prodrug thereof.

In embodiments, the compound of Formula (I) is selected from S1, S2, S5, S6, S7, S8, S9, S11, S12, S15, S16, S17, S25, S30-S34, S41-S75, or a pharmaceutically acceptable salt, solvate, tautomer, N-oxide, stereoisomer, metabolite, polymorph or prodrug thereof.

Forms of the Compound

In the case of compounds that are solids, it will be understood by those skilled in the art that the inventive compounds, agents and salts may exist in different crystalline or polymorphic forms, all of which are intended to be within the scope of the present invention and specified formulae.

The invention includes all crystalline forms of a compound of Formula (I) including anhydrous crystalline forms, hydrates, solvates and mixed solvates. If any of these crystalline forms demonstrates polymorphism, all polymorphs are within the scope of this invention.

Formula (I) is intended to cover, where applicable, solvated as well as unsolvated forms of the compounds. Thus, Formula (I) includes compounds having the indicated structures, including the hydrated or solvated forms, as well as the non-hydrated and non-solvated forms.

The compounds of Formula (I) or salts, tautomers, N-oxides, polymorphs or prodrugs thereof may be provided in the form of solvates. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF), acetic acid, and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the invention.

Basic nitrogen-containing groups may be quaternized with such agents as $C_{1-6}$alkyl halide, such as methyl, ethyl, propyl, and butyl chlorides, bromides and iodides; dialkyl sulfates like dimethyl and diethyl sulfate; and others.

Nitrogen containing groups may also be oxidised to form an N-oxide.

The compound of Formula (I) or salts, tautomers, N-oxides, solvates and/or prodrugs thereof that form crystalline solids may demonstrate polymorphism. All polymorphic forms of the compounds, salts, tautomers, N-oxides, solvates and/or prodrugs are within the scope of the invention.

The compound of Formula (I) may demonstrate tautomerism. Tautomers are two interchangeable forms of a molecule that typically exist within an equilibrium. Any tautomers of the compounds of Formula (I) are to be understood as being within the scope of the invention.

The compound of Formula (I) may contain one or more stereocentres. All stereoisomers of the compounds of formula (I) are within the scope of the invention. Stereoisomers include enantiomers, diastereomers, geometric isomers (E and Z olephinic forms and cis and trans substitution patterns) and atropisomers. In some embodiments, the compound is a stereoisomerically enriched form of the compound of formula (I) at any stereocentre. The compound may be enriched in one stereoisomer over another by at least about 60, 70, 80, 90, 95, 98 or 99%.

The compound of Formula (I) or its salts, tautomers, solvates, N-oxides, and/or stereoisomers, may be isotopically enriched with one or more of the isotopes of the atoms present in the compound. For example, the compound may be enriched with one or more of the following minor isotopes: $^2H$, $^3H$, $^{13}C$, $^{14}C$, $^{15}N$, $^{17}O$ and/or $^{18}F$, preferably $^2H$. An isotope may be considered enriched when its abundance is greater than its natural abundance.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four)amino acid residues which are covalently joined to free amino, and amido groups of compounds of Formula (I). The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of Formula (I) through the carbonyl carbon prodrug sidechain.

Compositions, Formulations and Modes of Administration

The compounds of formula (I) can be administered alone or in the form of a pharmaceutical composition. In practice, the compounds of formula (I) are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, there is provided a pharmaceutical composition comprising a compound of formula (I) or a pharmaceutically acceptable salt, stereoisomer, solvate, metabolite, or polymorph thereof, and at least one pharmaceutically acceptable excipient.

Pharmaceutical compositions of the disclosure typically include a therapeutically effective amount of one or more active ingredients in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial perilymph, possibly supplemented with other materials common in compositions for parenteral administration. Neutral buffered saline or saline mixed with serum albumin are further exemplary vehicles.

Pharmaceutical compositions of the present disclosure additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired.

Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminium hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present in the composition, according to the judgment of the formulator.

Various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

A compound of formula (I) may be administered in any form and route which makes the compound bioavailable.

Compositions described herein may be administered systemically or directly to the site of condition or disease.

Compositions described herein may be formulated from compounds according to Formula (I) for any appropriate route of administration including, for example, oral, rectal, nasal, vaginal, topical (including transdermal, buccal, ocular and sublingual), parenteral (including subcutaneous, intraperitoneal, intradermal, intravascular (for example, intravenous), intramuscular, spinal, intracranial, intrathecal, intraocular, periocular, intraorbital, intrasynovial and intraperitoneal injection, intracisternal injection as well as any other similar injection or infusion techniques), inhalation, insufflation, infusion or implantation techniques (e.g., as sterile injectable aqueous or non-aqueous solutions or suspensions). In some embodiments, compositions described herein may be administered orally, nasally, intravenously, intramuscularly, topically, subcutaneously, rectally, vaginally or by urethral application.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such Formulations may also comprise one or more demulcents, preservatives, flavouring agents and/or colouring agents.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical Formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A pharmaceutical composition may be formulated as inhaled formulations, including sprays, mists, or aerosols. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable Formulations, wherein the carrier is a liquid, for administration, as for example, a nasal spray or as nasal drops, include aqueous or oily solutions of the active ingredient.

Compositions suitable for rectal administration are preferably presented as unit dose suppositories. These may be prepared by at least partially dispersing the active in one or more lipophilic bases and then shaping the mixture.

Pharmaceutical compositions may be formulated as sustained release formulations such as a capsule that creates a slow release of active following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of active release. The amount of active contained within a sustained release formulation depends upon, for example, the site of implantation, the rate and expected duration of release and the nature of the condition to be treated.

One skilled in the art can readily select the proper form and route of administration depending on the particular characteristics of the compound selected, the disease or condition to be treated, the stage of the disease or condition, and other relevant circumstances.

It will be understood, that the specific dose level for any particular patient will depend upon a variety of factors including the activity of the specific compound employed, the age, body weight, general health, sex, diet, time of administration, route of administration, number of doses, and rate of excretion, drug combination (i.e. other drugs being used to treat the patient), and the severity of the particular disorder undergoing therapy.

The phrase "therapeutically effective amount" generally refers to an amount of one or more active ingredients of the invention that (i) treats the particular disease, condition, or disorder, (ii) attenuates, ameliorates, or eliminates one or more sign or symptoms of the particular disease, condition, or disorder, or (iii) delays the onset of one or more sign or symptoms of the particular disease, condition, or disorder described herein.

Typically, a therapeutically effective dosage is formulated to contain a concentration (by weight) of at least about 0.1% up to about 50% or more, and all combinations and subcombinations of ranges therein. The compositions can be formulated to contain one or more actives described herein in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

The frequency of administration may be once daily, 2, 3 or 4 times daily. The treatment period may be for the duration of the detectable disease.

In some embodiments, the pharmaceutical composition comprises a compound according to any one of the herein disclosed embodiments, or a pharmaceutically acceptable salt, solvate, tautomer, N-oxide, stereoisomer, metabolite, polymorph or prodrug thereof, an additional therapeutic agent, and a pharmaceutically acceptable excipient.

The additional agent may be any suitable agent described herein. In some embodiments, the additional agent is a psychoactive drug, including those described herein. In some embodiments, the additional agent is useful for treatment of a disease, disorder or condition by activation of a serotonin receptor, including those described herein. In some embodiments, the additional agent is selected from any one of the following, including those described herein: an agent for a mental illness and/or a neuropsychiatric condition; an agent for psychosis and/or psychotic symptoms; an agent for attention deficit hyperactivity disorder and/or attention deficit disorder; an agent for dementia and/or Alzheimer's disease; and an agent for an addiction disorder.

Applications

The present disclosure provides methods of using the compounds of formula (I) and compositions as described in any one of the foregoing paragraphs. The present disclosure also provides methods of delivering to a subject in need thereof a compound of formula (I) or a composition (e.g., an effective amount of the compound or composition) of the present disclosure.

In another aspect, the present disclosure provides methods of treating a disease in a subject in need thereof comprising administering to the subject in need thereof an effective amount (e.g., therapeutically effective amount) of a compound or composition (e.g., pharmaceutical composition) of the present disclosure.

In another aspect, the present disclosure provides methods of preventing a disease in a subject in need thereof comprising administering to the subject in need thereof an effective amount (e.g., therapeutically effective amount) of a compound of formula (I) or composition (e.g., pharmaceutical composition) of the present disclosure.

In another aspect, provided herein are uses of the compounds of formula (I) or compositions of the present disclosure in the manufacture of a medicament for use in a method (e.g., method of delivering an active agent to a subject in need thereof, method of treating a disease in a subject in need thereof, method of preventing a disease in a subject in need thereof) of the present disclosure.

In another aspect, provided herein are uses of the compounds of formula (I) or compositions of the present disclosure in a method (e.g., method of delivering an active agent to a subject in need thereof, method of treating a disease in a subject in need thereof, method of preventing a disease in a subject in need thereof) of the present disclosure.

In certain embodiments, the effective amount is effective in treating the disease. In certain embodiments, the effective amount is effective in preventing the disease. In another aspect, the present disclosure provides a method of treating a disease, disorder or condition by activation of a serotonin receptor, the method comprising administering to a subject in need thereof a compound of formula (I) or a pharmaceutical composition as described herein.

In another aspect, the present disclosure provides a method of preventing a disease, disorder or condition by activation of a serotonin receptor, the method comprising administering to a subject in need thereof a compound of formula (I) or a pharmaceutical composition as described herein.

In another aspect, the present disclosure provides method of treating a disease, disorder or condition by activation of a serotonin receptor, the method comprising administering to a subject in need thereof a compound of formula (I) or a pharmaceutical composition as described herein, in combination with another known agent useful for treatment of a disease, disorder or condition by activation of a serotonin receptor. The other known agents useful for treatment of a disease, disorder or condition by activation of a serotonin receptor may be any suitable agents known in the art, including those described herein.

In another aspect, the present disclosure provides method of preventing a disease, disorder or condition by activation of a serotonin receptor, the method comprising administering to a subject in need thereof a compound of formula (I) or a pharmaceutical composition as described herein, in combination with another known agent useful for prevention of a disease, disorder or condition by activation of a serotonin receptor.

In certain embodiments, the serotonin receptor is $5-HT_{2A}$.

In certain embodiments, the serotonin receptor is one or both of $5-HT_{2A}$ and $5-HT_{2C}$. Additionally, or alternatively, in some embodiments, the serotonin receptor is not $5-HT_{2B}$.

In some embodiments, the compound of formula (I) of the present disclosure is selective towards the $5-HT_{2A}$ receptor over one or both of the $5-HT_{2C}$ receptor and the $5-HT_{2B}$ receptor, preferably over the $5-HT_{2B}$ receptor. In some embodiments, the compound of formula (I) is selective towards the $5-HT_{2C}$ receptor over one or both of the $5-HT_{2A}$ receptor and the $5-HT_{2B}$ receptor, preferably over the $5-HT_{2B}$ receptor. In some embodiments, the compound of formula (I) is selective toward the $5-HT_{2A}$ receptor and $5-HT_{2C}$ receptor over the $5-HT_{2B}$ receptor.

In some embodiments, the compound of formula (I) of the present disclosure exhibits an $EC_{50}$ value for the $5-HT_{2A}$ receptor of less than about 1 mM, less than about 100 μM, less than about 10 μM, less than about 1 μM, or less than about 100 nM, or less than about 10 nM, as determined by an assay described herein, for example an assay of calcium flux activity such as measuring changes in intracellular calcium. In some embodiments, the compound of formula (I) exhibits an $EC_{50}$ for the $5-HT_{2A}$ receptor of less than about 1 mM, less than about 900 μM, less than about 800 μM, less than about 700 μM, less than about 600 μM, less than about 500 μM, less than about 400 μM, less than about 300 μM, less than about 200 μM, less than about 100 μM, less than about 90 μM, less than about 80 M, less than about 70 μM, less than about 60 μM, less than about 50 μM, less than about 40 µM, less than about 30 µM, less than about 20 µM, less than about 10 µM, less than about 9 µM, less than about 8 µM, less than about 7 µM, less than about 6 µM, less than about 5 µM, less than about 4 µM, less than about 3 µM, less than about 2 µM, less than about 1 µM, less than about 900 nM, less than about 800 nM, less than about 700 nM, less than about 600 nM, less than about 500 nM, less than about 400 nM, less than about 300 nM, less than about 200 nM, or less than about 100 nM, or any equivalent unit of measure (e.g., mol/L), as determined by an assay of calcium flux activity or IP1 accumulation.

In some embodiments, the compound of formula (I) of the present disclosure exhibits an $EC_{50}$ value for the 5-$HT_{2C}$ receptor of less than about 1 mM, less than about 100 µM, less than about 10 µM, less than about 1 µM, or less than about 100 nM, or less than about 10 nM, as determined by an assay described herein, for example an assay of calcium flux activity such as measuring changes in intracellular calcium. In some embodiments, the compound of formula (I) exhibits an $EC_{50}$ for the 5-$HT_{2C}$ receptor of less than about 1 mM, less than about 900 µM, less than about 800 µM, less than about 700 µM, less than about 600 µM, less than about 500 µM, less than about 400 µM, less than about 300 µM, less than about 200 µM, less than about 100 µM, less than about 90 µM, less than about 80 µM, less than about 70 µM, less than about 60 µM, less than about 50 M, less than about 40 µM, less than about 30 µM, less than about 20 µM, less than about 10 µM, less than about 9 µM, less than about 8 µM, less than about 7 M, less than about 6 µM, less than about 5 µM, less than about 4 µM, less than about 3 µM, less than about 2 µM, less than about 1 µM, less than about 900 nM, less than about 800 nM, less than about 700 nM, less than about 600 nM, less than about 500 nM, less than about 400 nM, less than about 300 nM, less than about 200 nM, or less than about 100 nM, or any equivalent unit of measure (e.g., mol/L), as determined by an assay of calcium flux activity.

In some embodiments, the compound of formula (I) of the present disclosure exhibits an $EC_{50}$ value for the 5-$HT_{2B}$ receptor of greater than about 1 µM, greater than about 10 µM, or greater than about 100 µM, as determined by an assay described herein, for example an assay of calcium flux activity such as measuring changes in intracellular calcium.

In some embodiments, the disease, disorder or condition that is treated by activation of a serotonin receptor is a mental illness or a neuropsychiatric condition. Accordingly, the present application also includes a method of treating a mental illness or a neuropsychiatric condition comprising administering to a subject in need thereof a compound of formula (I) or a composition as described herein. The present application also includes a use of a compound of formula (I) of the present disclosure for treatment of a mental illness or a neuropsychiatric condition, as well as a use of a compound of formula (I) of the present disclosure for the preparation of a medicament for treatment of a mental illness or a neuropsychiatric condition. The application further includes a compound of formula (I) of the present disclosure for use in treating a mental illness or a neuropsychiatric condition.

In some embodiments, the disease, disorder or condition that is treated by activation of a serotonin receptor is a mental illness or a neuropsychiatric condition and compound of formula (I) of the present disclosure is administered in combination with one or more additional agents for a mental illness or a neuropsychiatric condition. The one or more additional agents for a mental illness or a neuropsychiatric condition may be any suitable agents known in the art, including those described herein. In some embodiments, the additional agents for a mental illness or a neuropsychiatric condition is selected from antipsychotics, including typical antipsychotics and atypical antipsychotics; antidepressants including selective serotonin reuptake inhibitors (SSRIs) and selective norepinephrine reuptake inhibitors (SNRIs), tricyclic antidepressants and monoamine oxidase inhibitors (MAOIs) (e.g. bupropion); anti-anxiety medication including benzodiazepines such as alprazolam; agents for an addiction disorder such as alcohol addiction (e.g., disulfiram), nicotine dependence (e.g., varenicline) and opioid use disorder (e.g., methadone, buprenorphine, buprenorphine-naloxone and buprenorphine long-acting injection); mood stabilizers such as lithium and anticonvulsants such carbamazepine, divalproex (valproic acid), lamotrigine, gabapentin and topiramate.

In some embodiments, the disease, disorder or condition that is treated by activation of a serotonin receptor is neurodegeneration. Accordingly, the present application also includes a method of treating neurodegeneration comprising administering to a subject in need thereof a compound of formula (I) or a composition as described herein. The present application also includes a use of a compound of formula (I) of the present disclosure for treatment of neurodegeneration, as well as a use of a compound of formula (I) of the present disclosure for the preparation of a medicament for treatment neurodegeneration. The application further includes a compound of formula (I) of the present disclosure for use in treating neurodegeneration. In some embodiments, the disease, disorder or condition that is treated by activation of a serotonin receptor is reduced brain-derived neurotrophic factor (BDNF), mammalian target of rapamycin (mTOR) activation and/or inflammation.

In some embodiments, the disease, disorder or condition that is treated by activation of a serotonin receptor comprises cognitive impairment; ischemia including stroke; neurodegeneration; refractory substance use disorders; sleep disorders; pain, such as social pain, acute pain, cancer pain, chronic pain, breakthrough pain, bone pain, soft tissue pain, nerve pain, referred pain, phantom pain, neuropathic pain, cluster headaches and migraine; obesity and eating disorders; epilepsies and seizure disorders; neuronal cell death; excitotoxic cell death; or a combination thereof.

In some embodiments, the disease, disorder or condition that is treated by activation of a serotonin receptor is psychosis or psychotic symptoms. Accordingly, the present application also includes a method of treating psychosis or psychotic symptoms comprising administering to a subject in need thereof a compound of formula (I) or a composition as described herein. The present application also includes a use of a compound of formula (I) of the present disclosure for treatment of psychosis or psychotic symptoms, as well as a use of a compound of formula (I) of the present disclosure for the preparation of a medicament for treatment of psychosis or psychotic symptoms. The application further includes a compound of formula (I) of the present disclosure for use in treating psychosis or psychotic symptoms.

In some embodiments, the disease, disorder or condition that is treated by activation of a serotonin receptor is psychosis or psychotic symptoms and the compound of formula (I) of the present disclosure is administered in combination with one or more additional agents for psychosis or psychotic symptoms. The one or more additional agents for psychosis or psychotic symptoms may be any suitable agents known in the art, including those described herein. In some embodiments, the additional agents for psychosis or psychotic symptoms are selected typical antipsychotics and atypical antipsychotics. The typical antipsychotics may be selected from acepromazine, acetophenazine, benperidol, bromperidol, butaperazine, carfenazine, chlorproethazine, chlorpromazine, chlorprothixene, clopenthixol, cyamemazine, dixyrazine, droperidol, fluanisone, flupentixol, fluphenazine, fluspirilene, haloperidol, levomepromazine, lenperone, loxapine, mesoridazine, metitepine, molindone, moperone, oxypertine, oxyprotepine, penfluridol, perazine, periciazine, perphenazine, pimozide, pipamperone, piperacetazine, pipotiazine, prochlorperazine, promazine, prothipendyl, spiperone, sulforidazine, thiopropazate, thioproperazine, thioridazine, thiothixene, timiperone, trifluoperazine, trifluperidol, triflupromazine and zuclopenthixol and combinations thereof. The atypical antipsychotics may be selected from amoxapine, amisulpride, aripiprazole, asenapine, blonanserin, brexpiprazole, cariprazine, carpipramine, clocapramine, clorotepine, clotiapine, clozapine, iloperidone, levosulpiride, lurasidone, melperone, mosapramine, nemonapride, olanzapine, paliperidone, perospirone, quetiapine, remoxipride, reserpine, risperidone, sertindole, sulpiride, sultopride, tiapride, veralipride, ziprasidone and zotepine, and combinations thereof.

In some embodiments, administering to said subject in need thereof a therapeutically effective amount of the compound of formula (I) of the present disclosure does not result in a worsening of psychosis or psychotic symptoms such as, but not limited to, hallucinations and delusions. In some embodiments, administering to said subject in need thereof a therapeutically effective amount of the compound of formula (I) results in an improvement of psychosis or psychotic symptoms such as, but not limited to, hallucinations and delusions. In some embodiments, administering to said subject in need thereof a therapeutically effective amount of the compounds of formula (I) results in an improvement of psychosis or psychotic symptoms.

In some embodiments, the disease, disorder or condition that is treated by activation of a serotonin receptor is a central nervous system (CNS) disease, disorder or condition and/or a neurological disease, disorder or condition. Accordingly, the present application also includes a method of treating a CNS disease, disorder or condition and/or a neurological disease, disorder or condition comprising administering a therapeutically effective amount of compound of formula (I) or a composition of the present disclosure to a subject in need thereof. The present application also includes a use of compound of formula (I) of the present disclosure for treatment a CNS disease, disorder or condition and/or a neurological disease, disorder or condition, as well as a use of compound of formula (I) of the present disclosure for the preparation of a medicament for treatment of a CNS disease, disorder or condition and/or a neurological disease, disorder or condition. The application further includes a compound of formula (I) of the present disclosure of the application for use in treating a CNS disease, disorder or condition and/or a neurological disease, disorder or condition.

In some embodiments, the disease, disorder or condition that is treated by activation of a serotonin receptor is a central nervous system (CNS) disease, disorder or condition and/or a neurological disease, disorder or condition and the compound of formula (I) of the present disclosure is administered in combination with one or more additional agents for a central nervous system (CNS) disease, disorder or condition and/or a neurological disease, disorder or condition. The one or more additional agents for a central nervous system (CNS) disease, disorder or condition and/or a neurological disease, disorder or condition may be any suitable agents known in the art, including those described herein. In some embodiments, the additional agents for a central nervous system (CNS) disease, disorder or condition and/or a neurological disease, disorder or condition are selected from lithium, olanzapine, quetiapine, risperidone, aripiprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Non limiting examples of standard of care therapy for depression are sertraline, fluoxetine, escitalopram, venlafaxine, or aripiprazole. Non-limiting examples of standard of care therapy for depression are citalopram, escitalopram, fluoxetine, paroxetine, diazepam, or sertraline.

In some embodiments, the disease, disorder or condition that is treated by activation of a serotonin receptor is selected from attention deficit hyperactivity disorder and attention deficit disorder and a combination thereof. Accordingly, the present application also includes a method of treating attention deficit hyperactivity disorder and/or attention deficit disorder comprising administering to a subject in need thereof a compound of formula (I) or a composition as described herein. The present application also includes a use of a compound of formula (I) of the present disclosure for treatment of attention deficit hyperactivity disorder and/or attention deficit disorder, as well as a use of a compound of formula (I) of the present disclosure for the preparation of a medicament for treatment of attention deficit hyperactivity disorder and/or attention deficit disorder. The application further includes a compound of formula (I) of the present disclosure for use in treating attention deficit hyperactivity disorder and/or attention deficit disorder.

In some embodiments, the disease, disorder or condition that is treated by activation of a serotonin receptor is attention deficit hyperactivity disorder and/or attention deficit disorder and a combination thereof and the compound of formula (I) of the present disclosure is administered in combination with one or more additional agents for attention deficit hyperactivity disorder and/or attention deficit disorder and a combination thereof. The one or more additional agents for attention deficit hyperactivity disorder and/or attention deficit disorder may be any suitable agents known in the art, including those described herein. In some embodiments, the additional agents for attention deficit hyperactivity disorder and/or attention deficit disorder and a combination thereof are selected from methylphenidate, dexamphetamine, lisdexamfetine, atomoxetine and amphetamine and a combination thereof.

In some embodiments, the disease, disorder or condition that is treated by activation of a serotonin receptor is selected from dementia and Alzheimer's disease and a combination thereof. Accordingly, the present application also includes a method of treating dementia and/or Alzheimer's disease comprising administering to a subject in need thereof a compound of formula (I) or a composition as described herein. The present application also includes a use of a compound of formula (I) of the present disclosure for treatment of dementia and/or Alzheimer's disease, as well as a use of a compound of formula (I) of the present disclosure for the preparation of a medicament for treatment of dementia and/or Alzheimer's disease. The application further includes a compound of formula (I) of the present disclosure for use in treating dementia and/or Alzheimer's disease.

In some embodiments, the disease, disorder or condition that is treated by activation of a serotonin receptor is dementia or Alzheimer's disease and the compound of formula (I) of the present disclosure is administered in combination with one or more additional agents for dementia or Alzheimer's disease. The one or more additional agents for dementia or Alzheimer's disease may be any suitable agents known in the art, including those described herein. In some embodiments, the additional agents for dementia and Alzheimer's disease are selected from acetylcholinesterase inhibitors, NMDA antagonists and nicotinic agonists. The acetylcholinesterase inhibitors may be selected from donepezil, galantamine, rivastigmine, and phenserine, and combinations thereof. The NMDA antagonists may be selected from MK-801, ketamine, phencyclidine, and memantine, and combinations thereof. The nicotinic agonists may be selected from nicotine, nicotinic acid, nicotinic alpha7 agonists, or alpha2 beta4 agonists or a combination thereof.

In another aspect, the present disclosure provides a method of treating a mental illness, the method comprising administering to a subject in need thereof a compound of formula (I) or a pharmaceutical composition as described herein. In another aspect, the present disclosure provides a method of preventing a mental illness, the method comprising administering to a subject in need thereof a compound of formula (I) or a pharmaceutical composition as described herein. The mental illness may be a neuropsychiatric condition.

In certain embodiments, the mental illness is selected from anxiety disorders such as generalized anxiety disorder, panic disorder, social anxiety disorder and specific phobias; depression such as, hopelessness, loss of pleasure, fatigue and suicidal thoughts; mood disorders, such as depression, bipolar disorder, cancer-related depression, anxiety and cyclothymic disorder; psychotic disorders, such as hallucinations, delusions, mania, schizophrenia, schizoaffective disorder, schizophreniform Disorder; impulse control and addiction disorders, such as pyromania (starting fires), kleptomania (stealing) and compulsive gambling; alcohol addiction; drug addiction, such as opioid addiction/dependence, nicotine dependence, cocaine dependence, marijuana abuse and so on; smoking cessation; personality disorders, such as antisocial personality disorder, aggression, obsessive-compulsive personality disorder and paranoid personality disorder; obsessive-compulsive disorder (OCD), such as thoughts or fears that cause a subject to perform certain rituals or routines; post-traumatic stress disorder (PTSD); stress response syndromes (formerly called adjustment disorders); dissociative disorders, formerly called multiple personality disorder, or "split personality," and depersonalization disorder; factitious disorders; sexual and gender disorders, such as sexual dysfunction, gender identity disorder and the paraphilias; somatic symptom disorders, formerly known as a psychosomatic disorder or somatoform disorder.

In certain embodiments, the mental illness is selected from hallucinations and delusions and a combination thereof. In these embodiments, the hallucinations may be selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations and chronoceptive hallucinations, and a combination thereof.

In another aspect, the present disclosure provides a method for treating a central nervous system (CNS) disease, disorder or condition and/or a neurological disease, disorder or condition, the method comprising administering to a subject in need thereof a compound of formula (I) or a pharmaceutical composition as described herein.

In another aspect, the present disclosure provides a method for preventing a central nervous system (CNS) disease, disorder or condition and/or a neurological disease, disorder or condition, the method comprising administering to a subject in need thereof a compound of formula (I) or a pharmaceutical composition as described herein.

In some embodiments, the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; Tic disorder; schizophrenia; autism spectrum disorders; tuberous sclerosis; Rett syndrome; cerebral palsy; disorders of the reward system including eating disorders such as anorexia nervosa and bulimia nervosa; binge eating disorder, trichotillomania, dermotillomania, nail biting; migraine; fibromyalgia; and peripheral neuropathy of any etiology, and combinations thereof.

In another aspect, the present disclosure provides a method for increasing neuronal plasticity, the method comprising contacting a neuronal cell with a compound of formula (I) or a pharmaceutical composition as described herein, in an amount sufficient to increase neuronal plasticity of the neuronal cell. "Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In another aspect the present disclosure provides methods of treating weight, comprising administering an effective amount of a compound of the invention to a subject in need thereof. Treatment of weight may include treating weight gain; weight loss; metabolic disorder; weight gain associated with pharmaceutical intervention; weight gain associated with a mental illness (including those described herein); eating disorders such as anorexia, bulimia, cachexia, etc.; eating behaviour; obesity; diabetes; insulin resistance; prediabetes; glucose intolerance; hyperlipidemia; and cardiovascular disease.

In another aspect, the present disclosure provides a method for increasing dendritic spine density, the method comprising contacting a neuronal cell with a compound of formula (I) or a pharmaceutical composition as described herein, in an amount sufficient to increase dendritic spine density of the neuronal cell.

In certain embodiments, the compound of formula (I) produces a maximum number of dendritic crossings with an increase of greater than 1.0 fold by a Sholl Analysis.

In another aspect the present disclosure provides a method for activating a serotonin receptor in a cell, either in a biological sample or in a patient, comprising administering a compound of formula (I) as defined in any one of the herein disclosed embodiments to the cell. The serotonin receptor may be a 5-HT receptor subtype, preferably one or both of $5-HT_{2A}$ and $5-HT_{2C}$.

In some embodiments, effective amounts vary according to factors such as the disease state, age, sex and/or weight of the subject or species. In some embodiments, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated and the like, but can nevertheless be routinely determined by one skilled in the art.

In some embodiments, the compounds of formula (I) of the present disclosure are administered one, two, three or four times a year. In some embodiments, the compounds of the present disclosure are administered at least once a week. However, in another embodiment, the compounds are administered to the subject from about one time per two weeks, three weeks or one month. In another embodiment, the compounds are administered about one time per week to about once daily. In another embodiment, the compounds are administered 1, 2, 3, 4, 5 or 6 times daily. The length of the treatment period depends on a variety of factors, such as the severity of the disease, disorder or condition, the age of the subject, the concentration and/or the activity of the compounds of the application and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In some embodiments, the compounds of the application are administered at doses that are hallucinogenic or psychotomimetic and taken in conjunction with psychotherapy or therapy and may occur once, twice, three, or four times a year. However, in some embodiments, the compounds are administered to the subject once daily, once every two days, once every 3 days, once a week, once every two weeks, once a month, once every two months, or once every three months at doses that are not hallucinogenic or psychotomimetic.

A compound of formula (I) of the present disclosure may be either used alone or in combination with other known agents useful for treating diseases, disorders or conditions by activation of a serotonin receptor, such as the compounds of the present disclosure. When used in combination with other known agents useful in treating diseases, disorders by activation of a serotonin receptor, it is an embodiment that a compound of formula (I) is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In some embodiments, a compound of formula (I) of the present disclosure is administered with another therapeutic agent simultaneously or sequentially in separate unit dosage forms or together in a single unit dosage form. Accordingly, the present application provides a single unit dosage form comprising one or more compounds of formula (I) as described herein, an additional therapeutic agent and a pharmaceutically acceptable carrier.

In some embodiments, the compounds of the application are used or administered in an effective amount which comprises administration of doses or dosage regimens that are devoid of clinically meaningful psychedelic/psychotomimetic actions. In some embodiments, the compounds of the application are used or administered in an effective amount which comprises administration of doses or dosage regimens that provide clinical effects similar to those exhibited by a human plasma psilocin Cmax of 4 ng/ml or less and/or human $5-HT_{2A}$ human CNS receptor occupancy of 40% or less or those exhibited by a human plasma psilocin Cmax of 1 ng/ml or less and/or human $5-HT_{2A}$ human CNS receptor occupancy of 30% or less. In some embodiments, the compounds of the application are used or administered in an effective amount which comprises administration of doses or dosage regimens that provide clinical effects similar to those exhibited by a human plasma psilocin Tmax in excess of 60 minutes, in excess of 120 minutes or in excess of 180 minutes.

Kit

In another embodiment there is provided a kit or article of manufacture including one or more compounds, pharmaceutically acceptable salt, stereoisomer, solvate, metabolite, or polymorph, and/or pharmaceutical compositions as described above.

In other embodiments there is provided a kit for use in a therapeutic application mentioned above, the kit including:
  a container holding one or more compounds, pharmaceutically acceptable salt, stereoisomer, solvate, metabolite, or polymorph and/or pharmaceutical compositions as described herein;
  a label or package insert with instructions for use.

It will be understood that the invention disclosed and defined in this specification extends to all alternative combinations of two or more of the individual features mentioned or evident from the text or drawings. All of these different combinations constitute various alternative aspects of the invention.

EXAMPLES

Scheme 1: Compounds of general formula (I) can be synthesised from the appropriately substituted aza-indole following the outlined sequence of steps in Scheme 1 or similar as one skilled in the art may consider. A similar sequence of synthetic transformations as outlined in Scheme 1 proved to be a viable method of accessing compounds of general formula (I). Friedel-crafts acylation of aza-indole starting material 7 provides access to intermediate 8 which can be subjected to chemoselective silane reduction conditions to provide the alkyl chloride intermediate 9. Nucleophilic displacement of the alkyl chloride with a substituted amine provides compounds of general formula (I) (exemplified by P-3). One skilled in the art will recognise that utilising differentially substituted amines would allow access to compounds of general formula (I) as disclosed herein.

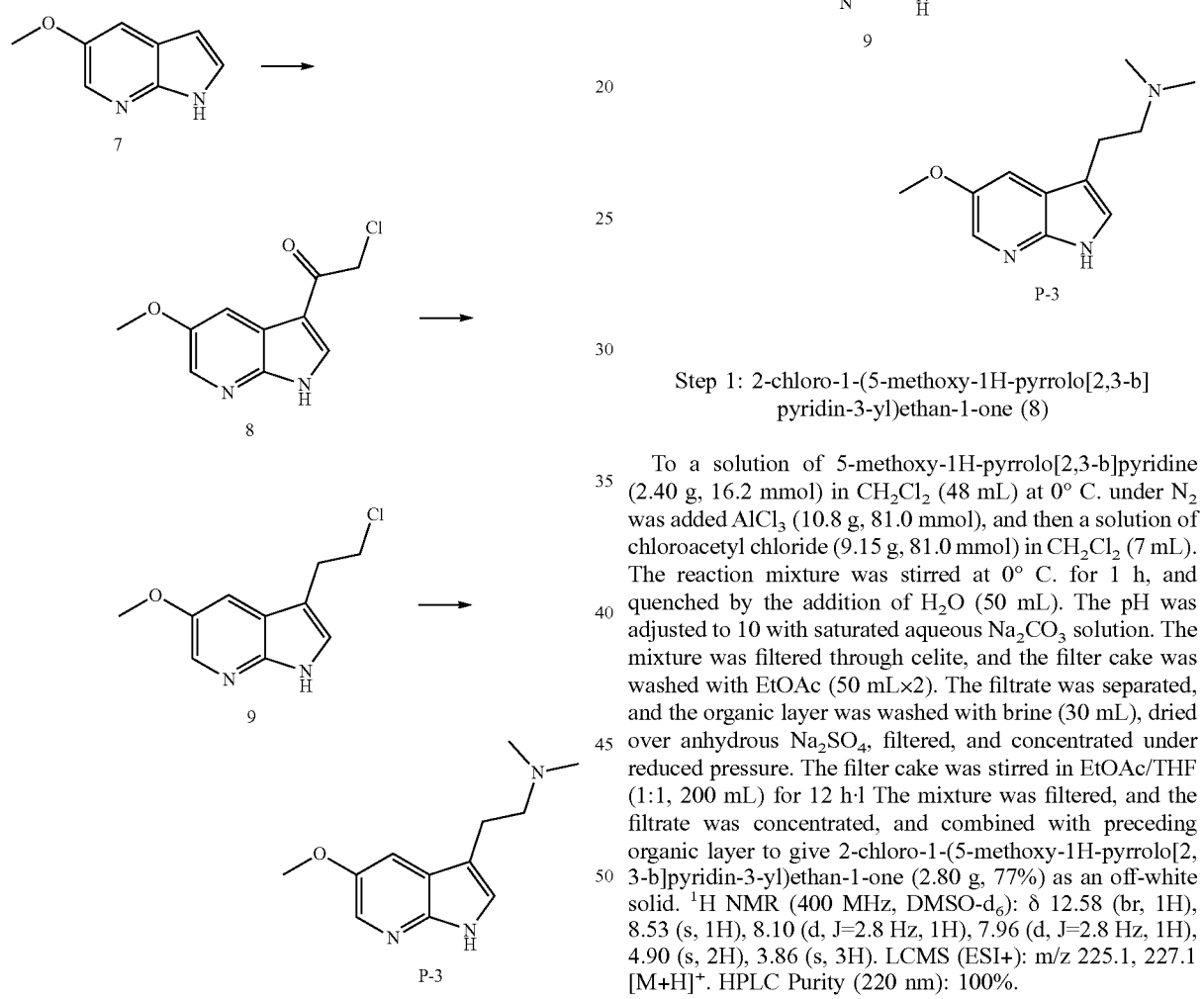

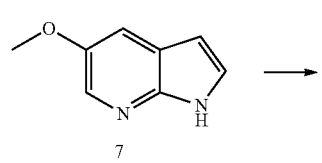

Step 1: 2-chloro-1-(5-methoxy-1H-pyrrolo[2,3-b]pyridin-3-yl)ethan-1-one (8)

To a solution of 5-methoxy-1H-pyrrolo[2,3-b]pyridine (2.40 g, 16.2 mmol) in $CH_2Cl_2$ (48 mL) at 0° C. under $N_2$ was added $AlCl_3$ (10.8 g, 81.0 mmol), and then a solution of chloroacetyl chloride (9.15 g, 81.0 mmol) in $CH_2Cl_2$ (7 mL). The reaction mixture was stirred at 0° C. for 1 h, and quenched by the addition of $H_2O$ (50 mL). The pH was adjusted to 10 with saturated aqueous $Na_2CO_3$ solution. The mixture was filtered through celite, and the filter cake was washed with EtOAc (50 mL×2). The filtrate was separated, and the organic layer was washed with brine (30 mL), dried over anhydrous $Na_2SO_4$, filtered, and concentrated under reduced pressure. The filter cake was stirred in EtOAc/THF (1:1, 200 mL) for 12 h·1 The mixture was filtered, and the filtrate was concentrated, and combined with preceding organic layer to give 2-chloro-1-(5-methoxy-1H-pyrrolo[2,3-b]pyridin-3-yl)ethan-1-one (2.80 g, 77%) as an off-white solid. $^1H$ NMR (400 MHz, DMSO-$d_6$): δ 12.58 (br, 1H), 8.53 (s, 1H), 8.10 (d, J=2.8 Hz, 1H), 7.96 (d, J=2.8 Hz, 1H), 4.90 (s, 2H), 3.86 (s, 3H). LCMS (ESI+): m/z 225.1, 227.1 [M+H]$^+$. HPLC Purity (220 nm): 100%.

Step 2: 3-(2-chloroethyl)-5-methoxy-1H-pyrrolo[2,3-b]pyridine (9)

To a solution of 2-chloro-1-(5-methoxy-1H-pyrrolo[2,3-b]pyridin-3-yl)ethan-1-one 8 (1.40 g, 6.23 mmol) in TFA (10 mL) was added $Et_3SiH$ (5.07 g, 43.6 mmol). The reaction mixture was stirred at 25° C. for 12 h. The reaction mixture was adjusted to pH 9 with saturated aqueous $Na_2CO_3$ solution and extracted with EtOAc (80 mL×2). The combined organic layers were washed with brine (50 mL), dried over $Na_2SO_4$, filtered, and concentrated in vacuo to give crude 3-(2-chloroethyl)-5-methoxy-1H-pyrrolo[2,3-b]pyridine 9 (1.40 g) as an off-white solid. $^1$H NMR (400 MHz, DMSO-$d_6$): δ11.29 (br, 1H), 7.94 (d, J=2.8 Hz, 1H), 7.60 (d, J=2.4 Hz, 1H), 7.32 (d, J=2.4 Hz, 1H), 3.82-3.87 (m, 5H), 3.12 (t, J=7.4 Hz, 2H). LCMS (ESI+): m/z 211.1, 213.1 [M+H]$^+$. HPLC Purity (220 nm): 98.5%

Step 3: 2-(5-methoxy-1H-pyrrolo[2,3-b]pyridin-3-yl)-N,N-dimethylethan-1-amine (P-3)

To a mixture of crude 3-(2-chloroethyl)-5-methoxy-1H-pyrrolo[2,3-b]pyridine (1.40 g) in Me$_2$NH (2.0 M in THF, 28 mL) was added NaI (996 mg, 6.65 mmol) and the mixture was stirred at 90° C. for 12 h. The mixture was filtered, and the filter cake was washed with THF (10 mL). The filtrate was evaporated, and the crude product was purified by preparative HPLC (column: Waters Xbridge BEH C18 (250*50 mm*10 μm); mobile phase: [water (NH$_3$ aq.+ NH$_4$HCO$_3$)-ACN]; B: 1-30%, 10 min) to afford 2-(5-methoxy-1H-pyrrolo[2,3-b]pyridin-3-yl)-N,N-dimethylethan-1-amine P-3 (397 mg, 29% over 2 steps) as a brown solid. $^1$H NMR (400 MHz, MeOD-$d_4$): δ 7.91 (d, J=2.8 Hz, 1H), 7.56 (d, J=2.8 Hz, 1H), 7.19 (s, 1H), 3.89 (s, 3H), 2.89-2.93 (m, 2H), 2.63-2.67 (m, 2H), 2.35 (s, 6H). LCMS (ESI+): R$_T$=0.79 min, m/z 220.2 [M+H]$^+$. HPLC Purity (220 nm): 100%.

Step 3a: 2-(5-methoxy-1H-pyrrolo[2,3-b]pyridin-3-yl)-N,N-dimethylethan-1-amine Hydrochloride (P-3·HCl)

To an ice cold (0° C.) solution of 2-(5-methoxy-1H-pyrrolo[2,3-b]pyridin-3-yl)-N,N-dimethylethan-1-amine (100 mg, 0.45 mmol) in anhydrous Et$_2$O (5 mL) and abs. EtOH (1 mL) was added 2 M HCl in Et$_2$O dropwise over 10 min until the pH of the reaction solution was acidic. The resulting precipitate was collected by filtration and dried overnight in a vacuum desiccator to afford 2-(5-methoxy-1H-pyrrolo[2,3-b]pyridin-3-yl)-N,N-dimethylethan-1-amine as the hydrochloride salt (78 mg, 68%) which was a white solid. $^1$H NMR (400 MHz, MeOD-$d_4$): δ 7.91 (d, J=2.8 Hz, 1H), 7.56 (d, J=2.8 Hz, 1H), 7.19 (s, 1H), 3.89 (s, 3H), 2.96-2.87 (m, 2H), 2.69-2.60 (m, 2H), 2.35 (s, 6H). HPLC Purity (220 nm): 99.7%.

Scheme 2: In some circumstances, an alternative synthesis for compounds of general formula (I) was utilised as outlined in Scheme 2. Nucleophilic displacement of the chloride of intermediate 8 by appropriately substituted amines generated aminoethan-1-ones. Subsequent two-step reductions allowed access to compounds of general formula (I) (exemplified by P-17). One skilled in the art will recognise that utilising differentially substituted amines would allow access to compounds of general formula (I) as disclosed herein.

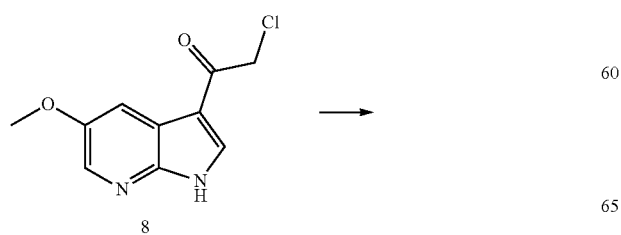

8

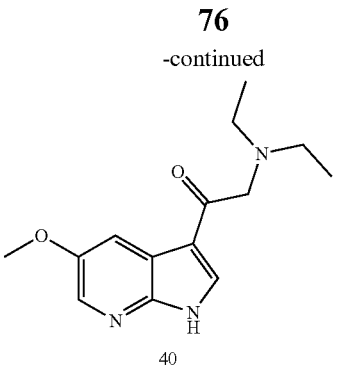

40

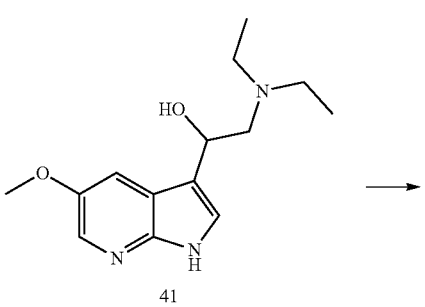

41

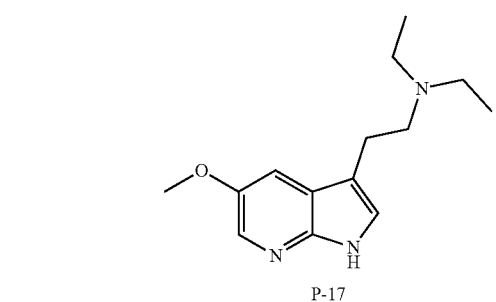

P-17

2(5-methoxy-1H-pyrrolo[2,3-b]pyrdin-3-yl)-N,N-diethylethan-1-amine (P-17)

8

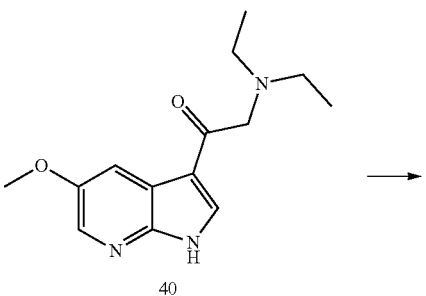

40

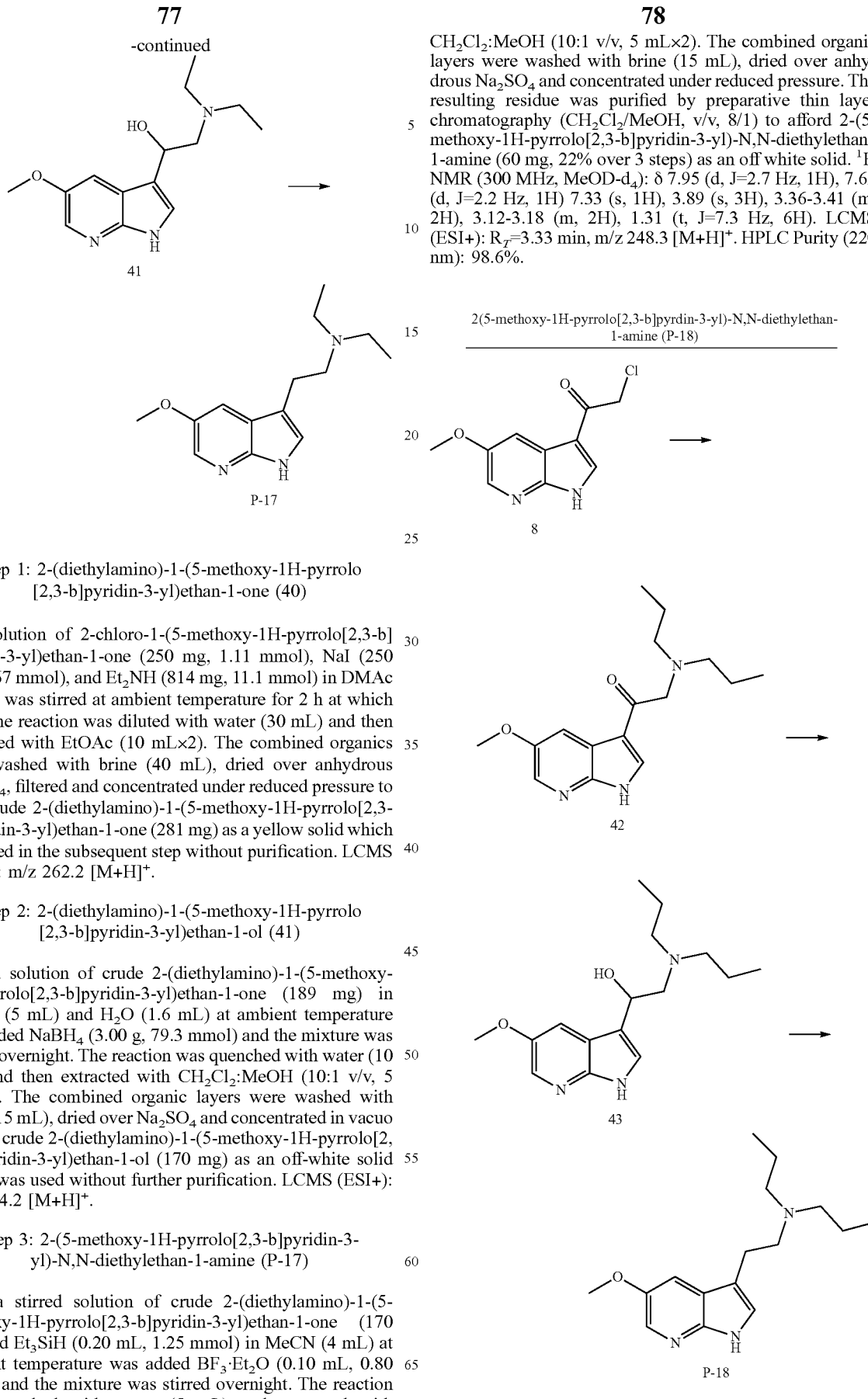

Step 1: 2-(diethylamino)-1-(5-methoxy-1H-pyrrolo[2,3-b]pyridin-3-yl)ethan-1-one (40)

A solution of 2-chloro-1-(5-methoxy-1H-pyrrolo[2,3-b]pyridin-3-yl)ethan-1-one (250 mg, 1.11 mmol), NaI (250 mg, 1.67 mmol), and Et₂NH (814 mg, 11.1 mmol) in DMAc (7 mL) was stirred at ambient temperature for 2 h at which point the reaction was diluted with water (30 mL) and then extracted with EtOAc (10 mL×2). The combined organics were washed with brine (40 mL), dried over anhydrous Na₂SO₄, filtered and concentrated under reduced pressure to give crude 2-(diethylamino)-1-(5-methoxy-1H-pyrrolo[2,3-b]pyridin-3-yl)ethan-1-one (281 mg) as a yellow solid which was used in the subsequent step without purification. LCMS (ESI+): m/z 262.2 [M+H]⁺.

Step 2: 2-(diethylamino)-1-(5-methoxy-1H-pyrrolo[2,3-b]pyridin-3-yl)ethan-1-ol (41)

To a solution of crude 2-(diethylamino)-1-(5-methoxy-1H-pyrrolo[2,3-b]pyridin-3-yl)ethan-1-one (189 mg) in MeOH (5 mL) and H₂O (1.6 mL) at ambient temperature was added NaBH₄ (3.00 g, 79.3 mmol) and the mixture was stirred overnight. The reaction was quenched with water (10 mL) and then extracted with CH₂Cl₂:MeOH (10:1 v/v, 5 mL×2). The combined organic layers were washed with brine (15 mL), dried over Na₂SO₄ and concentrated in vacuo to give crude 2-(diethylamino)-1-(5-methoxy-1H-pyrrolo[2,3-b]pyridin-3-yl)ethan-1-ol (170 mg) as an off-white solid which was used without further purification. LCMS (ESI+): m/z 264.2 [M+H]⁺.

Step 3: 2-(5-methoxy-1H-pyrrolo[2,3-b]pyridin-3-yl)-N,N-diethylethan-1-amine (P-17)

To a stirred solution of crude 2-(diethylamino)-1-(5-methoxy-1H-pyrrolo[2,3-b]pyridin-3-yl)ethan-1-one (170 mg) and Et₃SiH (0.20 mL, 1.25 mmol) in MeCN (4 mL) at ambient temperature was added BF₃·Et₂O (0.10 mL, 0.80 mmol) and the mixture was stirred overnight. The reaction was quenched with water (5 mL) and extracted with CH₂Cl₂:MeOH (10:1 v/v, 5 mL×2). The combined organic layers were washed with brine (15 mL), dried over anhydrous Na₂SO₄ and concentrated under reduced pressure. The resulting residue was purified by preparative thin layer chromatography (CH₂Cl₂/MeOH, v/v, 8/1) to afford 2-(5-methoxy-1H-pyrrolo[2,3-b]pyridin-3-yl)-N,N-diethylethan-1-amine (60 mg, 22% over 3 steps) as an off white solid. ¹H NMR (300 MHz, MeOD-d₄): δ 7.95 (d, J=2.7 Hz, 1H), 7.62 (d, J=2.2 Hz, 1H) 7.33 (s, 1H), 3.89 (s, 3H), 3.36-3.41 (m, 2H), 3.12-3.18 (m, 2H), 1.31 (t, J=7.3 Hz, 6H). LCMS (ESI+): R$_T$=3.33 min, m/z 248.3 [M+H]⁺. HPLC Purity (220 nm): 98.6%.

2(5-methoxy-1H-pyrrolo[2,3-b]pyrdin-3-yl)-N,N-diethylethan-1-amine (P-18)

Step 2-(dipropylamino)-1-(5-methoxy-1H-pyrrolo[2,3-b]pyridin-3-yl)ethan-1-one (42)

A solution of 2-chloro-1-(5-methoxy-1H-pyrrolo[2,3-b]pyridin-3-yl)ethan-1-one (250 mg, 1.11 mmol), NaI (250 mg, 1.67 mmol) in DMAc (7 mL) was added dipropylamine (1.13 g, 11.1 mmol) and the mixture was stirred at room temperature for 2 h·w The reaction was quenched with water (30 mL) and then extracted with EtOAc (10 mL×2). The combined organic layers were washed with brine (40 mL), dried over anhydrous Na$_2$SO$_4$ and concentrated under reduced pressure to give crude 2-(dipropylamino)-1-(5-methoxy-1H-pyrrolo[2,3-b]pyridin-3-yl)ethan-1-one (350 mg) as a yellow solid which was used in the subsequent step without purification. LCMS (ESI+): m/z 290.4 [M+H]$^+$.

Step 2: 2-(dipropylamino)-1-(5-methoxy-1H-pyrrolo[2,3-b]pyridin-3-yl)ethan-1-ol (43)

To a solution of crude 2-(dipropylamino)-1-(5-methoxy-1H-pyrrolo[2,3-b]pyridin-3-yl)ethan-1-one (350 mg) in MeOH (5 mL) at ambient temperature was added NaBH$_4$ (3.00 g, 79.3 mmol) and the mixture was stirred overnight. The reaction was quenched with water (10 mL) and then extracted with CH$_2$Cl$_2$:MeOH (10:1 v/v, 5 mL×2). The combined organic layers were washed with brine (30 mL), dried over Na$_2$SO$_4$ and concentrated in vacuo to give crude 2-(dipropylamino)-1-(5-methoxy-1H-pyrrolo[2,3-b]pyridin-3-yl)ethan-1-ol (280 mg) that was used without further purification. LCMS (ESI+): m/z 292.3 [M+H]$^+$.

Step 3: 2-(5-methoxy-1H-pyrrolo[2,3-b]pyridin-3-yl)-N,N-dipropylethan-1-amine (P-18)

To a stirred solution of crude 2-(dipropylamino)-1-(5-methoxy-1H-pyrrolo[2,3-b]pyridin-3-yl)ethan-1-ol (280 mg) and Et$_3$SiH (0.40 mL, 2.50 mmol) in MeCN (6 mL) at ambient temperature was added BF$_3$·Et$_2$O (0.30 mL, 2.43 mmol) and the mixture was stirred at room temperature overnight. The reaction was quenched with H$_2$O (5 mL) and then extracted with CH$_2$Cl$_2$:MeOH (10:1 v/v, 5 mL×2). The combined organic layers were washed with brine (15 mL) before being dried over anhydrous Na$_2$SO$_4$ and concentrated under reduced pressure. The resulting residue was purified by preparative thin layer chromatography (CH$_2$Cl$_2$/MeOH, v/v, 8/1) to afford 2-(5-methoxy-1H-pyrrolo[2,3-b]pyridin-3-yl)-N,N-dipropylethan-1-amine (80 mg, 26% over 3 steps) as an off white solid. $^1$H NMR (300 MHz, MeOD-d$_4$): δ 7.95 (d, J=2.6 Hz, 1H), 7.64 (d, J=2.6 Hz, 1H), 7.34 (s, 1H), 3.89 (s, 3H), 3.41-3.47 (m, 2H), 3.15-3.21 (m, 6H), 1.75 (sext, J=7.3 Hz, 4H), 1.00 (t, J=7.3 Hz, 6H). LCMS (ESI+): m/z 276.3 [M+H]$^+$. HPLC Purity (220 nm): 97.8%.

Scheme 3: In some circumstances, access to compounds of general formula (I) via Scheme 3 required the introduction of an appropriate protecting group for the reactive pyrrolo amine. Base mediated SEM protection of common intermediate 8 generated the protected aza-indole 44. This intermediate proved amenable to the previously described synthetic route (Scheme 5) involving nucleophilic displacement of the chloride of intermediate 44 by appropriately substituted amines. Subsequent two-step reductions simultaneously removed the SEM protecting group providing access to compounds of general formula (I) (exemplified by P-19). One skilled in the art will recognise that utilising differentially substituted amines would allow access to alternative derivatives of general formula (I) as disclosed herein.

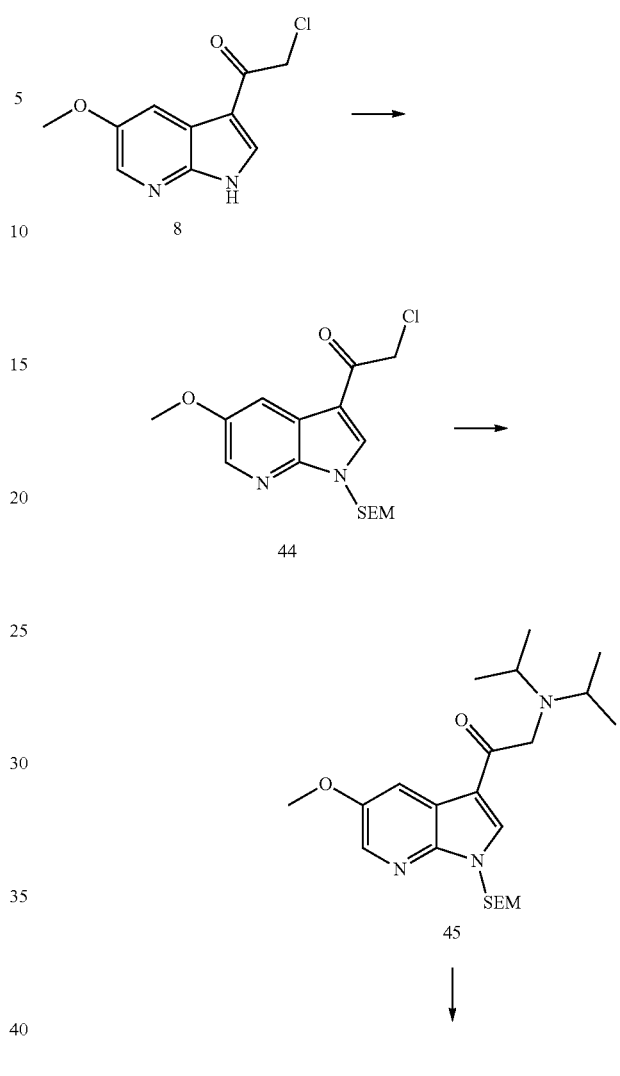

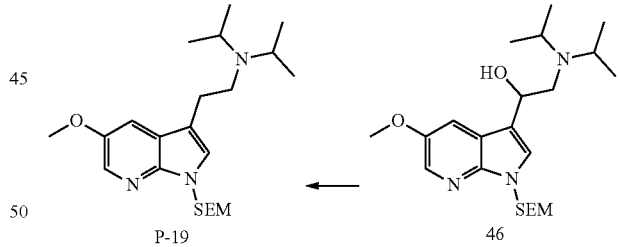

N-isopropyl-N-(2-(5-methoxy-1H-pyrrolo[2,3-b]pyridin-3-yl)ethyl)propan-2-amine (P-19)

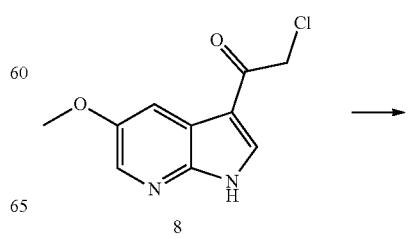

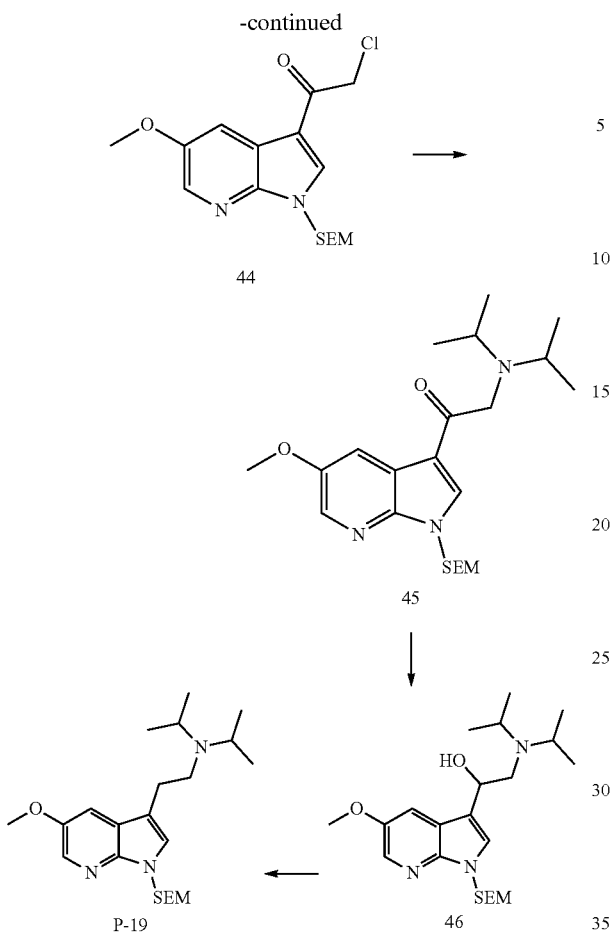

Step 1: 2-chloro-1-(5-methoxy-1-((2-(trimethylsilyl)ethoxy)methyl)-1H-pyrrolo[2,3-b]pyridin-3-yl)ethan-1-one (44)

A solution of 2-chloro-1-(5-methoxy-1H-pyrrolo[2,3-b]pyridin-3-yl)ethan-1-one (1 g, 4.45 mmol) and DIPEA (3.00 mL, 22.0 mmol) in DMAc (10 mL) was treated with (2-(chloromethoxy)ethyl)trimethylsilane (2.50 mL, 14.1 mmol) at 0° C. and then stirred at ambient temperature for 5 h. The reaction was then quenched with $H_2O$ (30 mL) and extracted with EtOAc (10 mL×2). The combined organic layer was washed with brine (40 mL), dried over anhydrous $Na_2SO_4$ and concentrated under reduced pressure. The residue was subjected to column chromatography (Petroleum ether: EtOAc-7:1) to afford crude 2-chloro-1-(5-methoxy-1-((2-(trimethylsilyl)ethoxy)methyl)-1H-pyrrolo[2,3-b]pyridin-3-yl)ethan-1-one (420 mg) which was used in the subsequent step without further purification. LCMS (ESI+): m/z 355.3, 357.2 [M+H]⁺.

Step 2: 2-(diisopropylamino)-1-(5-methoxy-1-((2-(trimethylsilyl)ethoxy)methyl)-1H-pyrrolo[2,3-b]pyridin-3-yl)ethan-1-one (45)

A solution of crude 2-chloro-1-(5-methoxy-1-((2-(trimethylsilyl)ethoxy)methyl)-1H-pyrrolo[2,3-b]pyridin-3-yl)ethan-1-one (410 mg), NaI (410 mg, 2.74 mmol), and diisopropylamine (2.07 mL, 14.8 mmol) in DMAc (5 mL) was stirred at ambient temperature for 3 h. The reaction was quenched with water (30 mL) and then extracted with EtOAc (10 mL×2). The combined organics were washed with brine (40 mL), dried over anhydrous $Na_2SO_4$ and concentrated under reduced pressure. The residue was purified by flash column chromatography (petroleum ether/EtOAc, v/v, 3/1) to give crude 2-(diisopropylamino)-1-(5-methoxy-1-((2-(trimethylsilyl)ethoxy)methyl)-1H-pyrrolo[2,3-b]pyridin-3-yl)ethan-1-one (146 mg) LCMS (ESI+): m/z 420.5 [M+H]⁺.

Step 3: 2-(diisopropylamino)-1-(5-methoxy-1-((2-(trimethylsilyl)ethoxy)methyl)-1H-pyrrolo[2,3-b]pyridin-3-yl)ethan-1-ol (46)

To a solution of crude 2-(diisopropylamino)-1-(5-methoxy-1-((2-(trimethylsilyl)ethoxy)methyl)-1H-pyrrolo[2,3-b]pyridin-3-yl)ethan-1-one (145 mg) in MeOH (2 mL) and $H_2O$ (0.4 mL) at ambient temperature was added $NaBH_4$ (3.00 g, 79.3 mmol) which was stirred overnight. The reaction was quenched with water (10 mL) and then extracted with $CH_2Cl_2$:MeOH (10:1 v/v, 5 mL×2). The combined organic layers were washed with brine (30 mL), dried over anhydrous $Na_2SO_4$ and concentrated in vacuo to give crude 2-(diisopropylamino)-1-(5-methoxy-1-((2-(trimethylsilyl)ethoxy)methyl)-1H-pyrrolo[2,3-b]pyridin-3-yl)ethan-1-ol (110 mg) which was used in the subsequent step without further purification. LCMS (ESI+): m/z 422.4 [M+H]⁺.

Step 4: N-isopropyl-N-(2-(5-methoxy-1H-pyrrolo[2,3-b]pyridin-3-yl)ethyl)propan-2-amine (P-19)

To a stirred solution of crude 2-(diisopropylamino)-1-(5-methoxy-1-((2-(trimethylsilyl)ethoxy)methyl)-1H-pyrrolo[2,3-b]pyridin-3-yl)ethan-1-ol (110 mg) and $Et_3SiH$ (300 mg, 2.58 mmol) in MeCN (2 mL) at ambient temperature was added $BF_3 \cdot Et_2O$ (0.20 mL, 1.62 mmol) and the mixture was stirred overnight. The reaction was quenched with $H_2O$ (5 mL) and extracted with $CH_2Cl_2$:MeOH (10:1 v/v, 5 mL×2). The combined organic layers were washed with brine (15 mL), dried over anhydrous $Na_2SO_4$ and concentrated under reduced pressure. The resulting residue was purified by preparative thin layer chromatography ($CH_2Cl_2$:MeOH, v/v, 8/1) to afford N-isopropyl-N-(2-(5-methoxy-1H-pyrrolo[2,3-b]pyridin-3-yl)ethyl)propan-2-amine (20 mg, 2% over 4 steps) as an off white solid. ¹H-NMR (300 MHz, MeOD-$d_4$): δ 7.96 (d, J=2.5 Hz, 1H), 7.55 (d, J=2.4 Hz, 1H), 7.36 (s, 1H), 3.89 (s, 3H), 3.79-3.83 (m, 2H), 3.36-3.41 (m, 2H), 3.13-3.18 (m, 2H), 1.42 (d, J=6.6 Hz, 12H). LCMS (ESI+): m/z 276.4 [M+H]⁺. HPLC Purity (220 nm): 97.4%.

N-ethyl-2-(5-methoxy-1H-pyrrolo[2,3-b]pyridin-3-yl)-N-methylethan-1-amine (P-20)

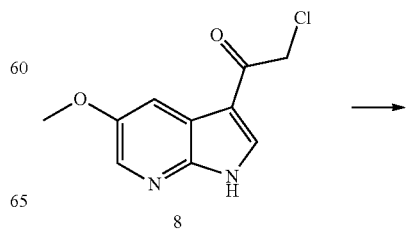

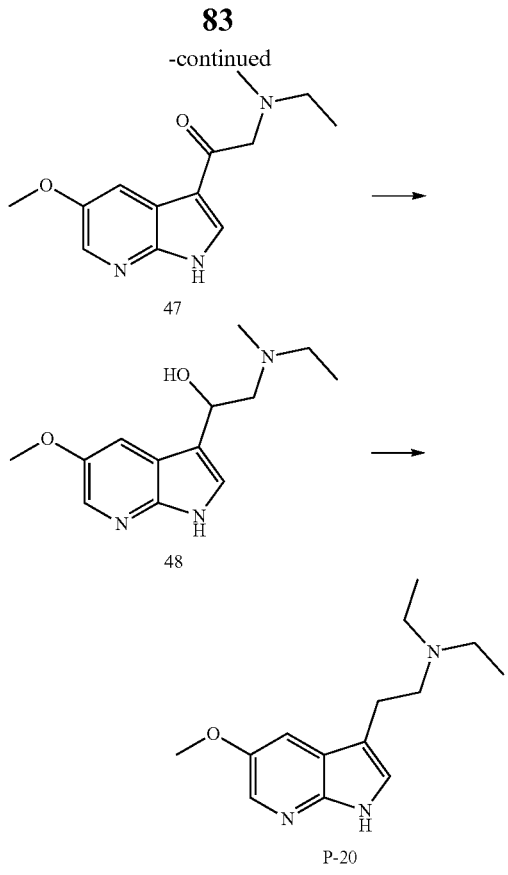

Step 1: 2-(ethyl(methyl)amino)-1-(5-methoxy-1H-pyrrolo[2,3-b]pyridin-3-yl)ethan-1-one (47)

A solution of 2-chloro-1-(5-methoxy-1H-pyrrolo[2,3-b]pyridin-3-yl)ethan-1-one (250 mg, 1.11 mmol), NaI (250 mg, 1.67 mmol), and ethyl(methyl)amine (658 mg, 11.1 mmol) in DMAc (7 mL) was stirred at ambient temperature for 2 h. The reaction was diluted with water (30 mL) and then extracted with EtOAc (10 mL×2). The combined organics were washed with brine (40 mL), dried over anhydrous $Na_2SO_4$ and concentrated under reduced pressure to give crude 2-(ethyl(methyl)amino)-1-(5-methoxy-1H-pyrrolo[2,3-b]pyridin-3-yl)ethan-1-one (216 mg) as a yellow solid that was used in the subsequent step without purification. LCMS (ESI+): m/z 248.3 $[M+H]^+$.

Step 2: 2-(ethyl(methyl)amino)-1-(5-methoxy-1H-pyrrolo[2,3-b]pyridin-3-yl)ethan-1-ol (48)

To a solution of crude 2-(ethyl(methyl)amino)-1-(5-methoxy-1H-pyrrolo[2,3-b]pyridin-3-yl)ethan-1-one (205 mg) in $MeOH/H_2O$ (6/2 v/v, 8 mL) at ambient temperature was added $NaBH_4$ (3.00 g, 79.3 mmol) and the mixture was stirred overnight. The reaction was quenched with water (10 mL) and then extracted with $CH_2Cl_2$:MeOH (10:1 v/v, 5 mL×2). The combined organics were washed with brine (30 mL), dried over anhydrous $Na_2SO_4$ and concentrated in vacuo to give crude 2-(dipropylamino)-1-(5-methoxy-1H-pyrrolo[2,3-b]pyridin-3-yl)ethan-1-ol (185 mg) as a white solid that was used in the next step without further purification. LCMS (ESI+): m/z 250.2 $[M+H]^+$.

Step 3: N-ethyl-2-(5-methoxy-1H-pyrrolo[2,3-b]pyridin-3-yl)-N-methylethan-1-amine (P-20·HCl)

To a stirred solution of crude 2-(ethyl(methyl)amino)-1-(5-methoxy-1H-pyrrolo[2,3-b]pyridin-3-yl)ethan-1-ol (185 mg) and $Et_3SiH$ (0.40 mL, 2.5 mmol) in MeCN (4 mL) at ambient temperature was added $BF_3·Et_2O$ (0.50 mL, 4.05 mmol) and the mixture was stirred overnight. The reaction was quenched with sat. aq. $Na_2CO_3$ (5 mL) and then extracted with $CH_2Cl_2$:MeOH (10:1 v/v, 5 mL×2). The combined organic layers were washed with brine (15 mL) before being dried over anhydrous $Na_2SO_4$ and concentrated under reduced pressure. The resulting residue was purified by preparative thin layer chromatography ($CH_2Cl_2$/MeOH, v/v, 8/1). The HCl salt was recovered after treatment with HCl/MeOH (1 mL) to provide N-ethyl-2-(5-methoxy-1H-pyrrolo[2,3-b]pyridin-3-yl)-N-methylethan-1-amine hydrochloride as an off-white solid (30 mg, 12% over 3 steps). $^1H$ NMR (300 MHz, MeOD-$d_4$): δ 8.56 (d, J=2.1 Hz, 1H), 8.25 (d, J=2.0 Hz, 1H), 7.66 (s, 1H), 4.00 (s, 3H), 3.33-3.55 (m, 4H), 3.13-3.22 (m, 2H), 2.92 (s, 3H), 1.34 (t, J=7.3 Hz, 3H). LCMS (ESI+): m/z 234.2 $[M+H]^+$. HPLC Purity (220 nm): 98.6%.

N-(2-(5-methoxy-1H-pyrrolo[2,3-b]pyridin-3-yl)ethyl)-N-methylpropan-2-amine (P-21)

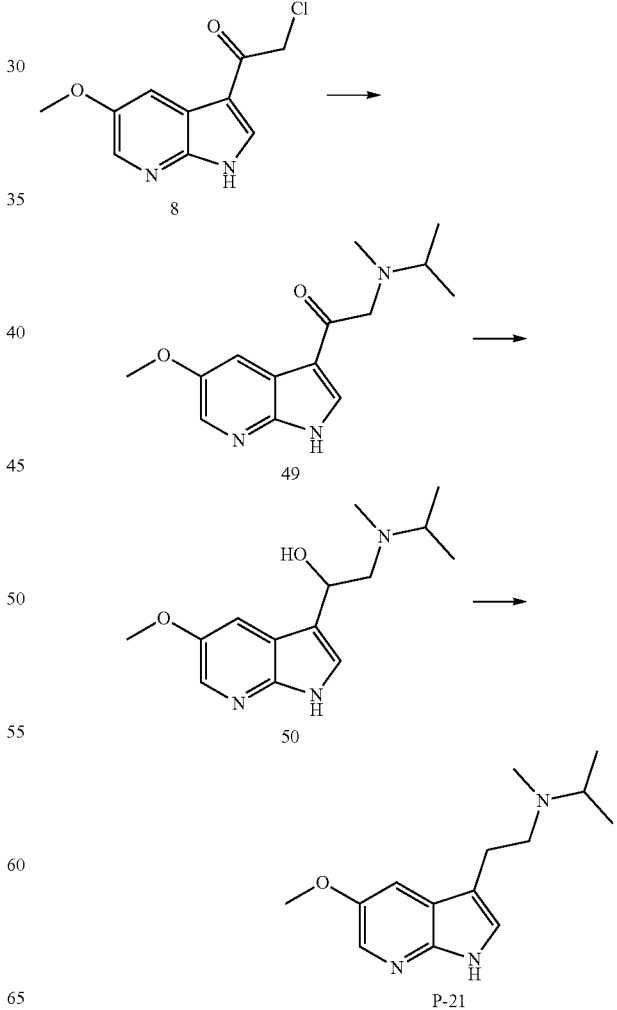

Step 1: 2-(isopropyl(methyl)amino)-1-(5-methoxy-1H-pyrrolo[2,3-b]pyridin-3-yl)ethan-1-one (49)

A solution of 2-chloro-1-(5-methoxy-1H-pyrrolo[2,3-b]pyridin-3-yl)ethan-1-one (300 mg, 1.33 mmol), NaI (300 mg, 2.00 mmol), and methyl(propan-2-yl)amine (977 mg, 13.4 mmol) in DMAc (8 mL) was stirred at ambient temperature for 2 h. The reaction was quenched with water (30 mL) and then extracted with EtOAc (10 mL×2). The combined organic layers were washed with brine (20 mL), dried over anhydrous $Na_2SO_4$ and concentrated under reduced pressure to give crude 2-(isopropyl(methyl)amino)-1-(5-methoxy-1H-pyrrolo[2,3-b]pyridin-3-yl)ethan-1-one (275 mg) as a yellow solid that was used in the subsequent step without purification. LCMS (ESI+): m/z 262.2 $[M+H]^+$.

Step 2: 2-(isopropyl(methyl)amino)-1-(5-methoxy-1H-pyrrolo[2,3-b]pyridin-3-yl)ethan-1-ol (50)

To a solution of crude 2-(isopropyl(methyl)amino)-1-(5-methoxy-1H-pyrrolo[2,3-b]pyridin-3-yl)ethan-1-one (275 mg, 1.05 mmol) in $MeOH/H_2O$ (8 mL, v/v, 6/2) at ambient temperature was added $NaBH_4$ (3.00 g, 79.3 mmol). The resulting mixture was stirred at ambient temperature overnight. The reaction was quenched with water (10 mL) and extracted with $CH_2Cl_2$:MeOH (10:1 v/v, 5 mL×2). The combined organic layers were washed with brine (30 mL), dried over anhydrous $Na_2SO_4$ and concentrated in vacuo to give crude 2-(isopropyl(methyl)amino)-1-(5-methoxy-1H-pyrrolo[2,3-b]pyridin-3-yl)ethan-1-ol (207 mg) as a white solid that was used in the next step without further purification. LCMS (ESI+): m/z 264.3 $[M+H]^+$.

Step 3: N-(2-(5-methoxy-1H-pyrrolo[2,3-b]pyridin-3-yl)ethyl)-N-methylpropan-2-amine (P-21)

To a stirred solution of crude 2-(isopropyl(methyl)amino)-1-(5-methoxy-1H-pyrrolo[2,3-b]pyridin-3-yl)ethan-1-ol (207 mg) and $Et_3SiH$ (0.40 mL, 2.50 mmol) in MeCN (4 mL) at ambient temperature was added $BF_3·Et_2O$ (0.30 mL, 2.43 mmol) and the mixture was stirred overnight. The reaction was quenched with sat. aq. $Na_2CO_3$ (5 mL) and then extracted with $CH_2Cl_2$:MeOH (10:1 v/v, 2×5 mL). The combined organic layers were washed with brine (10 mL), dried over anhydrous $Na_2SO_4$ and concentrated in vacuo. The resulting residue was purified by preparative thin layer chromatography ($CH_2Cl_2$/MeOH, v/v, 8/1) to afford N-(2-(5-methoxy-1H-pyrrolo[2,3-b]pyridin-3-yl)ethyl)-N-methylpropan-2-amine (32 mg, 10% over 3 steps) as an off white solid. $^1H$ NMR (300 MHz, MeOD-$d_4$): δ 7.95 (d, J=2.4 Hz, 1H), 7.65 (d, J=2.5 Hz, 1H), 7.34 (s, 1H), 3.89 (s, 3H), 3.64-3.72 (m, 1H), 3.34-3.44 (m, 2H), 3.12-3.23 (m, 2H), 2.85 (s, 3H), 1.32 (d, J=6.0 Hz, 6H). LCMS (ESI+): m/z 248.3 $[M+H]^+$. HPLC Purity (220 nm): 96%.

N,N-dimethyl-2-(5-methyl-1H-pyrrolo[2,3-b]pyridin-3-yl)ethan-1-amine (P-22)

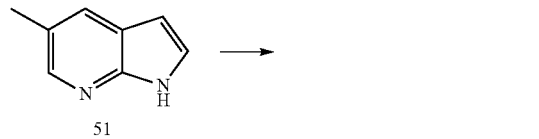

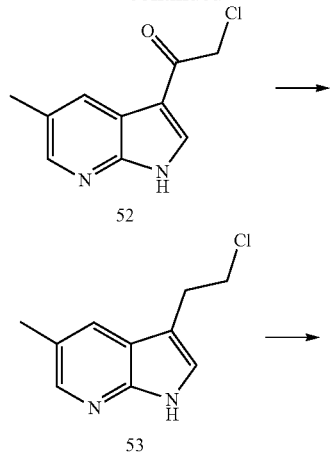

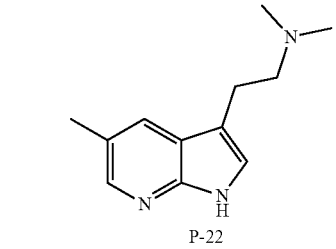

Step 1: 2-chloro-1-(5-methyl-1H-pyrrolo[2,3-b]pyridin-3-yl)ethan-1-one (52)

A mixture of 5-methyl-1H-pyrrolo[2,3-b]pyridine (500 mg, 3.78 mmol) in $CH_2Cl_2$ (15 mL) was degassed and purged with $N_2$ three times before adding $AlCl_3$ (2.52 g, 18.9 mmol) at 0° C. under $N_2$. After stirring at 0° C. for 5 min, was added 2-chloroacetyl chloride (1.28 g, 11.3 mmol) at 0° C. and then the mixture was stirred at ambient temperature for 2 h. The reaction was quenched with water (15 mL) at 0° C. and then adjusted to pH 9 with aqueous $Na_2CO_3$, filtered and the filter cake washed with EtOAc (30 ml×4). The aqueous phase was separated and extracted with EtOAc (20 mL×3). The combined organics were washed with brine (10 mL×2), dried over anhydrous $Na_2SO_4$ and concentrated under reduced pressure to provide crude 2-chloro-1-(5-methyl-1H-pyrrolo[2,3-b]pyridin-3-yl)ethan-1-one (650 mg) as a yellow solid which was used in the next step without purification.

Step 2: 3-(2-chloroethyl)-5-methyl-1H-pyrrolo[2,3-b]pyridine (53)

To a solution of 2-chloro-1-(5-methyl-1H-pyrrolo[2,3-b]pyridin-3-yl)ethan-1-one (650 mg) in TFA (10 mL) was added $Et_3SiH$ (5.10 g, 43.9 mmol) and the reaction was stirred at 70° C. for 12 h. The reaction mixture was then concentrated under reduced pressure and the residue was adjusted to pH 9 with saturated $Na_2CO_3$ solution and then extracted with EtOAc (10 mL×3). The combined organics were washed with brine (10 mL×2), dried over anhydrous $Na_2SO_4$ and concentrated under reduced pressure. The residue was purified by column chromatography (Petroleum ether/EtOAc, v/v, 10:1 to 1:1) to afford 3-(2-chloroethyl)-5-methyl-1H-pyrrolo[2,3-b]pyridine (350 mg) as an off-white solid. LCMS (ESI+): m/z 195.1 $[M+H]^+$.

Step 3: 2-(5-methyl-1H-pyrrolo[2,3-b]pyridin-3-yl)-N,N-dimethylethan-1-amine (P-22)

To a solution of 3-(2-chloroethyl)-5-methyl-1H-pyrrolo[2,3-b]pyridine (200 mg) in THF (3 mL) was added NaI (462 mg, 3.08 mmol) and 2 M Me$_2$NH in THF (1.03 mL, 2.06 mmol) which was stirred at 90° C. for 12 h in a sealed tube. The reaction mixture was diluted with water (20 mL) and then extracted with EtOAc (5 mL×3). The combined organics were washed with brine (5 mL×2), dried over anhydrous Na$_2$SO$_4$ and concentrated under reduced pressure. The residue was purified by preparative HPLC (column: Waters Xbridge (150*25 mm*5 μm); mobile phase: [water (NH$_3$)-ACN]; B: 12-42%, 9 min) to provide 2-(5-methyl-1H-pyrrolo[2,3-b]pyridin-3-yl)-N,N-dimethylethan-1-amine (25 mg, 6% over 3 steps) as an off-white solid. $^1$H NMR (400 MHz, CDCl$_3$): δ 9.11 (br s, 1H), 8.13 (d, J=2.0 Hz, 1H), 7.71 (s, 1H), 7.10 (s, 1H), 2.89-2.93 (m, 2H), 2.62-2.66 (m, 2H), 2.44 (s, 3H), 2.36 (s, 6H). LCMS (ESI+): m/z 204.0 [M+H]$^+$. HPLC Purity (220 nm): 96.5%

N-ethyl-N-methyl-2-(5-methyl-1H-pyrrolo[2,3-b]pyridin-3-yl)ethan-1-amine (P-23)

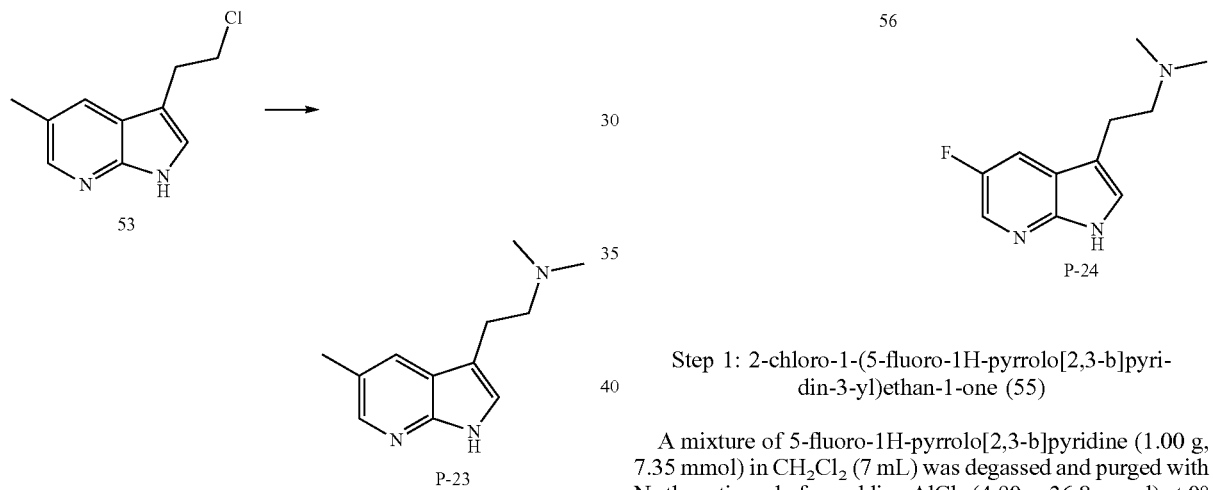

Step 1: N-ethyl-N-methyl-2-(5-methyl-1H-pyrrolo[2,3-b]pyridin-3-yl)ethan-1-amine (P-23)

To a solution of 3-(2-chloroethyl)-5-methyl-1H-pyrrolo[2,3-b]pyridine (200 mg, 1.03 mmol) in DMF (3 mL) was added K$_2$CO$_3$ (213 mg, 1.54 mmol) and ethyl(methyl)amine (182 mg, 3.08 mmol) which was stirred at 50° C. for 12 h. The reaction mixture was diluted with water (20 mL) and then extracted with EtOAc (5 mL×3). The combined organics were washed with brine (5 mL×2), dried over anhydrous Na$_2$SO$_4$ and concentrated under reduced pressure. The residue was purified by preparative HPLC (column: Waters Xbridge (150*25 mm*5 μm); mobile phase: [water (NH$_4$HCO$_3$)-ACN]; B: 12-42%, 9 min) to provide N-ethyl-N-methyl-2-(5-methyl-1H-pyrrolo[2,3-b]pyridin-3-yl)ethan-1-amine (25 mg, 5% over 3 steps) as a yellow oil. $^1$H NMR (400 MHz, CDCl$_3$): δ 9.08 (br s, 1H), 8.14 (d, J=1.6 Hz, 1H), 7.72 (s, 1H), 7.11 (s, 1H), 2.99-2.86 (m, 2H), 2.76-2.67 (m, 2H), 2.57 (q, J=7.2 Hz, 2H), 2.45 (s, 3H), 2.38 (s, 3H), 1.13 (t, J=7.2 Hz, 3H). LCMS (ESI+): m/z 218.0 [M+H]$^+$. HPLC Purity (220 nm): 98.2%.

N,N-dimethyl-2-(5-fluoro-1H-pyrrolo[2,3-b]pyridin-3-yl)ethan-1-amine (P-24)

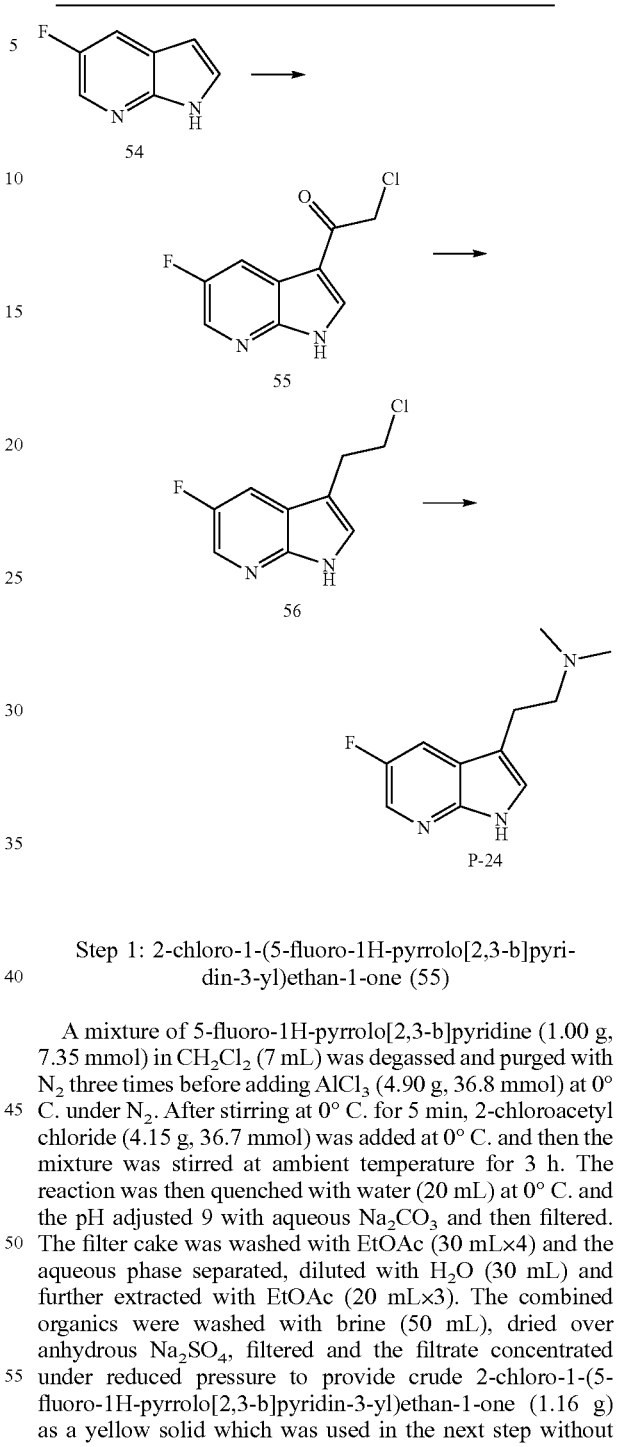

Step 1: 2-chloro-1-(5-fluoro-1H-pyrrolo[2,3-b]pyridin-3-yl)ethan-1-one (55)

A mixture of 5-fluoro-1H-pyrrolo[2,3-b]pyridine (1.00 g, 7.35 mmol) in CH$_2$Cl$_2$ (7 mL) was degassed and purged with N$_2$ three times before adding AlCl$_3$ (4.90 g, 36.8 mmol) at 0° C. under N$_2$. After stirring at 0° C. for 5 min, 2-chloroacetyl chloride (4.15 g, 36.7 mmol) was added at 0° C. and then the mixture was stirred at ambient temperature for 3 h. The reaction was then quenched with water (20 mL) at 0° C. and the pH adjusted 9 with aqueous Na$_2$CO$_3$ and then filtered. The filter cake was washed with EtOAc (30 mL×4) and the aqueous phase separated, diluted with H$_2$O (30 mL) and further extracted with EtOAc (20 mL×3). The combined organics were washed with brine (50 mL), dried over anhydrous Na$_2$SO$_4$, filtered and the filtrate concentrated under reduced pressure to provide crude 2-chloro-1-(5-fluoro-1H-pyrrolo[2,3-b]pyridin-3-yl)ethan-1-one (1.16 g) as a yellow solid which was used in the next step without purification.

Step 2: 3-(2-chloroethyl)-5-fluoro-1H-pyrrolo[2,3-b]pyridine (56)

To a solution of 2-chloro-1-(5-fluoro-1H-pyrrolo[2,3-b]pyridin-3-yl)ethan-1-one (1.16 g, 5.46 mmol) in TFA (10 mL) was added Et$_3$SiH (3.64 g, 31.3 mmol) and the reaction was stirred at ambient temperature for 12 h. The reaction mixture was adjusted to pH 9 with saturated Na$_2$CO$_3$ solution, diluted with H₂O (50 mL) and then extracted with EtOAc (75 mL×3). The combined organics were washed with brine (50 mL), dried over anhydrous Na₂SO₄, filtered and the filtrate concentrated under reduced pressure. The residue triturated with MTBE: Petroleum ether (1:5 v/v, 20 mL) at ambient temperature for 30 min and filtered to afford 3-(2-chloroethyl)-5-fluoro-1H-pyrrolo[2,3-b]pyridine (389 mg) as a yellow solid. LCMS (ESI+): m/z 199.0 [M+H]⁺

Step 3: 2-(5-fluoro-1H-pyrrolo[2,3-b]pyridin-3-yl)-N,N-dimethylethan-1-amine (P-24)

To a solution of 3-(2-chloroethyl)-5-fluoro-1H-pyrrolo[2,3-b]pyridine (50.0 mg, 0.25 mmol) in THF (5 mL) was added NaI (56.6 mg, 0.39 mmol) and 2 M Me₂NH in THF (0.5 mL, 1.01 mmol) which was stirred at 100° C. for 12 h in a sealed tube. The reaction mixture was then diluted with water (20 mL) and then extracted with EtOAc (20 ml×5). The combined organics were washed with brine (50 mL), dried over anhydrous Na₂SO₄, filtered and the filtrate concentrated under reduced pressure. The residue was purified by preparative HPLC (column: Waters Xbridge (150*25 mm*5 μm); mobile phase: [water (NH₃)-ACN]; B: 18-48%, 10 min) to provide 2-(5-fluoro-1H-pyrrolo[2,3-b]pyridin-3-yl)-N,N-dimethylethan-1-amine (10.3 mg, 5% over 3 steps) as a yellow solid. ¹H NMR (400 MHz, CDCl₃): δ 9.11 (br, 1H), 8.17 (t, J=2.2 Hz, 1H), 7.60 (dd, J=8.9, 2.7 Hz, 1H), 7.21 (d, J=2.4 Hz, 1H), 2.89 (t, J=7.6 Hz, 2H), 2.62 (t, J=6.9 Hz, 2H), 2.35 (s, 6H). ¹⁹F NMR (400 MHz, CDCl₃): δ −139.4. LCMS (ESI+): m/z 208.2 [M+H]⁺. HPLC Purity (220 nm): 98.0%.

N-ethyl-N-methyl-2-(5-fluoro-1H-pyrrolo[2,3-b]pyridin-3-yl)ethan-1-amine (P-25)

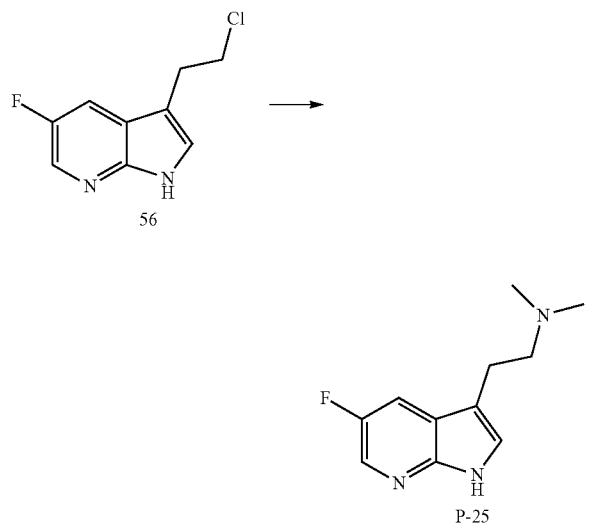

Step 1: N-ethyl-N-methyl-2-(5-fluoro-1H-pyrrolo[2,3-b]pyridin-3-yl)ethan-1-amine (P-25)

To a solution of 3-(2-chloroethyl)-5-fluoro-1H-pyrrolo[2,3-b]pyridine (200 mg, 1.01 mmol) in DMF (5 mL) was added K₂CO₃ (306 mg, 2.21 mmol) and ethyl(methyl)amine (238 mg, 4.03 mmol) which was stirred at 50° C. for 12 h in a sealed tube. The reaction mixture was then diluted with water (20 mL) and extracted with EtOAc (20 mL×5). The combined organics were washed with brine (50 mL), dried over anhydrous Na₂SO₄, filtered and the filtrate concentrated under reduced pressure. The residue was purified by preparative HPLC (column: Waters Xbridge (150*25 mm*5 μm); mobile phase: [water (aq. NH₃)-ACN]; B: 18-48%, 10 min) to provide N-ethyl-N-methyl-2-(5-fluoro-1H-pyrrolo[2,3-b]pyridin-3-yl)ethan-1-amine (57.0 mg, 7% over 3 steps) as a yellow solid. ¹H NMR (400 MHz, CDCl₃): δ 9.19 (br s, 1H), 8.16 (t, J=2.2 Hz, 1H), 7.61 (dd, J=8.9, 2.6 Hz, 1H), 7.20 (d, J=2.1 Hz, 1H), 2.87-2.91 (m, 2H), 2.66-2.70 (m, 2H), 2.53 (q, J=7.2 Hz, 2H), 2.34 (s, 3H), 1.11 (t, J=7.2 Hz, 3H). ¹⁹F NMR (400 MHz, CDCl₃): δ −139.4. LCMS (ESI+): m/z 222.2 [M+H]⁺. HPLC Purity (220 nm): 98.0%.

Scheme 4: Compounds of general formula (I) can be synthesised from the appropriately substituted aza-indole following the outlined sequence of steps in Scheme 4 or similar as one skilled in the art may consider. In a similar fashion to the steps outlined in Scheme 4, Friedel-crafts acylation of aza-indole starting material 10 provides access to intermediate 11 which can be subjected to chemoselective silane reduction conditions to provide the alkyl chloride intermediate 12. Nucleophilic displacement of the alkyl chloride with a substituted amine provides compounds of general formula (I) (exemplified by P-4).

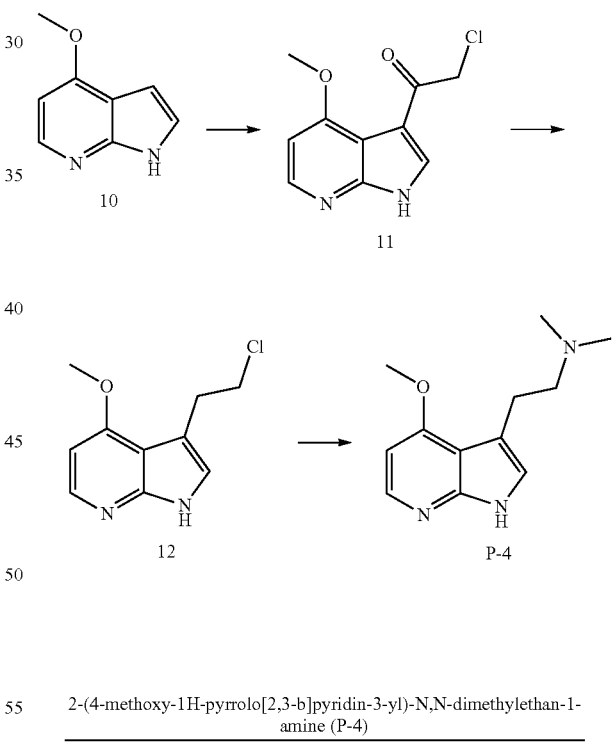

2-(4-methoxy-1H-pyrrolo[2,3-b]pyridin-3-yl)-N,N-dimethylethan-1-amine (P-4)

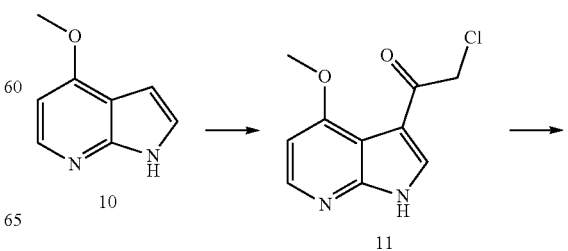

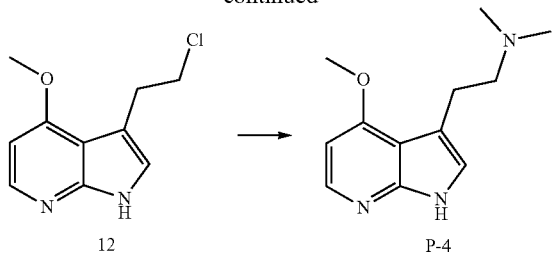

Step 1: 2-chloro-1-(4-methoxy-1H-pyrrolo[2,3-b]pyridin-3-yl)ethan-1-one (11)

To a solution of 4-methoxy-1H-pyrrolo[2,3-b]pyridine (2.20 g, 14.8 mmol) in CH$_2$Cl$_2$ (14 mL) was added AlCl$_3$ (9.90 g, 74.2 mmol) and chloroacetyl chloride (8.39 g, 74.2 mmol). The mixture was stirred at 0° C. for 1.5 h. The reaction mixture was quenched by addition of H$_2$O (20 mL) at 0° C., and then adjusted to pH 9 with saturated aqueous Na$_2$CO$_3$ solution. The mixture was filtered and extracted with EtOAc (50 mL×2). The combined organic layers were washed with brine (30 mL), dried over Na$_2$SO$_4$, filtered, and set aside. The filter cake was triturated with THF/EtOAc (1:1, 100 mL) at 20° C. for 2 h. The filter liquor was combined with organic layers and concentrated in vacuo to give the title compound (3.10 g, 93%) as a light-yellow solid. $^1$H NMR: (400 MHz, DMSO-d$_6$): δ 12.5 (br s, 1H), 8.27 (s, 1H), 8.21 (d, J=5.6 Hz, 1H), 6.84 (d, J=5.6 Hz, 1H), 4.97 (s, 2H), 3.95 (s, 3H). LCMS (ESI+): m/z 225.1 [M+H]$^+$.

Step 2: 3-(2-chloroethyl)-4-methoxy-1H-pyrrolo[2,3-b]pyridine (12)

To a solution of 2-chloro-1-(4-methoxy-1H-pyrrolo[2,3-b]pyridin-3-yl)ethan-1-one (2.26 g, 10.1 mmol) in TFA (13.2 mL) was added Et$_3$SiH (8.19 g, 70.4 mmol). The mixture was stirred at 20° C. for 16 h. The reaction mixture was adjusted to pH=9 with saturated aqueous Na$_2$CO$_3$ solution, then extracted with EtOAc (50 mL×2). The combined organic layers were washed with brine (30 mL), dried over Na$_2$SO$_4$, filtered, and concentrated in vacuum to give 3-(2-chloroethyl)-4-methoxy-1H-pyrrolo[2,3-b]pyridine (12) (2.00 g, 94%) as red solid. $^1$H NMR: (400 MHz, DMSO-d$_6$): δ 8.06 (d, J=5.6 Hz, 1H), 7.14 (d, J=1.6 Hz, 1H), 6.63 (d, J=5.6 Hz, 1H), 5.20 (br s, 1H), 3.93 (s, 3H), 3.81 (t, J=7.4 Hz, 2H), 3.16 (t, J=7.4 Hz, 2H). LCMS (ESI+): m/z 211.1 [M+H]$^+$.

Step 3: 2-(4-methoxy-1H-pyrrolo[2,3-b]pyridin-3-yl)-N,N-dimethylethan-1-amine (P-4)

A solution of 3-(2-chloroethyl)-4-methoxy-1H-pyrrolo[2,3-b]pyridine (1.6 g, 7.6 mmol) in 2 M Me$_2$NH in THF (32.3 mL, 8.5 eq., 64.6 mmol) was treated with sodium iodide (1.14 g, 7.6 mmol) and stirred under reflux for 24 h. Upon completion, the reaction mixture was filtered, and the filter cake was eluted with THF (20 mL). The combined filtrate was concentrated in vacuo and the residue was purified by preparative HPLC (column: Waters Xbridge Prep OBD C18 150*40 mm*10 um; mobile phase: [water (NH$_4$HCO$_3$)-ACN]; B: 1%-30%, 8 min) to afford 2-(4-methoxy-1H-pyrrolo[2,3-b]pyridin-3-yl)-N,N-dimethylethan-1-amine (0.6 g, 2.74 mmol) as a light yellow solid (600 mg, 36%). $^1$H-NMR (400 MHz, MeOD-d$_4$): δ 8.03 (d, J=5.6 Hz, 1H), 7.00 (s, 1H), 6.64 (d, J=5.6 Hz, 1H), 4.00 (s, 3H), 2.96-3.03 (m, 2H), 2.60-2.68 (m, 2H), 2.34 (s, 6H). LCMS (ESI+): m/z 220.2 [M+H]$^+$. HPLC purity (220 nm): 100%.

Step 3a: 2-(4-methoxy-1H-pyrrolo[2,3-b]pyridin-3-yl)-N,N-dimethylethan-1-amine Hydrochloride (P-4·HCl)

To an ice cold (0° C.) solution of 2-(4-methoxy-1H-pyrrolo[2,3-b]pyridin-3-yl)-N,N-dimethylethan-1-amine (0.2 g, 0.91 mmol) in anhydrous Et$_2$O (5 mL) and abs. EtOH (1 mL) was added 2 M HCl in Et$_2$O dropwise over 10 min until the pH of the reaction solution was acidic. The resulting precipitate was collected by filtration and dried overnight in a vacuum desiccator to afford 2-(4-methoxy-1H-pyrrolo[2,3-b]pyridin-3-yl)-N,N-dimethylethan-1-amine as the hydrochloride salt (120 mg, 52%) which was a white solid. $^1$H NMR (400 MHz, DMSO-d$_6$): δ 12.47 (s, 1H), 10.55 (br. s, 1H), 8.38 (d, J=6.6 Hz, 1H), 7.40 (d, J=2.2 Hz, 1H), 7.07 (d, J=6.6 Hz, 1H), 4.15 (s, 3H), 3.30-3.16 (m, 4H), 2.81 (d, J=4.8 Hz, 6H). $^{13}$C NMR (100 MHz, DMSO-d$_6$): δ 164.3, 142.3, 138.8, 124.1, 111.1, 110.1, 99.1, 57.2, 57.1, 42.1, 21.0. HPLC Purity (220 nm): 96.7%.

N,N-diethyl-2-(4-methoxy-1H-pyrrolo[2,3-b]pyridin-3-yl)ethan-1-amine (P-26)

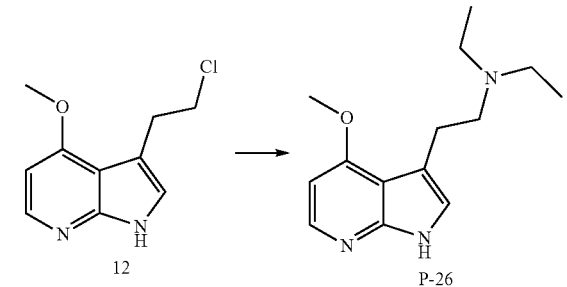

To a solution of 3-(2-chloroethyl)-4-methoxy-1H-pyrrolo[2,3-b]pyridine (500 mg, 2.37 mmol) in THF (5 mL) was added NaI (534 mg, 3.56 mmol) and Et$_2$NH (1.74 g, 23.8 mmol) and the mixture was stirred at 100° C. for 48 h. The mixture was then filtered and the filter cake was washed with THF (5 mL). The filtrate was concentrated under reduced pressure and the residue was purified by preparative HPLC (column: Waters Xbridge (150*25 mm*5 μm); mobile phase: [water (NH$_4$HCO$_3$)-ACN]; B: 5-35%, 9 min) to afford N,N-diethyl-2-(4-methoxy-1H-pyrrolo[2,3-b]pyridin-3-yl)ethan-1-amine (P-26) (100 mg, 17%) as a light yellow solid. $^1$H NMR (400 MHz, MeOD-d$_4$): δ 8.05 (d, J=5.7 Hz, 1H), 7.02 (s, 1H), 6.66 (d, J=5.7 Hz, 1H), 4.02 (s, 3H), 2.97-3.02 (m, 2H), 2.81-2.85 (m, 2H), 2.74 (q, J=7.2 Hz, 4H), 1.16 (t, J=7.2 Hz, 6H). LCMS (ESI+): m/z 248.1 [M+H]$^+$. HPLC Purity (220 nm): 96.9%.

N-isopropyl-N-(2-(4-methoxy-1H-pyrrolo[2,3-b]pyridin-3-yl)ethyl)propan-2-amine (P-27)

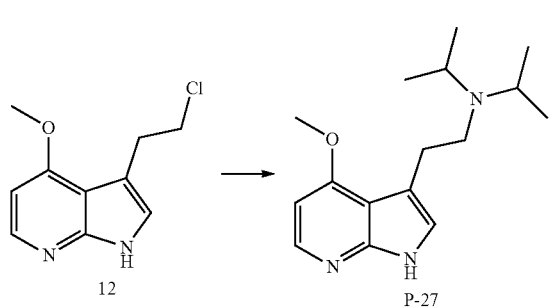

To a solution of 3-(2-chloroethyl)-4-methoxy-1H-pyrrolo[2,3-b]pyridine (500 mg, 2.37 mmol) in THF (5 mL) was added NaI (534 mg, 3.56 mmol) and diisopropyl amine (2.40 g, 23.7 mmol) and the mixture was stirred at 100° C. for 48 h. The mixture was then filtered, and the filter cake was washed with THF (5 mL). The filtrate was concentrated under reduced pressure and the residue was purified by preparative HPLC (Column: Waters Xbridge (150*25 mm*5 μm); mobile phase: [water (NH$_4$HCO$_3$)-ACN]; B: 10-40%, 9 min) to afford N-isopropyl-N-(2-(4-methoxy-1H-pyrrolo[2,3-b]pyridin-3-yl)ethyl)propan-2-amine (P-27) (14.4 mg, 2%) as a light yellow solid. $^1$H NMR (400 MHz, MeOD-d$_4$): δ 8.04 (br d, J=3.2 Hz, 1H), 7.00 (s, 1H), 6.65 (d, J=5.7 Hz, 1H), 4.00 (s, 3H), 3.16 (hept, J=6.5 Hz, 2H), 2.90-2.94 (m, 2H), 2.72-2.77 (m, 2H), 1.14 (d, J=6.5 Hz, 12H). LCMS (ESI+): m/z 276.1 [M+H]$^+$. HPLC Purity (220 nm): 97.1%.

N-ethyl-2-(4-methoxy-1H-pyrrolo[2,3-b]pyridin-3-yl)-N-methylethan-1-amine (P-28)

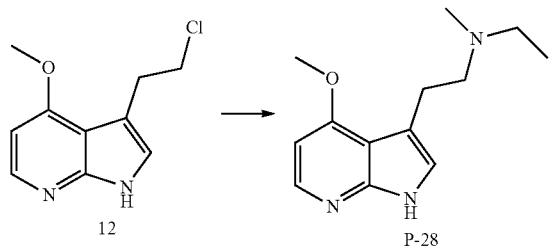

To a solution of 3-(2-chloroethyl)-4-methoxy-1H-pyrrolo[2,3-b]pyridine (200 mg, 0.95 mmol) in THF (2 mL) was added NaI (213 mg, 1.42 mmol) and ethyl(methyl)amine (561 mg, 9.49 mmol) and the mixture was stirred at 100° C. for 48 h. The mixture was then filtered, and the filter cake was washed with THF (2 mL). The filtrate was concentrated under reduced pressure and the residue was purified by preparative HPLC (column: Waters Xbridge (150*25 mm*5 μm); mobile phase: [water (NH$_4$HCO$_3$)-ACN]; B: 5-35%, 9 min) to afford N-ethyl-2-(4-methoxy-1H-pyrrolo[2,3-b]pyridin-3-yl)-N-methylethan-1-amine (P-28) (64.0 mg, 29%) as a light yellow solid. $^1$H NMR (400 MHz, MeOD-d$_4$): δ 8.07 (d, J=5.7 Hz, 1H), 7.08 (s, 1H), 6.68 (d, J=5.7 Hz, 1H), 4.03 (s, 3H), 3.06-3.14 (m, 2H), 2.96-3.03 (m, 2H), 2.87 (q, J=7.2 Hz, 2H), 2.60 (s, 3H), 1.23 (t, J=7.2 Hz, 3H). LCMS (ESI+): m/z 233.15 [M+H]$^+$. HPLC Purity (220 nm): 96.9%.

N-(2-(4-methoxy-1H-pyrrolo[2,3-b]pyridin-3-yl)ethyl)-N-methylpropan-2-amine (P-29)

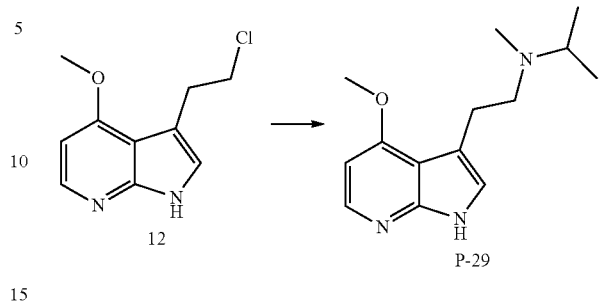

To a solution of 3-(2-chloroethyl)-4-methoxy-1H-pyrrolo[2,3-b]pyridine (150 mg, 0.71 mmol) in THF (2 mL) was added NaI (160 mg, 1.07 mmol) and methyl(propan-2-yl)amine (521 mg, 7.12 mmol) and the mixture was stirred at 100° C. for 48 h. The mixture was filtered, and the filter cake was washed with THF (1.5 mL). The filtrate was concentrated under reduced pressure and the residue was purified by preparative HPLC (column: Waters Xbridge Prep OBD C18 (150*40 mm*10 μm); mobile phase: [water (NH$_4$HCO$_3$)-ACN]; B: 0-30%, 15 min) to afford N-(2-(4-methoxy-1H-pyrrolo[2,3-b]pyridin-3-yl)ethyl)-N-methylpropan-2-amine (P-29) (120 mg, 68%) as a light yellow solid. $^1$H NMR (400 MHz, MeOD-d$_4$): δ 8.04 (d, J=5.7 Hz, 1H), 7.01 (s, 1H), 6.65 (d, J=5.7 Hz, 1H), 4.01 (s, 3H), 2.95-3.00 (m, 3H), 2.71-2.76 (m, 2H), 2.37 (s, 3H), 1.10 (d, J=6.5 Hz, 6H). LCMS (ESI+): m/z 248.1 [M+H]$^+$. HPLC Purity (220 nm): 96.2%.

N,N-dimethyl-2-(4-methyl-1H-pyrrolo[2,3-b]pyridin-3-yl)ethan-1-amine (P-30)

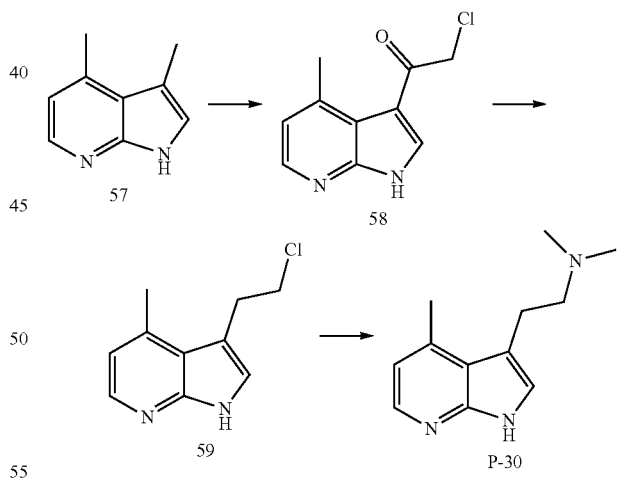

Step 1: 2-chloro-1-(4-methyl-1H-pyrrolo[2,3-b]pyridin-3-yl)ethan-1-one (58)

A mixture of 4-methyl-1H-pyrrolo[2,3-b]pyridine (500 mg, 3.78 mmol) in CH$_2$Cl$_2$ (15 mL) was degassed and purged with N$_2$ three times before adding AlCl$_3$ (2.52 g, 18.9 mmol) at 0° C. under N$_2$. After stirring at 0° C. for 5 min, 2-chloroacetyl chloride (1.28 g, 11.3 mmol) was added at 0° C. and then the mixture was stirred at room temperature for 2 h under N$_2$. The reaction was then cooled to 0° C. before being quenched with water (20 mL) followed by addition of sat. aq. Na$_2$CO$_3$ until the solution was at pH 9. The mixture was then filtered and the filter cake was washed with EtOAc (30 mL×4) and the aqueous phase separated and extracted with EtOAc (20 mL×3). The combined organics were washed with brine (15 mL×2), dried over anhydrous Na$_2$SO$_4$, filtered and the filtrate concentrated under reduced pressure to provide crude 2-chloro-1-(4-methyl-1H-pyrrolo[2,3-b]pyridin-3-yl)ethan-1-one (58) (850 mg) as a yellow solid which was used in the next step without purification.

Step 2: 3-(2-chloroethyl)-4-methyl-1H-pyrrolo[2,3-b]pyridine (59)

To a solution of 2-chloro-1-(4-methyl-1H-pyrrolo[2,3-b]pyridin-3-yl)ethan-1-one (800 mg) in TFA (10 mL) was added Et$_3$SiH (4.11 g, 35.3 mmol) and the reaction was stirred at 70° C. for 12 h. The reaction mixture was then concentrated under reduced pressure and the residue was adjusted to pH 9 with sat. aq. Na$_2$CO$_3$ solution and then extracted with EtOAc (10 mL×3). The combined organics were washed with brine (10 mL×2), dried with anhydrous Na$_2$SO$_4$ before being filtered and the filtrate concentrated under reduced pressure. The residue was purified by column chromatography (petroleum ether: EtOAc 10:1 to 1:2) to afford 3-(2-chloroethyl)-4-methyl-1H-pyrrolo[2,3-b]pyridine (59) (310 mg, 42% over 2 steps) as a white solid. LCMS (ESI+): m/z 195.0

Step 3: N,N-dimethyl-2-(4-methyl-1H-pyrrolo[2,3-b]pyridin-3-yl)ethan-1-amine (P-30)

A mixture of 3-(2-chloroethyl)-4-methyl-1H-pyrrolo[2,3-b]pyridine (50.0 mg, 257 μmol), K$_2$CO$_3$ (53.3 mg, 0.39 mmol) and Me$_2$NH (23.3 mg, 0.52 mmol) in THF (4 mL) and DMF (2 mL) was stirred at 50° C. for 12 h in a sealed tube. The reaction mixture was then diluted with water (20 mL) and then extracted with EtOAc (5 mL×3). The combined organics were washed with brine (5 mL×2), dried over anhydrous Na$_2$SO$_4$ and concentrated under reduced pressure. The residue was purified by preparative HPLC (column: Waters Xbridge (150*25 mm*5 μm); mobile phase: [water (NH$_3$)-ACN]; B: 18-48%, 10 min) to provide N,N-dimethyl-2-(4-methyl-1H-pyrrolo[2,3-b]pyridin-3-yl)ethan-1-amine (P-30) (15.0 mg, 14%) as a white solid. $^1$H NMR (400 MHz, CDCl$_3$): δ 8.84 (br s., 1H), 8.13 (d, J=4.8 Hz, 1H), 7.08 (br s, 1H), 6.82 (d, J=4.8 Hz, 1H), 3.07-3.11 (m, 2H), 2.70 (s, 3H) 2.65-2.69 (m, 2H), 2.39 (s, 6H). LCMS (ESI+): m/z 204.0. HPLC Purity (220 nm): 99.6%.

N-ethyl-N-methyl-2-(4-methyl-1H-pyrrolo[2,3-b]pyridin-3-yl)ethan-1-amine (P-31)

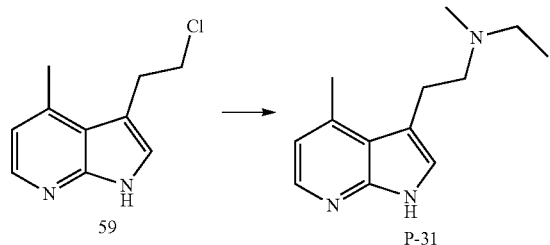

Step 1: N-ethyl-N-methyl-2-(5-methyl-1H-pyrrolo[2,3-b]pyridin-3-yl)ethan-1-amine (P-31)

To a solution of 3-(2-chloroethyl)-4-methyl-1H-pyrrolo[2,3-b]pyridine (150 mg, 771 μmol) in DMF (3 mL) was added K$_2$CO$_3$ (160 mg, 1.16 mmol) and ethyl(methyl)amine (137 mg, 2.32 mmol) which was stirred at 50° C. for 12 h. The reaction mixture was then diluted with water (20 mL) and then extracted with EtOAc (5 mL×3). The combined organics were washed with brine (5 mL×2), dried over anhydrous Na$_2$SO$_4$ and concentrated under reduced pressure. The residue was purified by preparative HPLC (column: Waters Xbridge (150*25 mm*5 μm); mobile phase: [water (NH$_4$HCO$_3$)-ACN]; B: 10-40%, 9 min) to provide N-ethyl-N-methyl-2-(5-methyl-1H-pyrrolo[2,3-b]pyridin-3-yl)ethan-1-amine (P-31) (30.0 mg, 18%) as an off-white solid. $^1$H NMR (400 MHz, CDCl$_3$) δ 9.32 (br s, 1H), 8.13 (d, J=4.8 Hz, 1H), 7.09 (s, 1H), 6.82 (d, J=4.9 Hz, 1H), 3.07-3.11 (m, 2H), 2.69-2.73 (m, 2H), 2.71 (s, 3H), 2.57 (q, J=7.1 Hz, 2H), 2.38 (s, 3H), 1.13 (t, J=7.2 Hz, 3H). LCMS (ESI+): m/z 218.0 [M+H]$^+$. HPLC Purity (220 nm): 96.7%.

N,N-dimethyl-2-(4-fluoro-1H-pyrrolo[2,3-b]pyridin-3-yl)ethan-1-amine (P-32)

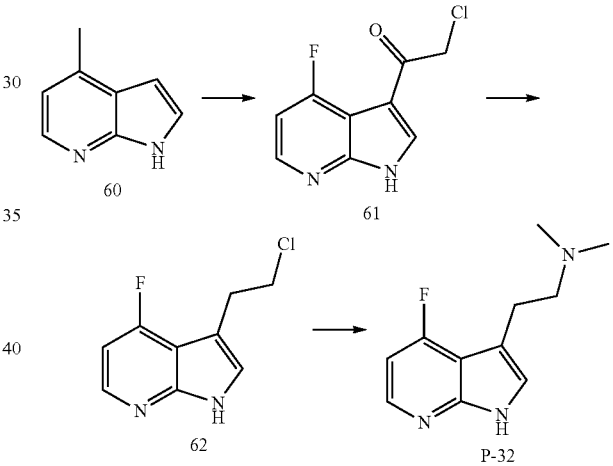

Step 1: 2-chloro-1-(4-fluoro-1H-pyrrolo[2,3-b]pyridin-3-yl)ethan-1-one (61)

A mixture of 4-fluoro-1H-pyrrolo[2,3-b]pyridine (700 mg, 5.14 mmol) in CH$_2$Cl$_2$ (15 mL) was degassed and purged with N$_2$ three times before adding AlCl$_3$ (3.43 g, 25.7 mmol) at 0° C. under N$_2$. After stirring at 0° C. for 5 min, 2-chloroacetyl chloride (2.90 g, 25.7 mmol) was added at 0° C. and then the mixture was stirred at ambient temperature for 6 h under N$_2$ atmosphere. The reaction was then cooled to 0° C., quenched with water (20 mL), and adjusted to pH 9 with sat. aq. Na$_2$CO$_3$ before being filtered. The filter cake was washed with EtOAc (30 mL×4) and the aqueous phase separated, diluted with water (30 mL) and extracted with EtOAc (20 mL×3). The combined organics were washed with brine (50 mL), dried over anhydrous Na$_2$SO$_4$ and concentrated under reduced pressure to provide crude 2-chloro-1-(4-fluoro-1H-pyrrolo[2,3-b]pyridin-3-yl)ethan-1-one (61) (727 mg) as a yellow solid which was used in the next step without purification.

Step 2: 3-(2-chloroethyl)-4-fluoro-1H-pyrrolo[2,3-b]pyridine (62)

To a solution of 2-chloro-1-(4-fluoro-1H-pyrrolo[2,3-b]pyridin-3-yl)ethan-1-one (700 mg) in TFA (10 mL) was added Et$_3$SiH (2.91 g, 25.0 mmol) and the reaction was stirred at 25° C. for 12 h. The reaction mixture was adjusted to pH 9 with satd. aq. Na$_2$CO$_3$ solution, diluted with H$_2$O (50 mL), and then extracted with EtOAc (75 mL×3). The combined organics were washed with brine (50 mL), dried over anhydrous Na$_2$SO$_4$ and concentrated under reduced pressure. The residue was triturated with 1:5 MTBE/Petroleum ether (1/5 v/v, 20 mL) at ambient temperature for 30 min and filtered to afford crude 3-(2-chloroethyl)-4-fluoro-1H-pyrrolo[2,3-b]pyridine (62) (580 mg) as a yellow solid. LCMS (ESI+): m/z 199.1 [M+H]$^+$.

Step 3: 2-(4-fluoro-1H-pyrrolo[2,3-b]pyridin-3-yl)-N,N-dimethylethan-1-amine (P-32)

To a solution of crude 3-(2-chloroethyl)-4-fluoro-1H-pyrrolo[2,3-b]pyridine (200 mg) in DMF (5 mL) was added K$_2$CO$_3$ (306 mg, 2.21 mmol) and 2 M dimethylamine in THF (2.01 mL) which was stirred at 50° C. for 12 h in a sealed tube. The reaction mixture was diluted with water (20 mL) and then extracted with EtOAc (20 mL×5). The combined organics were washed with brine (50 mL), dried over anhydrous Na$_2$SO$_4$ and concentrated under reduced pressure. The residue was purified by preparative HPLC (column: Waters Xbridge (150*25 mm*5 μm); mobile phase: [water (NH$_3$)-ACN]; B: 18-48%, 10 min) to provide 2-(4-fluoro-1H-pyrrolo[2,3-b]pyridin-3-yl)-N, N-dimethylethan-1-amine (P-32) (34.1 mg, 10% over 3 steps) as a yellow solid. $^1$H NMR (400 MHz, CDCl$_3$): δ 9.15 (br s, 1H), 8.21 (dd, J=7.8, 5.5 Hz, 1H), 7.11 (s, 1H), 6.77 (dd, J=10.3, 5.5 Hz, 1H), 3.02-3.06 (m, 2H), 2.69-2.73 (m, 2H), 2.39 (s, 6H). $^{19}$F NMR (400 MHz, CDCl$_3$): δ −112.5. LCMS (ESI+): m/z 208.2 [M+H]$^+$. HPLC Purity (220 nm): 96.6%.

N-ethyl-N-methyl-2-(4-fluoro-1H-pyrrolo[2,3-b]pyridin-3-yl)ethan-1-amine (P-33)

Step 1: N-ethyl-N-methyl-2-(4-fluoro-1H-pyrrolo[2,3-b]pyridin-3-yl)ethan-1-amine (P-33)

To a solution of crude 3-(2-chloroethyl)-4-fluoro-1H-pyrrolo[2,3-b]pyridine (200 mg) in DMF (5 mL) was added K$_2$CO$_3$ (306 mg, 2.21 mmol) and ethyl(methyl)amine (238 mg, 4.03 mmol) which was stirred at 50° C. for 12 h in a sealed tube. The reaction mixture was then diluted with water (20 mL) and then extracted with EtOAc (20 mL×5). The combined organics were washed with brine (50 mL), dried over anhydrous Na$_2$SO$_4$, filtered and filtrate concentrated under reduced pressure. The residue was purified by preparative HPLC (column: Waters Xbridge (150*25 mm*5 μm); mobile phase: [water (NH$_3$)-ACN]; B: 20-50%, 10 min) to provide N-ethyl-N-methyl-2-(4-fluoro-1H-pyrrolo[2,3-b]pyridin-3-yl)ethan-1-amine (P-33, 34.1 mg, 9% over 3 steps) as a pink solid. $^1$H NMR (400 MHz, CDCl$_3$): δ 9.25 (br s, 1H), 8.21 (dd, J=7.7, 5.5 Hz, 1H), 7.10 (s, 1H), 6.77 (dd, J=10.3, 5.5 Hz, 1H), 3.01-3.05 (m, 2H), 2.74-2.77 (m, 2H), 2.59 (q, J=7.0 Hz, 2H) 2.39 (s, 3H), 1.13 (t, J=7.2 Hz, 3H). $^{19}$F NMR (400 MHz, CDCl$_3$): δ −112.4. LCMS (ESI+): m/z 222 [M+H]$^+$. HPLC Purity (220 nm): 98.8%.

The following compounds S1 to S75 may be prepared by similar routes.

| Compound No. | Structure |
|---|---|
| S1 | 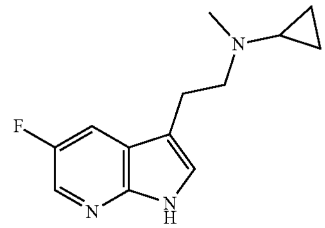 [SMILES: CN(CCc1c[nH]c2ncc(F)cc12)C1CC1] |
| S2 | 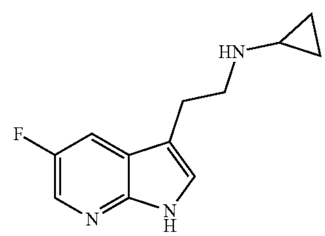 [SMILES: Fc1cnc2[nH]cc(CCNC3CC3)c2c1] |
| S3 | 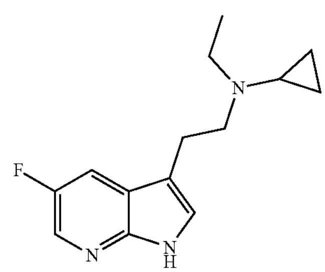 [SMILES: CCN(CCc1c[nH]c2ncc(F)cc12)C1CC1] |
| S4 | 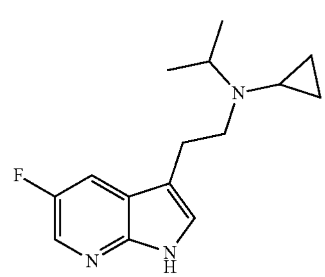 [SMILES: CC(C)N(CCc1c[nH]c2ncc(F)cc12)C1CC1] |

| Compound No. | Structure |
|---|---|
| S5 | 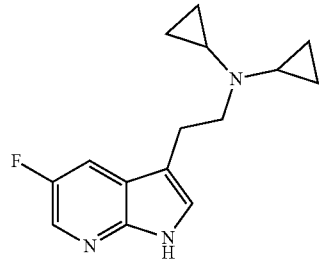 |
| S6 | 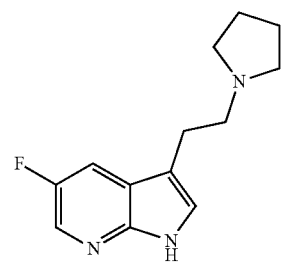 |
| S7 | 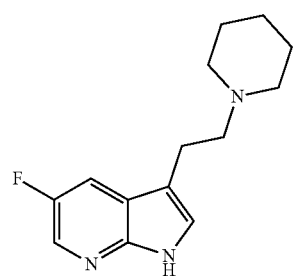 [SMILES: Fc1cnc2[nH]cc(CCN3CCCCC3)c2c1] |
| S8 | 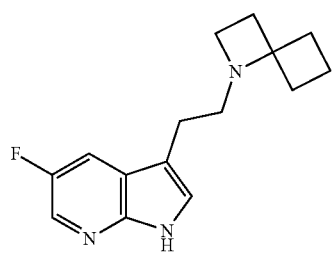 [SMILES: Fc1cnc2[nH]cc(CCN3CCC34CCC4)c2c1] |
| S9 | 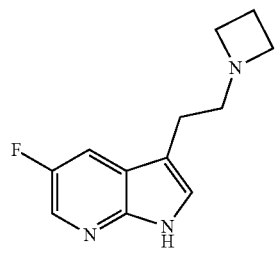 |
| S11 | 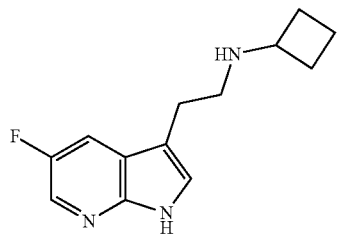 [SMILES: Fc1cnc2[nH]cc(CCNC3CCC3)c2c1] |
| Compound No. | Structure |
|---|---|
| S12 | 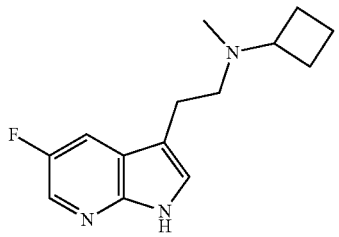 [SMILES: CN(CCc1c[nH]c2ncc(F)cc12)C1CCC1] |
| S13 | 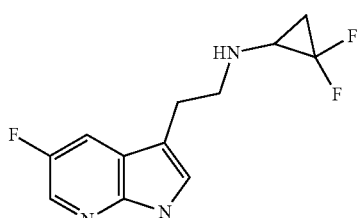 |
| S14 | 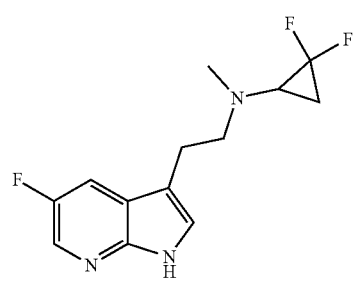 [SMILES: CN(CCc1c[nH]c2ncc(F)cc12)C1CC1(F)F] |
| S15 | 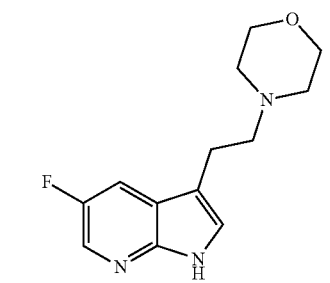 [SMILES: Fc1cnc2[nH]cc(CCN3CCOCC3)c2c1] |
| S16 | 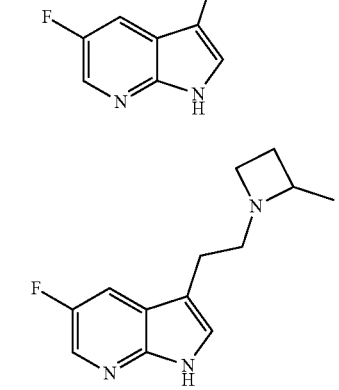 |
| S17 | 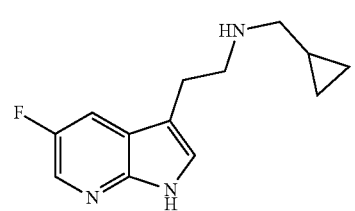 [SMILES: Fc1cnc2[nH]cc(CCNCC3CC3)c2c1] |

| Compound No. | Structure |
|---|---|
| S18 | 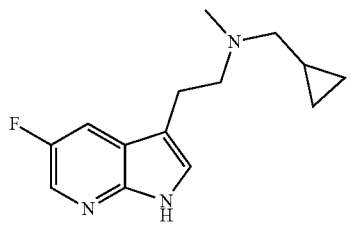 [SMILES: CN(CCc1c[nH]c2ncc(F)cc12)CC1CC1] |
| S19 | 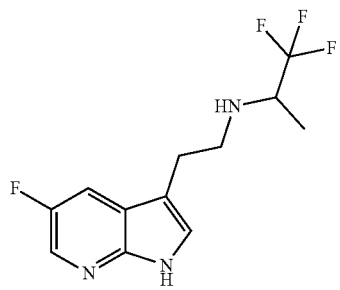 |
| S20 | 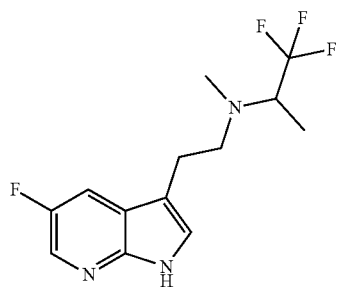 |
| S21 | 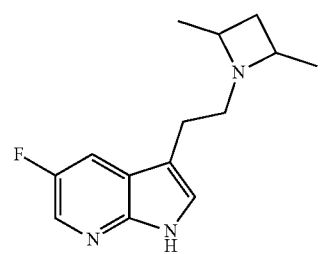 [SMILES: CC1CC(C)N1CCc1c[nH]c2ncc(F)cc12] |
| S22 | 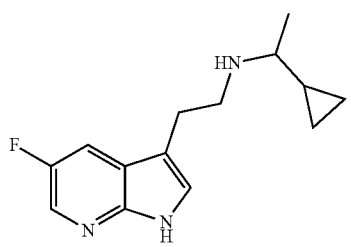 [SMILES: CC(NCCc1c[nH]c2ncc(F)cc12)C1CC1] |
| S23 | 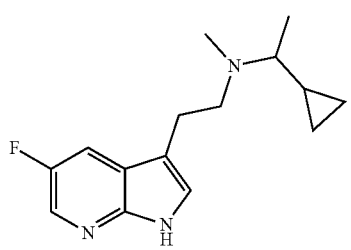 [SMILES: CC(C1CC1)N(C)CCc1c[nH]c2ncc(F)cc12] |
| Compound No. | Structure |
|---|---|
| S24 | 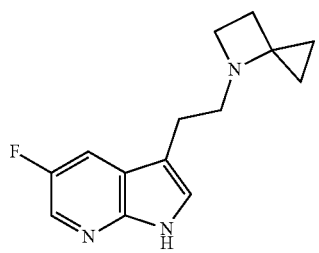 [SMILES: Fc1cnc2[nH]cc(CCN3CCC34CC4)c2c1] |
| S25 | 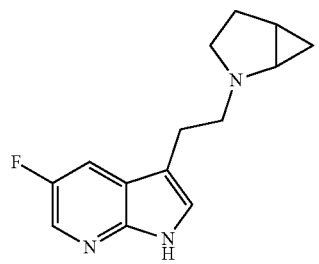 [SMILES: Fc1cnc2[nH]cc(CCN3CCC4CC43)c2c1] |
| S26 | 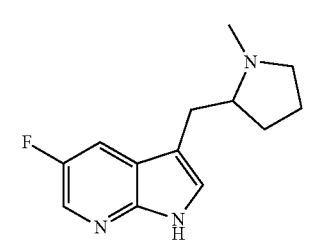 [SMILES: CN1CCCC1Cc1c[nH]c2ncc(F)cc12] |
| S27 | 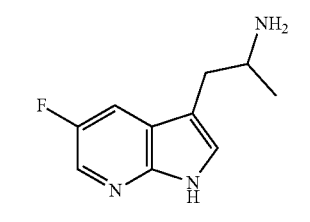 |
| S28 | 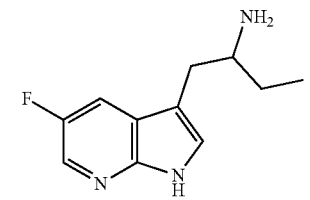 |
| S29 | 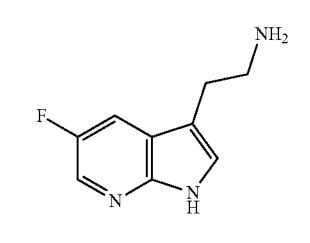 [SMILES: NCCc1c[nH]c2ncc(F)cc12] |

| Compound No. | Structure |
|---|---|
| S30 | 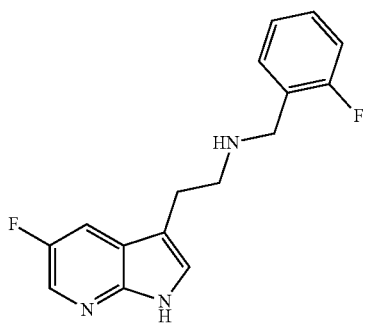 [SMILES: Fc1cnc2[nH]cc(CCNCc3ccccc3F)c2c1] |
| S31 | 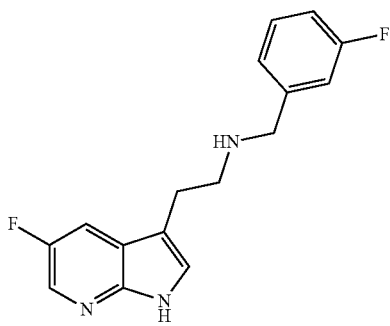 [SMILES: Fc1cccc(CNCCc2c[nH]c3ncc(F)cc23)c1] |
| S32 | 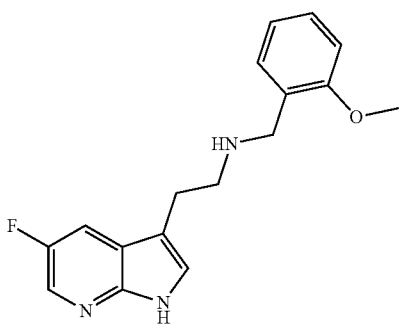 [SMILES: COc1ccccc1CNCCc1c[nH]c2ncc(F)cc12] |
| S33 | 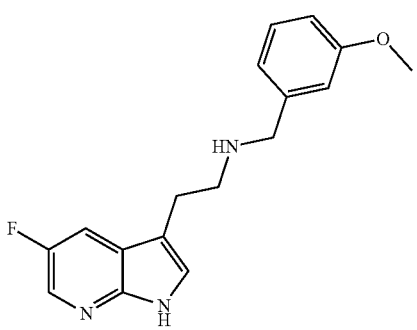 [SMILES: COc1cccc(CNCCc2c[nH]c3ncc(F)cc23)c1] |
| Compound No. | Structure |
|---|---|
| S34 | 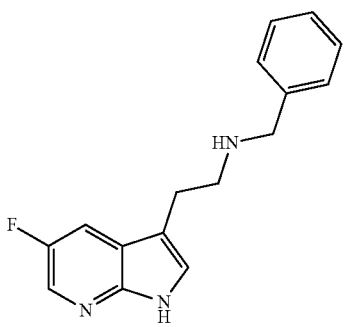 [SMILES: Fc1cnc2[nH]cc(CCNCc3ccccc3)c2c1] |
| S35 | 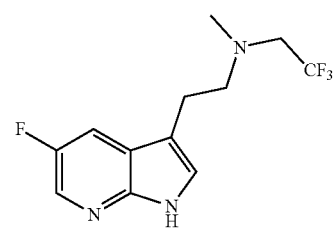 [SMILES: CN(CCc1c[nH]c2ncc(F)cc12)CC(F)(F)F] |
| S36 | 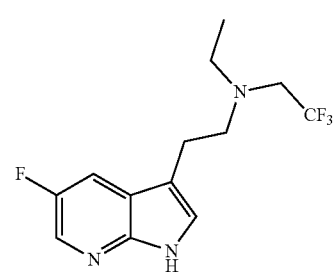 [SMILES: CCN(CCc1c[nH]c2ncc(F)cc12)CC(F)(F)F] |
| S37 | 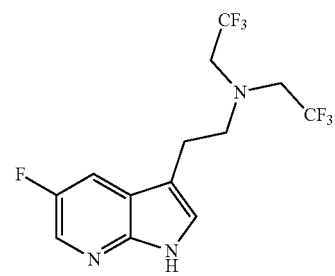 |
| S38 | 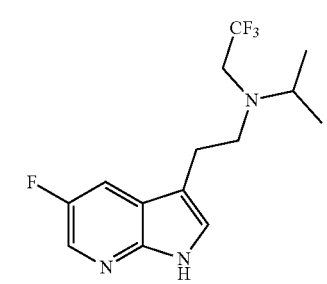 [SMILES: CC(C)N(CCc1c[nH]c2ncc(F)cc12)CC(F)(F)F] |

| Compound No. | Structure |
|---|---|
| S39 | 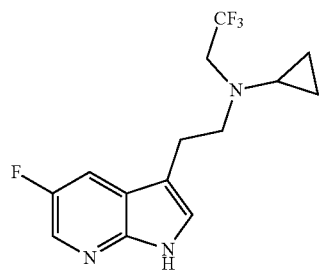 [SMILES: Fc1cnc2[nH]cc(CCN(CC(F)(F)F)C3CC3)c2c1] |
| S40 | 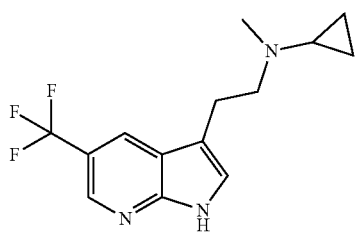 [SMILES: CN(CCc1c[nH]c2ncc(C(F)(F)F)cc12)C1CC1] |
| S41 | 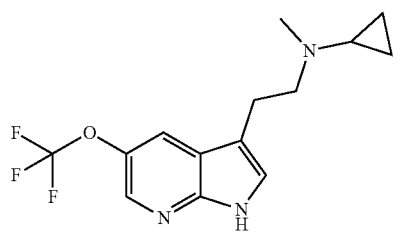 [SMILES: CN(CCc1c[nH]c2ncc(OC(F)(F)F)cc12)C1CC1] |
| S42 | 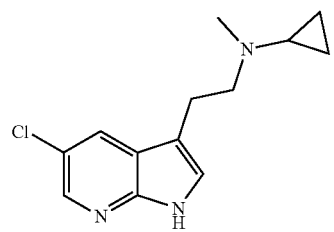 [SMILES: CN(CCc1c[nH]c2ncc(Cl)cc12)C1CC1] |
| S43 | 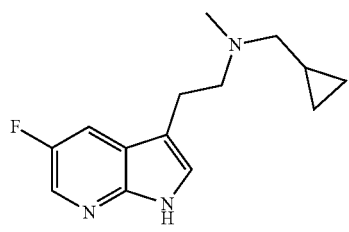 [SMILES: CN(CCc1c[nH]c2ncc(F)cc12)CC1CC1] |
| S44 | 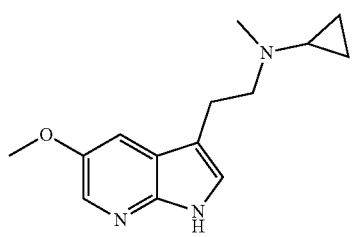 [SMILES: COc1cnc2[nH]cc(CCN(C)C3CC3)c2c1] |
| Compound No. | Structure |
|---|---|
| S45 | 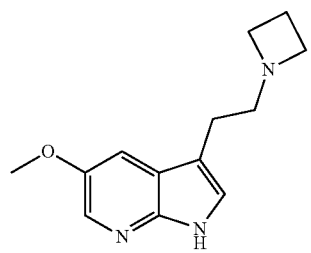 [SMILES: COc1cnc2[nH]cc(CCN3CCC3)c2c1] |
| S46 | 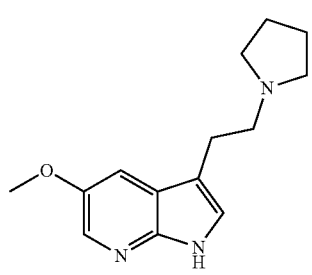 [SMILES: COc1cnc2[nH]cc(CCN3CCCC3)c2c1] |
| S47 | 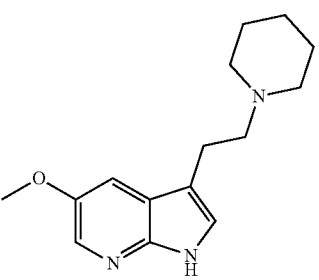 [SMILES: COc1cnc2[nH]cc(CCN3CCCCC3)c2c1] |
| S48 | 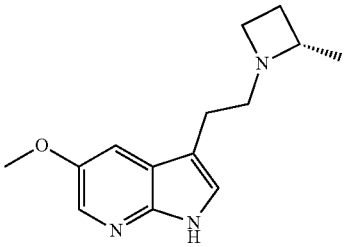 |
| S49 | 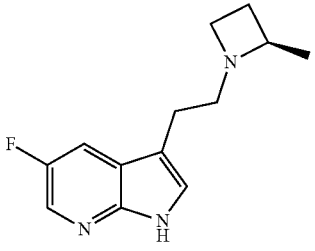 [SMILES: C[C@@H]1CCN1CCc1c[nH]c2ncc(F)cc12] |

| Compound No. | Structure |
|---|---|
| S50 | 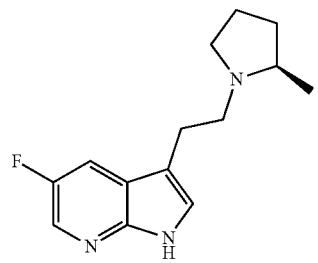 [SMILES: C[C@@H]1CCCN1CCc1c[nH]c2ncc(F)cc12] |
| S51 | 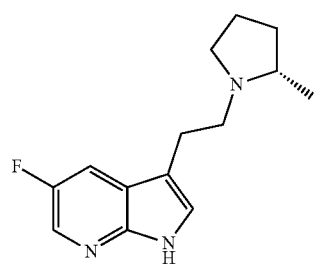 [SMILES: C[C@H]1CCCN1CCc1c[nH]c2ncc(F)cc12] |
| S52 | 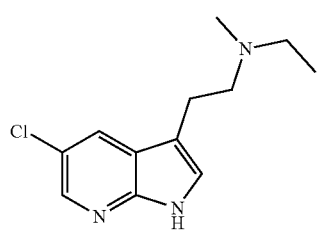 [SMILES: CCN(C)CCc1c[nH]c2ncc(Cl)cc12] |
| S53 | 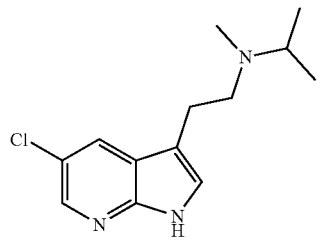 [SMILES: CC(C)N(C)CCc1c[nH]c2ncc(Cl)cc12] |
| S54 | 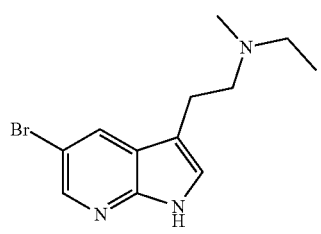 |
| S55 | 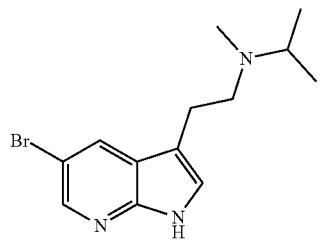 |
| Compound No. | Structure |
|---|---|
| S56 | 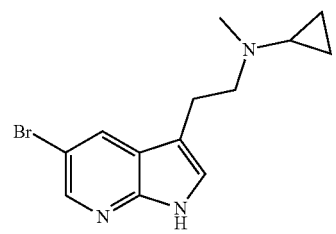 |
| S57 | 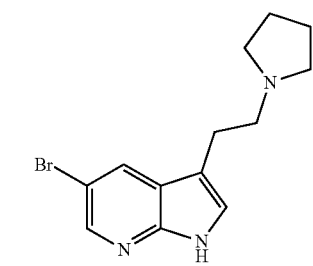 [SMILES: Brc1cnc2[nH]cc(CCN3CCCC3)c2c1] |
| S58 | 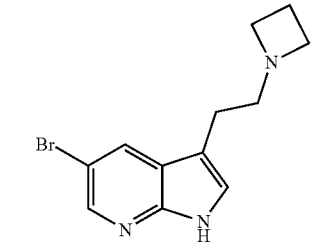 [SMILES: Brc1cnc2[nH]cc(CCN3CCC3)c2c1] |
| S59 | 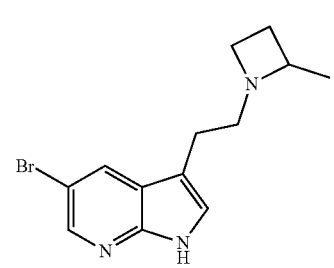 [SMILES: CC1CCN1CCc1c[nH]c2ncc(Br)cc12] |
| S60 | 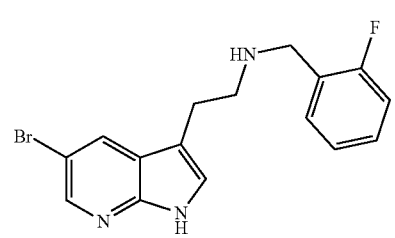 [SMILES: Fc1ccccc1CNCCc1c[nH]c2ncc(Br)cc12] |
| S61 | 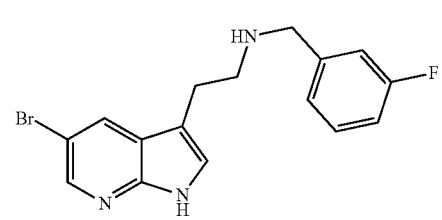 [SMILES: Fc1cccc(CNCCc2c[nH]c3ncc(Br)cc23)c1] |

| Compound No. | Structure |
|---|---|
| S62 | 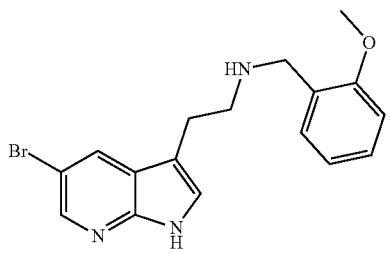 [SMILES: COc1ccccc1CNCCc1c[nH]c2ncc(Br)cc12] |
| S63 | 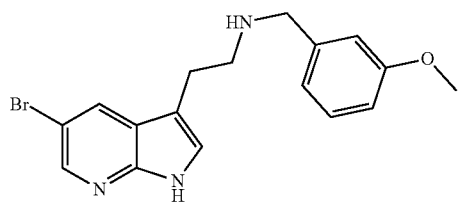 [SMILES: COc1cccc(CNCCc2c[nH]c3ncc(Br)cc23)c1] |
| S64 | 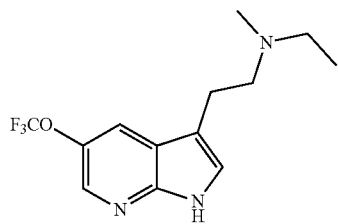 [SMILES: CCN(C)CCc1c[nH]c2ncc(OC(F)(F)F)cc12] |
| S65 | 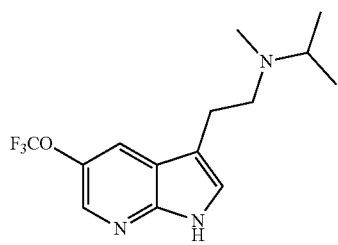 [SMILES: CC(C)N(C)CCc1c[nH]c2ncc(OC(F)(F)F)cc12] |
| S66 | 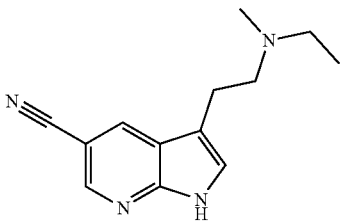 [SMILES: CCN(C)CCc1c[nH]c2ncc(C#N)cc12] |
| S67 | 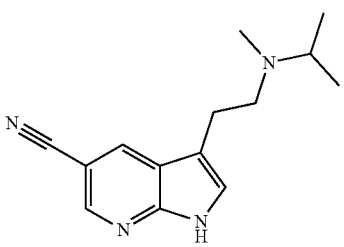 [SMILES: CC(C)N(C)CCc1c[nH]c2ncc(C#N)cc12] |
| S68 | 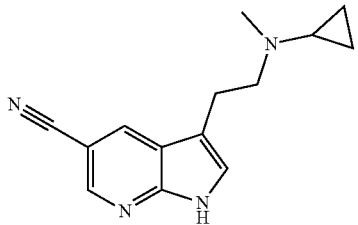 [SMILES: CN(CCc1c[nH]c2ncc(C#N)cc12)C1CC1] |
| S69 | 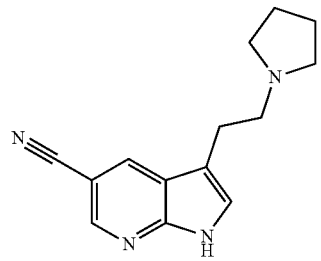 [SMILES: N#Cc1cnc2[nH]cc(CCN3CCCC3)c2c1] |
| S70 | 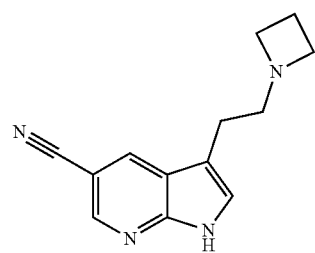 [SMILES: N#Cc1cnc2[nH]cc(CCN3CCC3)c2c1] |
| S71 | 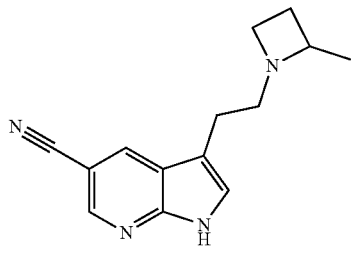 [SMILES: CC1CCN1CCc1c[nH]c2ncc(C#N)cc12] |
| S72 | 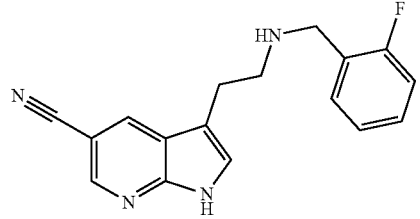 [SMILES: N#Cc1cnc2[nH]cc(CCNCc3ccccc3F)c2c1] |
| S73 | 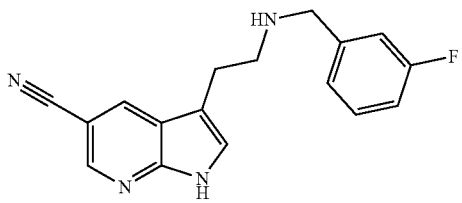 [SMILES: N#Cc1cnc2[nH]cc(CCNCc3cccc(F)c3)c2c1] |

| Compound No. | Structure |
|---|---|
| S74 | 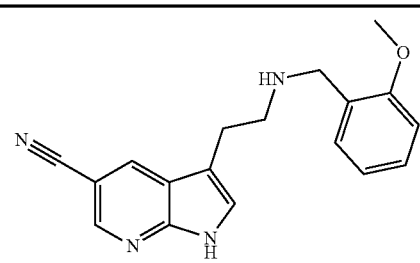 |
| S75 | 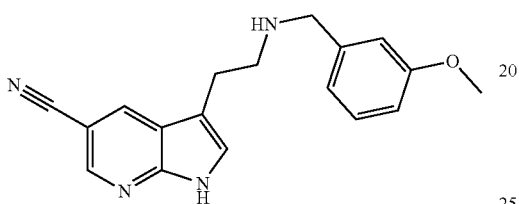 |

| Condition | Instrument | Column | Mobile Phase (A/B) | Time Program |
|---|---|---|---|---|
| A | Shimadzu LC-20AD XR, 8030 triple quadrupole mass spectrometer | Waters XSelect C18 (3.5 μm, 1.6 × 150 mm) [25° C.] | 0.1% FA in H₂O/0.1% FA in MeCN | 5-100% B over 7 minutes (1 mL/min) |
| B | Agilent 1260 HPLC, 6125B single quadrupole mass spectrometer | Phenomenex Luna C18 (5 μm, 2.0 × 50 mm) [40° C.] | 0.4% TFA in H₂O/0.2% TFA in MeCN | 5-95% B over 3 minutes (1 mL/min) |
| C | Waters AQUITY UPLC with QDa mass spectrometer | Waters XBridge BEH C18 (2.5 μm, 2.1 × 50 mm) [35° C.] | 2 mM NH4OAc in 0.1% FA in H₂O/0.1% FA in MeCN | 5-100% B over 2.1 minutes (0.55 mL/min) |

9:1 solution of methanol to 15 M aqueous ammonia. LCMS was carried out using the following conditions.

GENERAL

In the examples below, unless otherwise stated, temperatures are given in degrees Celsius (° C.); operations were carried out at room or ambient temperature, "rt," or "RT," (typically a range of from about 18-25° C.; evaporation of solvent was carried out using a rotary evaporator under reduced pressure (typically, 4.5-30 mm Hg) with a bath temperature of up to 60° C.; the course of reactions was typically followed by thin layer chromatography (TLC); melting points are uncorrected; products exhibited satisfactory $^1$H NMR and/or microanalytical data; and the following conventional abbreviations are also used: L (litres), mL (millilitres), mmol (millimoles), g (grams), mg (milligrams), min (minutes), and h (hours).

Unless otherwise specified, all solvents and reagents were purchased from suppliers and used without further purification. Reactions were conducted under a blanket of nitrogen unless otherwise stated. Compounds were visualized under UV lamp (254 nm). $^1$H NMR spectra were recorded on a 300 MHz, 400 MHz, or 600 MHz NMR instrument as indicated. Column and flash chromatography was performed using SiO₂ as the stationary phase and "MeOH/NH₃" refers to a Compounds of general formula (I) can be synthesised from an appropriately substituted 6,5-aromatic system following the steps outlined in Schemes 5 and 6 below or similar as one skilled in the art may consider. Various substituted 6,5-aromatic systems are commercially available or may be prepared by techniques known in the art, for example as described in Whelligan D et al (Journal of Organic Chemistry, Volume 75, 1 Jan. 2010, Pages 11-15).

Compounds of general formula (I) can be synthesised from an appropriately substituted 6,5-aromatic system following the steps outlined in Schemes 5 and 6 below or similar as one skilled in the art may consider.

Scheme 5: Compounds of general formula (I) can be synthesised via an appropriately substituted 1H-pyrrolo[2,3-b]pyridine system following the outlined sequence of steps in Scheme 5 or similar as one skilled in the art may consider. Amination of an appropriately 5-substituted 2-chloropyridine can be achieved by a palladium catalysed cross coupling with diphenylmethanimine followed by hydrolysis under acidic conditions to provide Int. 1. Regioselective bromination allows for alkynylation via a Sonogashira coupling to provide Int. 3. Cyclisation under basic conditions yields substituted 1H-pyrrolo[2,3-b]pyridine Int. 4 that can be acylated using Friedel-Crafts methodology. Reduction and subsequent nucleophilic substitution allows access to compounds of general formula (I).

Scheme 5

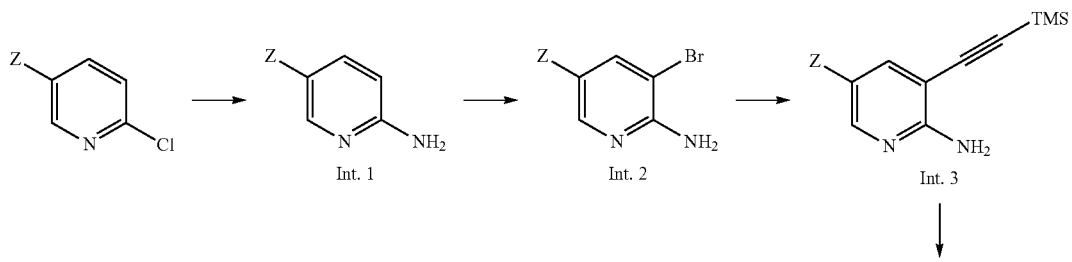

113

-continued

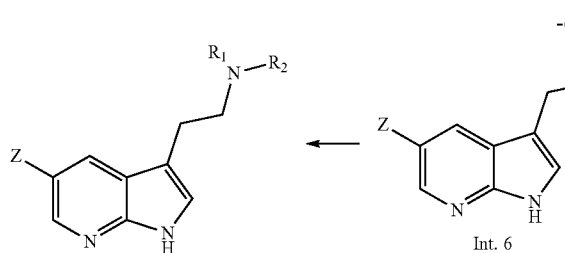 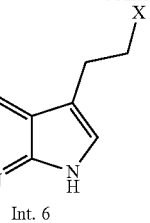 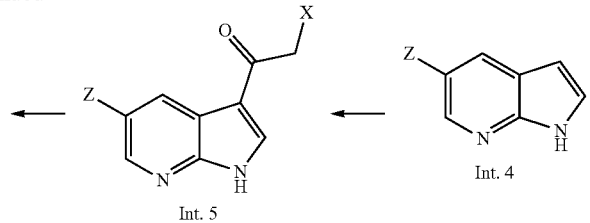

Int. 6    Int. 5    Int. 4

Scheme 6: Compounds of general formula (I) can be synthesised from alkylhalides as outlined in the following steps or similar as one skilled in the art may consider. Access to a primary amine intermediate can be achieved via a Gabriel synthesis which can then be subjected to sequential reductive alkylations with a desired carbonyl and reducing agent to provide compounds of general formula (I) (exemplified by Example S30).

Scheme 6

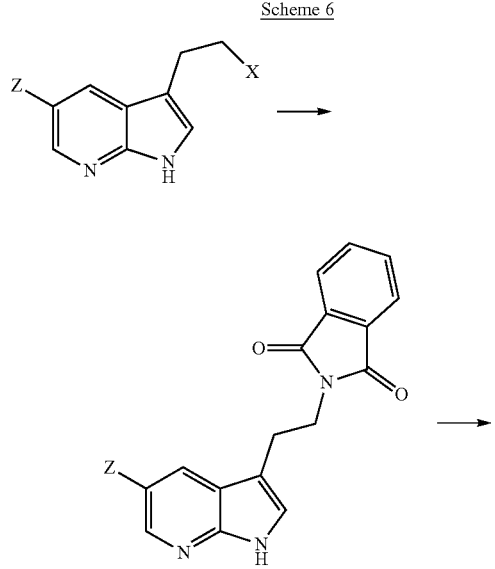

-continued

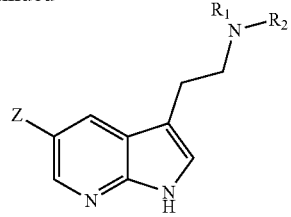

General Procedure A: Preparation of 2-Halo-1-(1H-pyrrolo[2,3-b]pyridin-3-yl)ethanones To an ice-cold solution of appropriately substituted 1H-pyrrolo[2,3-b]pyridine (1 eq.) in anhydrous $CH_2Cl_2$ (5 mL per mmol of 1H-pyrrolo[2,3-b]pyridine) was added $AlCl_3$ (3.5 eq.) portion wise. The reaction mixture was heated to reflux and a solution of bromoacetyl bromide or chloroacetyl chloride (1 eq.) in anhydrous $CH_2Cl_2$ (1 mL per mmol acyl halide) was added dropwise over 10 min. The reaction was allowed to stir at reflux for 1 h at which point the reaction was cooled to RT before being poured onto ice. The crude product was obtained by collecting the resultant precipitate by filtration or by extraction with EtOAc (3×10 V). The crude product was then purified by column chromatography (20% to 50% EtOAc in Hexanes) to give the desired compounds.

General Procedure B: Preparation of 2-Haloethyl-1H-pyrrolo[2,3-b]pyridines

A solution of the appropriately substituted 1H-pyrrolo[2,3-b]pyridin-3-yl ethanones (1 eq.) in $Et_3SiH$ (1 mL per mmol) and trifluoroacetic acid (1 mL per mmol) was heated to 70° C. for up to 16 h. The reaction was quenched by addition of saturated $NaHCO_3$ until slightly alkaline (pH=8-9) and extracted with $Et_2O$ (1.5 V). The combined organics were washed with brine before being dried over $Na_2SO_4$ or $MgSO_4$, filtered, and the filtrate concentrated via rotary evaporation. The resultant crude mass was then purified by column chromatography (0% to 10% EtOAc in Hexanes) to give the desired compounds.

General Procedure C: Alkylation of 2-haloethyl-1H-pyrrolo[2,3-b]pyridines Using Freebase Amines

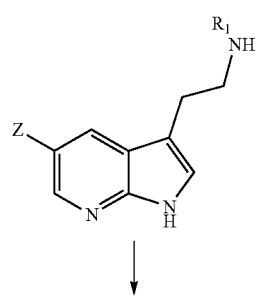

To a pressure tube containing a solution of the appropriately substituted alkylhalide (1 eq.) and NaI (1 eq.) in DMF (2 mL per mmol) was added an appropriately substituted amine (3 eq.) and the sealed vessel was heated to 70° C. until complete. The reaction was then cooled, poured into $H_2O$ (10 V), diluted with saturated aq. $Na_2CO_3$ (5 V), and adjusted to pH 12 with dropwise 15% aq. NaOH, which was then extracted with EtOAc (3×10 V). The combined organics were subsequently washed with saturated aq. $Na_2CO_3$ (5×2 V), $H_2O$ (1×2 V), brine (2×4 V), before being dried ($Na_2SO_4$ or $MgSO_4$), filtered, and the filtrate concentrated under reduced pressure. The resultant crude mass was then purified by column chromatography (0.1% to 10% MeOH/$NH_3$ in $CH_2Cl_2$) to give the desired products.

General Procedure D: Alkylation of 2-haloethyl-1H-pyrrolo[2,3-b]pyridines Using Amine Hydrochlorides To a pressure tube containing a solution of the appropriately substituted alkylhalide (1 eq.) and NaI (1 eq.) in DMF (2 mL per mmol) was added an appropriately substituted amine hydrochloride (1.3-1.5 eq.) and $iPr_2NEt$ (3 eq.) and the sealed vessel was heated to 70° C. until complete. The reaction was then cooled, poured into $H_2O$ (10 V), diluted with saturated aq. $Na_2CO_3$ (5 V), and adjusted to pH 12 with dropwise 15% aq. NaOH, which was then extracted with EtOAc (3×10 V). The combined organics were subsequently washed with saturated aq. $Na_2CO_3$ (5×2 V), $H_2O$ (1×2 V), brine (2×4 V), before being dried ($Na_2SO_4$ or $MgSO_4$), filtered, and the filtrate concentrated under reduced pressure. The resultant crude mass was then purified by column chromatography (0.1% to 10% MeOH/$NH_3$ in $CH_2Cl_2$) to give the desired products.

General Procedure E: Formulation of Hydrochloride Salts from Amines

Starting freebase amine was dissolved in a minimal amount of solvent (MeOH, iPrOH or mixture thereof) and acidified to pH 1 by dropwise addition of concentrated HCl (37%). Precipitation was initiated by addition of $Et_2O$ and the mixture was left to stand at 0° C. The product was collected by vacuum filtration and washed with $Et_2O$.

General Procedure F: Formulation of Fumaric Acid and Maleic Acid Salts from Amines A solution of freebase amine in a minimal amount of solvent (acetone or iPrOH) was added to a hot solution of fumaric acid or maleic acid in either acetone or iPrOH (1-3 eq., 0.02-0.2 M) and the mixture was heated to between 40-60° C. The mixture was cooled and precipitation was initiated by addition of $Et_2O$ or hexane and then left to stand at 0° C. The product was collected by vacuum filtration and washed with $Et_2O$.

Example 1: Synthesis of N-(2-(5-fluoro-1H-pyrrolo[2,3-b]pyridin-3-yl)ethyl)-N-methylcyclopropanamine (S1)

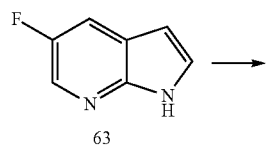

63

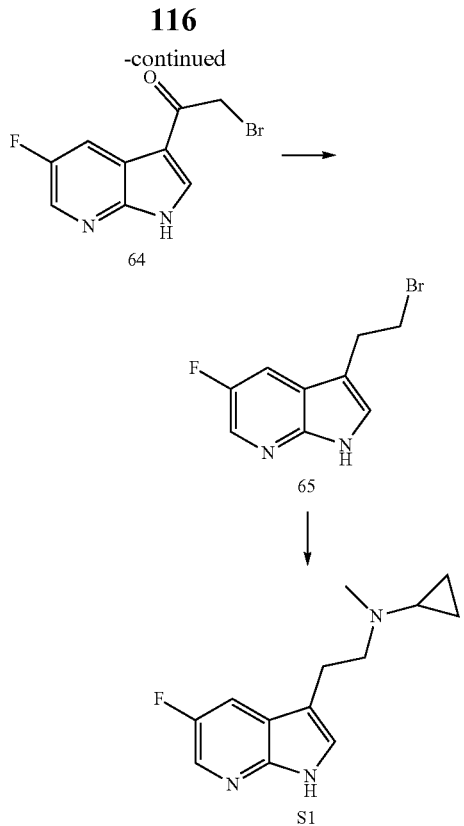

Step 1: 2-bromo-1-(5-fluoro-1H-pyrrolo[2,3-b]pyridin-3-yl)ethan-1-one (64)

The title compound was synthesised according to General Procedure A with 5-fluoro-1H-pyrrolo[2,3-b]pyridine (2.28 g, 16.7 mmol) resulting in the title compound as a pale brown solid (2.2 g, 51%). $^1$H NMR (400 MHz, $CDCl_3$): δ 10.22 (s, 1H), 8.45 (dd, J=8.5, 2.7 Hz, 1H), 8.34-8.28 (m, 1H), 8.18 (s, 1H), 4.31 (s, 2H).

Step 2: 3-(2-bromoethyl)-5-fluoro-1H-pyrrolo[2,3-b]pyridine (65)

The title compound was synthesized according to General Procedure B with 2-bromo-1-(5-fluoro-1H-pyrrolo[2,3-b]pyridin-3-yl)ethan-1-one (1 g, 3.9 mmol) resulting in the title compound as white crystalline needles (0.8 g, 85%). $^1$H NMR (400 MHz, DMSO-$d_6$): δ 11.64 (s, 1H), 8.24-8.12 (m, 1H), 8.00-7.90 (m, 1H), 7.49 (d, J=2.6 Hz, 1H), 3.75 (t, J=7.3 Hz, 2H), 3.23 (td, J=7.3, 0.8 Hz, 2H); $^{13}$C NMR (101 MHz, DMSO-$d_6$): δ 155.3 (d, J=238.4 Hz), 145.8, 131.1 (d, J=29.0 Hz), 127.2, 119.6 (d, J=6.9 Hz), 112.9 (d, J=20.6 Hz), 111.5 (d, J=4.3 Hz), 34.7, 29.0.

Step 3: N-(2-(5-fluoro-1H-pyrrolo[2,3-b]pyridin-3-yl)ethyl)-N-methylcyclopropanamine Hydrochloride (S1·HCl)

The title compound was synthesised according to General Procedure D utilising 3-(2-bromoethyl)-5-fluoro-1H-pyrrolo[2,3-b]pyridine (0.4 g, 1.65 mmol), N-methylcyclopropanamine hydrochloride (266 mg, 2.5 mmol) and $iPr_2NEt$ (0.86 mL, 4.9 mmol) which upon purification generated the title compound as a colourless oil (293 mg, 76%) which was then formulated as the hydrochloride salt as per General Procedure E (180 mg, 54%) as a white crystalline solid. LCMS (Condition A): $t_R$ (3.210 min) m/z=234.15 [M+H]$^+$; $^1$H NMR (400 MHz, DMSO-d$_6$): δ 11.69 (s, 1H), 10.78 (s, 1H), 8.21 (dd, J=2.8, 1.7 Hz, 1H), 8.02 (dd, J=9.6, 2.8 Hz, 1H), 7.51 (d, J=2.5 Hz, 1H), 3.49-3.40 (m, 2H), 3.31-3.12 (m, 2H), 2.97-2.86 (m, 4H), 1.30-1.19 (m, 1H), 1.10-0.99 (m, 1H), 0.96-0.76 (m, 2H); $^{13}$C NMR (101 MHz, DMSO-d$_6$): δ 155.2 (d, J=238.6 Hz), 145.9, 131.5, 127.0, 119.5 (d, J=6.9 Hz), 112.9 (d, J=20.7 Hz), 109.1, 56.6, 41.3, 39.1, 20.4, 5.5, 3.6.

Example 2: Synthesis N-(2-(5-fluoro-1H-pyrrolo[2,3-b]pyridin-3-yl)ethyl)cyclopropanamine (S2)

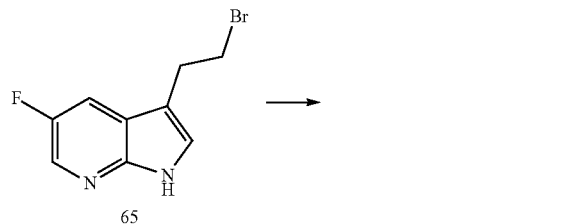

Step 1: N-(2-(5-fluoro-1H-pyrrolo[2,3-b]pyridin-3-yl)ethyl)cyclopropanamine Fumarate (S2·Fumarate)

Cyclopropylamine (0.13 mL, 1.81 mmol) was added to a solution of 3-(2-bromoethyl)-5-fluoro-1H-pyrrolo[2,3-b]pyridine (0.2 g, 0.82 mmol) in DMF (5 mL). This solution was heated to 80° C. for 4 h in a pressure tube. The reaction was then allowed to cool, and then poured into H$_2$O (50 mL) before being extracted with EtOAc (3×20 mL). The combined organics were washed sequentially with H$_2$O (3×100 mL), brine (1×100 mL) before being dried (MgSO$_4$), filtered and concentrated under reduced pressure. The resultant oil was purified by column chromatography (1-10% MeOH/NH$_3$ in CH$_2$Cl$_2$) to give the title compound as a colourless oil which was then formulated as the fumarate salt as per General Procedure F (115 mg, 39%) as a white crystalline solid. LCMS (Condition A): $t_R$ (3.162 min) m/z=220.10 [M+H]$^+$; $^1$H NMR (400 MHz, DMSO-d$_6$): δ 11.56 (s, 1H), 8.16 (dd, J=2.6, 1.8 Hz, 1H), 7.88 (dd, J=9.6, 2.7 Hz, 1H), 7.42 (d, J=2.4 Hz, 1H), 6.54 (s, 3H), 3.11-2.98 (m, 2H), 2.96-2.81 (m, 2H), 2.46-2.36 (m, 1H), 0.62-0.44 (m, 4H).

Example 5: Synthesis N-cyclopropyl-N-(2-(5-fluoro-1H-pyrrolo[2,3-b]pyridin-3-yl)ethyl)cyclopropanamine (S5)

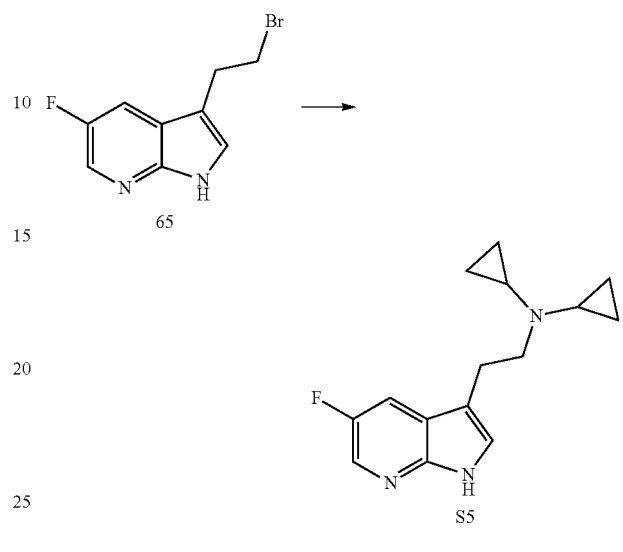

Step 1: N-cyclopropyl-N-(2-(5-fluoro-1H-pyrrolo[2,3-b]pyridin-3-yl)ethyl)cyclopropanamine Hydrochloride (S5·HCl)

The title compound was synthesised according to General Procedure D utilising 3-(2-bromoethyl)-5-fluoro-1H-pyrrolo[2,3-b]pyridine (0.2 g, 0.82 mmol), N-cyclopropylcyclopropanamine hydrochloride (143 mg, 1.07 mmol), NaI (123 mg, 0.82 mmol), and iPr$_2$NEt (0.43 mL, 2.46 mmol) which upon purification generated the title compound as a colourless oil which was then formulated as the hydrochloride salt as per General Procedure E (85 mg, 35%) as a white crystalline solid. LCMS (Condition A): $t_R$ (3.504 min) m/z=260.10 [M+H]$^+$; $^1$H NMR (400 MHz, DMSO-d$_6$): δ 11.72 (s, 1H), 10.89 (s, 1H), 8.30-8.12 (m, 1H), 8.01 (dd, J=9.5, 2.7 Hz, 1H), 7.53 (d, J=2.3 Hz, 1H), 3.54-3.39 (m, 2H), 3.34-3.23 (m, 2H), 3.10-2.97 (m, 2H), 1.30-1.13 (m, 4H), 0.94-0.75 (m, 4H); $^{13}$C NMR (101 MHz, DMSO-d$_6$): δ 154.7 (d, J=238.7 Hz), 145.3, 130.8 (d, J=29.1 Hz), 126.6, 119.1 (d, J=6.8 Hz), 112.5 (d, J=20.7 Hz), 108.9 (d, J=4.4 Hz), 56.5, 38.1, 19.8, 3.4, 3.2.

Example 6: Synthesis 5-fluoro-3-(2-(pyrrolidin-1-yl)ethyl)-1H-pyrrolo[2,3-b]pyridine (S6)

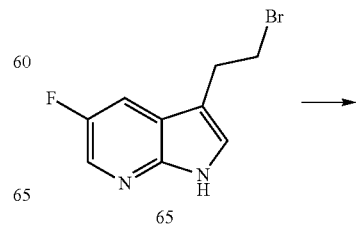

Step 1: 5-fluoro-3-(2-(pyrrolidin-1-yl)ethyl)-1H-pyrrolo[2,3-b]pyridine fumarate (S6·Fumarate)

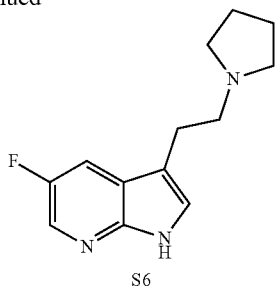

Pyrrolidine (0.15 mL, 1.81 mmol) was added to a solution of 3-(2-bromoethyl)-5-fluoro-1H-pyrrolo[2,3-b]pyridine (0.2 g, 0.82 mmol) in DMF (5 mL). This solution was heated to 80° C. for 4 h in a pressure tube. The reaction was then allowed to cool, and then poured into H$_2$O (50 mL) before being extracted with EtOAc (3×20 mL). The combined organics were washed sequentially with H$_2$O (3×100 mL), brine (1×100 mL) before being dried (MgSO$_4$), filtered and concentrated under reduced pressure. The resultant oil was purified by column chromatography (1-10% MeOH/NH$_3$ in CH$_2$Cl$_2$) to give the title compound as a colourless oil which was then formulated as the fumarate salt as per General Procedure F (120 mg, 53%) as a white crystalline solid. LCMS (Condition A): $t_R$ (3.114 min) m/z=234.10 [M+H]$^+$; $^1$H NMR (400 MHz, DMSO-d$_6$): δ 11.59 (s, 1H), 8.18 (dd, J=2.8, 1.7 Hz, 1H), 7.93 (dd, J=9.7, 2.8 Hz, 1H), 7.44 (d, J=2.5 Hz, 1H), 6.53 (s, 2H), 3.11-3.05 (m, 2H), 3.05-2.93 (m, 6H), 1.88-1.80 (m, 4H).

Example 7: Synthesis 5-fluoro-3-(2-(piperidin-1-yl)ethyl)-1H-pyrrolo[2,3-b]pyridine (S7)

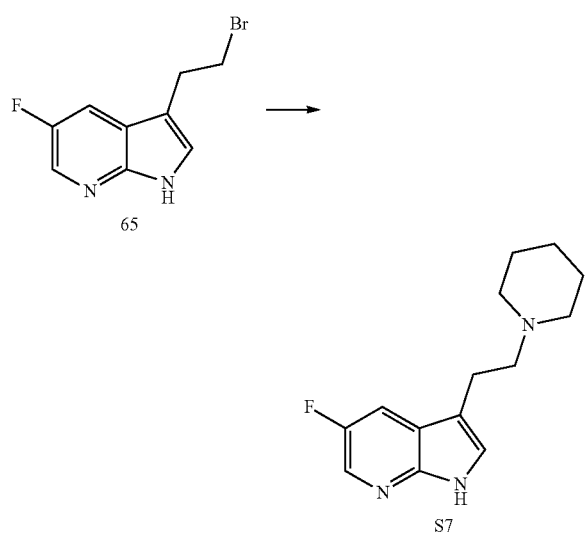

Step 1: 5-fluoro-3-(2-(piperidin-1-yl)ethyl)-1H-pyrrolo[2,3-b]pyridine Fumarate (S7·Fumarate)

Piperidine (0.18 mL, 2.2 eq., 1.81 mmol) was added to a solution of 3-(2-bromoethyl)-5-fluoro-1H-pyrrolo[2,3-b]pyridine (0.2 g, 0.82 mmol) in DMF (5 mL). This solution was heated to 80° C. for 4 h in a pressure tube. The reaction was then allowed to cool, and then poured into H$_2$O (50 mL) before being extracted with EtOAc (3×20 mL). The combined organics were washed sequentially with H$_2$O (3×100 mL), brine (1×100 mL) before being dried (MgSO$_4$), filtered, and the filtrate concentrated under reduced pressure. The resultant oil was purified by column chromatography (1-10% MeOH/NH$_3$ in CH$_2$Cl$_2$) to give the title compound as a colourless oil which was then formulated as the fumarate salt as per General Procedure F (110 mg, 37%) as a white crystalline solid. LCMS (Condition A): $t_R$ (3.315 min) m/z=248.15 [M+H]$^+$; $^1$H NMR (400 MHz, DMSO-d$_6$): δ 11.56 (s, 1H), 8.17 (dd, J=2.8, 1.7 Hz, 1H), 7.90 (dd, J=9.7, 2.8 Hz, 1H), 7.42 (d, J=2.5 Hz, 1H), 6.55 (s, 2H), 2.98-2.81 (m, 4H), 2.77 (m, 4H), 1.68-1.60 (m, 4H), 1.49-1.46 (m, 2H).

Example 8: Synthesis 3-(2-(1-azaspiro[3.3]heptan-1-yl)ethyl)-5-fluoro-1H-pyrrolo[2,3-b]pyridine (S8)

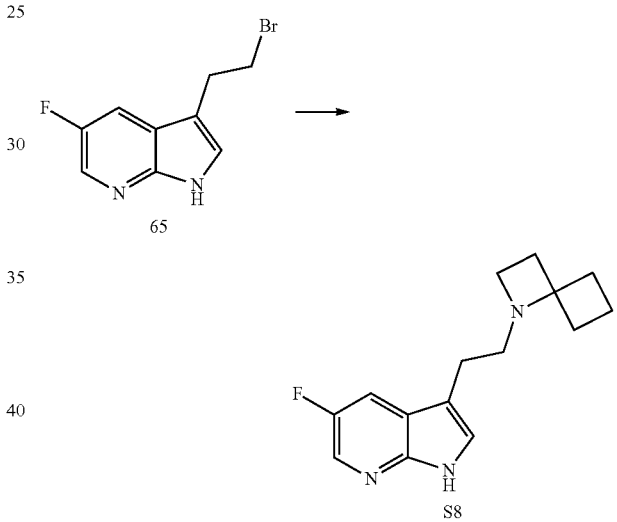

Step 1: 3-(2-(1-azaspiro[3.3]heptan-1-yl)ethyl)-5-fluoro-1H-pyrrolo[2,3-b]pyridine Hydrochloride (S8·HCl)

The title compound was synthesised according to General Procedure D utilising 3-(2-bromoethyl)-5-fluoro-1H-pyrrolo[2,3-b]pyridine (0.2 g, 0.82 mmol), 1-azaspiro[3.3]heptane hydrochloride (143 mg, 1.07 mmol), NaI (123 mg, 0.82 mmol) and iPr$_2$NEt (0.43 mL, 2.46 mmol) which upon purification generated the title compound as a pale yellow oil which was then formulated as the hydrochloride salt as per General Procedure E (109 mg, 45%) as a brown solid. LCMS (Condition A): $t_R$ (3.493 min) m/z=260.10 [M+H]$^+$; $^1$H NMR (400 MHz, DMSO-d$_6$): δ 11.70 (s, 1H), 10.71 (s, 1H), 8.20 (dd, J=2.8, 1.7 Hz, 1H), 8.06-7.98 (m, 1H), 7.51 (d, J=2.5 Hz, 1H), 3.97-3.70 (m, 2H), 3.50-3.41 (m, 1H), 3.25-3.11 (m, 1H), 3.03-2.91 (m, 2H), 2.66 (q, J=10.5 Hz, 1H), 2.61-2.45 (m, 3H), 2.18-2.06 (m, 2H), 1.84-1.66 (m, 2H).

Example 9: Synthesis 3-(2-(azetidin-1-yl)ethyl)-5-fluoro-1H-pyrrolo[2,3-b]pyridine (S9)

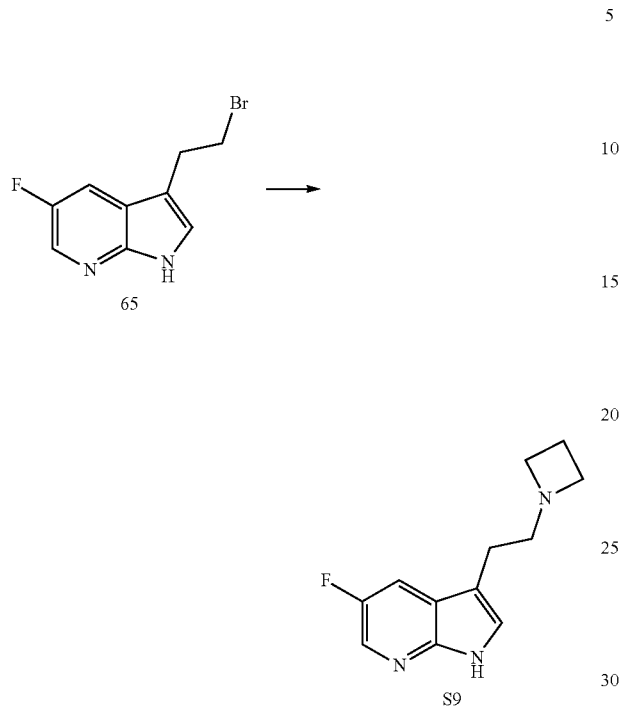

Step 1: 3-(2-(azetidin-1-yl)ethyl)-5-fluoro-1H-pyrrolo[2,3-b]pyridine (S9)

The title compound was synthesised according to General Procedure C utilising 3-(2-bromoethyl)-5-fluoro-1H-pyrrolo[2,3-b]pyridine (0.5 g, 2.06 mmol), azetidine (0.69 mL, 10.3 mmol), however MeCN was used as the solvent instead of DMF. Upon purification the title compound was a yellow solid (230 mg, 44%). $^1$H NMR (400 MHz, DMSO-$d_6$): δ 11.45 (s, 1H), 8.19-8.05 (m, 1H), 7.81 (dd, J=9.7, 2.8 Hz, 1H), 7.43-7.25 (m, 1H), 3.08 (t, J=6.9 Hz, 4H), 2.67-2.54 (m, 4H), 1.93 (p, J=6.9 Hz, 2H).

Step 2: 3-(2-(azetidin-1-yl)ethyl)-5-fluoro-1H-pyrrolo[2,3-b]pyridine Fumarate (S9-fumarate)

3-(2-(azetidin-1-yl)ethyl)-5-fluoro-1H-pyrrolo[2,3-b]pyridine (430 mg, 1.96 mmol) was formulated as the fumarate salt according to General Procedure F which was isolated as an off-white solid (540 mg, 82%). LCMS (Condition A): $t_R$ (2.999 min) m/z=220.10 [M+H]$^+$; $^1$H NMR (400 MHz, DMSO-$d_6$): δ 11.59 (s, 1H), 8.20-8.08 (m, 1H), 7.92 (dd, J=9.7, 2.7 Hz, 1H), 7.41 (d, J=2.4 Hz, 1H), 6.53 (s, 2H), 3.69 (t, J=7.7 Hz, 4H), 3.14-3.04 (m, 2H), 2.85-2.74 (m, 2H), 2.18 (p, J=7.7 Hz, 2H); $^{13}$C NMR (101 MHz, DMSO-$d_6$): δ 167.6, 154.8 (d, J=238.3 Hz), 145.5, 134.9, 130.6 (d, J=28.9 Hz), 126.4, 119.2 (d, J=6.8 Hz), 112.4 (d, J=20.6 Hz), 109.6, 55.8, 53.5, 21.2, 16.4; $^1$H qNMR Purity: 99.2% (ERETIC).

Example 11: Synthesis N-(2-(5-fluoro-1H-pyrrolo[2,3-b]pyridin-3-yl)ethyl)cyclobutanamine (S11)

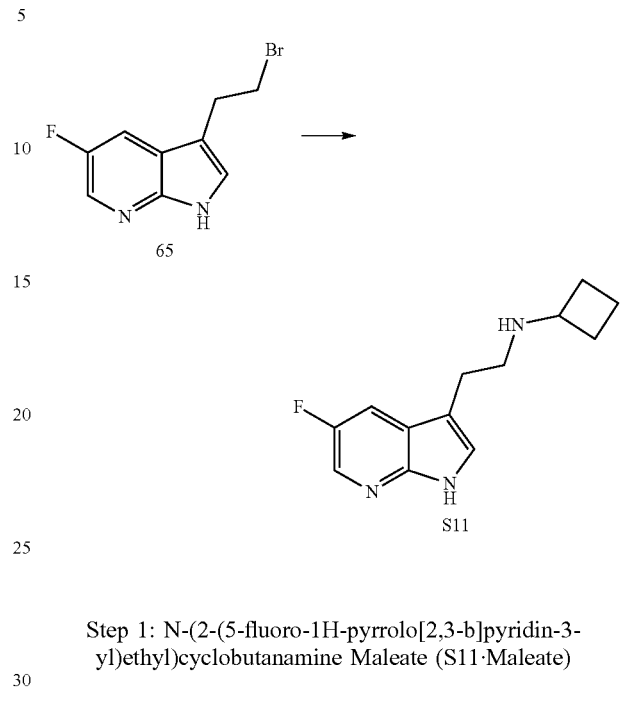

Step 1: N-(2-(5-fluoro-1H-pyrrolo[2,3-b]pyridin-3-yl)ethyl)cyclobutanamine Maleate (S11·Maleate)

The title compound was synthesised according to General Procedure D utilising 3-(2-bromoethyl)-5-fluoro-1H-pyrrolo[2,3-b]pyridine (0.2 g, 0.82 mmol), cyclobutylamine hydrochloride (115 mg, 1.07 mmol), NaI (123 mg, 0.82 mmol) and iPr$_2$NEt (0.43 mL, 2.46 mmol) which upon purification generated the title compound as a colourless oil which was then formulated as the maleate salt as per General Procedure F (75 mg, 25%) as a white crystalline solid. LCMS (Condition A): $t_R$ (3.337 min) m/z=234.15 [M+H]$^+$; $^1$H NMR (400 MHz, DMSO-$d_6$): δ 11.69 (s, 1H), 8.54 (s, 1H), 8.33-8.12 (m, 1H), 7.91 (dd, J=9.6, 2.8 Hz, 1H), 7.48 (d, J=2.5 Hz, 1H), 6.02 (s, 2H), 3.73 (p, J=8.0 Hz, 1H), 3.09 (t, J=7.4 Hz, 2H), 2.97 (t, J=7.5 Hz, 2H), 2.27-2.01 (m, 4H), 1.86-1.68 (m, 2H); $^{13}$C NMR (101 MHz, DMSO-$d_6$): δ 167.2, 154.8 (d, J=238.5 Hz), 145.5, 136.1, 130.8 (d, J=28.9 Hz), 126.9, 119.1 (d, J=6.8 Hz), 112.3 (d, J=20.7 Hz), 108.4 (d, J=4.4 Hz), 50.8, 44.3, 26.0, 21.8, 14.5.

Example 12: Synthesis N-(2-(5-fluoro-1H-pyrrolo[2,3-b]pyridin-3-yl)ethyl)-N-methylcyclobutanamine (S12)

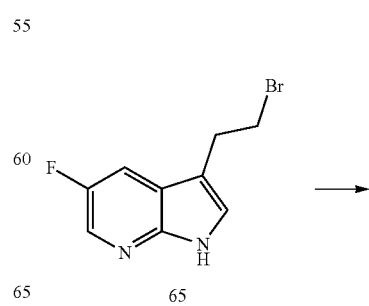

-continued

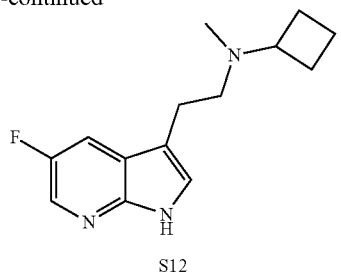

S12

Step 1: N-(2-(5-fluoro-1H-pyrrolo[2,3-b]pyridin-3-yl)ethyl)-N-methylcyclobutanamine Hydrochloride (S12·HCl)

The title compound was synthesised according to General Procedure D utilising 3-(2-bromoethyl)-5-fluoro-1H-pyrrolo[2,3-b]pyridine (0.2 g, 0.82 mmol), N-methylcyclobutanamine hydrochloride (130 mg, 1.07 mmol), NaI (123 mg, 0.82 mmol) and iPr$_2$NEt (0.43 mL, 2.46 mmol) which upon purification generated the title compound as a pale yellow oil which was then formulated as the hydrochloride salt as per General Procedure E (192 mg, 73%) as a colourless solid. LCMS (Condition A): t$_R$ (3.895 min) m/z=300.15 [M+H]$^+$; $^1$H NMR (400 MHz, DMSO-d$_6$): δ 11.71 (s, 1H), 11.07 (s, 1H), 8.31-8.13 (m, 1H), 8.03 (dd, J=9.6, 2.7 Hz, 1H), 7.51 (d, J=2.5 Hz, 1H), 3.78-3.60 (m, 1H), 3.30-2.96 (m, 4H), 2.69 (d, J=5.0 Hz, 3H), 2.46-2.27 (m, 2H), 2.27-2.07 (m, 2H), 1.82-1.53 (m, 2H); $^{13}$C NMR (101 MHz, DMSO-d$_6$): δ 154.8 (d, J=238.8 Hz), 145.3, 130.8 (d, J=29.0 Hz), 126.7, 119.2 (d, J=7.3 Hz), 112.6 (d, J=21.3 Hz), 108.7 (d, J=4.4 Hz), 58.5, 52.0, 35.6, 25.5, 25.1, 19.6, 13.0.

Example 15: Synthesis 4-(2-(5-fluoro-1H-pyrrolo[2,3-b]pyridin-3-yl)ethyl) morpholine (S15)

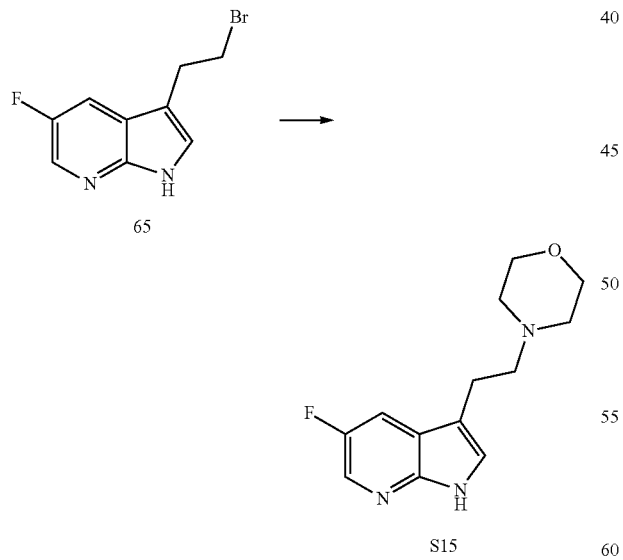

S15

Step 1: 4-(2-(5-fluoro-1H-pyrrolo[2,3-b]pyridin-3-yl)ethyl) morpholine (S15)

The title compound was synthesised according to General Procedure C utilising 3-(2-bromoethyl)-5-fluoro-1H-pyrrolo[2,3-b]pyridine (0.2 g, 0.82 mmol), morpholine (0.21 mL, 2.47 mmol) and NaI (123 mg, 0.82 mmol) which upon purification generated the title compound as a white solid (180 mg, 88%). LCMS (Condition A): t$_R$ (2.954 min) m/z=250.15 [M+H]$^+$; $^1$H NMR (400 MHz, DMSO-d$_6$): δ 11.48 (s, 1H), 8.20-8.10 (m, 1H), 7.84 (dd, J=9.7, 2.7 Hz, 1H), 7.39 (s, 1H), 3.64-3.53 (m, 4H), 2.87-2.77 (m, 2H), 2.60-2.52 (m, 2H), 2.44 (s, 4H); $^{13}$C NMR (101 MHz, DMSO-d$_6$): δ 154.7 (d, J=238.1 Hz), 145.4, 130.3 (d, J=28.9 Hz), 125.8, 119.6 (d, J=6.7 Hz), 112.3 (d, J=20.5 Hz), 112.0 (d, J=4.3 Hz), 66.3, 58.8, 53.3, 22.0.

Example 16: Synthesis of 3-(2-(2-methylazetidin-1-yl)ethyl)-5-fluoro-1H-pyrrolo[2,3-b]pyridine (S16)

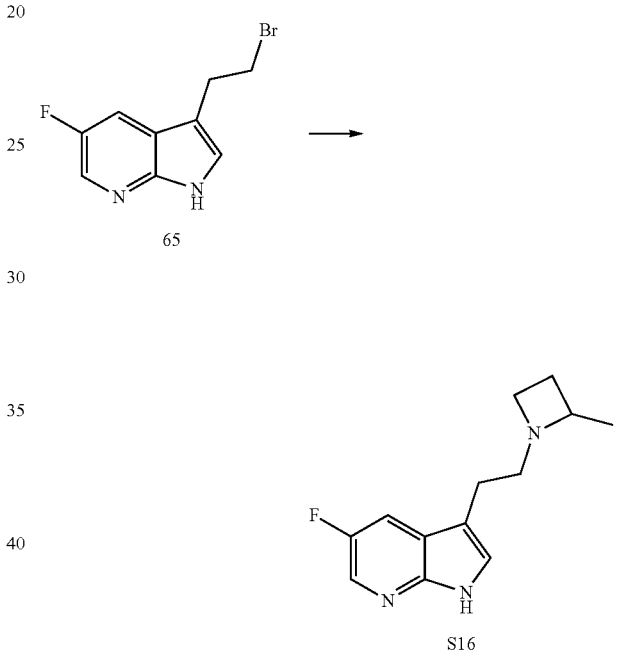

S16

Step 1: 3-(2-(2-methylazetidin-1-yl)ethyl)-5-fluoro-1H-pyrrolo[2,3-b]pyridine Hydrochloride (S16·HCl)

The title compound was synthesised according to General Procedure D utilising 3-(2-bromoethyl)-5-fluoro-1H-pyrrolo[2,3-b]pyridine (0.2 g, 0.82 mmol), 2-methylazetidine hydrochloride (115 mg, 1.07 mmol), NaI (123 mg, 0.82 mmol) and iPr$_2$NEt (0.43 mL, 2.46 mmol) which upon purification generated the title compound as a pale yellow oil which was then formulated as the hydrochloride salt as per General Procedure E (94 mg, 42%) as an off-white solid. LCMS (Condition A): t$_R$ (3.127 min) m/z=234.15 [M+H]$^+$; $^1$H NMR (400 MHz, DMSO-d$_6$): δ 11.70 (s, 1H), 10.88 (s, 1H), 8.20 (dd, J=2.5, 1.8 Hz, 1H), 8.04 (dd, J=9.6, 2.6 Hz, 1H), 7.48 (d, J=2.5 Hz, 1H), 4.54-4.33 (m, 1H), 3.95-3.68 (m, 2H), 3.55-3.20 (m, 2H), 3.07-2.88 (m, 2H), 2.45-2.29 (m, 1H), 2.23-2.03 (m, 1H), 1.51 (d, J=6.6 Hz, 3H).

Example 17: Synthesis N-(cyclopropylmethyl)-2-(5-fluoro-1H-pyrrolo[2,3-b]pyridin-3-yl)ethan-1-amine (S17)

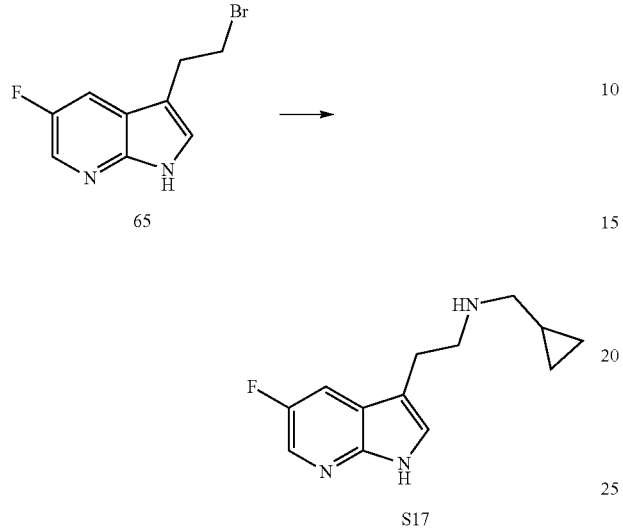

Step 1: N-(cyclopropylmethyl)-2-(5-fluoro-1H-pyrrolo[2,3-b]pyridin-3-yl)ethan-1-amine (S17)

The title compound was synthesised according to General Procedure C utilising 3-(2-bromoethyl)-5-fluoro-1H-pyrrolo[2,3-b]pyridine (0.2 g, 0.82 mmol), N-(cyclopropylmethyl)amine (0.21 mL, 2.47 mmol) and NaI (123 mg, 0.82 mmol) which upon purification generated the title compound as a light yellow oil (150 mg, 78%). $^1$H NMR (400 MHz, DMSO-$d_6$): δ 11.48 (s, 1H), 8.14 (dd, J=2.7, 1.7 Hz, 1H), 7.83 (dd, J=9.7, 2.7 Hz, 1H), 7.36 (s, 1H), 2.84-2.73 (m, 4H), 2.40 (d, J=6.6 Hz, 2H), 0.95-0.77 (m, 1H), 0.45-0.29 (m, 2H), 0.13--0.02 (m, 2H); $^{13}$C NMR (101 MHz, DMSO-$d_6$): δ 154.7 (d, J=238.1 Hz), 145.5, 130.3 (d, J=28.9 Hz), 125.8, 119.6 (d, J=6.6 Hz), 112.3 (d, J=18.2 Hz), 112.2 (d, J=2.1 Hz), 54.0, 49.8, 25.5, 11.2, 3.2.

Step 2: N-(cyclopropylmethyl)-2-(5-fluoro-1H-pyrrolo[2,3-b]pyridin-3-yl)ethan-1-amine Hydrochloride (S17·HCl)

N-(cyclopropylmethyl)-2-(5-fluoro-1H-pyrrolo[2,3-b]pyridin-3-yl)ethan-1-amine (140 mg, 0.60 mmol) was formulated as the hydrochloride salt as per General Procedure E (77 mg, 48%) as an off-white solid. LCMS (Condition A): $t_R$ (3.348 min) m/z=234.15 [M+H]$^+$; $^1$H NMR (400 MHz, DMSO-$d_6$): δ 11.73 (s, 1H), 9.21 (s, 2H), 8.24-8.16 (m, 1H), 8.04 (dd, J=9.6, 2.7 Hz, 1H), 7.49 (d, J=2.5 Hz, 1H), 3.22-2.96 (m, 4H), 2.84-2.74 (m, 2H), 1.21-0.99 (m, 1H), 0.66-0.47 (m, 2H), 0.46-0.29 (m, 2H). $^{13}$C NMR (101 MHz, DMSO-$d_6$): δ 154.7 (d, J=238.5 Hz), 145.2, 130.5 (d, J=29.2 Hz), 126.8, 119.4 (d, J=6.8 Hz), 112.8 (d, J=20.8 Hz), 109.0 (d, J=4.3 Hz), 51.1, 46.5, 41.9, 21.6, 7.0, 4.0. $^1$H qNMR Purity: 92.9% (ERETIC).

Example 25: Synthesis 3-(2-(2-azabicyclo[3.1.0]hexan-2-yl)ethyl)-5-fluoro-1H-pyrrolo[2,3-b]pyridine (S25)

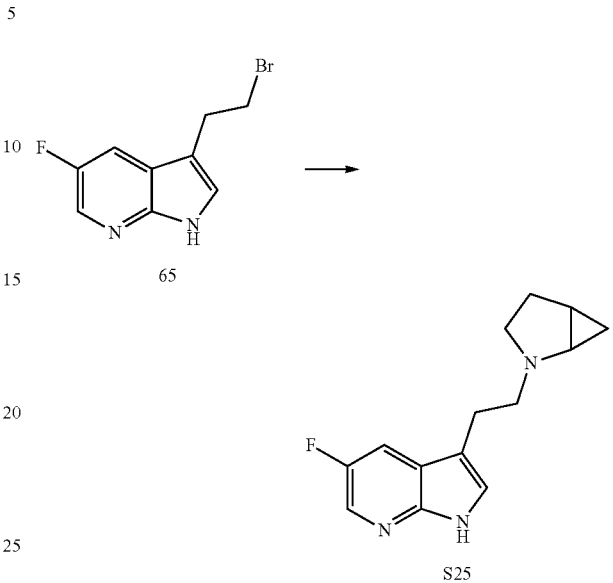

Step 1: 3-(2-(2-azabicyclo[3.1.0]hexan-2-yl)ethyl)-5-fluoro-1H-pyrrolo[2,3-b]pyridine (S25)

A solution of 3-(2-bromoethyl)-5-fluoro-1H-pyrrolo[2,3-b]pyridine (250 mg, 1.03 mmol) in acetonitrile (5 mL) was treated with 2-azabicyclo[3.1.0]hexane hydrochloride (246 mg, 2.06 mmol) and iPr$_2$NEt (0.9 mL, 5.14 mmol) and the reaction was stirred at RT for 48 h. The reaction was diluted with half saturated aq. NH$_4$Cl (100 mL) and then extracted with CH$_2$Cl$_2$ (25 mL×3) followed by iPrOH:CHCl$_3$ (1:3, 25 mL×3). The combined organic layer was concentrated and the residue was purified by flash chromatography (1% to 8% MeOH/NH$_3$ in CH$_2$Cl$_2$) to afford the title compound as an off-white solid (210 mg, 83%). $^1$H NMR (400 MHz, CDCl$_3$): δ 9.43 (s, 1H), 8.20-8.01 (m, 1H), 7.63 (ddd, J=8.9, 2.8, 0.6 Hz, 1H), 7.24 (d, J=2.3 Hz, 1H), 3.16-2.95 (m, 3H), 2.94-2.79 (m, 3H), 2.15-1.94 (m, 2H), 1.90 (dd, J=11.4, 6.9 Hz, 1H), 1.58-1.47 (m, 1H), 0.71 (ddd, J=6.6, 4.3, 2.7 Hz, 1H), 0.20 (dt, J=8.1, 5.9 Hz, 1H); $^{13}$C NMR (101 MHz, CDCl$_3$): δ 155.6 (d, J=241.4 Hz), 145.7, 131.6 (d, J=29.5 Hz), 124.5, 120.2 (d, J=6.3 Hz), 113.1, 113.0 (d, J=20.5 Hz), 55.1, 48.8, 40.7, 26.8, 25.1, 15.4, 2.0.

Step 2: 3-(2-(2-azabicyclo[3.1.0]hexan-2-yl)ethyl)-5-fluoro-1H-pyrrolo[2,3-b]pyridine Fumarate (S25·Fumarate)

3-(2-(2-azabicyclo[3.1.0]hexan-2-yl)ethyl)-5-fluoro-1H-pyrrolo[2,3-b]pyridine (185 mg, 0.75 mmol) was formulated as the fumarate salt as per General Procedure F (162 mg, 59%) as a white solid. LCMS (Condition A): $t_R$ (3.216 min) m/z=246.15 [M+H]$^+$; $^1$H NMR (400 MHz, DMSO-$d_6$): δ 11.55 (s, 1H), 8.16 (dd, J=2.6, 1.8 Hz, 1H), 7.88 (dd, J=9.7, 2.7 Hz, 1H), 7.43 (d, J=2.5 Hz, 1H), 6.57 (s, 2H), 3.23-3.07 (m, 1H), 3.02 (td, J=6.0, 2.6 Hz, 1H), 2.99-2.88 (m, 4H), 2.32-2.17 (m, 1H), 2.01-1.77 (m, 2H), 1.57-1.44 (m, 1H), 0.85 (ddd, J=6.5, 4.5, 2.6 Hz, 1H), 0.30 (dt, J=8.1, 6.1 Hz, 1H); $^{13}$C NMR (101 MHz, DMSO-$d_6$): δ 167.1, 154.7 (d, J=238.3 Hz), 145.5, 134.6, 130.5 (d, J=28.9 Hz), 126.1, 119.4 (d, J=6.8 Hz), 112.4 (d, J=20.5 Hz), 110.8 (d, J=4.4 Hz), 53.8, 47.8, 40.0, 25.8, 23.3, 14.9, 2.2; $^1$H qNMR Purity: 100% (ERETIC).

Example 30: Synthesis of 2-(5-fluoro-1H-pyrrolo[2,3-b]pyridin-3-yl)-N-(2-fluorobenzyl)ethan-1-amine (S30)

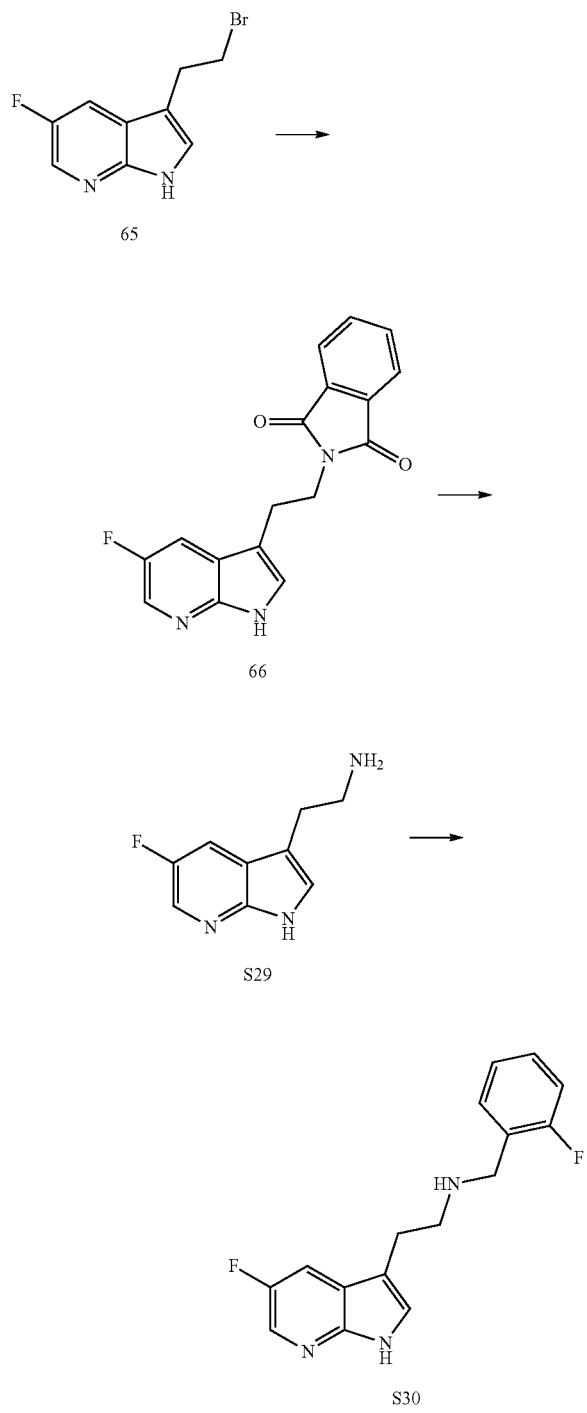

Step 1: 2-(2-(5-fluoro-1H-pyrrolo[2,3-b]pyridin-3-yl)ethyl)isoindoline-1,3-dione (66)

Potassium phthalimide (1.01 g, 4.95 mmol) was added to a solution of 3-(2-bromoethyl)-5-fluoro-1H-pyrrolo[2,3-b]pyridine (0.8 g, 3.29 mmol) in DMF (5 mL). This solution was heated to 80° C. for 4 h in a pressure tube. The reaction was then allowed to cool, and poured into H$_2$O (50 mL) before being extracted with EtOAc (3×20 mL). The combined organics were washed sequentially with H$_2$O (3×100 mL), brine (1×100 mL) before being dried (MgSO$_4$) and concentrated under reduced pressure. The resultant oil was purified by column chromatography (10% MeOH/CH$_2$Cl$_2$) to give the desired compound as a yellow solid.

Step 2: 2-(5-fluoro-1H-pyrrolo[2,3-b]pyridin-3-yl)ethan-1-amine (S29)

To a solution of 2-(2-(5-fluoro-1H-pyrrolo[2,3-b]pyridin-3-yl)ethyl)isoindoline-1,3-dione (800 mg, 2.59 mmol) in EtOH (10 mL) was added hydrazine monohydrate (1.25 mL, 25.9 mmol) and the resulting mixture was refluxed for 16 h. The cooled reaction mixture was filtered, and the filtrate concentrated in vacuo. The residue was purified by flash chromatography (5-20% MeOH in CH$_2$Cl$_2$) to give the title compound $^1$H NMR (400 MHz, DMSO-d$_6$): δ 8.19-8.06 (m, 1H), 7.83 (dd, J=9.7, 2.8 Hz, 1H), 7.35 (s, 1H), 3.17 (s, 2H), 2.85-2.76 (m, 2H), 2.76-2.64 (m, 2H).

Step 3: 2-(5-fluoro-1H-pyrrolo[2,3-b]pyridin-3-yl)-N-(2-fluorobenzyl)ethan-1-amine (S30)

To a stirred solution of 2-(5-fluoro-1H-pyrrolo[2,3-b]pyridin-3-yl)ethan-1-amine (160 mg, 0.89 mmol) in MeOH (10 mL) at 0° C. was added NaCNBH$_3$ (56 mg, 0.89 mmol) followed by a solution of 2-fluorobenzaldehyde (111 mg, 0.89 mmol) in MeOH (5.0 mL) dropwise and the mixture was stirred at RT for 16 h. The reaction was quenched by addition of 2 M NaOH (4.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-10% MeOH/NH$_3$ in CH$_2$Cl$_2$) to provide 2-(5-fluoro-1H-pyrrolo[2,3-b]pyridin-3-yl)-N-(2-fluorobenzyl)ethan-1-amine (127 mg, 50%) as a clear, yellow viscous oil. $^1$H NMR (400 MHz, CDCl$_3$): δ 9.05 (br s, 1H), 8.16-8.15 (m, 1H), 7.55 (ddd, J=8.9, 2.7, 0.7 Hz, 1H), 7.31-7.26 (m, 1H), 7.25-7.18 (m, 2H), 7.08 (td, J=7.5, 1.2 Hz, 1H), 7.00 (ddd, J=10.3, 8.1, 1.2 Hz, 1H), 3.88 (s, 2H), 3.00-2.88 (m, 4H).

Step 4: 2-(5-fluoro-1H-pyrrolo[2,3-b]pyridin-3-yl)-N-(2-fluorobenzyl)ethan-1-amine Fumarate (S30·Fumarate)

2-(5-fluoro-1H-pyrrolo[2,3-b]pyridin-3-yl)-N-(2-fluorobenzyl)ethan-1-amine (122 mg, 0.43 mmol) was formulated as the fumarate salt according to General Procedure F which was isolated as off-white crystals (92 mg, 51%). LCMS (Condition A): t$_R$ (3.770 min) m/z=288.10 [M+H]$^+$; $^1$H NMR (400 MHz, DMSO-d$_6$): δ 11.56 (br s, 1H), 8.16 (dd, J=2.7, 1.7 Hz, 1H), 7.52 (td, J=7.5, 1.8 Hz, 1H), 7.41 (d, J=2.5 Hz, 1H), 7.40-7.33 (m, 1H), 7.25-7.15 (m, 2H), 6.56 (s, 2H), 4.00 (s, 2H), 3.05-2.89 (m, 4H).

Example 31: Synthesis of 2-(5-fluoro-1H-pyrrolo[2,3-b]pyridin-3-yl)-N-(3-fluorobenzyl) ethan-1-amine (S31)

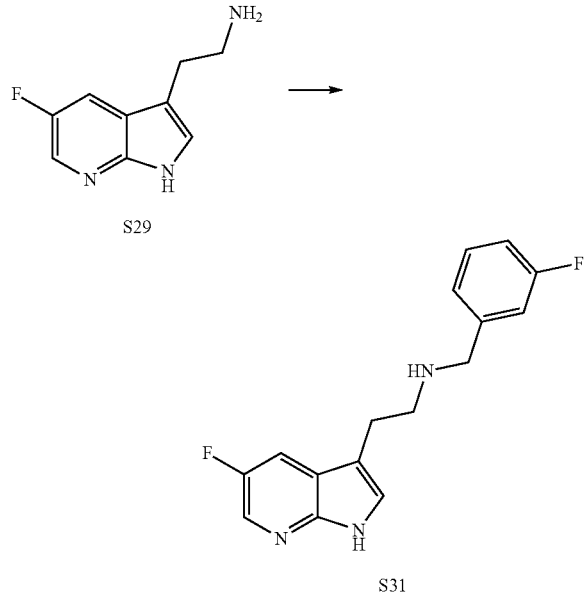

Example 32: Synthesis of 2-(5-fluoro-1H-pyrrolo[2,3-b]pyridin-3-yl)-N-(2-methoxybenzyl)ethan-1-amine (S32)

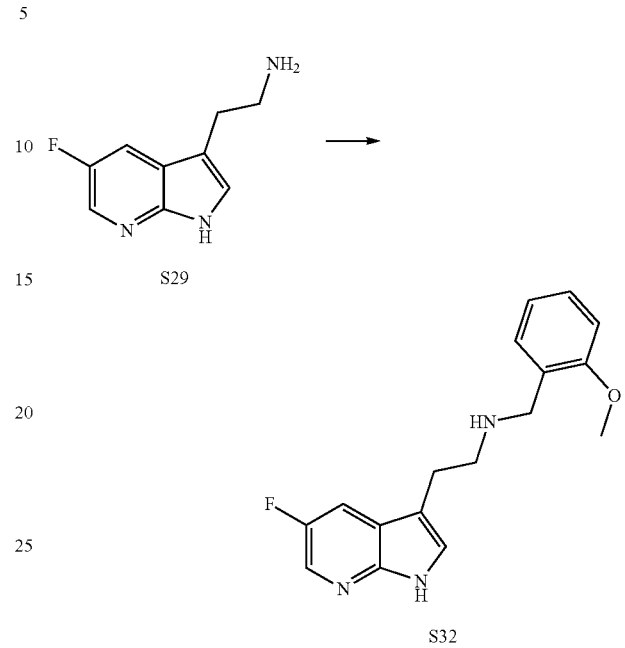

Step 1: 2-(5-fluoro-1H-pyrrolo[2,3-b]pyridin-3-yl)-N-(3-fluorobenzyl)ethan-1-amine (S31)

To a stirred solution of 2-(5-fluoro-1H-pyrrolo[2,3-b]pyridin-3-yl)ethan-1-amine (160 mg, 0.89 mmol) in MeOH (10 mL) at 0° C. was added NaCNBH$_3$ (56 mg, 0.89 mmol) followed by a solution of 3-fluorobenzaldehyde (111 mg, 0.89 mmol) in MeOH (5.0 mL) dropwise and the mixture was stirred at RT for 16 h. The reaction was quenched by addition of 2 M NaOH (4.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-10% MeOH/NH$_3$ in CH$_2$Cl$_2$) to provide 2-(5-fluoro-1H-pyrrolo[2,3-b]pyridin-3-yl)-N-(3-fluorobenzyl)ethan-1-amine (61 mg, 24%) as a clear, yellow viscous oil.

$^1$H NMR (400 MHz, CDCl$_3$): δ 8.99 (br s, 1H), 8.20-8.15 (m, 1H), 7.58 (ddd, J=9.0, 2.7, 0.7 Hz, 1H), 7.28-7.22 (m, 2H), 7.21 (d, J=2.4 Hz, 1H), 7.07-6.97 (m, 2H), 6.96-6.89 (m, 1H), 3.81 (s, 2H), 2.98-2.89 (m, 4H).

Step 2: 2-(5-fluoro-1H-pyrrolo[2,3-b]pyridin-3-yl)-N-(3-fluorobenzyl)ethan-1-amine Fumarate (S31-fumarate)

2-(5-fluoro-1H-pyrrolo[2,3-b]pyridin-3-yl)-N-(3-fluorobenzyl)ethan-1-amine (56 mg, 0.20 mmol) was formulated as the fumarate salt according to General Procedure F which was isolated as off-white crystals (55 mg, 70%). LCMS (Condition A): t$_R$ (3.856 min) m/z=288.10 [M+H]$^+$; $^1$H NMR (400 MHz, DMSO-d$_6$): δ 11.56 (br s, 1H), 8.16 (dd, J=2.8, 1.7 Hz, 1H), 7.84 (dd, J=9.6, 2.8 Hz, 1H), 7.44-7.34 (m, 2H), 7.30-7.21 (m, 2H), 7.17-7.08 (m, 1H), 6.53 (s, 2H), 3.97 (s, 3H), 3.01-2.88 (m, 4H).

Step 1: 2-(5-fluoro-1H-pyrrolo[2,3-b]pyridin-3-yl)-N-(2-methoxybenzyl)ethan-1-amine (S32)

To a stirred solution of 2-(5-fluoro-1H-pyrrolo[2,3-b]pyridin-3-yl)ethan-1-amine (160 mg, 0.89 mmol) in MeOH (10 mL) at 0° C. was added NaCNBH$_3$ (56 mg, 0.89 mmol) followed by a solution of 2-methoxybenzaldehyde (122 mg, 0.89 mmol) in MeOH (5.0 mL) dropwise and the mixture was stirred at RT for 16 h. The reaction was quenched by addition of 2 M NaOH (4.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-10% MeOH/NH$_3$ in CH$_2$Cl$_2$) to provide 2-(5-fluoro-1H-pyrrolo[2,3-b]pyridin-3-yl)-N-(2-methoxybenzyl)ethan-1-amine (134 mg, 50%) as a yellow viscous oil. $^1$H NMR (400 MHz, CDCl$_3$): δ 9.07 (br s, 1H), 8.13-8.08 (m, 1H), 7.49 (dd, J=9.0, 2.7 Hz, 1H), 7.26-7.17 (m, 3H), 6.90 (td, J=7.4, 1.1 Hz, 1H), 6.77 (dd, J=8.1, 1.1 Hz, 1H), 3.86 (s, 2H), 3.63 (s, 3H), 2.95 (s, 4H).

Step 2: 2-(5-fluoro-1H-pyrrolo[2,3-b]pyridin-3-yl)-N-(2-methoxybenzyl)ethan-1-amine Fumarate (S32·Fumarate)

2-(5-fluoro-1H-pyrrolo[2,3-b]pyridin-3-yl)-N-(2-methoxybenzyl)ethan-1-amine (129 mg, 0.43 mmol) was formulated as the fumarate salt according to General Procedure F which was isolated as white crystals (107 mg, 60%). LCMS (Condition A): t$_R$ (3.907 min) m/z=300.15 [M+H]$^+$; $^1$H NMR (400 MHz, DMSO-d$_6$): δ 11.63-11.58 (m, 1H), 8.17 (t, J=2.2 Hz, 1H), 7.85 (dd, J=9.6, 2.8 Hz, 1H), 7.42 (d, J=2.4 Hz, 1H), 7.37 (dd, J=7.5, 1.7 Hz, 1H), 7.32

(td, J=7.8, 1.7 Hz, 1H), 7.00 (d, J=8.2 Hz, 1H), 6.94 (td, J=7.4, 1.0 Hz, 1H), 6.51 (s, 2H), 3.98 (s, 2H), 3.75 (s, 3H), 3.07-2.92 (m, 4H).

Example 33: Synthesis of 2-(5-fluoro-1H-pyrrolo[2,3-b]pyridin-3-yl)-N-(3-methoxybenzyl)ethan-1-amine (S33)

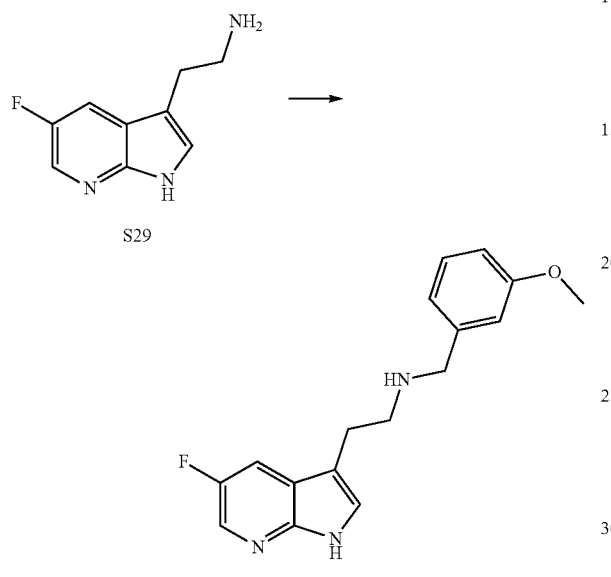

Step 1: 2-(5-fluoro-1H-pyrrolo[2,3-b]pyridin-3-yl)-N-(3-methoxybenzyl)ethan-1-amine (S33)

To a stirred solution of 2-(5-fluoro-1H-pyrrolo[2,3-b]pyridin-3-yl)ethan-1-amine (128 mg, 0.71 mmol) in MeOH (10 mL) at 0° C. was added NaCNBH$_3$ (45 mg, 0.71 mmol) followed by a solution of 3-methoxybenzaldehyde (97 mg, 0.71 mmol) in MeOH (5.0 mL) dropwise and the mixture was stirred for two hours at room temperature. The reaction was quenched by addition of 2 M NaOH (4.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-10% MeOH/NH$_3$ in CH$_2$Cl$_2$) to provide 2-(5-fluoro-1H-pyrrolo[2,3-b]pyridin-3-yl)-N-(3-methoxybenzyl)ethan-1-amine (46 mg, 21%) as a clear viscous oil. $^1$H NMR (400 MHz, CDCl$_3$): δ 9.01 (br s, 1H), 8.10 (t, J=2.2 Hz, 1H), 7.55 (dd, J=8.9, 2.7 Hz, 1H), 7.25-7.18 (m, 2H), 6.89-6.85 (m, 2H), 6.82-6.77 (m, 1H), 3.84 (s, 2H), 3.78 (s, 3H), 3.03-2.91 (m, 4H).

Step 2: 2-(5-fluoro-1H-pyrrolo[2,3-b]pyridin-3-yl)-N-(3-methoxybenzyl)ethan-1-amine Maleate (S33·Maleate)

2-(5-fluoro-1H-pyrrolo[2,3-b]pyridin-3-yl)-N-(3-methoxybenzyl)ethan-1-amine (46 mg, 0.15 mmol) was formulated as the maleate salt according to General Procedure F which was isolated as white crystals (37 mg, 58%). LCMS (Condition A): $t_R$ (3.895 min) m/z=300.15 [M+H]$^+$;

$^1$H NMR (400 MHz, DMSO-d$_6$): δ 11.68 (s, 1H), 8.77 (br s, 1H), 8.20 (dd, J=2.8, 1.7 Hz, 1H), 7.87 (dd, J=9.6, 2.7 Hz, 1H), 7.48 (d, J=2.5 Hz, 1H), 7.41-7.32 (m, 1H), 7.10-7.07 (m, 1H), 7.06-7.03 (m, 1H), 7.00 (ddd, J=8.4, 2.6, 0.9 Hz, 1H), 6.02 (s, 2H), 4.17 (s, 2H), 3.77 (s, 3H), 3.25-3.17 (m, 2H), 3.08-2.99 (m, 2H).

Example 34: Synthesis of N-benzyl-2-(5-fluoro-1H-pyrrolo[2,3-b]pyridin-3-yl)ethan-1-amine (S34)

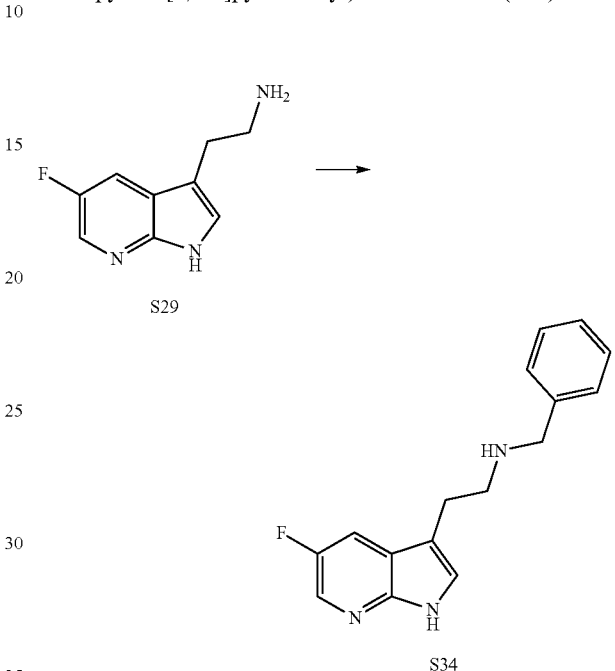

Step 1: N-benzyl-2-(5-fluoro-1H-pyrrolo[2,3-b]pyridin-3-yl)ethan-1-amine (S34)

To a stirred solution of 2-(5-fluoro-1H-pyrrolo[2,3-b]pyridin-3-yl)ethan-1-amine (128 mg, 0.71 mmol) in MeOH (10 mL) at 0° C. was added NaCNBH$_3$ (45 mg, 0.71 mmol) followed by a solution of benzaldehyde (76 mg, 0.71 mmol) in MeOH (5.0 mL) dropwise and the mixture was stirred for two hours at room temperature. The reaction was quenched by addition of 2 M NaOH (4.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-10% MeOH/NH$_3$ in CH$_2$Cl$_2$) to provide N-benzyl-2-(5-fluoro-1H-pyrrolo[2,3-b]pyridin-3-yl)ethan-1-amine (72 mg, 37%) as a slightly yellow viscous oil which solidified overnight. $^1$H NMR (400 MHz, CDCl$_3$): δ 9.01 (br s, 1H), 8.16 (t, J=2.2 Hz, 1H), 7.57 (dd, J=9.0, 2.7 Hz, 1H), 7.33-7.22 (m, 5H), 7.19 (d, J=2.3 Hz, 1H), 3.83 (s, 2H), 3.01-2.88 (m, 4H).

Step 2: N-benzyl-2-(5-fluoro-1H-pyrrolo[2,3-b]pyridin-3-yl)ethan-1-amine Fumarate (S34·Fumarate)

N-benzyl-2-(5-fluoro-1H-pyrrolo[2,3-b]pyridin-3-yl)ethan-1-amine (68 mg, 0.25 mmol) was formulated as the fumarate salt according to General Procedure F which was isolated as white crystals (66 mg, 68%). LCMS (Condition A): $t_R$ (3.776 min) m/z=270.10 [M+H]$^+$; $^1$H NMR (400

MHz, DMSO-d$_6$): δ 11.58 (s, 1H), 8.16 (dd, J=2.8, 1.7 Hz, 1H), 7.45-7.40 (m, 3H), 7.39-7.29 (m, 3H), 6.52 (s, 2H), 3.99 (s, 2H), 3.05-2.91 (m, 4H).

Example 41: Synthesis of N-methyl-N-(2-(5-(trifluoromethoxy)-1H-pyrrolo[2,3-b]pyridin-3-yl)ethyl)cyclopropanamine (S41)

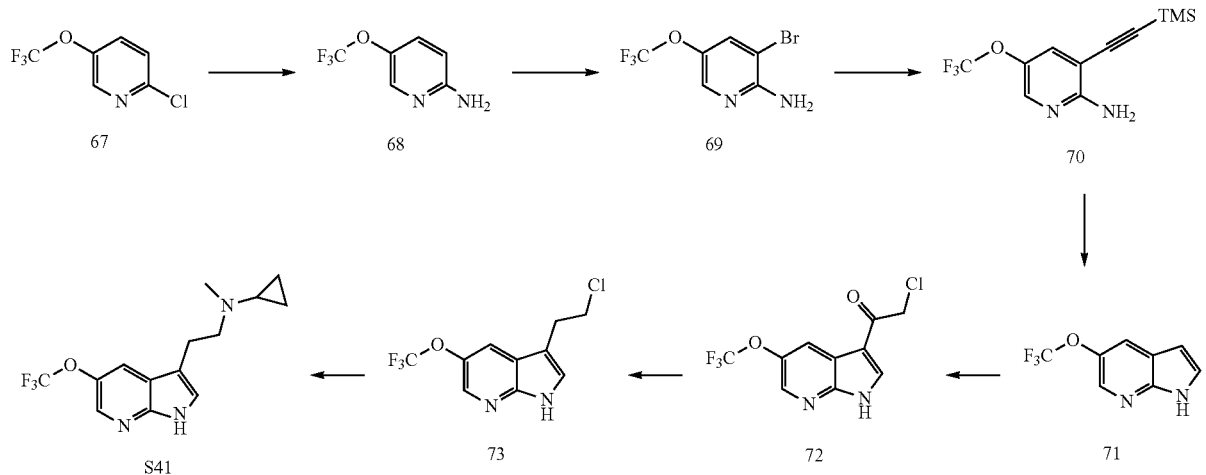

Step 1: 5-(trifluoromethoxy)pyridin-2-amine (68)

To a solution of 2-chloro-5-(trifluoromethoxy)pyridine (10.0 g, 50.6 mmol), diphenylmethanimine (11.0 g, 60.8 mmol, 10.2 mL) and t-BuOK (11.4 g, 101 mmol) in toluene (70 mL) was added DPEPhos (1.09 g, 2.02 mmol), Pd$_2$(dba)$_3$ (927 mg, 1.01 mmol, 0.02 eq) and the mixture was stirred at 80° C. for 2 hrs. The mixture was filtered and the filter cake was washed with EtOAc (20 mL). The filtrate was treated with 3 M aq. HCl (800 mL) and stirred at 50° C. for 1 h. The reaction mixture was cooled to RT and the phases were separated. The aqueous phase was adjusted pH to 9 with aq. NaOH and extracted with EtOAc (2×10 mL). The combined organics were dried over anhydrous Na$_2$SO$_4$ and concentrated under reduced pressure to provide crude 5-(trifluoromethoxy)pyridin-2-amine (10.0 g) as a brown oil.

Step 2: 3-bromo-5-(trifluoromethoxy)pyridin-2-amine (69)

To a solution of 5-(trifluoromethoxy)pyridin-2-amine (9.00 g, 50.5 mmol) in CH$_2$Cl$_2$ (63 mL) was added NBS (8.99 g, 50.5 mmol) and the mixture was stirred at 25° C. for 10 h. The reaction mixture was concentrated under reduced pressure and the residue was purified by column chromatography (petroleum ether/EtOAc-100:1 to 0:1) to provide 3-bromo-5-(trifluoromethoxy)pyridin-2-amine (1.20 g, 9%) as yellow solid. $^1$H NMR (400 MHz CDCl$_3$): δ 8.00 (d, J=2.0 Hz, 1H), 7.62 (d, J=1.7 Hz, 1H), 5.27-4.84 (m, 2H).

Step 3: 5-(trifluoromethoxy)-3-((trimethylsilyl)ethynyl)pyridin-2-amine (70)

To a solution of 3-bromo-5-(trifluoromethoxy)pyridin-2-amine (1.00 g, 3.89 mmol), ethynyltrimethylsilane (1.15 g, 11.7 mmol, 1.62 mL) and Et$_3$N (1.18 g, 11.7 mmol, 1.62 mL) in DMF (5.0 mL) was added CuI (74.1 mg, 0.39 mmol), Pd(PPh$_3$)$_2$Cl$_2$ (137 mg, 0.20 mmol) and the mixture was stirred at 105° C. for 6 h under nitrogen atmosphere. The reaction mixture was filtered and the filter cake was washed with EtOAc (20 mL). The filtrate was concentrated under reduced pressure and the residue was purified by column chromatography (petroleum ether/EtOAc-100:1 to 0:1) to provide crude 5-(trifluoromethoxy)-3-((trimethylsilyl)ethynyl)pyridin-2-amine (1.00 g) as a brown solid. $^1$H NMR (400 MHz CDCl$_3$): δ 7.96 (d, J=2.4 Hz, 1H), 7.46-7.41 (m, 1H), 5.13 (br s, 2H), 0.31-0.26 (m, 9H).

Step 4: 5-(trifluoromethoxy)-1H-pyrrolo[2,3-b]pyridine (71)

To a solution of 5-(trifluoromethoxy)-3-((trimethylsilyl)ethynyl)pyridin-2-amine (1.00 g, 3.65 mmol) in NMP (7.0 mL) was added t-BuOK (2.05 g, 18.2 mmol) and the mixture was stirred at 130° C. for 4 h. The reaction mixture was poured into H$_2$O (20 mL) and then extracted with EtOAc (3×10 mL). The combined organics were washed with brine (10 mL), dried over anhydrous Na$_2$SO$_4$ and concentrated under reduced pressure. The residue was purified by column chromatography (petroleum ether/EtOAc—80:1 to 0:1) to provide 5-(trifluoromethoxy)-1H-pyrrolo[2,3-b]pyridine (500 mg, 68%) as a light yellow solid. $^1$H NMR: (400 MHz CDCl$_3$): δ 10.1-9.67 (m, 1H), 8.29 (d, J=1.9 Hz, 1H), 7.86 (s, 1H), 7.52-7.40 (m, 1H), 6.57 (dd, J=1.90, 3.5 Hz, 1H).

Step 5: 2-chloro-1-(5-(trifluoromethoxy)-1H-pyrrolo[2,3-b]pyridin-3-yl)ethan-1-one (72)

To a solution of 5-(trifluoromethoxy)-1H-pyrrolo[2,3-b]pyridine (300 mg, 1.48 mmol) in CH$_2$Cl$_2$ (10 mL) was added AlCl$_3$ (989 mg, 7.42 mmol, 406 μL) at 0° C. under nitrogen atmosphere and the mixture was stirred at 0° C. for 30 minutes before adding 2-chloroacetyl chloride (503 mg, 4.45 mmol, 355 μL) dropwise. The reaction mixture was stirred at 50° C. for 10 h and then quenched with H$_2$O (50 mL). The mixture was extracted with EtOAc (2×20 mL) and the combined organics were dried over anhydrous Na$_2$SO$_4$ and concentrated under reduced pressure to provide 2-chloro-1-(5-(trifluoromethoxy)-1H-pyrrolo[2,3-b]pyridin-3-yl)ethan-1-one (300 mg, 73% yield) as a light yellow solid. $^1$H NMR (400 MHz CDCl$_3$): δ 11.2-10.8 (m, 1H), 8.63 (d, J=1.4 Hz, 1H), 8.38 (d, J=2.3 Hz, 1H), 8.24 (s, 1H), 4.57-4.51 (m, 2H).

Step 6: 3-(2-chloroethyl)-5-(trifluoromethoxy)-1H-pyrrolo[2,3-b]pyridine (73)

To a solution of 2-chloro-1-(5-(trifluoromethoxy)-1H-pyrrolo[2,3-b]pyridin-3-yl)ethan-1-one (300 mg, 1.08 mmol) in TFA (3.00 mL) was added Et$_3$SiH (751 mg, 6.46 mmol, 1.03 mL) and the reaction mixture was stirred at 70° C. for 10 h. The reaction mixture was quenched with H$_2$O (5 mL), adjusted pH to 8 with aq. NaHCO$_3$ and extracted with EtOAc (3×30 mL). The combined organics were washed with brine (20 mL), dried over Na$_2$SO$_4$ and concentrated under reduced pressure. The residue was purified by column chromatography (petroleum ether/EtOAc-80:1 to 0:1) to provide 3-(2-chloroethyl)-5-(trifluoromethoxy)-1H-pyrrolo[2,3-b]pyridine (200 mg, 70%) as a light yellow solid.

Step 7: N-methyl-N-(2-(5-(trifluoromethoxy)-1H-pyrrolo[2,3-b]pyridin-3-yl)ethyl)cyclopropanamine (S41)

To a solution of 3-(2-chloroethyl)-5-(trifluoromethoxy)-1H-pyrrolo[2,3-b]pyridine (100 mg, 0.38 mmol) and N-methylcyclopropanamine (54 mg, 0.76 mmol) in DMF (2.00 mL) was added K$_2$CO$_3$ (104 mg, 0.76 mmol) and the mixture was stirred at 50° C. for 10 h. The reaction mixture was quenched with H$_2$O (30 mL) and extracted with EtOAc (2×10 mL). The combined organics were washed with brine (10 mL), dried over Na$_2$SO$_4$ and concentrated under reduced pressure. The residue was purified by prep-HPLC (column: Waters Xbridge Prep OBD C18 150×40 mm, 10 um; mobile phase: [H$_2$O (10 mM NH$_4$HCO$_3$)-MeCN]; gradient: 20%-60% B over 8.0 min) to provide N-methyl-N-(2-(5-(trifluoromethoxy)-1H-pyrrolo[2,3-b]pyridin-3-yl)ethyl)cyclopropanamine (20 mg, 2%) as a yellow solid. $^1$H NMR (400 MHz CDCl$_3$): δ 9.09 (br s, 1H), 8.25 (d, J=1.9 Hz, 1H), 7.80 (s, 1H), 7.25 (d, J=1.7 Hz, 1H), 3.05-2.83 (m, 4H), 2.49 (s, 3H), 1.76 (br d, J=1.1 Hz, 1H), 0.54 (br d, J=6.2 Hz, 4H); $^{19}$F NMR (376 MHz CDCl$_3$): δ −58.6; LCMS (Condition B): t$_R$ (1.906 min) m/z=300 [M+H]$^+$.

Example 42: Synthesis of N-(2-(5-chloro-1H-pyrrolo[2,3-b]pyridin-3-yl)ethyl)-N-methylcyclopropanamine (S42)

Step 1: 2-chloro-1-(5-chloro-1H-pyrrolo[2,3-b]pyridin-3-yl)ethan-1-one (75)

To a solution of 5-chloro-1H-pyrrolo[2,3-b]pyridine (5.00 g, 32.7 mmol) in CH$_2$Cl$_2$ (35 mL) was added AlCl$_3$ (13.1 g, 98.3 mmol, 5.37 mL) at 0° C. under nitrogen atmosphere and the mixture was stirred at 0° C. for 30 min. Chloroacetyl chloride (7.40 g, 65.5 mmol, 5.22 mL) was added dropwise into the mixture which was then stirred at 25° C. for 10 h. The reaction mixture was quenched with H$_2$O (50 mL), filtered and the filter cake was washed with H$_2$O (2×10 mL), collected and dried under vacuum to provide 2-chloro-1-(5-chloro-1H-pyrrolo[2,3-b]pyridin-3-yl)ethan-1-one (7.00 g, 93%) as a light yellow solid. $^1$H NMR (400 MHz, DMSO-d$_6$): δ 12.91 (br s, 1H), 8.67 (d, J=3.3 Hz, 1H), 8.43 (d, J=2.3 Hz, 1H), 8.38 (d, J=2.4 Hz, 1H), 4.94 (s, 2H).

Step 2: 5-chloro-3-(2-chloroethyl)-1H-pyrrolo[2,3-b]pyridine (76)

To a solution of 2-chloro-1-(5-chloro-1H-pyrrolo[2,3-b]pyridin-3-yl)ethan-1-one (2.00 g, 8.73 mmol) in TFA (10.0 mL) was added Et$_3$SiH (10.1 g, 87.3 mmol, 13.9 mL) at 20° C. under nitrogen atmosphere and the mixture was stirred at 70° C. for 10 h. The reaction mixture was concentrated under reduced pressure, and the residue was adjusted pH to 8-9 with aq. Na$_2$CO$_3$. The mixture was filtered and the filter cake was collected and dried under vacuum to provide 5-chloro-3-(2-chloroethyl)-1H-pyrrolo[2,3-b]pyridine (1.20 g, 64%) as a light yellow solid. $^1$H NMR (400 MHz, DMSO-d$_6$): δ 11.8-11.6 (m, 1H), 8.23-8.09 (m, 2H), 7.53-7.40 (m, 1H), 3.86 (t, J=7.1 Hz, 2H), 3.13 (t, J=7.10 Hz, 2H).

Step 3: N-(2-(5-chloro-1H-pyrrolo[2,3-b]pyridin-3-yl)ethyl)-N-methylcyclopropanamine (S42)

To a solution of 5-chloro-3-(2-chloroethyl)-1H-pyrrolo[2,3-b]pyridine (200 mg, 0.93 mmol) and N-methylcyclopropanamine (132 mg, 1.86 mmol) in DMF (5.00 mL) was added K$_2$CO$_3$ (257 mg, 1.86 mmol) at 20° C. under nitrogen atmosphere and the mixture was stirred at 50° C. for 10 h. The reaction mixture was quenched with H$_2$O (30 mL), extracted with EtOAc (2×10 mL). The combined organics were washed with brine (10 mL), dried over Na$_2$SO$_4$ and concentrated under reduced pressure. The residue was purified by prep-HPLC (column: Waters Xbridge Prep OBD C18 150×40 mm, 10 um; mobile phase: [H$_2$O (10 mM NH$_4$HCO$_3$)-MeCN]; gradient: 30%-65% B over 8.0 min) to provide N-(2-(5-chloro-1H-pyrrolo[2,3-b]pyridin-3-yl)ethyl)-N-methylcyclopropanamine (20 mg, 9%) as a yellow solid. LCMS (Condition B): t$_R$ (1.71 min) m/z=250.0, 252.0 [M+H]$^+$, [M+2+H]$^+$; $^1$H NMR (400 MHz, CDCl$_3$): δ 9.55 (br s, 1H), 8.25 (d, J=2.0 Hz, 1H), 7.89 (d, J=2 Hz, 1H), 7.19 (s, 1H), 2.93-2.85 (m, 4H), 2.46 (s, 3H), 1.74-1.70 (m, 1H), 0.54-0.44 (m, 4H).

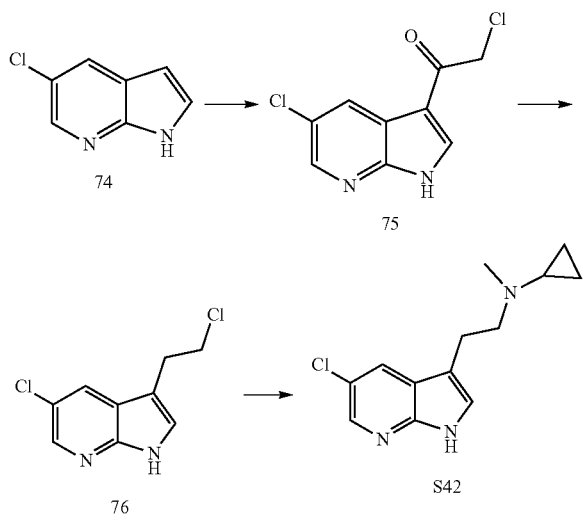

Example 43: Synthesis of N-(cyclopropylmethyl)-2-(5-fluoro-1H-pyrrolo[2,3-b]pyridin-3-yl)-N-methyl-ethan-1-amine (S43)

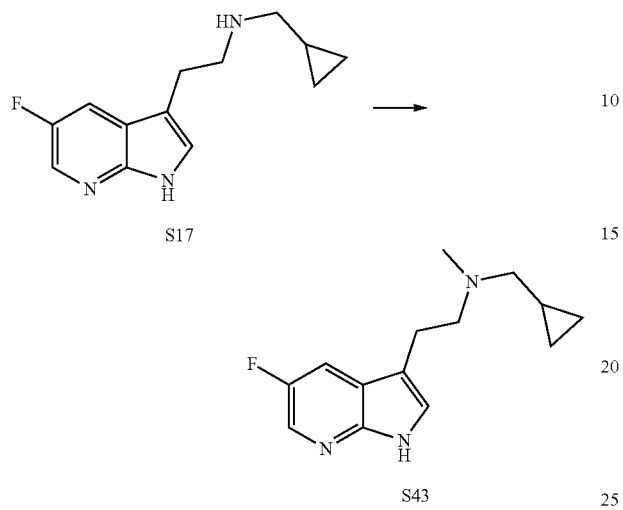

A solution of N-(cyclopropylmethyl)-2-(5-fluoro-1H-pyrrolo[2,3-b]pyridin-3-yl)ethan-1-amine (142 mg, 0.69 mmol) in CH$_2$Cl$_2$ (3 mL) was treated with NaBH(OAc)$_3$ (194 mg, 0.91 mmol) and 40% w/w aq. formaldehyde (69 μL, 0.91 mmol) and the mixture was stirred at RT for 16 h. The reaction mixture was quenched by addition of 1 M aq. NaOH (10 mL) and then extracted with CH$_2$Cl$_2$ (3×10 mL). The combined organics were washed with brine (10 mL), dried over anhydrous Na$_2$SO$_4$ and concentrated under reduced pressure. The residue was dissolved in ethylenediamine (1.5 mL) and stirred at room temperature for 4 h and then concentrated under a stream of nitrogen gas. The residue was diluted with water (5 mL) and extracted with CH$_2$Cl$_2$ (3×10 mL). The combined organics were washed with brine (10 mL), dried over anhydrous Na$_2$SO$_4$ and concentrated under reduced pressure. The crude material was purified by flash chromatography (0-10% MeOH/NH$_3$ in CH$_2$Cl$_2$) to provide N-(cyclopropylmethyl)-2-(5-fluoro-1H-pyrrolo[2,3-b]pyridin-3-yl)-N-methylethan-1-amine (70 mg, 46%) as a colourless oil. $^1$H NMR (400 MHz, CDCl$_3$): δ 9.20 (s, 1H), 8.17 (ddd, J=2.5, 1.8, 0.5 Hz, 1H), 7.61 (ddd, J=9.0, 2.6, 0.7 Hz, 1H), 7.21 (d, J=2.4 Hz, 1H), 2.95-2.86 (m, 2H), 2.80-2.71 (m, 2H), 2.44 (s, 3H), 2.37 (d, J=6.6 Hz, 2H), 0.92 (ttt, J=8.0, 6.6, 4.9 Hz, 1H), 0.61-0.48 (m, 2H), 0.19-0.10 (m, 2H).

Example 44: Synthesis of N-(2-(5-methoxy-1H-pyrrolo[2,3-b]pyridin-3-yl)ethyl)-N-methylcyclopropanamine Fumarate (S44·Fumarate)

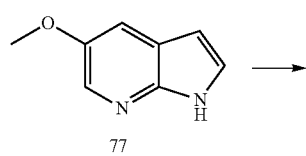

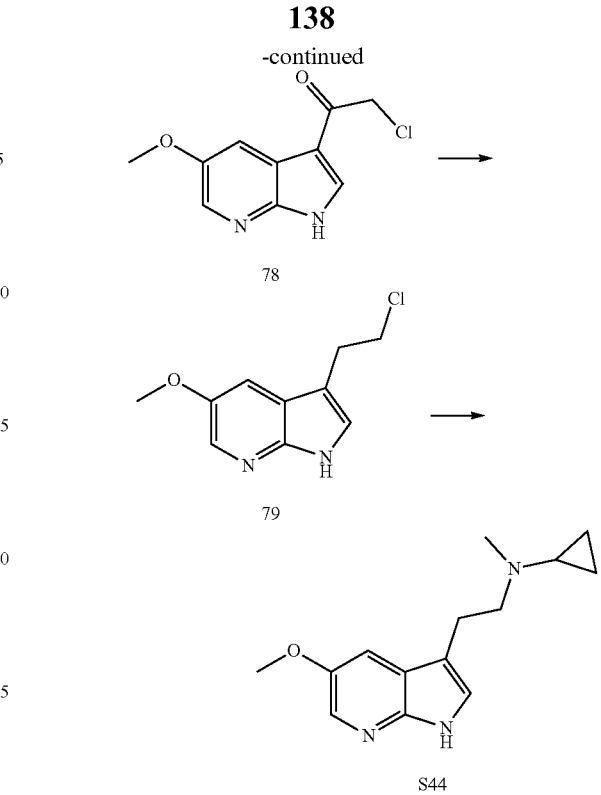

Step 1: 2-chloro-1-(5-methoxy-1H-pyrrolo[2,3-b]pyridin-3-yl)ethan-1-one (78)

An ice-cold solution of 5-methoxy-1H-pyrrolo[2,3-b]pyridine (500 mg, 3.37 mmol) in CH$_2$Cl$_2$ (10 mL) was treated with AlCl$_3$ (2.25 g, 16.9 mmol), followed by 2-chloroacetyl chloride (1.34 mL, 16.9 mmol), diluted 1:1 by volume with CH$_2$Cl$_2$, under nitrogen. The reaction was stirred cold and TLC 15 mins after addition of the chloride indicated reaction was complete. The reaction was added dropwise to ice-water under vigorous stirring and the residue in the flask washed in with minimal CH$_2$Cl$_2$. The mixture was then adjusted to pH 8-9 with saturated aq. NaHCO$_3$ slowly whilst stirring vigorously. The mixture was then filtered through celite and the filter cake was washed with EtOAc. The filtrate layers were separated, the organic layer washed with water (2×20 mL) and then brine (50 mL), then dried over anhydrous Na$_2$SO$_4$, filtered, and the filtrate concentrated in vacuo. The slightly yellow solid was triturated with refluxing CH$_2$Cl$_2$ and then filtered when cooled to afford the title compound as a white solid (740 mg, 98%). $^1$H NMR (400 MHz, DMSO-d$_6$): δ 12.56 (s, 1H), 8.52 (d, J=3.2 Hz, 1H), 8.10 (d, J=2.8 Hz, 1H), 7.97 (d, J=2.8 Hz, 1H), 4.89 (s, 2H), 3.86 (s, 3H); $^{13}$C NMR (101 MHz, DMSO-d$_6$): δ 186.3, 152.7, 143.9, 135.3, 134.9, 118.0, 112.0, 111.4, 55.8, 46.1.

Step 2: 3-(2-chloroethyl)-5-methoxy-1H-pyrrolo[2,3-b]pyridine (79)

The title compound was synthesized according to General Procedure B with 2-chloro-1-(5-methoxy-1H-pyrrolo[2,3-b]pyridin-3-yl)ethan-1-one (500 mg, 2.23 mmol) resulting in the title compound as a white solid (465 mg, quant.). $^1$H NMR (400 MHz, CDCl$_3$): δ 9.99 (s, 1H), 8.09 (d, J=2.8 Hz, 1H), 7.44 (d, J=2.8 Hz, 1H), 7.23 (s, 1H), 3.91 (s, 3H), 3.76

(t, J=7.2 Hz, 2H), 3.19 (t, J=7.2 Hz, 2H); $^{13}$C NMR (101 MHz, CDCl$_3$): δ 151.4, 143.9, 132.9, 124.3, 120.1, 110.9, 110.9, 56.8, 44.6, 29.2.

Step 3: N-(2-(5-methoxy-1H-pyrrolo[2,3-b]pyridin-3-yl)ethyl)-N-methylcyclopropanamine Fumarate (S44·Fumarate)

The title compound was synthesised according to General Procedure D utilising 3-(2-chloroethyl)-5-methoxy-1H-pyrrolo[2,3-b]pyridine (290 mg, 1.38 mmol), N-methylcyclopropanamine hydrochloride (296 mg, 2.75 mmol) and iPr$_2$NEt (0.72 mL, 4.13 mmol) which upon purification generated the title compound as a colourless oil (250 mg, 74%) which was then formulated as the fumarate salt as per General Procedure F (70 mg, 27%) as colourless crystals. LCMS (Condition A): $t_R$ (3.388 min) m/z=246.15 [M+H]$^+$; $^1$H NMR (400 MHz, DMSO-d$_6$): δ 11.15 (s, 1H), 7.93 (d, J=2.7 Hz, 1H), 7.48 (d, J=2.7 Hz, 1H), 7.22 (d, J=2.4 Hz, 1H), 6.61 (s, 2H), 3.82 (s, 3H), 2.84 (s, 4H), 2.41 (s, 3H), 1.84 (tt, J=6.7, 3.7 Hz, 1H), 0.57-0.28 (m, 4H); $^{13}$C NMR (101 MHz, DMSO-d$_6$): δ 166.2, 150.2, 144.1, 134.1, 132.6, 123.9, 119.2, 111.0, 109.4, 57.8, 56.0, 42.1, 38.2, 22.4, 6.3.

Example 45: Synthesis of 3-(2-(azetidin-1-yl)ethyl)-5-methoxy-1H-pyrrolo[2,3-b]pyridine (S45)

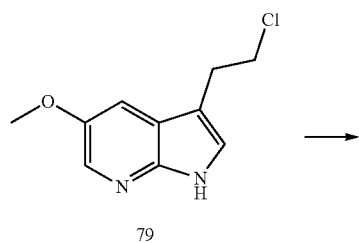

79

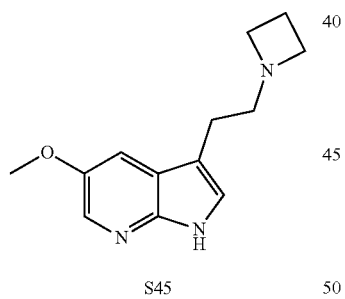

S45

Step 1: 3-(2-(azetidin-1-yl)ethyl)-5-methoxy-1H-pyrrolo[2,3-b]pyridine (S45)

The title compound was synthesised according to General Procedure C utilising 3-(2-chloroethyl)-5-methoxy-1H-pyrrolo[2,3-b]pyridine (500 mg, 2.37 mmol) and azetidine (0.48 mL, 7.12 mmol), however MeCN was used as the solvent instead of DMF. Upon purification the title compound was a yellow oil (125 mg, 23%). $^1$H NMR (400 MHz, DMSO-d$_6$): δ 9.37 (s, 1H), 8.10-8.00 (m, 1H), 7.40 (d, J=2.5 Hz, 1H), 7.10 (d, J=2.2 Hz, 1H), 3.89 (s, 3H), 3.23 (t, J=7.0 Hz, 4H), 2.87-2.58 (m, 4H), 2.09 (p, J=7.0 Hz, 2H); $^{13}$C NMR (101 MHz, CDCl$_3$): δ 151.1, 144.5, 133.5, 123.1, 119.9, 112.5, 110.4, 60.3, 56.7, 55.5, 24.1, 18.0.

Step 2: 3-(2-(azetidin-1-yl)ethyl)-5-methoxy-1H-pyrrolo[2,3-b]pyridine Oxalate (S45·Oxalate)

A solution of 3-(2-(azetidin-1-yl)ethyl)-5-methoxy-1H-pyrrolo[2,3-b]pyridine (105 mg, 0.45 mmol) dissolved in minimal warm isopropanol was filtered through a cotton plug directly into a warm solution of oxalic acid (61 mg, 0.68 mmol) in acetone (10 mL). The vial was then sealed, the suspension was heated to reflux, and then allowed to cool to RT. The precipitate was collected by filtration under vacuum and washed with cold acetone to afford the title compound as the oxalate salt which was a white solid (106 mg, 73%). $^1$H NMR (400 MHz, DMSO-d$_6$): δ 11.12 (s, 1H), 7.69 (d, J=8.7 Hz, 1H), 7.37 (d, J=2.7 Hz, 1H), 6.56 (d, J=8.7 Hz, 1H), 4.04 (t, J=8.1 Hz, 4H), 3.90 (s, 3H), 3.47 (t, J=7.5 Hz, 2H), 2.90 (t, J=7.4 Hz, 2H), 2.33 (p, J=8.1 Hz, 2H); $^{13}$C NMR (101 MHz, DMSO-d$_6$): δ 164.6, 158.7, 140.7, 126.0, 124.7, 122.7, 108.7, 104.6, 54.3, 53.7, 52.6, 19.6, 16.0.

Example 46: Synthesis of 5-methoxy-3-(2-(pyrrolidin-1-yl)ethyl)-1H-pyrrolo[2,3-b]pyridine Dihydrochloride (S46)

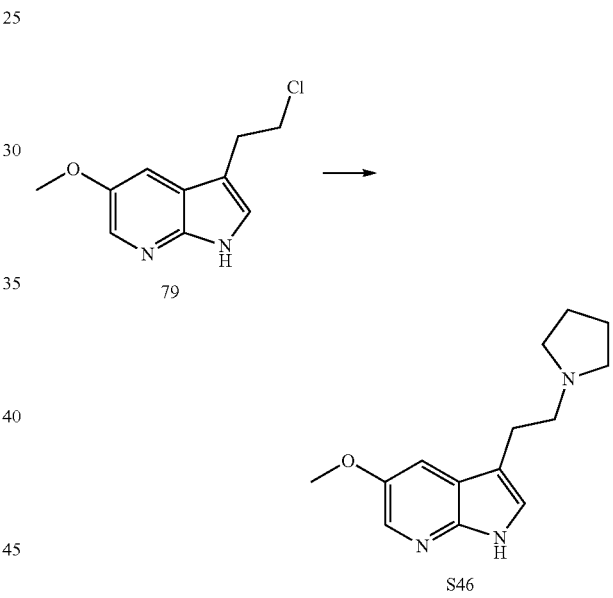

79

S46

Step 1: 5-methoxy-3-(2-(pyrrolidin-1-yl)ethyl)-1H-pyrrolo[2,3-b]pyridine Dihydrochloride (S46·2HCl)

The title compound was synthesised according to General Procedure C utilising 3-(2-chloroethyl)-5-methoxy-1H-pyrrolo[2,3-b]pyridine (100 mg, 0.48 mmol) and pyrrolidine (169 mg, 2.37 mmol) which upon purification generated the title compound as a yellow oil which was then formulated as the dihydrochloride salt as per General Procedure E (27 mg, 17%) as an off-white solid. $^1$H NMR (400 MHz, DMSO-d$_6$): δ 11.73 (s, 1H), 10.92 (s, 1H), 8.06 (d, J=2.6 Hz, 1H), 7.96 (d, J=2.6 Hz, 1H), 7.43 (d, J=2.4 Hz, 1H), 3.88 (s, 3H), 3.60-3.47 (m, 2H), 3.45-3.29 (m, 2H), 3.22-3.10 (m, 2H), 3.10-2.98 (m, 2H), 2.09-1.78 (m, 4H); $^{13}$C NMR (101 MHz, DMSO-d$_6$): δ 150.4, 141.5, 129.7, 126.0, 120.7, 113.3, 108.8, 56.5, 53.8, 52.8, 22.8, 21.3; $^1$H qNMR Purity: 96.7% (ERETIC).

141

Example 47: Synthesis of 5-methoxy-3-(2-(piperidin-1-yl)ethyl)-1H-pyrrolo[2,3-b]pyridine (S47)

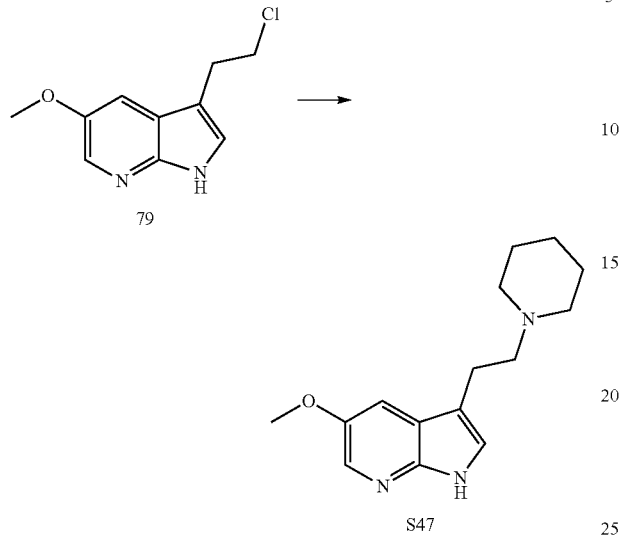

Step 1: 5-methoxy-3-(2-(piperidin-1-yl)ethyl)-1H-pyrrolo[2,3-b]pyridine Dihydrochloride (S47·2HCl)

The title compound was synthesised according to General Procedure C utilising 3-(2-chloroethyl)-5-methoxy-1H-pyrrolo[2,3-b]pyridine (100 mg, 0.48 mmol) and piperidine (202 mg, 2.37 mmol) which upon purification generated the title compound as a yellow oil which was then formulated as the dihydrochloride salt as per General Procedure E (55 mg, 37%) as an off-white solid. LCMS (Condition A): $t_R$ (3.443 min) m/z=260.15 [M+H]$^+$; $^1$H NMR (400 MHz, DMSO-d$_6$): δ 11.75 (s, 1H), 10.82 (s, 1H), 8.07 (d, J=2.6 Hz, 1H), 8.04 (d, J=2.6 Hz, 1H), 7.42 (d, J=2.5 Hz, 1H), 3.88 (s, 3H), 3.61-3.39 (m, 2H), 3.37-3.17 (m, 4H), 3.01-2.78 (m, 2H), 1.95-1.64 (m, 5H), 1.55-1.27 (m, 1H); $^{13}$C NMR (101 MHz, DMSO-d$_6$): δ 150.3, 141.2, 129.5, 125.9, 120.8, 113.6, 108.9, 56.5, 54.4, 51.7, 22.3, 21.5, 19.5; $^1$H qNMR Purity: 100% (ERETIC).

Example 48: Synthesis of (S)-5-fluoro-3-(2-(2-methylazetidin-1-yl)ethyl)-1H-pyrrolo[2,3-b]pyridine (S48)

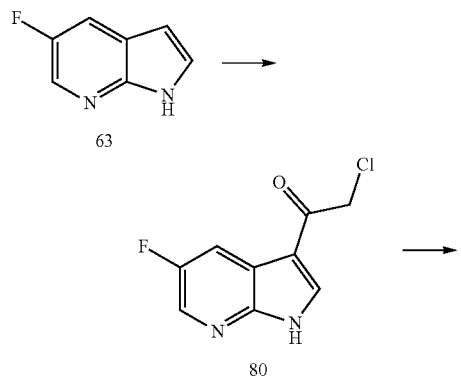

142

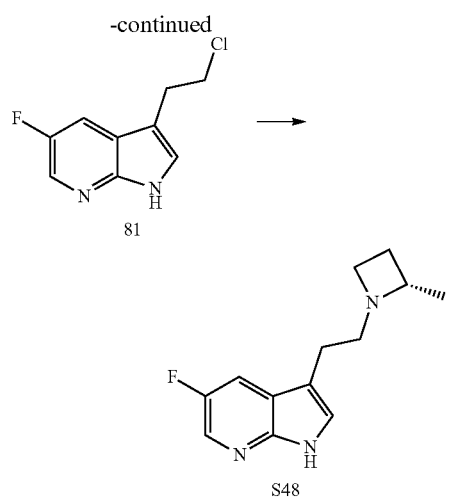

Step 1: 2-chloro-1-(5-fluoro-1H-pyrrolo[2,3-b]pyridin-3-yl)ethan-1-one (80)

A mixture of 5-fluoro-1H-pyrrolo[2,3-b]pyridine (1.00 g, 7.35 mmol) in CH$_2$Cl$_2$ (7 mL) was degassed and purged with N$_2$ three times before adding AlCl$_3$ (4.90 g, 36.8 mmol) at 0° C. under N$_2$. After stirring at 0° C. for 5 min, 2-chloroacetyl chloride (4.15 g, 36.7 mmol) was added at 0° C. and then the mixture was stirred at RT for 3 h. The reaction was then quenched with water (20 mL) at 0° C. and the pH adjusted 9 with aqueous Na$_2$CO$_3$ and then filtered. The filter cake was washed with EtOAc (4×30 mL) and the aqueous phase separated, diluted with H$_2$O (30 mL) and further extracted with EtOAc (3×20 mL). The combined organics were washed with brine (50 mL), dried over anhydrous Na$_2$SO$_4$, filtered and the filtrate concentrated under reduced pressure to provide crude 2-chloro-1-(5-fluoro-1H-pyrrolo[2,3-b]pyridin-3-yl)ethan-1-one (1.16 g) as a yellow solid which was used in the next step without purification.

Step 2: 3-(2-chloroethyl)-5-fluoro-1H-pyrrolo[2,3-b]pyridine (81)

To a solution of 2-chloro-1-(5-fluoro-1H-pyrrolo[2,3-b]pyridin-3-yl)ethan-1-one (1.16 g, 5.46 mmol) in TFA (10 mL) was added Et$_3$SiH (3.64 g, 31.3 mmol) and the reaction was stirred at RT for 12 h. The reaction mixture was adjusted to pH 9 with saturated aq. Na$_2$CO$_3$ solution, diluted with H$_2$O (50 mL) and then extracted with EtOAc (3×75 m). The combined organics were washed with brine (50 mL), dried over anhydrous Na$_2$SO$_4$, filtered and the filtrate concentrated under reduced pressure. The residue triturated with MTBE: petroleum ether (1:5 v/v, 20 mL) at ambient temperature for 30 min and filtered to afford 3-(2-chloroethyl)-5-fluoro-1H-pyrrolo[2,3-b]pyridine (389 mg) as a yellow solid. LCMS (Condition A): m/z=199.0 [M+H]$^+$.

Step 3: (S)-5-fluoro-3-(2-(2-methylazetidin-1-yl)ethyl)-1H-pyrrolo[2,3-b]pyridine Dihydrochloride (S48·2HCl)

The title compound was synthesised according to General Procedure D utilising 3-(2-chloroethyl)-5-fluoro-1H-pyrrolo[2,3-b]pyridine (100 mg, 0.50 mmol), (S)-2-methylazetidine hydrochloride (108 mg, 1.01 mmol) and Et$_3$N (0.15 mL, 1.11 mmol) which upon purification generated the title compound as a yellow oil which was then formulated as the dihydrochloride salt as per General Procedure E (25 mg, 18%) as colourless crystals. LCMS (Condition A): $t_R$ (3.748 min) m/z=234.15 [M+H]$^+$; $^1$H NMR (400 MHz, DMSO-d$_6$): δ 11.71 (s, 1H), 10.91 (s, 1H), 8.26-8.14 (m, 1H), 8.04 (dd, J=9.6, 2.6 Hz, 1H), 7.48 (d, J=2.5 Hz, 1H), 4.57-4.30 (m, 1H), 3.94-3.70 (m, 2H), 3.55-3.18 (m, 2H), 3.05-2.86 (m, 2H), 2.45-2.27 (m, 1H), 2.20-2.01 (m, 1H), 1.50 (d, J=6.6 Hz, 3H); $^{13}$C NMR (101 MHz, DMSO-d$_6$): δ 154.7 (d, J=238.4 Hz), 145.3, 130.7 (d, J=29.1 Hz), 126.7, 119.1 (d, J=6.8 Hz), 112.8 (d, J=20.9 Hz), 108.6 (d, J=4.3 Hz), 65.1, 53.1, 49.9, 24.1, 20.2, 18.3; $^1$H qNMR Purity: 96.6% (ERETIC).

Example 49: Synthesis of (R)-5-fluoro-3-(2-(2-methylazetidin-1-yl)ethyl)-1H-pyrrolo[2,3-b]pyridine (S49)

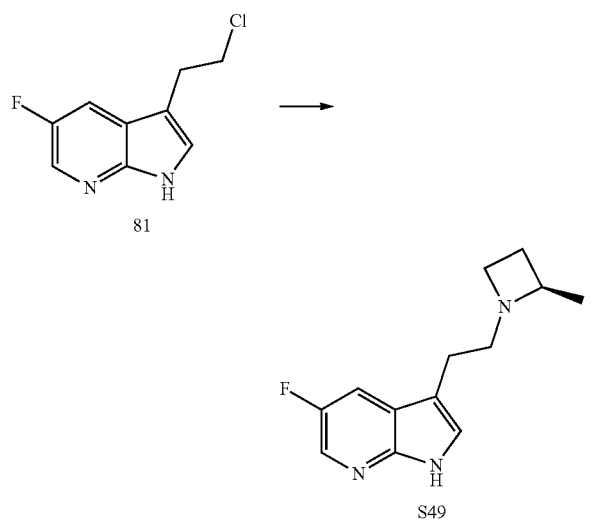

Step 1: (R)-5-fluoro-3-(2-(2-methylazetidin-1-yl)ethyl)-1H-pyrrolo[2,3-b]pyridine Dihydrochloride (S49·2HCl)

The title compound was synthesised according to General Procedure D utilising 3-(2-chloroethyl)-5-fluoro-1H-pyrrolo[2,3-b]pyridine (100 mg, 0.50 mmol), (R)-2-methylazetidine hydrochloride (108 mg, 1.01 mmol) and Et$_3$N (0.15 mL, 1.11 mmol) which upon purification generated the title compound as a yellow oil which was then formulated as the hydrochloride salt as per General Procedure E (25 mg, 18%) which were colourless crystals. LCMS: $t_R$ (3.754 min) m/z=234.15 [M+H]$^+$; $^1$H NMR (400 MHz, DMSO-d$_6$): δ 11.71 (s, 1H), 10.94 (s, 1H), 8.26-8.15 (m, 1H), 8.04 (dd, J=9.6, 2.6 Hz, 1H), 7.48 (d, J=2.5 Hz, 1H), 4.54-4.33 (m, 1H), 3.92-3.71 (m, 2H), 3.56-3.18 (m, 2H), 3.10-2.85 (m, 2H), 2.45-2.27 (m, 1H), 2.23-2.00 (m, 1H), 1.51 (d, J=6.6 Hz, 3H); $^{13}$C NMR (101 MHz, DMSO-d$_6$): δ 154.7 (d, J=238.4 Hz), 145.3, 130.7 (d, J=29.1 Hz), 126.7, 119.1 (d, J=7.0 Hz), 112.8 (d, J=20.7 Hz), 108.6 (d, J=4.3 Hz), 65.1, 53.1, 49.9, 24.1, 20.2, 18.3; $^1$H qNMR Purity: 95.8% (ERETIC).

Example 50: Synthesis of (R)-5-fluoro-3-(2-(2-methylpyrrolidin-1-yl)ethyl)-1H-pyrrolo[2,3-b]pyridine (S50)

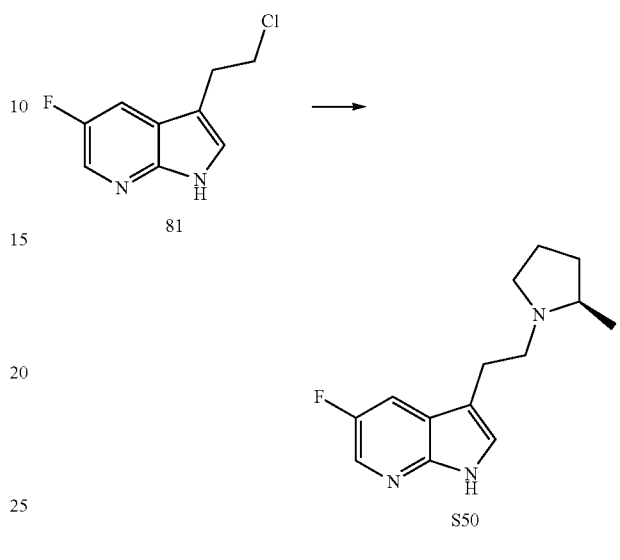

Step 1: (R)-5-fluoro-3-(2-(2-methylpyrrolidin-1-yl)ethyl)-1H-pyrrolo[2,3-b]pyridine Dihydrochloride (S50·2HCl)

The title compound was synthesised according to General Procedure D utilising 3-(2-chloroethyl)-5-fluoro-1H-pyrrolo[2,3-b]pyridine (100 mg, 0.50 mmol), (R)-2-methylpyrrolidine hydrochloride (122 mg, 1.01 mmol) and Et$_3$N (0.15 mL, 1.11 mmol) which upon purification generated the title compound as a yellow oil which was then formulated as the hydrochloride salt as per General Procedure E (42 mg, 29%) as colourless crystals. LCMS: $t_R$ (3.863 min) m/z=248.15 [M+H]$^+$; $^1$H NMR (400 MHz, DMSO-d$_6$): δ 11.72 (s, 1H), 10.74 (s, 1H), 8.28-8.13 (m, 1H), 8.04 (dd, J=9.6, 2.6 Hz, 1H), 7.52 (d, J=2.5 Hz, 1H), 3.73-3.57 (m, 1H), 3.54-3.35 (m, 2H), 3.27-3.07 (m, 4H), 2.25-2.12 (m, 1H), 2.03-1.87 (m, 2H), 1.70-1.57 (m, 1H), 1.42 (d, J=6.5 Hz, 3H); $^{13}$C NMR (101 MHz, DMSO-d$_6$): δ 154.7 (d, J=238.4 Hz), 145.2, 130.7 (d, J=29.1 Hz), 126.7, 119.2 (d, J=6.8 Hz), 112.7 (d, J=20.6 Hz), 108.9 (d, J=4.3 Hz), 63.4, 52.2, 52.0, 31.0, 21.1, 21.0, 15.4; $^1$H qNMR Purity: 95.6% (ERETIC).

Example 51: Synthesis of (S)-5-fluoro-3-(2-(2-methylpyrrolidin-1-yl)ethyl)-1H-pyrrolo[2,3-b]pyridine (S51)

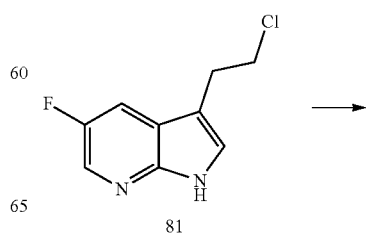

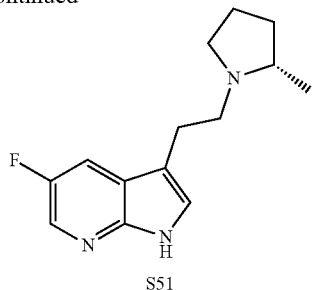

Step 1: (S)-5-fluoro-3-(2-(2-methylpyrrolidin-1-yl)ethyl)-1H-pyrrolo[2,3-b]pyridine Fumarate (S51·Fumarate)

The title compound was synthesised according to General Procedure D utilising 3-(2-chloroethyl)-5-fluoro-1H-pyrrolo[2,3-b]pyridine (100 mg, 0.50 mmol), (S)-2-methylpyrrolidine hydrochloride (122 mg, 1.01 mmol) and Et$_3$N (0.15 mL, 1.11 mmol) which upon purification generated the title compound as a yellow oil which was then formulated as the fumarate salt as per General Procedure F (40 mg, 13%) as colourless crystals. LCMS: t$_R$ (3.856 min) m/z=248.15 [M+H]$^+$; $^1$H NMR (400 MHz, DMSO-d$_6$): δ 11.56 (s, 1H), 8.16 (dd, J=2.6, 1.8 Hz, 1H), 7.91 (dd, J=9.7, 2.7 Hz, 1H), 7.44 (d, J=2.4 Hz, 1H), 6.54 (s, 2H), 3.50-3.32 (m, 1H), 3.31-3.15 (m, 1H), 3.10-2.81 (m, 3H), 2.79-2.61 (m, 2H), 2.10-1.93 (m, 1H), 1.89-1.68 (m, 2H), 1.57-1.35 (m, 1H), 1.18 (d, J=6.3 Hz, 3H); $^{13}$C NMR (76 MHz, DMSO-d$_6$): δ 167.2, 154.7 (d, J=238.5 Hz), 145.4, 134.7, 130.5 (d, J=28.9 Hz), 126.1, 119.3 (d, J=6.9 Hz), 112.4 (d, J=20.6 Hz), 110.5 (d, J=4.1 Hz), 60.9, 52.8, 52.5, 31.7, 22.6, 21.2, 17.0; $^1$H qNMR Purity: 100% (ERETIC).

Example 52: Synthesis of 2-(5-chloro-1H-pyrrolo[2,3-b]pyridin-3-yl)-N-ethyl-N-methylethan-1-amine (S52)

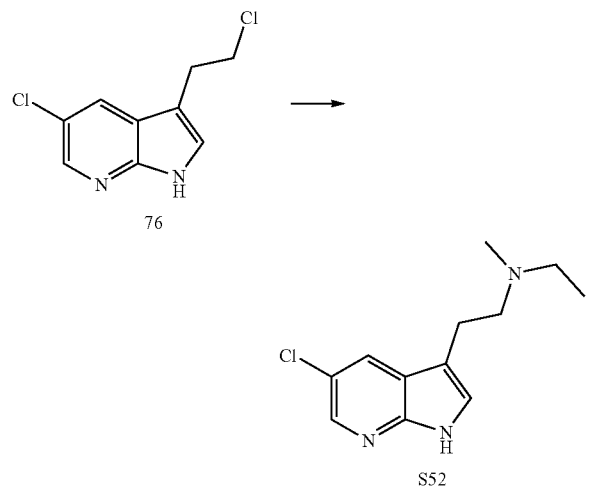

To a solution of 5-chloro-3-(2-chloroethyl)-1H-pyrrolo[2,3-b]pyridine (200 mg, 0.93 mmol) and N-methylethanamine (110 mg, 1.86 mmol, 159 µL) in DMF (5.00 mL) was added K$_2$CO$_3$ (257 mg, 1.86 mmol) and the mixture was stirred at 50° C. for 10 hrs. The reaction mixture was quenched with H$_2$O (30 mL) and extracted with EtOAc (2×10 mL). The combined organics were washed with brine (10 mL), dried over Na$_2$SO$_4$ and concentrated under reduced pressure. The residue was purified by prep-HPLC (column: Waters Xbridge Prep OBD C18 150×40 mm, 10 um; mobile phase: [H$_2$O (10 mM NH$_4$HCO$_3$)-MeCN]; gradient: 20%-60% B over 8.0 min) to provide 2-(5-chloro-1H-pyrrolo[2,3-b]pyridin-3-yl)-N-ethyl-N-methylethan-1-amine (20.0 mg, 10% yield) as a yellow solid. LCMS (Condition B): t$_R$ (1.633 min) m/z=238 [M+H]$^+$; $^1$H NMR (400 MHz CDCl$_3$): δ 9.51 (br s, 1H), 8.24 (d, J=2.3 Hz, 1H), 7.90 (d, J=2.1 Hz, 1H), 7.20 (d, J=2.0 Hz, 1H), 2.95-2.86 (m, 2H), 2.75-2.65 (m, 2H), 2.55 (q, J=7.2 Hz, 2H), 2.36 (s, 3H), 1.12 (t, J=7.1 Hz, 3H).

Example 53: Synthesis of N-(2-(5-chloro-1H-pyrrolo[2,3-b]pyridin-3-yl)ethyl)-N-methylpropan-2-amine (S53)

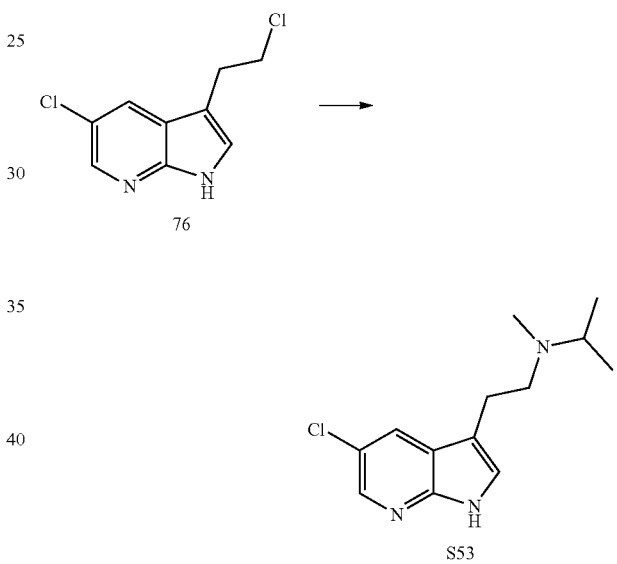

To a solution of 5-chloro-3-(2-chloroethyl)-1H-pyrrolo[2,3-b]pyridine (200 mg, 929 µmol) and N-methylpropan-2-amine (136 mg, 1.86 mmol, 193 µL) in DMF (5.00 mL) was added K$_2$CO$_3$ (257 mg, 1.86 mmol) at 20° C. under nitrogen atmosphere and the mixture was stirred at 50° C. for 10 hrs. The reaction mixture was quenched with H$_2$O (30 mL) and extracted with EtOAc (2×10 mL). The combined organics were washed with brine (10 mL), dried over Na$_2$SO$_4$ and concentrated under reduced pressure. The residue was purified by prep-HPLC (column: Waters Xbridge Prep OBD C18 150×40 mm, 10 um; mobile phase: [H$_2$O (10 mM NH$_4$HCO$_3$)-MeCN]; gradient: 25%-60% B over 8.0 min) to provide N-(2-(5-chloro-1H-pyrrolo[2,3-b]pyridin-3-yl)ethyl)-N-methylpropan-2-amine (20.0 mg, 9%) as a yellow solid. LCMS (Condition B): t$_R$ (1.34 min) m/z=252 [M+H]$^+$; $^1$H NMR (400 MHz CDCl$_3$): δ 9.63 (br s, 1H), 8.25 (d, J=2.1 Hz, 1H), 7.95-7.85 (m, 1H), 7.21 (s, 1H), 7.17 (m, 1H), 3.01-2.81 (m, 3H), 2.74-2.66 (m, 2H), 2.39-2.30 (m, 3H), 1.05 (d, J=6.6 Hz, 6H).

Example 54: Synthesis of 2-(5-bromo-1H-pyrrolo[2,3-b]pyridin-3-yl)-N-ethyl-N-methylethan-1-amine (S54)

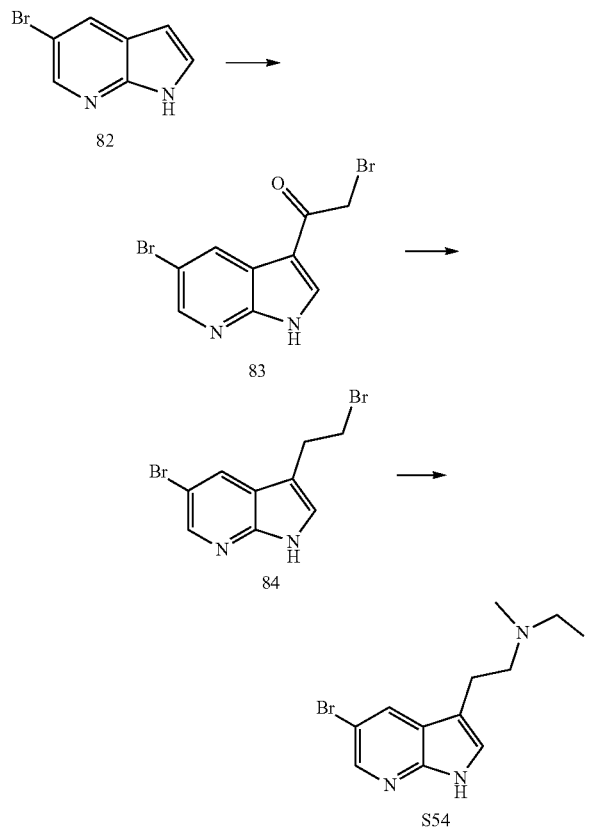

Step 1: 2-bromo-1-(5-bromo-1H-pyrrolo[2,3-b]pyridin-3-yl)ethan-1-one (83)

To a stirred solution of 5-bromo-1H-pyrrolo[2,3-b]pyridine (0.5 g, 2.53 mmol) in $CH_2Cl_2$ (27 mL) at 0° C. under nitrogen atmosphere was added $AlCl_3$ (1.01 g, 7.61 mmol). Then 2-bromoacetyl bromide (0.76 g, 3.80 mmol) was added at RT and then the mixture was stirred at 40° C. for 1 h. The reaction mixture was diluted with ice cold water (70 mL) and the precipitate was filtered and washed with 2-propanol to afford 2-bromo-1-(5-bromo-1H-pyrrolo[2,3-b]pyridin-3-yl)ethan-1-one (650 mg, 81%) as a white solid. LCMS (Condition C): $t_R$ (2.053 min) m/z=318.0 [M+H]$^+$; $^1$H NMR (400 MHz, DMSO-$d_6$): δ 12.93 (s, 1H), 8.70 (d, J=2.8 Hz, 1H), 8.56 (s, 1H), 8.45 (d, J=1.6 Hz, 1H), 4.71 (s, 2H).

Step 2: 5-bromo-3-(2-bromoethyl)-1H-pyrrolo[2,3-b]pyridine (84)

To a stirred solution of 2-bromo-1-(5-bromo-1H-pyrrolo[2,3-b]pyridin-3-yl)ethan-1-one (0.5 g, 1.57 mmol) was added TFA (7 mL) and triethylsilane (4 mL) portion wise at 0° C. and the resulting reaction mixture was stirred at RT for 48 h under nitrogen atmosphere. The reaction mixture quenched by dropwise addition of $NaHCO_3$ solution (150 mL) and then extracted with EtOAc (2×150 mL). The combined organics were dried over $Na_2SO_4$ and concentrated under reduced pressure. The crude material was purified by column chromatography (0% to 40% EtOAc in hexane) to afford 5-bromo-3-(2-bromoethyl)-1H-pyrrolo[2,3-b]pyridine (325 mg, 68%) as an off white solid. LCMS (Condition C): $t_R$ (1.726 min) m/z=302.6, 304.6, 306.5 [M+H]$^+$, [M+2+H]$^+$, [M+4+H]$^+$. $^1$H NMR (400 MHz, CDCl$_3$): δ 9.47 (s, 1H), 8.37 (d, J=2.0 Hz, 1H), 8.07 (d, J=1.6 Hz, 1H), 7.28-7.26 (m, 1H), 3.65 (t, J=7.2 Hz, 2H), 3.30 (t, J=7.2 Hz, 2H).

Step 3: 2-(5-bromo-1H-pyrrolo[2,3-b]pyridin-3-yl)-N-ethyl-N-methylethan-1-amine (S54)

To a stirred solution of 5-bromo-3-(2-bromoethyl)-1H-pyrrolo[2,3-b]pyridine (0.4 g, 1.31 mmol) in EtOH (13 mL) was added N-methylethanamine (0.18 g, 1.97 mmol) and NaI (0.19 g, 1.31 mmol) at RT and the reaction mixture was refluxed at 90° C. for 48 h. The reaction mixture was diluted with water (50 mL) and extracted with EtOAc (2×70 mL). The combined organics were dried over $Na_2SO_4$ and concentrated under reduced pressure. The crude material was purified by prep-HPLC to afford 2-(5-bromo-1H-pyrrolo[2,3-b]pyridin-3-yl)-N-ethyl-N-methylethan-1-amine (0.08 g, 22%) as a light brown sticky solid. LCMS: $t_R$ (1.049 min) m/z=281.8, 283.7 [M+H]$^+$, [M+2+H]$^+$; $^1$H NMR (400 MHz, DMSO-$d_6$): δ 11.61 (s, 1H), 8.22-8.20 (m, 2H), 7.37 (s, 1H), 2.83 (t, J=7.2 Hz, 2H), 2.66 (t, J=6.8 Hz, 2H), 2.52 (m, 2H), 2.29 (s, 3H), 1.01 (t, J=7.2 Hz, 3H).

Step 4: 2-(5-bromo-1H-pyrrolo[2,3-b]pyridin-3-yl)-N-ethyl-N-methylethan-1-amine Fumarate (S54·Fumarate)

To a stirred solution of 2-(5-bromo-1H-pyrrolo[2,3-b]pyridin-3-yl)-N-ethyl-N-methylethan-1-amine (0.08 g, 0.28 mmol) in acetone (2 mL) was added fumaric acid (0.03 g, 0.28 mmol) and the reaction mixture was refluxed at 100° C. for 10 min, then cooled and left to stand at RT for 16 h. The solid was triturated using acetone and dried under reduced pressure. The solid was dissolved in $H_2O$/MeCN and then lyophilised to afford 2-(5-bromo-1H-pyrrolo[2,3-b]pyridin-3-yl)-N-ethyl-N-methylethan-1-amine fumarate salt (82 mg, 70% yield) as a light brown solid. LCMS: $t_R$ (1.043 min) m/z=281.8, 283.7 [M+H]$^+$, [M+2+H]$^+$; $^1$H NMR (400 MHz, DMSO-$d_6$): δ 11.68 (s, 1H), 8.27-8.24 (m, 2H), 7.41 (s, 1H), 6.55 (s, 2H), 2.92 (s, 4H), 2.79-2.77 (m, 2H), 2.58-2.50 (m, 3H), 1.10 (t, J=7.2 Hz, 3H).

Example 55: Synthesis of N-(2-(5-bromo-1H-pyrrolo[2,3-b]pyridin-3-yl)ethyl)-N-methylpropan-2-amine (S55)

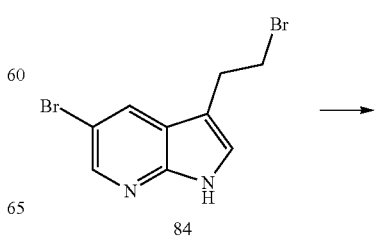

84

-continued

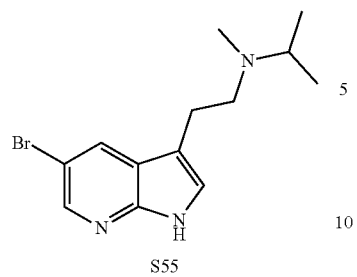

S55

Step 1: N-(2-(5-bromo-1H-pyrrolo[2,3-b]pyridin-3-yl)ethyl)-N-methylpropan-2-amine Formate (S55·Formate)

To a stirred solution of 5-bromo-3-(2-bromoethyl)-1H-pyrrolo[2,3-b]pyridine (0.3 g, 0.98 mmol) in EtOH (10 mL) was added NaI (0.15 g, 0.98 mmol) at 0° C. After 15 min, N-methylpropan-2-amine (0.22 g, 2.96 mmol) in EtOH (1 mL) was added and the mixture was stirred at 90° C. for 24 h. The reaction mixture was concentrated under reduced pressure, diluted with water (50 mL) and then extracted with EtOAc (2×50 mL). The combined organics were washed with saturated aq. NH$_4$Cl solution (2×50 mL), dried over Na$_2$SO$_4$ and concentrated under reduced pressure. The crude material was purified by reverse phase column chromatography (product eluted at 5% MeCN in 0.1% FA in water) to afford N-(2-(5-bromo-1H-pyrrolo[2,3-b]pyridin-3-yl)ethyl)-N-methylpropan-2-amine formate (0.075 g, 26%) as a white gum. LCMS (Condition C): t$_R$ (1.074 min) m/z=295.8, 297.7 [M+H]$^+$, [M+2+H]$^+$; $^1$H NMR (400 MHz, DMSO-d$_6$): δ 11.72 (s, 1H), 8.29 (s, 1H), 8.23 (s, 1H), 8.19 (s, 1H), 7.44 (s, 1H), 3.34-3.30 (m, 1H), 3.00 (s, 4H), 2.54 (s, 3H), 1.13 (d, J=6.4 Hz, 6H).

Step 2: N-(2-(5-bromo-1H-pyrrolo[2,3-b]pyridin-3-yl)ethyl)-N-methylpropan-2-amine Fumarate (S55·Fumarate)

To a stirred solution of N-(2-(5-bromo-1H-pyrrolo[2,3-b]pyridin-3-yl)ethyl)-N-methylpropan-2-amine (0.075 g, 0.25 mmol) in acetone (2.0 mL) was added fumaric acid (0.03 g, 0.25 mmol) and the reaction mixture was refluxed at 100° C. for 20 min, then cooled and left to stand at RT for 16 h. The solid was dried under reduced pressure, redissolved in MeCN:H$_2$O (1:1) and lyophilised to afford N-(2-(5-bromo-1H-pyrrolo[2,3-b]pyridin-3-yl)ethyl)-N-methylpropan-2-amine fumarate salt (83 mg, 75%) as a white solid. LCMS (Condition C): t$_R$ (1.067 min) m/z=295.8, 297.7 [M+H]$^+$, [M+2+H]$^+$; $^1$H NMR (400 MHz, DMSO-d$_6$): δ 11.76 (s, 1H), 8.34 (s, 1H), 8.26 (s, 1H), 7.46 (s, 1H), 6.59 (s, 2H), 3.52-3.49 (m, 1H), 3.18-3.06 (m, 4H), 2.65 (s, 3H), 1.20 (d, J=6.8 Hz, 6H).

Example 56: Synthesis of N-(2-(5-bromo-1H-pyrrolo[2,3-b]pyridin-3-yl)ethyl)-N-methylcyclopropanamine (S56)

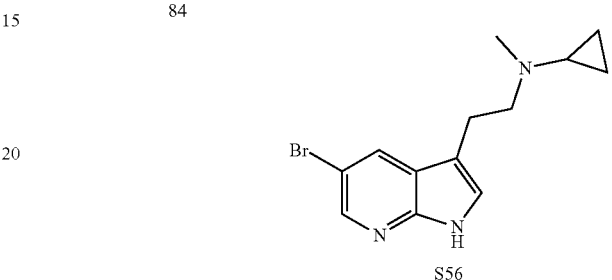

S56

Step 1: N-(2-(5-bromo-1H-pyrrolo[2,3-b]pyridin-3-yl)ethyl)-N-methylcyclopropanamine (S56)

To a stirred solution of 5-bromo-3-(2-bromoethyl)-1H-pyrrolo[2,3-b]pyridine (0.25 g, 0.82 mmol) in EtOH (10 mL) was added NaI (0.12 g, 0.82 mmol), Et$_3$N (0.26 g, 2.46 mmol) and N-methylcyclopropanamine (0.09 g, 1.23 mmol) at rt. The resulting mixture was stirred at 100° C. for 3 h under microwave irradiation. The reaction mixture was cooled to RT and concentrated under reduced pressure. The residue was treated with saturated aq. NH$_4$Cl solution (100 mL) and extracted with EtOAc (2×150 mL). The combined organics were dried over Na$_2$SO$_4$ and concentrated under reduced pressure, and the crude material was purified by column chromatography (70% EtOAc/hexane) to afford N-(2-(5-bromo-1H-pyrrolo[2,3-b]pyridin-3-yl)ethyl)-N-methylcyclopropanamine (0.12 g, 50%) as a yellow liquid. LCMS (Condition C): t$_R$ (1.068 min) m/z=293.8, 295.7 [M+H]$^+$, [M+2+H]$^+$; $^1$H NMR (400 MHz, DMSO-d$_6$): δ 11.58 (s, 1H), 8.22 (d, J=2.0 Hz, 1H), 8.16 (d, J=2.4 Hz, 1H), 7.34 (d, J=2.0 Hz, 1H), 2.82-2.74 (m, 4H), 2.34 (s, 3H), 1.71-1.68 (m, 1H), 0.44-0.40 (m, 2H), 0.28-0.24 (m, 2H).

Step 2: N-(2-(5-bromo-1H-pyrrolo[2,3-b]pyridin-3-yl)ethyl)-N-methylcyclopropanamine Fumarate (S56·Fumarate)

To a stirred solution of N-(2-(5-bromo-1H-pyrrolo[2,3-b]pyridin-3-yl)ethyl)-N-methylcyclopropanamine (0.11 g, 0.37 mmol) in acetone (2.0 mL) was added fumaric acid (0.04 g, 0.37 mmol) and the reaction mixture was refluxed at 90° C. for 20 min, then cooled and left to stand at RT for 16 h. The solid was triturated with acetone, dried under reduced pressure and lyophilised from MeCN:H$_2$O (1:1) to afford N-(2-(5-bromo-1H-pyrrolo[2,3-b]pyridin-3-yl)ethyl)-N-methylcyclopropanamine fumarate salt (0.12 g, 78%) as an off white solid. LCMS (Condition C): t$_R$ (1.090 min) m/z=293.7, 295.7 [M+H]$^+$, [M+2+H]$^+$; 1H NMR (400 MHz, DMSO-d$_6$): δ 11.58 (s, 1H), 8.22 (d, J=2.0 Hz, 1H), 8.16 (d, J=2.0 Hz, 1H), 7.34 (d, J=2.4 Hz, 1H), 6.60 (s, 2H), 2.85-2.75 (m, 4H), 2.36 (s, 3H), 1.77-1.74 (m, 1H), 0.46-0.42 (m, 2H), 0.32-0.29 (m, 2H).

Example 57: Synthesis of 5-bromo-3-(2-(pyrrolidin-1-yl)ethyl)-1H-pyrrolo[2,3-b]pyridine (S57)

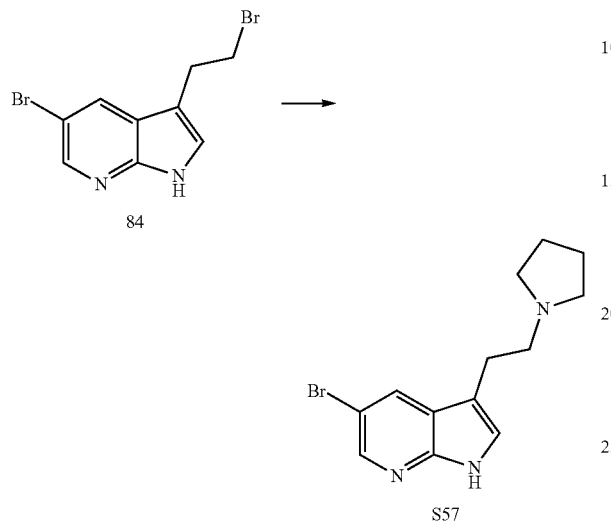

Step 1: 5-bromo-3-(2-(pyrrolidin-1-yl)ethyl)-1H-pyrrolo[2,3-b]pyridine (S57)

To a stirred solution of 5-bromo-3-(2-bromoethyl)-1H-pyrrolo[2,3-b]pyridine (0.4 g, 1.31 mmol) in EtOH (10 mL) was added NaI (0.19 g, 1.31 mmol) at RT under nitrogen atmosphere. After 5 min, pyrrolidine (0.14 g, 1.97 mmol) was added and the mixture was stirred at 90° C. for 16 h. The reaction mixture was concentrated under reduced pressure, treated with saturated aq. NH$_4$Cl solution (100 mL) and extracted with EtOAc (2×150 mL). The combined organics were dried over Na$_2$SO$_4$ and concentrated under reduced pressure to get crude material, which was purified by column chromatography (70% MeOH:CH$_2$Cl$_2$:NH$_4$OH (1:9:0.01) in CH$_2$Cl$_2$) to afford 5-bromo-3-(2-(pyrrolidin-1-yl)ethyl)-1H-pyrrolo[2,3-b]pyridine (0.15 g, 39%) as an off white solid. LCMS (Condition C): $t_R$ (1.533 min) m/z=294.0, 296.0 [M+H]$^+$, [M+2+H]$^+$; $^1$H NMR (400 MHz, DMSO-d$_6$): δ 11.80 (s, 1H), 8.33 (d, J=2.0 Hz, 1H), 8.28 (d, J=2.0 Hz, 1H), 7.49 (d, J=2.4 Hz, 1H), 3.63-3.57 (m, 2H), 3.58-3.41 (m, 2H), 3.10-3.03 (m, 4H), 2.09-1.93 (m, 2H), 1.85-1.82 (m, 2H).

Step 2: 5-bromo-3-(2-(pyrrolidin-1-yl)ethyl)-1H-pyrrolo[2,3-b]pyridine Fumarate (S57·Fumarate)

To a stirred solution of 5-bromo-3-(2-(pyrrolidin-1-yl)ethyl)-1H-pyrrolo[2,3-b]pyridine (0.15 g, 0.51 mmol) in acetone (2.0 mL) was added fumaric acid (0.06 g, 0.51 mmol) and the reaction mixture was refluxed at 80° C. for 10 min, then cooled and left to stand at RT for 16 h. The solid was triturated with acetone, dried under reduced pressure and lyophilised from MeCN:H$_2$O (1:1) to afford 5-bromo-3-(2-(pyrrolidin-1-yl)ethyl)-1H-pyrrolo[2,3-b]pyridine fumarate salt (0.3 g, quant.) as a white solid. LCMS (Condition C): $t_R$ (1.06 min) m/z=293.8, 295.7 [M+H]$^+$, [M+2+H]$^+$; $^1$H NMR (400 MHz, DMSO-d$_6$): δ 11.79 (s, 1H), 8.34 (s, 1H), 8.27 (d, J=1.6 Hz, 1H), 7.47 (s, 1H), 6.62 (s, 2H), 3.41-3.37 (m, 2H), 3.32-3.26 (m, 4H), 3.09 (t, J=8.2 Hz, 2H), 1.94 (s, 4H).

Example 58: Synthesis of 3-(2-(azetidin-1-yl)ethyl)-5-bromo-1H-pyrrolo[2,3-b]pyridine (S58)

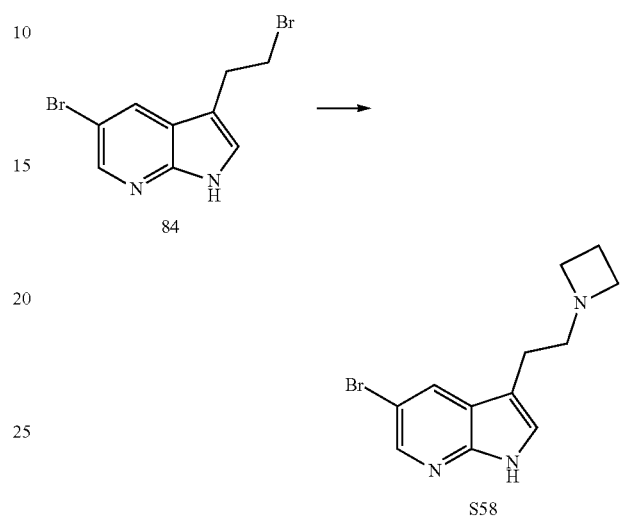

Step 1: 3-(2-(azetidin-1-yl)ethyl)-5-bromo-1H-pyrrolo[2,3-b]pyridine (S58)

To a stirred solution of 5-bromo-3-(2-bromoethyl)-1H-pyrrolo[2,3-b]pyridine (0.5 g, 1.64 mmol) in EtOH (15 mL) was added azetidine (0.28 g, 4.93 mmol) and NaI (0.24 g, 1.64 mmol) at RT and the reaction mixture was refluxed at 90° C. for 5 h. The reaction mixture was diluted with water (70 mL) and extracted with CH$_2$Cl$_2$ (2×50 mL). The combined organics were dried over Na$_2$SO$_4$ and concentrated under reduced pressure to get crude material, which was purified by reverse phase column chromatography (100% MeCN) to afford 3-(2-(azetidin-1-yl)ethyl)-5-bromo-1H-pyrrolo[2,3-b]pyridine (0.1 g, 22%) as a pale yellow sticky solid. LCMS (Condition C): $t_R$ (1.052 min) m/z=279.7, 281.7 [M+H]$^+$, [M+2+H]$^+$; $^1$H NMR (400 MHz, DMSO-d$_6$): δ 11.57 (s, 1H), 8.21 (d, J=2.0 Hz, 1H), 8.17 (d, J=2.0 Hz, 1H), 7.33 (d, J=1.6 Hz, 1H), 3.16-3.08 (m, 4H), 2.61 (s, 4H), 1.96-1.92 (m, 2H).

Step 2: 3-(2-(azetidin-1-yl)ethyl)-5-bromo-1H-pyrrolo[2,3-b]pyridine Fumarate (S58·Fumarate)

To a stirred solution of 3-(2-(azetidin-1-yl)ethyl)-5-bromo-1H-pyrrolo[2,3-b]pyridine (95 mg, 0.34 mmol) in acetone (1.4 mL) was added fumaric acid (40 mg, 0.34 mmol) and the reaction mixture was refluxed at 80° C. for 10 min, then cooled and left to stand at RT for 16 h. The solid was triturated with acetone, dried under reduced pressure and lyophilised from MeCN:H$_2$O (1:1) to afford 3-(2-(azetidin-1-yl)ethyl)-5-bromo-1H-pyrrolo[2,3-b]pyridine fumarate salt (94 mg, 70%) as a pale yellow solid. LCMS (Condition C): $t_R$ (1.070 min) m/z=279.7, 281.7 [M+H]$^+$, [M+2+H]$^+$; $^1$H NMR (400 MHz, DMSO-d$_6$): δ 11.68 (s, 1H), 8.27-8.22 (m, 2H), 7.38 (d, J=1.6 Hz, 1H), 6.52 (s, 2H), 3.54 (t, J=7.2 Hz, 4H), 2.97 (t, J=7.2 Hz, 2H), 2.75 (t, J=7.6 Hz, 2H), 2.14-2.08 (m, 2H).

Example 59: Synthesis of 5-bromo-3-(2-(2-methyl-azetidin-1-yl)ethyl)-1H-pyrrolo[2,3-b]pyridine (S59)

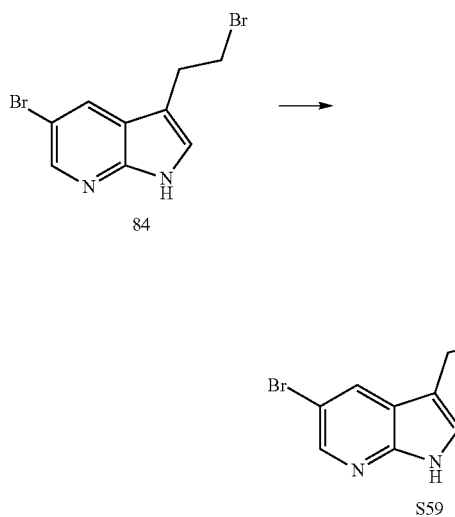

Step 1: 5-bromo-3-(2-(2-methylazetidin-1-yl)ethyl)-1H-pyrrolo[2,3-b]pyridine (S59)

To a stirred solution of 5-bromo-3-(2-bromoethyl)-1H-pyrrolo[2,3-b]pyridine (0.3 g, 0.99 mmol) in EtOH (3 mL) was added 2-methylazetidine hydrochloride (0.32 g, 2.96 mmol), Et₃N (0.2 mL, 1.97 mmol) and NaI (0.15 g, 0.99 mmol) and the reaction mixture was stirred at 100° C. for 1 h under microwave irradiation. The reaction mixture was concentrated under reduced pressure, diluted with water (100 mL) and extracted with 40% iPrOH in chloroform (4×100 mL). The combined organics were dried over Na₂SO₄ and concentrated under reduced pressure. The crude material was purified by prep HPLC purification (Mobile phase A: 5 mM NH₄HCO₃+0.05% NH₄OH in H₂O; Mobile phase B: MeCN: water (80:20)) to afford 5-bromo-3-(2-(2-methylazetidin-1-yl)ethyl)-1H-pyrrolo[2,3-b]pyridine (45 mg, 16%) as a yellow sticky solid. LCMS (Condition C): $t_R$ (1.113 min) m/z=293.7, 295.7 [M+H]⁺, [M+2+H]⁺; ¹H NMR (400 MHz, DMSO-d₆): δ 11.57 (s, 1H), 8.22-8.18 (m, 2H), 7.35 (d, J=2.4 Hz, 1H), 3.26 (t, J=2.0 Hz, 1H), 3.23-3.06 (m, 1H), 2.80-2.70 (m, 1H), 2.68-2.63 (m, 3H), 2.50-2.44 (m, 1H), 2.02-1.96 (m, 1H), 1.68-1.59 (m, 1H), 1.12 (d, J=6.0 Hz, 3H).

Step 2: 5-bromo-3-(2-(2-methylazetidin-1-yl)ethyl)-1H-pyrrolo[2,3-b]pyridine Fumarate (S59·Fumarate)

To a stirred solution of 5-bromo-3-(2-(2-methylazetidin-1-yl)ethyl)-1H-pyrrolo[2,3-b]pyridine (0.045 g, 0.15 mmol) in acetone (2 mL) was added fumaric acid (0.018 g, 0.15 mmol) and the mixture was refluxed at 80° C. for 10 min, then cooled and left to stand at RT for 16 h. The solid was triturated with acetone, dried under reduced pressure and lyophilised from MeCN:H₂O (1:1) to afford 5-bromo-3-(2-(2-methylazetidin-1-yl)ethyl)-1H-pyrrolo[2,3-b]pyridine fumarate salt (0.045 g, 76%) as a light brown solid. LCMS (Condition C): $t_R$ (1.080 min) m/z=293.8, 295.7 [M+H]⁺, [M+2+H]⁺; ¹H NMR (400 MHz, DMSO-d₆): δ 11.67 (s, 1H), 8.28-8.23 (m, 2H), 7.38 (s, 1H), 6.53 (s, 2H), 3.69-3.65 (m, 1H), 3.58-3.54 (m, 1H), 3.19-3.17 (m, 1H), 3.06-3.04 (m, 1H), 2.85-2.76 (m, 3H), 2.18-2.16 (m, 1H), 1.87-1.82 (m, 1H), 1.28-1.23 (, J=6.0 Hz, 3H).

Example 60: Synthesis of 2-(5-bromo-1H-pyrrolo[2,3-b]pyridin-3-yl)-N-(2-fluorobenzyl)ethan-1-amine (S60)

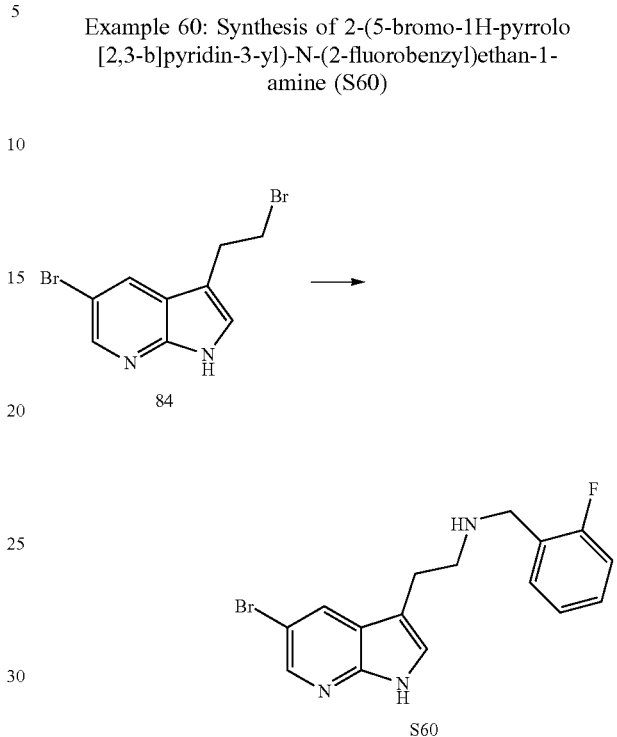

To a stirred solution of 5-bromo-3-(2-bromoethyl)-1H-pyrrolo[2,3-b]pyridine (0.4 g, 1.32 mmol) in EtOH (4 mL) was added (2-fluorophenyl) methanamine (0.49 g, 3.93 mmol) and NaI (0.19 g, 1.27 mmol) and the reaction mixture was refluxed at 90° C. for 48 h. The reaction mixture was concentrated under reduced pressure and the crude material was purified by column chromatography (45% MeOH: CH₂Cl₂:NH₄OH (1:9:0.1) in CH₂Cl₂) to afford 2-(5-bromo-1H-pyrrolo[2,3-b]pyridin-3-yl)-N-(2-fluorobenzyl)ethan-1-amine (0.14 g, 31%) as a light brown solid. LCMS (Condition C): $t_R$ (1.179 min) m/z=347.8, 349.7 [M+H]⁺, [M+2+H]⁺; ¹H NMR (400 MHz, DMSO-d₆): δ 11.60 (s, 1H), 8.22-8.17 (m, 2H), 7.44 (t, J=7.2 Hz, 1H), 7.35 (d, J=1.6 Hz, 1H), 7.30-7.26 (m, 1H), 7.17-7.11 (m, 2H), 3.80 (s, 2H), 2.89-2.82 (m, 4H).

Example 61: Synthesis of 2-(5-bromo-1H-pyrrolo[2,3-b]pyridin-3-yl)-N-(3-fluorobenzyl)ethan-1-amine (S61)

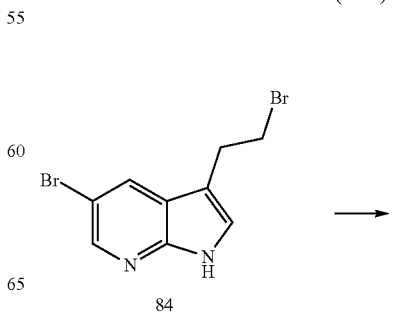

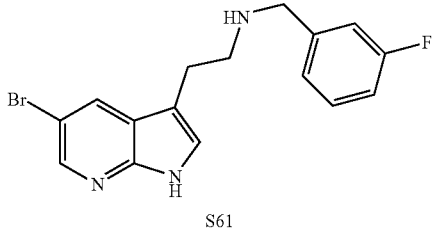

S61

Step 1: 2-(5-bromo-1H-pyrrolo[2,3-b]pyridin-3-yl)-N-(3-fluorobenzyl)ethan-1-amine (S61)

To a stirred solution of 5-bromo-3-(2-bromoethyl)-1H-pyrrolo[2,3-b]pyridine (0.5 g, 1.64 mmol) in EtOH (10 mL) was added NaI (0.24 g, 1.64 mmol) at 0° C. After 15 min, (3-fluorophenyl) methanamine (0.41 g, 3.29 mmol) was added at RT and the reaction mixture refluxed at 90° C. for 24 h. The reaction mixture was concentrated under reduced pressure, diluted with water (50 mL) and extracted with EtOAc (2×50 mL). The combined organics were washed with saturated NH$_4$Cl Solution (50 mL), dried over Na$_2$SO$_4$, and concentrated under reduced pressure. The crude material was purified by flash column chromatography (100% MeOH:CH$_2$Cl$_2$:NH$_4$OH (1:9:0.1) in CH$_2$Cl$_2$) to afford 2-(5-bromo-1H-pyrrolo[2,3-b]pyridin-3-yl)-N-(3-fluorobenzyl)ethan-1-amine (0.27 g, 57% yield) as a pale yellow sticky solid. LCMS (Condition C): t$_R$ (1.182 min) m/z=347.8, 349.8 [M+H]$^+$, [M+2+H]$^+$; $^1$H NMR (400 MHz, DMSO-d$_6$): δ 11.59 (s, 1H), 8.22 (d, J=2.0 Hz, 1H), 8.16 (d, J=2.0 Hz, 1H), 7.34-7.30 (m, 2H), 7.17-7.11 (m, 2H), 7.03 (t, J=7.2 Hz, 1H), 3.75 (s, 2H), 2.83-2.74 (m, 4H).

Step 2: 2-(5-bromo-1H-pyrrolo[2,3-b]pyridin-3-yl)-N-(3-fluorobenzyl)ethan-1-amine Fumarate (S61·Fumarate)

To a stirred solution 2-(5-bromo-1H-pyrrolo[2,3-b]pyridin-3-yl)-N-(3-fluorobenzyl)ethan-1-amine (0.27 g, 0.78 mmol) in acetone (2 mL) was added fumaric acid (0.09 g, 0.78 mmol) and the reaction mixture was refluxed at 100° C. for 5 min, then cooled and left to stand at RT for 16 h. The solid was dried under reduced pressure and then lyophilised from MeCN:H$_2$O (1:1) to afford 2-(5-bromo-1H-pyrrolo[2,3-b]pyridin-3-yl)-N-(3-fluorobenzyl)ethan-1-amine fumarate salt (0.22 g, 61%) as an off white solid. LCMS (Condition C): t$_R$ (1.887 min) m/z=347.8, 349.7 [M+H]$^+$, [M+2+H]$^+$; $^1$H NMR (400 MHz, DMSO-d$_6$): δ 11.66 (s, 1H), 8.24 (d, J=2.0 Hz, 1H), 8.20 (d, J=2.0 Hz, 1H), 7.41-7.36 (m, 2H), 7.28-7.20 (m, 2H), 7.12 (t, J=8.8 Hz, 1H), 6.55 (s, 2H), 3.93 (s, 2H), 2.91 (s, 4H).

Example 62: Synthesis of 2-(5-bromo-1H-pyrrolo[2,3-b]pyridin-3-yl)-N-(2-methoxybenzyl)ethan-1-amine (S62)

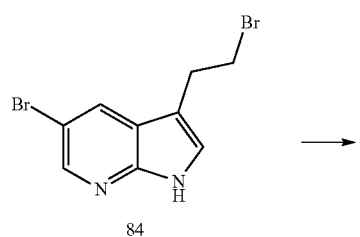

84

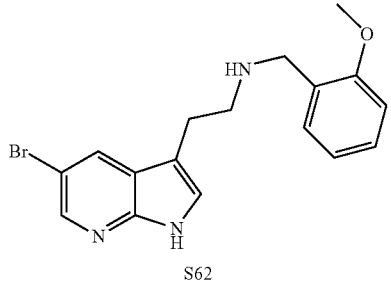

S62

Step 1: 2-(5-bromo-1H-pyrrolo[2,3-b]pyridin-3-yl)-N-(2-methoxybenzyl)ethan-1-amine (S62)

To a stirred solution of 5-bromo-3-(2-bromoethyl)-1H-pyrrolo[2,3-b]pyridine (0.4 g, 1.32 mmol) in EtOH (20 mL) was added NaI (0.19 g, 1.27 mmol) at under nitrogen atmosphere. After 15 min (2-methoxyphenyl) methanamine (0.54 g, 3.94 mmol) was added at 0° C. and the reaction mixture was stirred at 90° C. for 22 h. The reaction mixture was concentrated under reduced pressure, treated with saturated aq. NH$_4$Cl solution (20 mL) and extracted with EtOAc (30 mL). The combined organics were dried over Na$_2$SO$_4$ and concentrated under reduced pressure to get crude material, which was purified by flash column chromatography (70% MeOH:CH$_2$Cl$_2$:NH$_4$OH (1:9:0.01) in CH$_2$Cl$_2$) to afford 2-(5-bromo-1H-pyrrolo[2,3-b]pyridin-3-yl)-N-(2-methoxybenzyl)ethan-1-amine (0.2 g, 42%) as a pale yellow sticky solid. LCMS (Condition C): t$_R$ (1.219 min) m/z=359.9, 361.8 [M+H]$^+$, [M+2+H]$^+$; $^1$H NMR (400 MHz, DMSO-d$_6$): δ 11.59 (s, 1H), 8.22 (d, J=2.0 Hz, 1H), 8.14 (d, J=2.4 Hz, 1H), 7.33 (d, J=2.0, 1H), 7.26 (d, J=7.2 Hz, 1H), 7.21-7.17 (m, 1H), 6.92-6.85 (m, 2H), 3.68 (s, 5H), 2.81-2.76 (m, 4H).

Step 2: 2-(5-bromo-1H-pyrrolo[2,3-b]pyridin-3-yl)-N-(2-methoxybenzyl)ethan-1-amine Fumarate (S62·Fumarate)

To a stirred solution of 2-(5-bromo-1H-pyrrolo[2,3-b]pyridin-3-yl)-N-(2-methoxybenzyl)ethan-1-amine (0.2 g, 0.56 mmol) in acetone (2.0 mL) was added fumaric acid (0.06 g, 0.52 mmol) and the reaction mixture was refluxed at 60° C. for 10 min, then cooled and left to stand at RT for 16 h. The solid material was dried under reduced pressure and lyophilised from (MeCN:H$_2$O (1:1)) to afford 2-(5-bromo-1H-pyrrolo[2,3-b]pyridin-3-yl)-N-(2-methoxybenzyl)ethan-1-amine fumarate salt (0.22 g, 83%) as an off white solid. LCMS (Condition C): t$_R$ (1.210 min) m/z=359.9, 361.8 [M+H]$^+$, [M+2+H]$^+$; 1H NMR (400 MHz, DMSO-d$_6$): δ 11.73 (s, 1H), 8.27-8.21 (m, 2H), 7.41-7.32 (m, 3H), 7.02 (d, J=8.4 Hz, 1H), 6.95 (t, J=7.2 Hz, 1H), 6.54 (s, 2H), 4.01 (s, 2H), 3.77 (s, 3H), 3.04-2.99 (m, 4H).

Example 63: Synthesis of 2-(5-bromo-1H-pyrrolo[2,3-b]pyridin-3-yl)-N-(3-methoxybenzyl)ethan-1-amine (S63)

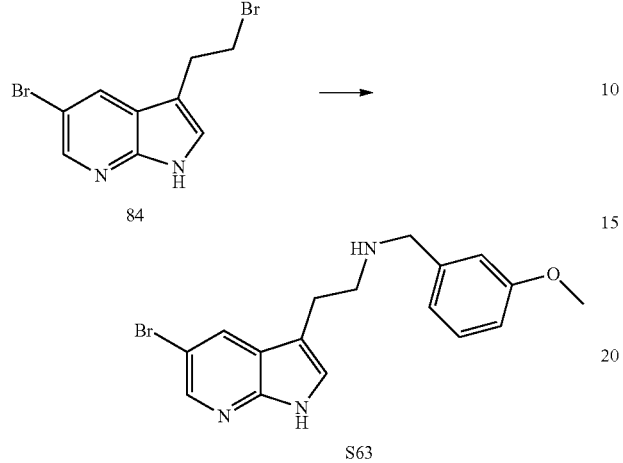

Step 1: 2-(5-bromo-1H-pyrrolo[2,3-b]pyridin-3-yl)-N-(3-methoxybenzyl)ethan-1-amine (S63)

To a stirred solution of 5-bromo-3-(2-bromoethyl)-1H-pyrrolo[2,3-b]pyridine (0.4 g, 1.32 mmol) in EtOH (6 mL) was added (3-methoxyphenyl) methanamine (0.54 g, 3.94 mmol) and NaI (0.19 g, 1.27 mmol) and the reaction mixture was stirred at RT for 18 h. The reaction mixture was quenched with aq. NH$_4$Cl solution (50 mL) and extracted with EtOAc (3×150 mL). The combined organics were dried over Na$_2$SO$_4$ and concentrated under reduced pressure and the crude material was purified by flash column chromatography (90% MeOH:CH$_2$Cl$_2$:NH$_4$OH (1:9:0.1) in CH$_2$Cl$_2$) to afford 2-(5-bromo-1H-pyrrolo[2,3-b]pyridin-3-yl)-N-(3-methoxybenzyl)ethan-1-amine (0.23 g, 49%) as a pale yellow sticky solid. LCMS (Condition C): t$_R$ (1.197 min) m/z=359.9, 361.9 [M+H]$^+$, [M+2+H]$^+$; $^1$H NMR (400 MHz, DMSO-d$_6$): δ 11.62 (s, 1H), 8.23 (d, J=2.0 Hz, 1H), 8.18 (d, J=2.0 Hz, 1H), 7.36 (d, J=2.0 Hz, 1H), 7.22 (t, J=7.6 Hz, 1H), 6.93-6.88 (m, 2H), 6.81-6.79 (m, 1H), 3.78 (s, 2H), 3.71 (s, 3H), 2.89-2.81 (m, 4H).

Step 2: 2-(5-bromo-1H-pyrrolo[2,3-b]pyridin-3-yl)-N-(3-methoxybenzyl)ethan-1-amine Fumarate (S63·Fumarate)

To a stirred solution of 2-(5-bromo-1H-pyrrolo[2,3-b]pyridin-3-yl)-N-(3-methoxybenzyl)ethan-1-amine (0.23 g, 0.64 mmol) in acetone (2 mL) was added fumaric acid (0.07 g, 0.60 mmol) and the reaction mixture was refluxed at 90° C. for 10 min, then cooled and left to stand at RT for 16 h. The solid was triturated with acetone, dried under reduced pressure and lyophilised from MeCN:H$_2$O (1:1) to afford 2-(5-bromo-1H-pyrrolo[2,3-b]pyridin-3-yl)-N-(3-methoxybenzyl)ethan-1-amine fumarate salt (0.23 g, 76%) as an off white solid. LCMS (Condition C): t$_R$ (1.193 min) m/z=359.9, 361.9 [M+H]$^+$, [M+2+H]$^+$; $^1$H NMR (400 MHz, DMSO-d$_6$): δ 11.70 (s, 1H), 8.27-8.20 (m, 2H), 7.41 (d, J=2.0 Hz, 1H), 7.29 (t, J=8.0 Hz, 1H), 7.04 (s, 1H), 6.99 (d, J=7.2 Hz, 1H), 6.90 (dd, J=8.4, 2.4 Hz, 1H), 6.56 (s, 2H), 3.99 (s, 2H), 3.74 (s, 3H), 3.05-2.98 (m, 4H).

Example 64: Synthesis of N-ethyl-N-methyl-2-(5-(trifluoromethoxy)-1H-pyrrolo[2,3-b]pyridin-3-yl)ethan-1-amine (S64)

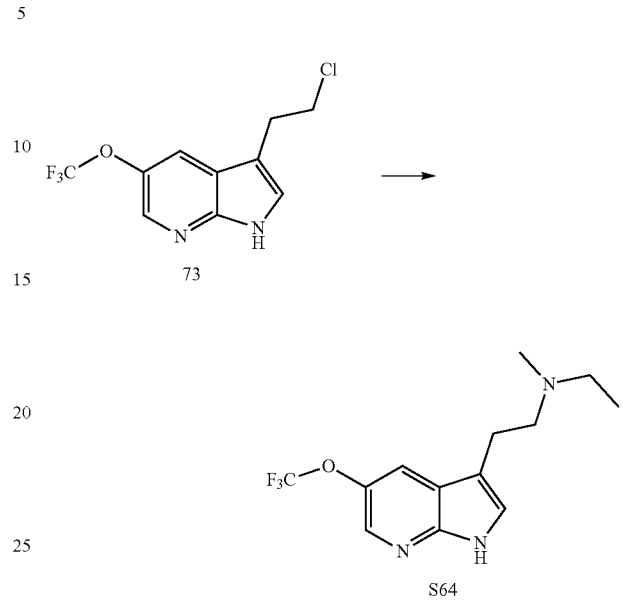

To a solution of 3-(2-chloroethyl)-5-(trifluoromethoxy)-1H-pyrrolo[2,3-b]pyridine (50 mg, 0.19 mmol) and N-methylethanamine (33 μL, 0.38 mmol) in DMF (2.00 mL) was added K$_2$CO$_3$ (52 mg, 0.38 mmol) and the mixture was stirred at 50° C. for 10 h. The reaction mixture was quenched with H$_2$O (30 mL) and extracted with EtOAc (2×10 mL). The combined organics were washed with brine (10 mL), dried over Na$_2$SO$_4$ and concentrated under reduced pressure. The residue was purified by prep-HPLC (column: Waters Xbridge Prep OBD C18 150×40 mm, 10 um; mobile phase: [H$_2$O (10 mM NH$_4$HCO$_3$)-MeCN]; gradient: 10%-40% B over 8.0 min) to provide N-ethyl-N-methyl-2-(5-(trifluoromethoxy)-1H-pyrrolo[2,3-b]pyridin-3-yl)ethan-1-amine (20 mg, 37%) as an off-white solid. LCMS (Condition B): t$_R$ (1.826 min) m/z=288 [M+H]$^+$; $^1$H NMR (400 MHz, CDCl$_3$): δ 8.88 (br s, 1H), 8.24 (s, 1H), 7.81 (s, 1H), 7.26 (s, 1H), 3.01-2.91 (m, 2H), 2.79-2.70 (m, 2H), 2.64-2.54 (m, 2H), 2.39 (s, 3H), 1.14 (t, J=7.1 Hz, 3H); $^{19}$F NMR (376 MHz, CDCl$_3$): δ −58.6.

Example 65: Synthesis of N-methyl-N-(2-(5-(trifluoromethoxy)-1H-pyrrolo[2,3-b]pyridin-3-yl)ethyl)propan-2-amine (S65)

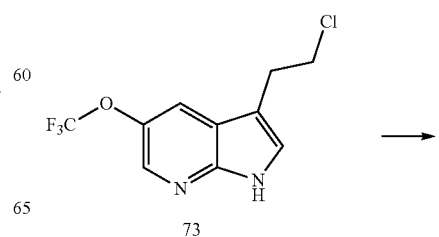

159
-continued

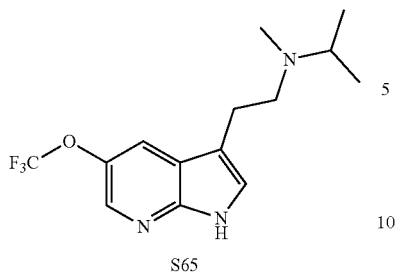

S65

To a solution of 3-(2-chloroethyl)-5-(trifluoromethoxy)-1H-pyrrolo[2,3-b]pyridine (100 mg, 0.38 mmol) and N-methylpropan-2-amine (55.3 mg, 0.76 mmol, 79 µL) in DMF (2.00 mL) was added $K_2CO_3$ (104 mg, 0.75 mmol) and the mixture was stirred at 50° C. for 10 h. The reaction mixture was quenched with $H_2O$ (30 mL) and extracted with EtOAc (2×10 mL). The combined organics were washed with brine (10 mL), dried over $Na_2SO_4$ and concentrated under reduced pressure. The residue was purified by prep-HPLC (column: Waters Xbridge Prep OBD C18 150×40 mm, 10 um; mobile phase: [$H_2O$ (10 mM $NH_4HCO_3$)-MeCN]; gradient: 20%-60% B over 8.0 min) to provide N-methyl-N-(2-(5-(trifluoromethoxy)-1H-pyrrolo[2,3-b]pyridin-3-yl)ethyl)propan-2-amine (20 mg, 18% yield) as a yellow solid. LCMS (Condition B): $t_R$ (1.90 min) m/z=302 [M+H]$^+$; $^1$H NMR (400 MHz, $CD_3CN$): δ 9.59 (br s, 1H), 8.19 (d, J=2.0 Hz, 1H), 7.92 (s, 1H), 7.32 (d, J=2.0 Hz, 1H), 2.88-2.78 (m, 3H), 2.69-2.62 (m, 2H), 2.24 (s, 3H), 0.94 (d, J=6.6 Hz, 6H); $^{19}$F NMR (376 MHz, $CDCl_3$): δ −59.3.

Example 66: Synthesis of 3-(2-(ethyl(methyl)amino)ethyl)-1H-pyrrolo[2,3-b]pyridine-5-carbonitrile (S66)

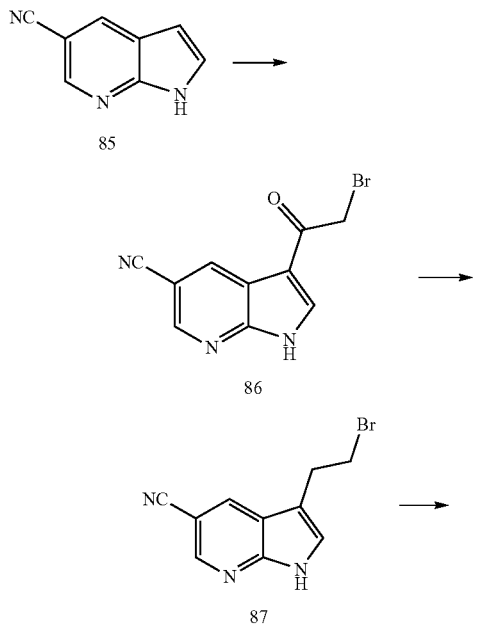

160
-continued

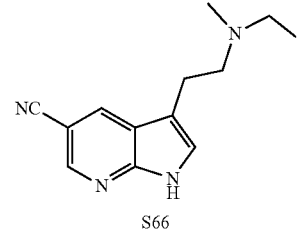

S66

Step 1: 3-(2-bromoacetyl)-1H-pyrrolo[2,3-b]pyridine-5-carbonitrile (86)

To a stirred solution of 1H-pyrrolo[2,3-b]pyridine-5-carbonitrile (0.5 g, 3.49 mmol) in $CS_2$ (150 mL) was added $AlCl_3$ (1.86 g, 14.0 mmol) at 0° C. under nitrogen atmosphere. After 30 min, 2-bromoacetyl bromide (1.75 g, 8.67 mmol) was added at 0° C. and the reaction mixture was stirred at RT for 16 h. The reaction mixture was quenched by dropwise addition of saturated aq. $NaHCO_3$ solution (120 mL) and then extracted with EtOAc (2×200 mL). The combined organics were dried over $Na_2SO_4$ then concentrated under reduced pressure and the crude material was purified by column chromatography (48% EtOAc/hexane) to afford 3-(2-bromoacetyl)-1H-pyrrolo[2,3-b]pyridine-5-carbonitrile (0.3 g, 33% yield) as an off white solid. LCMS (Condition B): $t_R$ (1.305 min) m/z=261.93, 263.83 [M−H]$^-$, [M+2−H]$^-$; $^1$H NMR (400 MHz, DMSO-$d_6$): δ 13.27 (s, 1H), 8.84 (d, J=3.2 Hz, 1H), 8.82 (d, J=2.0 Hz, 1H), 8.78 (d, J=2.0 Hz, 1H), 4.75 (s, 2H).

Step 2: 3-(2-bromoethyl)-1H-pyrrolo[2,3-b]pyridine-5-carbonitrile (87)

To a stirred solution of 3-(2-bromoacetyl)-1H-pyrrolo[2,3-b]pyridine-5-carbonitrile (0.6 g, 2.27 mmol) in TFA (5.0 mL) at 0° C. was added $Et_3SiH$ (2.0 mL) dropwise and the mixture was stirred at RT for 48 h under nitrogen atmosphere. The reaction mixture was quenched by dropwise addition of saturated $NaHCO_3$ solution (100 mL) and extracted with EtOAc (2×150 mL). The combined organics were dried over $Na_2SO_4$ then concentrated under reduced pressure and the crude material was purified by column chromatography (50% EtOAc/hexane) to afford 3-(2-bromoethyl)-1H-pyrrolo[2,3-b]pyridine-5-carbonitrile (0.4 g, 50%) as a white solid. LCMS (Condition C): $t_R$ (1.462 min) m/z=249.8, 251.8 [M+H]$^+$, [M+2+H]$^+$; $^1$H NMR (400 MHz, DMSO-$d_6$): δ 12.18 (s, 1H), 8.66 (d, J=4.0 Hz, 1H), 8.58 (d, J=1.6 Hz, 1H), 7.62 (d, J=2.0 Hz, 1H), 3.78 (t, J=7.2 Hz, 2H), 3.25 (t, J=7.2 Hz, 2H).

Step 3: 3-(2-(ethyl(methyl)amino)ethyl)-1H-pyrrolo[2,3-b]pyridine-5-carbonitrile (S66)

To a stirred solution of 3-(2-bromoethyl)-1H-pyrrolo[2,3-b]pyridine-5-carbonitrile (0.3 g, 1.20 mmol) in EtOH (10 mL) was added NaI (0.17 g, 1.13 mmol) at rt. After 10 min, N-methylethanamine (0.1 g, 1.69 mmol) was added and the mixture was stirred at 90° C. for 16 h. The reaction mixture was concentrated under reduced pressure, diluted with saturated aq. $NH_4Cl$ solution (150 mL) and extracted with 25% IPA in $CHCl_3$ (3×100 mL). The combined organic layers were dried over $Na_2SO_4$, concentrated under reduced pressure and the crude material was purified by flash column chromatography (product eluted at 35% MeOH:$CH_2Cl_2$:

NH$_4$OH (1:9:0.01) in CH$_2$Cl$_2$) to afford 3-(2-(ethyl(methyl)amino)ethyl)-1H-pyrrolo[2,3-b]pyridine-5-carbonitrile (0.13 g, 47%) as an off-white solid. LCMS (Condition C): t$_R$ (0.911 min) m/z=229.0 [M+H]$^+$; $^1$H NMR (400 MHz, DMSO-d$_6$): δ 8.52 (d, J=2.0 Hz, 1H), 8.45 (d, J=2.0 Hz, 1H), 7.45 (s, 1H), 3.05-3.01 (m, 2H), 2.88-2.84 (m, 2H), 2.71 (q, J=7.2 Hz, 2H), 2.47 (s, 3H), 1.18 (t, J=7.2 Hz, 3H).

Step 4: 3-(2-(ethyl(methyl)amino)ethyl)-1H-pyrrolo[2,3-b]pyridine-5-carbonitrile Fumarate (S66·Fumarate)

To a stirred solution of 3-(2-(ethyl(methyl)amino)ethyl)-1H-pyrrolo[2,3-b]pyridine-5-carbonitrile (0.13 g, 0.57 mmol) in acetone (2.0 mL) was added fumaric acid (0.07 g, 0.57 mmol) at RT and the reaction mixture was refluxed at 80° C. for 10 min, then cooled and left to stand at RT for 16 h. The solid was triturated with acetone, dried under reduced pressure and lyophilised from MeCN:H$_2$O (1:1) to afford 3-(2-(ethyl(methyl)amino)ethyl)-1H-pyrrolo[2,3-b]pyridine-5-carbonitrile fumarate salt (0.13 g, 66% yield) as a white solid. LCMS (Condition C): t$_R$ (0.931 min) m/z=228.93 [M+H]$^+$; $^1$H NMR (400 MHz, DMSO-d$_6$): δ 12.15 (s, 1H), 8.63 (d, J=1.6 Hz, 1H), 8.58 (d, J=1.6 Hz, 1H), 7.57 (s, 1H), 6.54 (s, 2H), 3.01 (s, 4H), 2.86 (q, J=7.2 Hz, 2H), 2.56 (s, 3H), 1.12 (t, J=7.2 Hz, 3H).

Example 67: Synthesis of 3-(2-(isopropyl(methyl)amino)ethyl)-1H-pyrrolo[2,3-b]pyridine-5-carbonitrile (S67)

(methyl)amino)ethyl)-1H-pyrrolo[2,3-b]pyridine-5-carbonitrile (0.29 g, 60%) as a pale yellow solid. LCMS (Condition C): t$_R$ (0.961 min) m/z=243.0 [M+H]$^+$; $^1$H NMR (400 MHz, DMSO-d$_6$): δ 12.03 (s, 1H), 8.57-8.53 (m, 2H), 7.50 (s, 1H), 2.86-2.78 (m, 3H), 2.65-2.63 (m, 2H), 2.22 (s, 3H), 0.93 (d, J=6.4 Hz, 6H).

Step 2: 3-(2-(isopropyl(methyl)amino)ethyl)-1H-pyrrolo[2,3-b]pyridine-5-carbonitrile Fumarate (S67·Fumarate)

To a stirred solution of 3-(2-(isopropyl(methyl)amino)ethyl)-1H-pyrrolo[2,3-b]pyridine-5-carbonitrile (0.28 g, 1.16 mmol) in acetone (2.0 mL) was added fumaric acid (0.14 g, 1.16 mmol) and the mixture was refluxed at 100° C. for 10 min, then cooled and left to stand at RT for 24 h. The solid was dried under reduced pressure and lyophilised from MeCN:H$_2$O (1:1) to afford 3-(2-(isopropyl(methyl)amino)ethyl)-1H-pyrrolo[2,3-b]pyridine-5-carbonitrile fumarate salt (0.3 g, 72%) as a white solid. LCMS (Condition C): t$_R$ (0.960 min) m/z=243.0 [M+H]$^+$; $^1$H NMR (400 MHz, DMSO-d$_6$): δ 12.14 (s, 1H), 8.61 (d, J=1.6 Hz, 1H), 8.57 (d, J=1.6 Hz, 1H), 7.56 (d, J=2.0 Hz, 1H), 6.53 (s, 2H), 3.23-3.19 (m, 1H), 2.99-2.91 (m, 4H), 2.461 (s, 3H), 1.07 (d, J=6.4 Hz, 6H).

Example 68: Synthesis of 3-(2-(cyclopropyl(methyl)amino)ethyl)-1H-pyrrolo[2,3-b]pyridine-5-carbonitrile (S68)

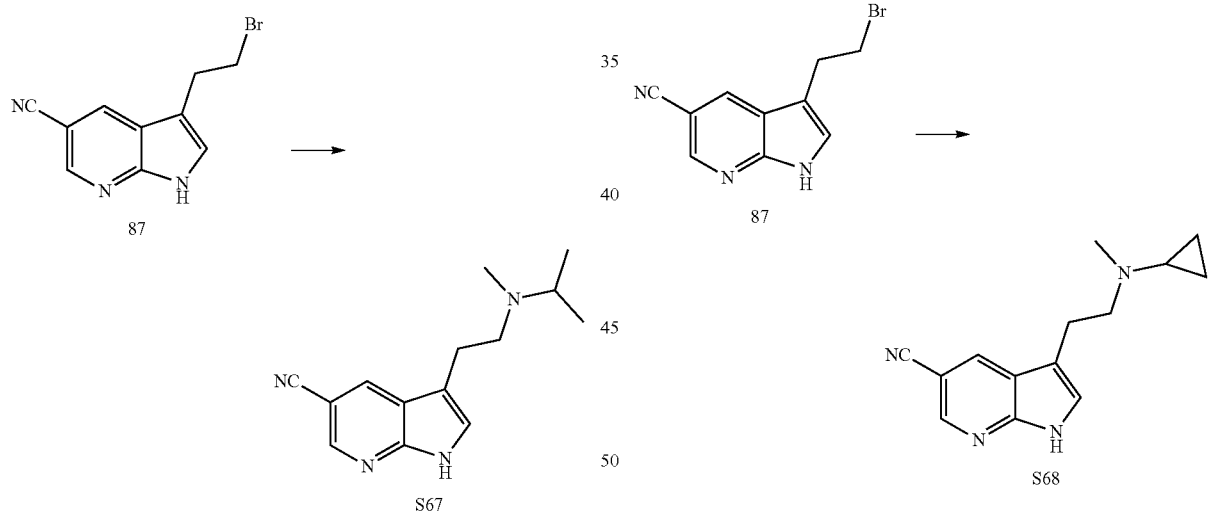

Step 1: 3-(2-(isopropyl(methyl)amino)ethyl)-1H-pyrrolo[2,3-b]pyridine-5-carbonitrile (S67)

To a stirred solution of 3-(2-bromoethyl)-1H-pyrrolo[2,3-b]pyridine-5-carbonitrile (0.5 g, 1.99 mmol) in EtOH (10 mL) was added NaI (0.30 g, 1.99 mmol) and N-methylpropan-2-amine (0.29 g, 3.99 mmol) and the mixture was stirred at 90° C. for 24 h. The reaction mixture was cooled to rt, poured into water (100 mL) and extracted with CH$_2$Cl$_2$ (2×50 mL). The combined organics were dried over Na$_2$SO$_4$, concentrated under reduced pressure and the crude material was purified by flash chromatography (20% MeOH in CH$_2$Cl$_2$ with 0.2% NH$_4$OH) to afford 3-(2-(isopropyl Step 1: 3-(2-(cyclopropyl(methyl)amino)ethyl)-1H-pyrrolo[2,3-b]pyridine-5-carbonitrile (S68)

To a stirred solution of 3-(2-bromoethyl)-1H-pyrrolo[2,3-b]pyridine-5-carbonitrile (0.31 g, 1.23 mmol) in EtOH (15 mL) was added NaI (0.18 g, 1.23 mmol) and Et$_3$N (0.52 ml, 3.71 mmol) at 0° C. under nitrogen atmosphere. After 20 min, a solution of N-methylcyclopropanamine (0.17 g, 2.47 mmol) in EtOH (2 mL) was added and the mixture was stirred at 90° C. for 24 h. The reaction mixture was cooled to RT, poured into water (70 mL) and extracted with CH$_2$Cl$_2$ (2×50 mL). The combined organics were dried over Na$_2$SO$_4$ and concentrated under reduced pressure. The crude material was purified by flash chromatography (SiO$_2$, 4% MeOH in $CH_2Cl_2$) to afford 3-(2-(cyclopropyl(methyl)amino)ethyl)-1H-pyrrolo[2,3-b]pyridine-5-carbonitrile (0.096 g, 32%) as an off white solid. LCMS (Condition C): $t_R$ (0.986 min) m/z=241.0 $[M+H]^+$; $^1$H NMR (400 MHz, DMSO-$d_6$): δ 12.02 (s, 1H), 8.55 (d, J=2.0 Hz, 1H), 8.52 (d, J=2.0 Hz, 1H), 7.49 (d, J=2.4 1H), 2.88-2.84 (m, 2H), 2.78-2.74 (m, 2H), 2.34 (s, 3H), 1.70-1.67 (m, 1H), 0.43-0.39 (m, 2H), 0.26-0.23 (m, 2H).

Step 2: 3-(2-(cyclopropyl(methyl)amino)ethyl)-1H-pyrrolo[2,3-b]pyridine-5-carbonitrile Fumarate (S68·Fumarate)

To a stirred solution of 3-(2-(cyclopropyl(methyl)amino)ethyl)-1H-pyrrolo[2,3-b]pyridine-5-carbonitrile (0.096 g, 0.39 mmol) in acetone (2.0 mL) was added fumaric acid (0.046 g, 0.39 mmol) and the reaction mixture was refluxed at 100° C. for 20 min, then cooled and left to stand at RT for 16 h. The solid was dried under reduced pressure and then lyophilised from $MeCN:H_2O$ (1:1) to afford 3-(2-(cyclopropyl(methyl)amino)ethyl)-1H-pyrrolo[2,3-b]pyridine-5-carbonitrile fumarate salt (0.12 g, 84%) as a white solid. LCMS (Condition C): $t_R$ (0.981 min) m/z=241.03 $[M+H]^+$; $^1$H NMR (400 MHz, DMSO-$d_6$): δ 12.04 (s, 1H), 8.56-8.52 (m, 2H), 7.49 (s, 1H), 6.61 (s, 2H), 2.891-2.86 (m, 2H), 2.83-2.79 (m, 2H), 2.37 (s, 3H), 1.79-1.75 (m, 1H), 0.46-0.42 (m, 2H), 0.30-0.29 (m, 2H).

Example 69: Synthesis of 3-(2-(cyclopropyl(methyl)amino)ethyl)-1H-pyrrolo[2,3-b]pyridine-5-carbonitrile (S69)

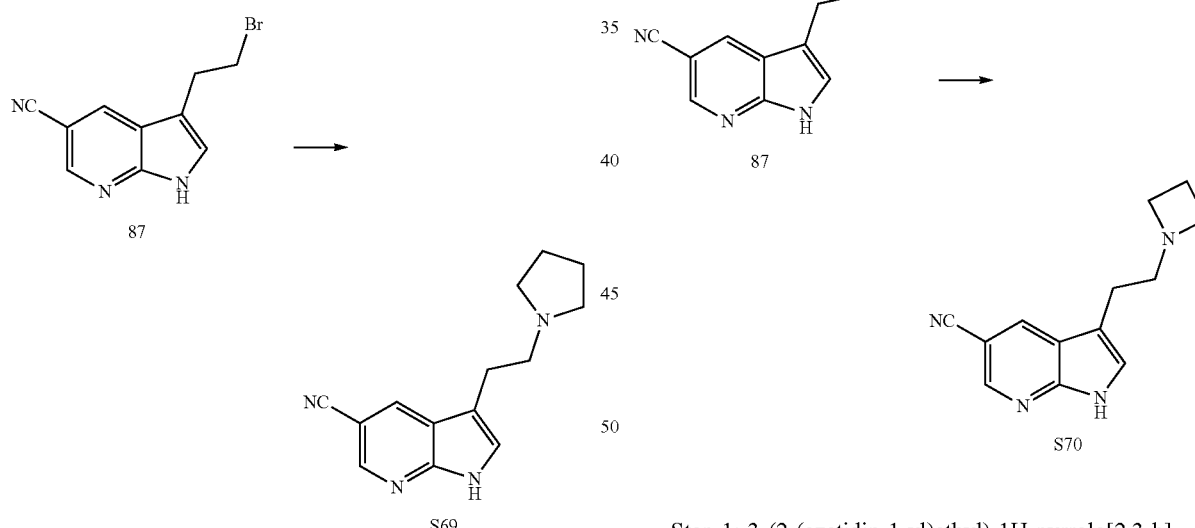

Step 1: 3-(2-(pyrrolidin-1-yl)ethyl)-1H-pyrrolo[2,3-b]pyridine-5-carbonitrile (S69)

To a stirred solution of 3-(2-bromoethyl)-1H-pyrrolo[2,3-b]pyridine-5-carbonitrile (0.36 g, 1.44 mmol) in EtOH (10 mL) was added NaI (0.21 g, 1.44 mmol) and pyrrolidine (0.15 g, 2.16 mmol) and the mixture was stirred at 90° C. for 16 h. The reaction mixture was cooled to rt, poured into water (150 mL) and extracted with 10% iPrOH in $CHCl_3$ (6×100 mL). The combined organics were dried over $Na_2SO_4$ and concentrated under reduced pressure. The crude material was purified by column chromatography ($SiO_2$, 8% MeOH in $CH_2Cl_2$) to afford 3-(2-(pyrrolidin-1-yl)ethyl)-1H-pyrrolo[2,3-b]pyridine-5-carbonitrile (0.12 g, 35%) as an off white solid. LCMS (Condition C): $t_R$ (0.946 min) m/z=241.0 $[M+H]^+$; $^1$H NMR (400 MHz, DMSO-$d_6$): δ 12.23 (s, 1H), 8.68 (d, J=1.6 Hz, 1H), 8.61 (d, J=2.0 Hz, 1H), 7.63 (d, J=2.0 Hz, 1H), 3.52-3.33 (m, 4H), 3.17-3.06 (m, 4H), 1.98-1.79 (m, 4H).

Step 2: 3-(2-(pyrrolidin-1-yl)ethyl)-1H-pyrrolo[2,3-b]pyridine-5-carbonitrile Fumarate (S69·Fumarate)

To a stirred solution of 3-(2-(pyrrolidin-1-yl)ethyl)-1H-pyrrolo[2,3-b]pyridine-5-carbonitrile (0.06 g, 0.25 mmol) in acetone (2.0 mL) was added fumaric acid (0.03 g, 0.24 mmol) and the reaction mixture was refluxed at 100° C. for 10 min, then cooled and left to stand at RT for 16 h. The solid was triturated with acetone, dried under reduced pressure and then lyophilised from 1:1 $MeCN:H_2O$ to afford 3-(2-(pyrrolidin-1-yl)ethyl)-1H-pyrrolo[2,3-b]pyridine-5-carbonitrile fumarate salt (75 mg, 80%) as a white solid. LCMS (Condition C): $t_R$ (0.983 min) m/z=240.9 $[M+H]^+$; $^1$H NMR (400 MHz, DMSO-$d_6$): δ 12.17 (s, 1H), 8.64 (d, J=1.6 Hz, 1H), 8.59 (d, J=2.0 Hz, 1H), 7.59 (d, J=2.0 Hz, 1H), 6.57 (s, 2H), 3.23-3.19 (m, 2H), 3.11-3.02 (m, 6H), 1.87 (s, 4H).

Example 70: Synthesis of 3-(2-(azetidin-1-yl)ethyl)-1H-pyrrolo[2,3-b]pyridine-5-carbonitrile (S70)

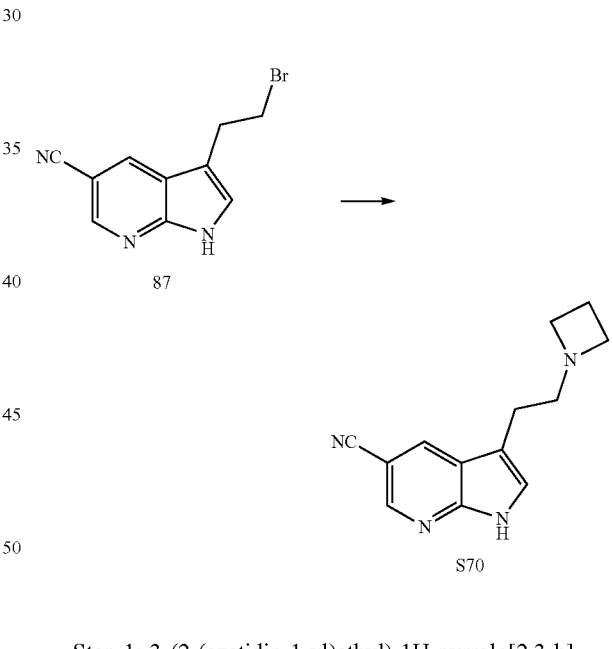

Step 1: 3-(2-(azetidin-1-yl)ethyl)-1H-pyrrolo[2,3-b]pyridine-5-carbonitrile (S70)

To a stirred solution of 3-(2-bromoethyl)-1H-pyrrolo[2,3-b]pyridine-5-carbonitrile (0.5 g, 1.99 mmol) in EtOH (15 mL) was added NaI (0.30 g, 1.99 mmol) at 0° C. under nitrogen atmosphere. After 15 min, azetidine (0.23 g, 3.99 mmol) was added and the resulting reaction mixture was stirred at 90° C. for 10 h. The reaction mixture was poured into water (100 mL) and extracted with $CH_2Cl_2$ (2×60 mL). The combined organics were dried over $Na_2SO_4$, concentrated under reduced pressure and the crude material was purified by flash chromatography (96% $MeOH:CH_2Cl_2$:$NH_4OH$ (1:9:0.1) in $CH_2Cl_2$) to afford 3-(2-(azetidin-1-yl)

ethyl)-1H-pyrrolo[2,3-b]pyridine-5-carbonitrile (0.06 g, 13%) as a white solid. LCMS (Condition C): t$_R$ (0.959 min) m/z=226.9 [M+H]$^+$; $^1$H NMR (400 MHz, DMSO-d$_6$): δ 12.03 (s, 1H), 8.56-8.54 (m, 2H), 7.48 (s, 1H), 3.11 (t, J=6.8 Hz, 4H), 2.66-2.62 (m, 4H), 1.95-1.92 (m, 2H).

Step 2: 3-(2-(azetidin-1-yl)ethyl)-1H-pyrrolo[2,3-b]pyridine-5-carbonitrile Fumarate (S70·Fumarate)

To a stirred solution of 3-(2-(azetidin-1-yl)ethyl)-1H-pyrrolo[2,3-b]pyridine-5-carbonitrile (0.06 g, 0.26 mmol) in acetone (2.0 mL) was added fumaric acid (0.03 g, 0.26 mmol) and the reaction mixture was refluxed at 80° C. for 10 min, then cooled and left to stand at RT for 16 h. The solid was dried under reduced pressure and lyophilised from MeCN:H$_2$O (1:1) to afford 3-(2-(azetidin-1-yl)ethyl)-1H-pyrrolo[2,3-b]pyridine-5-carbonitrile fumarate salt (0.07 g, 75% yield) as an off white solid. LCMS (Condition C): t$_R$ (0.958 min) m/z=225.9 [M+H]$^+$; $^1$H NMR (400 MHz, DMSO-d$_6$): δ 12.14 (s, 1H), 8.64-8.58 (m, 2H), 7.54 (s, 1H), 6.54 (s, 2H), 3.60 (t, J=6.8 Hz, 4H), 3.05-3.02 (m, 2H), 2.82 (t, J=7.2 Hz, 2H), 2.14 (t, J=7.6 Hz, 2H).

Example 71: Synthesis of 3-(2-(2-methylazetidin-1-yl)ethyl)-1H-pyrrolo[2,3-b]pyridine-5-carbonitrile (S71)

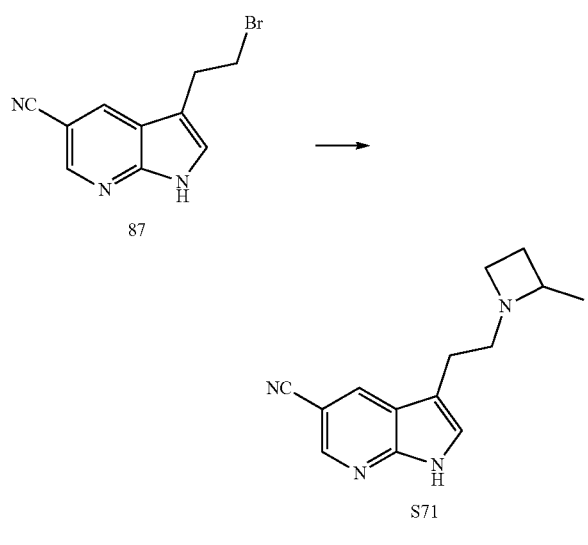

Step 1: 3-(2-(2-methylazetidin-1-yl)ethyl)-1H-pyrrolo[2,3-b]pyridine-5-carbonitrile (S71)

To a stirred solution of 3-(2-bromoethyl)-1H-pyrrolo[2,3-b]pyridine-5-carbonitrile (0.4 g, 1.59 mmol) in EtOH (4 mL) was added NaI (0.24 g, 1.59 mmol), Et$_3$N (0.4 mL, 3.19 mmol) and 2-methylazetidine hydrochloride (0.51 g, 4.79 mmol) and the reaction mixture was stirred at 100° C. for 2 h under microwave irradiation. The reaction mixture was concentrated under reduced pressure and the crude material was purified by reverse phase column chromatography (0.05% formic acid in H$_2$O/MeCN) to afford 3-(2-(2-methylazetidin-1-yl)ethyl)-1H-pyrrolo[2,3-b]pyridine-5-carbonitrile (0.1 g, 26%) as an off white solid. LCMS (Condition C): t$_R$ (0.990 min) m/z=241.0 [M+H]$^+$; $^1$H NMR (400 MHz, DMSO-d$_6$): δ 12.13 (s, 1H), 8.63 (d, J=1.6 Hz, 1H), 8.58 (d, J=1.6 Hz, 1H), 7.55 (s, 1H), 3.80-3.78 (m, 1H), 3.59-3.57 (m, 1H), 3.31-3.29 (m, 1H), 3.18-3.11 (m, 1H), 2.95-2.90 (m, 1H), 2.83 (t, J=7.6 Hz, 2H), 2.21-2.19 (m, 1H), 1.89-1.85 (m, 1H), 1.29 (d, J=6.4 Hz, 3H).

Example 72: Synthesis of 3-(2-((2-fluorobenzyl)amino)ethyl)-1H-pyrrolo[2,3-b]pyridine-5-carbonitrile (S72)

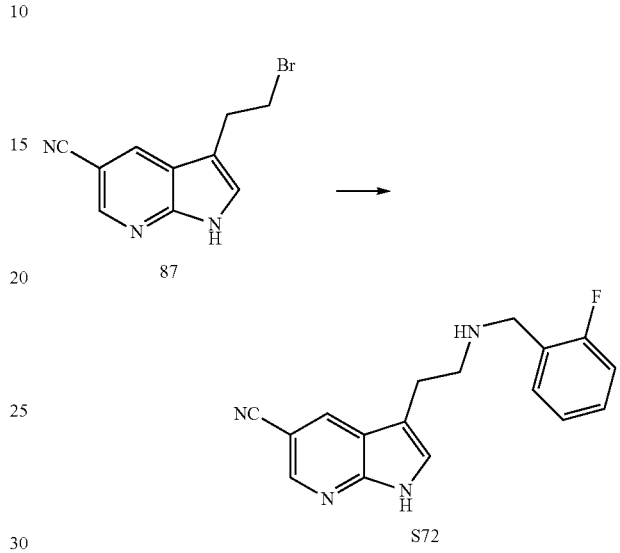

Step 1: 3-(2-((2-fluorobenzyl)amino)ethyl)-1H-pyrrolo[2,3-b]pyridine-5-carbonitrile (S72)

To a stirred solution of 3-(2-bromoethyl)-1H-pyrrolo[2,3-b]pyridine-5-carbonitrile (0.35 g, 1.39 mmol) in EtOH (10 mL) was added NaI (0.2 g, 1.39 mmol) at rt. After 10 min, (2-fluorophenyl) methanamine (0.26 g, 2.10 mmol) was added and the mixture was stirred at 90° C. for 16 h. The reaction mixture was concentrated under reduced pressure, treated with saturated aq. NH$_4$Cl solution (150 mL) and extracted with 20% MeOH in CH$_2$Cl$_2$ (3×100 mL). The combined organics were dried over Na$_2$SO$_4$ and concentrated under reduced pressure. The crude material was purified by column chromatography (30% MeOH:CH$_2$Cl$_2$:NH$_4$OH (1:9:0.1) in CH$_2$Cl$_2$) to afford 3-(2-((2-fluorobenzyl)amino)ethyl)-1H-pyrrolo[2,3-b]pyridine-5-carbonitrile (0.11 g, 27%) as an off-white solid. LCMS (Condition C): t$_R$ (1.542 min) m/z=294.82 [M+H]$^+$; $^1$H NMR (400 MHz, DMSO-d$_6$): δ 12.16 (br s, 1H), 8.57-8.53 (m, 2H), 7.50-7.43 (m, 2H), 7.32-7.26 (m, 1H), 7.16-7.11 (m, 2H), 3.83 (s, 2H), 2.92-2.84 (m, 4H).

Step 2: 3-(2-((2-fluorobenzyl)amino)ethyl)-1H-pyrrolo[2,3-b]pyridine-5-carbonitrile Fumarate (S72·Fumarate)

To a stirred solution of 3-(2-((2-fluorobenzyl)amino)ethyl)-1H-pyrrolo[2,3-b]pyridine-5-carbonitrile (0.11 g, 0.37 mmol) in acetone (2.0 mL) was added fumaric acid (0.043 g, 0.37 mmol) and the reaction mixture was refluxed at 70° C. for 10 min, then cooled and left to stand at RT for 16 h. The solid was triturated with acetone, dried under reduced pressure and then lyophilised from MeCN:H$_2$O (1:1) to afford 3-(2-((2-fluorobenzyl)amino)ethyl)-1H-pyrrolo[2,3-b]pyridine-5-carbonitrile fumarate salt (0.13 g, 85%) as an off white solid. LCMS (Condition C): $t_R$ (1.107 min) m/z=294.9 [M+H]$^+$; $^1$H NMR (400 MHz, DMSO-d$_6$): δ 12.14 (s, 1H), 8.57 (s, 2H), 7.56-7.52 (m, 2H), 7.38-7.35 (m, 1H), 7.23-7.18 (m, 2H), 6.57 (s, 2H), 4.01 (s, 2H), 3.05-2.99 (m, 4H).

Example 73: Synthesis of 3-(2-((3-fluorobenzyl)amino)ethyl)-1H-pyrrolo[2,3-b]pyridine-5-carbonitrile (S73)

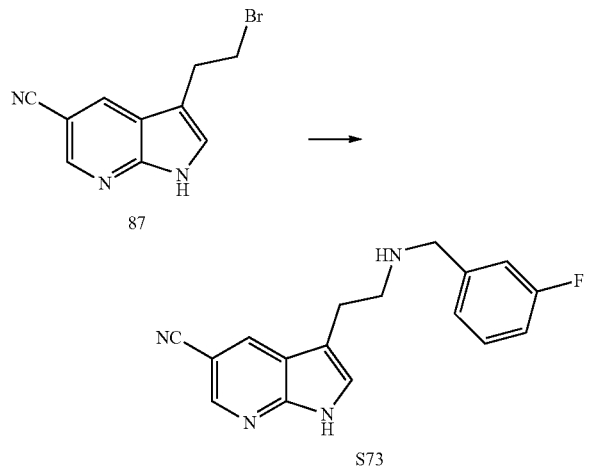

Step 1: 3-(2-((3-fluorobenzyl)amino)ethyl)-1H-pyrrolo[2,3-b]pyridine-5-carbonitrile (S73)

To a stirred solution of 3-(2-bromoethyl)-1H-pyrrolo[2,3-b]pyridine-5-carbonitrile (0.5 g, 1.99 mmol) in EtOH (10 mL) was added NaI (0.3 g, 1.99 mmol) at 0° C. under nitrogen atmosphere. After 15 min, (3-fluorophenyl) methenamine (0.75 g, 5.99 mmol) was added at 0° C. and the resulting reaction mixture was stirred at 90° C. for 24 h. The reaction mixture was concentrated under reduced pressure, diluted with water (100 mL) and extracted with EtOAc (3×100 mL). The combined organics were dried over Na$_2$SO$_4$ and concentrated under reduced pressure to get crude material, which was purified by flash column chromatography (product eluted at 8% MeOH in CH$_2$Cl$_2$ to afford 3-(2-((3-fluorobenzyl)amino)ethyl)-1H-pyrrolo[2,3-b]pyridine-5-carbonitrile (0.23 g, 39%) as an off white solid. LCMS (Condition C): $t_R$ (1.070 min) m/z=294.9 [M+H]$^+$; $^1$H NMR (400 MHz, DMSO-d$_6$): δ 12.03 (s, 1H), 8.55 (d, J=1.6 Hz, 1H), 8.51 (d, J=1.6 Hz, 1H), 7.78 (s, 1H), 7.35-7.27 (m, 1H), 7.13-7.10 (m, 2H), 7.03-6.98 (m, 1H), 3.73 (s, 2H), 2.89-2.83 (m, 2H), 2.80-2.74 (m, 2H).

Step 2: 3-(2-((3-fluorobenzyl)amino)ethyl)-1H-pyrrolo[2,3-b]pyridine-5-carbonitrile Fumarate (S73·Fumarate)

To a stirred solution of 3-(2-((3-fluorobenzyl)amino) ethyl)-1H-pyrrolo[2,3-b]pyridine-5-carbonitrile (0.23 g, 0.78 mmol) in acetone (2 mL) was added fumaric acid (0.09 g, 0.78 mmol) at 100° C. and the mixture was refluxed at 100° C. for 5 min, then cooled and left to stand at RT for 16 h. The solid was dried under reduced pressure and then lyophilised from MeCN:H$_2$O (1:1) to afford 3-(2-((3-fluorobenzyl)amino)ethyl)-1H-pyrrolo[2,3-b]pyridine-5-carbonitrile fumarate salt (0.28 g, 87%) as an off white solid. LCMS (Condition C): $t_R$ (1.102 min) m/z=294.9 [M+H]$^+$; $^1$H NMR (400 MHz, DMSO-d$_6$): δ 12.21 (s, 1H), 8.58-8.54 (m, 2H), 7.53 (s, 1H), 7.40-7.35 (m, 1H), 7.24-7.21 (m, 2H), 7.13-7.08 (m, 1H), 6.55 (s, 2H), 3.93 (s, 2H), 2.95 (s, 4H).

Example 74: Synthesis of 3-(2-((2-methoxybenzyl)amino)ethyl)-1H-pyrrolo[2,3-b]pyridine-5-carbonitrile (S74)

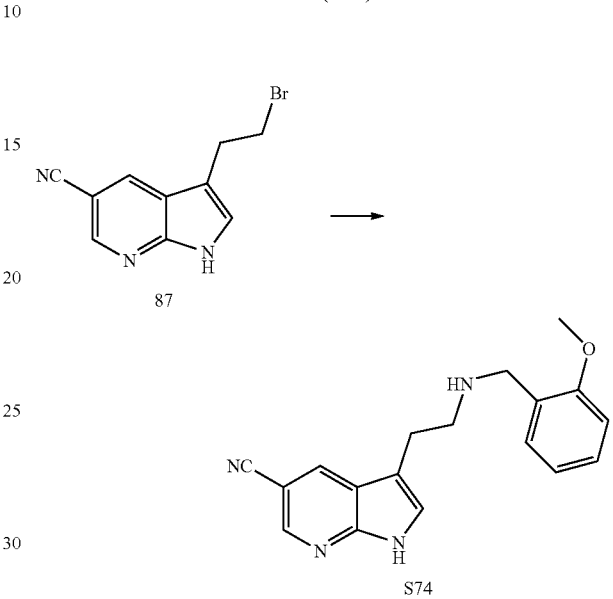

Step 1: 3-(2-((2-methoxybenzyl)amino)ethyl)-1H-pyrrolo[2,3-b]pyridine-5-carbonitrile (S74)

To a stirred solution of 3-(2-bromoethyl)-1H-pyrrolo[2,3-b]pyridine-5-carbonitrile (0.36 g, 1.43 mmol) in EtOH (10 mL) was added NaI (0.21 g, 1.43 mmol) at 0° C. After 20 min, (2-methoxyphenyl) methanamine (0.29 g, 2.15 mmol) in EtOH (2 mL) was added and the mixture was stirred at 90° C. for 24 h. The reaction mixture was cooled to rt, poured into water (100 mL) and extracted with CH$_2$Cl$_2$ (2×80 mL). The combined organics were dried over Na$_2$SO$_4$ and concentrated under reduced pressure. The crude material was purified by flash column chromatography (product eluted at 15% MeOH in CH$_2$Cl$_2$) to afford 3-(2-((2-methoxybenzyl)amino)ethyl)-1H-pyrrolo[2,3-b]pyridine-5-carbonitrile (0.07 g, 16%) as a pale yellow gum. LCMS (Condition C): $t_R$ (1.127 min) m/z=306.9 [M+H]$^+$; $^1$H NMR (400 MHz, DMSO-d$_6$): δ 12.03 (s, 1H), 8.54 (d, J=1.6 Hz, 1H), 8.48 (d, J=2.0 Hz, 1H), 7.47 (s, 1H), 7.26-7.17 (m, 2H), 6.90-6.84 (m, 2H), 3.68 (s, 5H), 2.85 (t, J=6.4 Hz, 2H), 2.78 (t, J=6.8 Hz, 2H).

Step 2: 3-(2-((2-methoxybenzyl)amino)ethyl)-1H-pyrrolo[2,3-b]pyridine-5-carbonitrile Fumarate (S74·Fumarate)

To a stirred solution of 3-(2-((2-methoxybenzyl)amino) ethyl)-1H-pyrrolo[2,3-b]pyridine-5-carbonitrile (0.07 g, 0.22 mmol) in acetone (2.0 mL) was added fumaric acid (0.026 g, 0.22 mmol) and the mixture was refluxed at 100° C. for 20 min, then cooled and left to stand at RT for 16 h. The material was dried under reduced pressure and then lyophilised from (MeCN:H$_2$O) to afford 3-(2-((2-methoxybenzyl)amino)ethyl)-1H-pyrrolo[2,3-b]pyridine-5-carbonitrile fumarate salt (0.084 g, 81%) as a white solid. LCMS: $t_R$ (1.164 min) m/z=306.9 [M+H]$^+$; $^1$H NMR (400 MHz, DMSO-d$_6$): δ 12.16 (s, 1H), 8.59-8.55 (m, 2H), 7.55 (s, 1H), 7.36-7.30 (m, 2H), 7.01-6.92 (m, 2H), 6.53 (s, 2H), 3.97 (s, 2H), 3.76 (s, 3H), 3.05-3.01 (m, 4H).

Example 75: Synthesis of 3-(2-((3-methoxybenzyl)amino)ethyl)-1H-pyrrolo[2,3-b]pyridine-5-carbonitrile (S75)

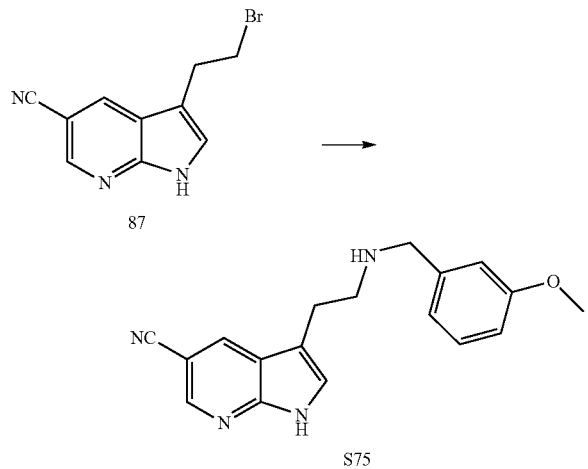

Step 1: 3-(2-((3-methoxybenzyl)amino)ethyl)-1H-pyrrolo[2,3-b]pyridine-5-carbonitrile (S75)

To a stirred solution of 3-(2-bromoethyl)-1H-pyrrolo[2,3-b]pyridine-5-carbonitrile (0.5 g, 1.99 mmol) in EtOH (15 mL) was added NaI (0.3 g, 1.9 mmol) at 0° C. under nitrogen atmosphere. After 10 min, (3-methoxyphenyl) methanamine (0.54 g, 3.99 mmol) was added and the reaction mixture to stirred at 90° C. for 20 h. The reaction mixture was poured into water (70 mL), extracted with CH$_2$Cl$_2$ (2×50 mL) and the combined organics were dried over Na$_2$SO$_4$ and concentrated under reduced pressure. The crude material was purified by flash column chromatography (product eluted at 49% MeOH: CH$_2$Cl$_2$:NH$_4$OH (1:9:0.1) in CH$_2$Cl$_2$) to afford 3-(2-((3-methoxybenzyl)amino)ethyl)-1H-pyrrolo[2,3-b]pyridine-5-carbonitrile (0.14 g, 23%) as a brown sticky liquid. LCMS (Condition C): $t_R$ (1.165 min) m/z=306.9 [M+H]$^+$; $^1$H NMR (400 MHz, DMSO-d$_6$): δ 12.03 (s, 1H), 8.55 (d, J=2.0 Hz, 1H), 8.51 (d, J=2.0 Hz, 1H), 7.49 (s, 1H), 7.18 (t, J=8.0, 1H), 6.88-6.84 (m, 2H), 6.77-6.75 (m, 1H), 3.70 (s, 5H), 2.86 (t, J=6.4 Hz, 2H), 2.77 (t, J=6.8 Hz, 2H).

Step 2: 3-(2-((3-methoxybenzyl)amino)ethyl)-1H-pyrrolo[2,3-b]pyridine-5-carbonitrile Fumarate (S75·Fumarate)

To a stirred solution of 3-(2-((3-methoxybenzyl)amino)ethyl)-1H-pyrrolo[2,3-b]pyridine-5-carbonitrile (0.14 g, 0.45 mmol) in acetone (2.0 mL) was added fumaric acid (0.053 g, 0.46 mmol) and the reaction mixture was refluxed at 80° C. for 10 min, then cooled and left to stand at RT for 16 h. The material was dried under reduced pressure and then lyophilised from MeCN:H$_2$O (1:1) to afford 3-(2-((3-methoxybenzyl)amino)ethyl)-1H-pyrrolo[2,3-b]pyridine-5-carbonitrile fumarate salt (0.15 g, 78%) as an off white solid. LCMS (Condition C): $t_R$ (1.152 min) m/z=306.9 [M+H]$^+$; $^1$H NMR (400 MHz, DMSO-d$_6$): δ 12.13 (s, 1H), 8.58-8.54 (m, 2H), 7.54 (s, 1H), 7.26 (t, J=8.0 Hz, 1H), 6.99-6.95 (m, 2H), 6.87-6.85 (m, 1H), 6.53 (s, 2H), 3.92 (s, 2H), 3.73 (s, 3H), 2.98 (s, 4H).

Functional Assays 5-HT$_{2A}$, 5-HT$_{2B}$ and 5-HT$_{2C}$ Receptors

Activity at 5-HT2A, 5-HT2B and 5-HT2C receptors was determined using a FLIPR Ca2+ flux assay at WuXi AppTec Co. Ltd. (Hong Kong) Discovery Biology Unit according to their standard protocols. Briefly, stably transfected cells expressing the receptor of interest (HEK293 for 5-HT2A and 5-HT2C; CHO-K1 for 5-HT2B) were grown and plated in a 384 well plate and incubated at 37° C. and 5% CO2 overnight. A 250 mM stock solution of probenecid in FLIPR calcium assay buffer (10 mL) was freshly prepared and combined with a fluorescent dye (Fluo-4 Direct) to give a final assay concentration of 2.5 mM. Reference compounds were 4-fold serially diluted and the screening compounds were 3-fold serially diluted in 100% DMSO for 10 points using Agilent Bravo, and 750 nL was added to a 384 well compound plate using Echo along with 30 μL assay buffer. The fluorescent dye was then added to the assay plate along with assay buffer to a final volume of 40 μL. The cell plate was incubated for 50 min at 37° C. and 5% CO$_2$ and placed into the FLIPR Tetra along with the compound plate. 10 μL of references and compounds were then transferred from the compound plate into the cell plate and the fluorescent signal was read.

Activation data are provided in a similar assay tested at a single 10 μM concentration.

Compounds P-1 to P-56 were prepared by similar synthesis to those described above.

TABLE 1

Agonist activity of exemplified compounds at selected serotonin (5-HT) receptors in Ca$^{2+}$ flux functional assays.

| Code | 5-HT2A | | 5-HT2B | | 5-HT2C | | 5-HT2B |
| | EC$_{50}$ (nM) | E$_{max}$ (%) | EC$_{50}$ (nM) | E$_{max}$ (%) | EC$_{50}$ (nM) | E$_{max}$ (%) | % Activation @ 10 μM |
|---|---|---|---|---|---|---|---|
| P-1 | 34.88 | 47.69 | >10000 | −1.07 | 18.79 | 74.29 | |
| P-2 | >10000 | 15.85 | >10000 | −0.67 | 2072 | 20.57 | |
| P-3 | 49.72 | 41.38 | >10000 | −0.67 | 121.1 | 41.19 | |
| P-4 | 1228 | 34.95 | >10000 | −0.27 | 240.9 | 17.91 | |
| P-5 | 24.42 | 56.19 | >10000 | −0.87 | 38.37 | 79.08 | |
| P-6 | 43.13 | 66.41 | >10000 | 0.34 | >10000 | −0.79 | |
| P-7 | >10000 | −0.3 | >10000 | 0.17 | 2343 | 40.16 | |
| P-8 | 202.9 | 69.97 | >10000 | 17.9 | 532.3 | 72.39 | |
| P-9 | 1023 | 37.3 | >10000 | 2.53 | >10000 | −30.53 | |

TABLE 1-continued

Agonist activity of exemplified compounds at selected serotonin (5-HT) receptors in $Ca^{2+}$ flux functional assays.

| Code | 5-HT2A $EC_{50}$ (nM) | 5-HT2A $E_{max}$ (%) | 5-HT2B $EC_{50}$ (nM) | 5-HT2B $E_{max}$ (%) | 5-HT2C $EC_{50}$ (nM) | 5-HT2C $E_{max}$ (%) | 5-HT2B % Activation @ 10 μM |
|---|---|---|---|---|---|---|---|
| P-10 | 6.110 | 82.81 | 283.6 | 47.12 | 68.63 | 99.11 | |
| P-11 | 4.165 | 99.06 | 52.18 | 92.13 | 91.13 | 96.32 | |
| P-12 | 6.956 | 85.65 | 22.23 | 101.87 | 199.6 | 110.09 | |
| P-13 | 10.08 | 79.64 | >10000 | 2.25 | 31.92 | 95.83 | |
| P-14 | 20.97 | 78.91 | >10000 | 1.06 | 139.0 | 98.26 | |
| P-17 | 279.5 | 84.66 | >10000 | 0.37 | >10000 | −0.53 | |
| P-18 | 85.53 | 89.44 | >10000 | 9.35 | >10000 | −0.33 | |
| P-19 | 72.86 | 112.37 | >10000 | 13.27 | >10000 | 0.16 | |
| P-20 | 93.26 | 76.74 | >10000 | 1.38 | >10000 | −0.08 | |
| P-21 | 108.6 | 79.80 | >10000 | 4.56 | >10000 | −0.15 | |
| P-22 | 690.9 | 55.49 | >10000 | 1.91 | >10000 | 0.27 | |
| P-23 | 1238 | 54.98 | >10000 | 0.88 | >10000 | −0.04 | |
| P-24 | 80.76 | 56.55 | >10000 | 6.16 | >10000 | 24.74 | |
| P-25 | 108.8 | 70.30 | >10000 | 8.23 | >10000 | 20.98 | |
| P-26 | 1619 | 58.34 | >10000 | 3.08 | >10000 | 0.90 | |
| P-27 | 856.9 | 80.23 | >10000 | 35.63 | >10000 | 0.54 | |
| P-28 | 781.7 | 70.54 | >10000 | 0.69 | >10000 | −0.06 | |
| P-29 | 555.4 | 71.56 | >10000 | 0.59 | >10000 | 0.48 | |
| P-30 | 387.3 | 56.61 | >10000 | 0.03 | >10000 | 1.04 | |
| P-31 | 1016 | 54.48 | >10000 | 1.01 | >10000 | 0.01 | |
| P-32 | 413.8 | 57.78 | >10000 | 0.14 | >10000 | 0.61 | |
| P-33 | 640.8 | 54.73 | >10000 | 0.01 | >10000 | 0.33 | |
| P-34 | 149.6 | 82.59 | >10000 | 14.70 | 681.6 | 91.66 | |
| P-35 | 78.99 | 82.20 | 78.45 | 74.65 | 7178 | 55.58 | |
| P-36 | 77.06 | 113.99 | 96.44 | 48.92 | >10000 | 38.38 | |
| P-37 | 86.83 | 82.79 | >10000 | 2.60 | 532.8 | 105.33 | |
| P-38 | 77.69 | 83.13 | 610.3 | 19.57 | 1922 | 70.16 | |
| P-39 | >10000 | 1.47 | NT | NT | NT | NT | |
| P-40 | >10000 | 0.75 | NT | NT | NT | NT | |
| P-42 | 2979 | 68.77 | >10000 | 0.24 | 3488 | 70.51 | |
| P-43 | 2183 | 38.93 | >10000 | 8.01 | >10000 | 28.82 | |
| P-44 | 259.3 | 97.62 | 490.3 | 39.36 | 1704 | 77.24 | |
| P-45 | 159.8 | 100.25 | >10000 | 8.93 | >10000 | 40.22 | |
| P-48 | 6986 | 58.60 | >10000 | 16.12 | >10000 | 4.22 | |
| P-49 | 1395 | 67.61 | >10000 | 30.67 | >10000 | −0.46 | |
| P-51 | 525.7 | 79.08 | >10000 | 30.87 | >10000 | 24.61 | |
| P-52 | 1840 | 77.29 | >10000 | 0.22 | >10000 | 0.09 | |
| P-55 | 255.8 | 58.72 | >10000 | 1.35 | 366.5 | 83.62 | |
| P-56 | 794.2 | 50.53 | >10000 | −0.39 | 1256 | 63.60 | |
| S1 | 33.7 | 82 | NT | NT | 1442 | 77 | 2 |
| S2 | 10.8 | 92 | NT | NT | 187 | 92 | 74 |
| S5 | 1067 | 82 | NT | NT | >10000 | 28 | NT |
| S6 | 37.9 | 81 | NT | NT | 1861 | 81 | 16 |
| S7 | 529 | 70 | NT | NT | >10000 | 2 | 0 |
| S8 | 354 | 56 | NT | NT | >10000 | 0 | NT |
| S9 | 21.0 | 83 | NT | NT | 1480 | 72 | NT |
| S11 | 136 | 80 | NT | NT | >10000 | 25 | NT |
| S12 | 79 | 84 | NT | NT | 3369 | 50 | NT |
| S15 | 1943 | 72 | NT | NT | >10000 | 0 | NT |
| S16 | 32.5 | 81 | NT | NT | 1102 | 60 | NT |
| S17 | 134 | 84 | NT | NT | 4118 | 35 | 7 |
| S25 | 8.98 | 87 | NT | NT | 76 | 84 | 41 |
| S30 | 26.9 | 82 | NT | NT | 512 | 83 | NT |
| S31 | 15.5 | 87 | NT | NT | 515 | 76 | NT |
| S32 | 3.31 | 94 | NT | NT | 206 | 89 | NT |
| S33 | 8.27 | 82 | NT | NT | 244 | 87 | NT |
| S34 | 18.0 | 90 | NT | NT | 319 | 84 | NT |
| S41 | 822 | 41 | NT | NT | >10000 | 0 | 0 |
| S42 | 143 | 58 | NT | NT | 1098 | 75 | 15 |
| S43 | 155 | 71 | NT | NT | 2741 | 55 | NT |
| S44 | 9.49 | 82 | NT | NT | 2835 | 45 | 1 |
| S45 | 24.0 | 86 | NT | NT | >10000 | 11 | 0 |
| S46 | 47.0 | 91 | NT | NT | 4169 | 43 | 3 |
| S47 | 673 | 65 | NT | NT | >10000 | 8 | 0 |
| S48 | 115 | 82 | NT | NT | 3962 | 44 | 2 |
| S49 | 65.7 | 78 | NT | NT | >10000 | 28 | 0 |
| S50 | 66.5 | 90 | NT | NT | 3978 | 44 | 2 |
| S51 | 394 | 86 | NT | NT | >10000 | 2 | 0 |
| S52 | 149 | 61 | NT | NT | 1947 | 49 | 3 |
| S53 | 115 | 84 | NT | NT | 2584 | 71 | 26 |
| S54 | 223 | 69 | NT | NT | >10000 | 19 | 1 |
| S55 | 158 | 73 | NT | NT | 3591 | 34 | 4 |

TABLE 1-continued

Agonist activity of exemplified compounds at selected serotonin (5-HT) receptors in $Ca^{2+}$ flux functional assays.

| Code | 5-HT2A $EC_{50}$ (nM) | 5-HT2A $E_{max}$ (%) | 5-HT2B $EC_{50}$ (nM) | 5-HT2B $E_{max}$ (%) | 5-HT2C $EC_{50}$ (nM) | 5-HT2C $E_{max}$ (%) | 5-HT2B % Activation @ 10 µM |
|---|---|---|---|---|---|---|---|
| S56 | 226 | 54 | NT | NT | 1850 | 45 | 2 |
| S57 | 897 | 86 | NT | NT | 3484 | 62 | 12 |
| S58 | 124 | 79 | NT | NT | 231 | 67 | 3 |
| S59 | 410 | 69 | NT | NT | >10000 | 19 | 0 |
| S60 | 285 | 66 | NT | NT | 1793 | 63 | 0 |
| S61 | 74.7 | 65 | NT | NT | 1924 | 73 | 0 |
| S62 | 7.86 | 78 | NT | NT | 480 | 85 | 1 |
| S63 | 104 | 63 | NT | NT | 2968 | 48 | 0 |
| S64 | 1673 | 47 | NT | NT | >10000 | 0 | 1 |
| S65 | 665 | 73 | NT | NT | >10000 | 0 | 1 |
| S66 | 1168 | 65 | NT | NT | >10000 | 1 | 0 |
| S67 | 609 | 80 | NT | NT | >10000 | 2 | 4 |
| S68 | 566 | 70 | NT | NT | 4570 | 44 | 11 |
| S69 | 1470 | 86 | NT | NT | >10000 | 0 | 0 |
| S70 | 681 | 78 | NT | NT | >10000 | 16 | 0 |
| S71 | 1137 | 81 | NT | NT | >10000 | 9 | 0 |
| S72 | 179 | 70 | NT | NT | 5067 | 47 | 0 |
| S73 | 134 | 66 | NT | NT | 7432 | 43 | 2 |
| S74 | 7.70 | 93 | NT | NT | 1879 | 88 | 15 |
| S75 | 44.4 | 79 | NT | NT | 3625 | 46 | 1 |

Example 76: In Vivo Pharmacokinetics Experiments

The study was conducted using established procedures in accordance with the Australian Code of Practice for the Care and Use of Animals for Scientific Purposes, and the study protocols were reviewed and approved by the Monash Institute of Pharmaceutical Sciences Animal Ethics Committee.

The systemic exposure of selected examples was studied in non-fasted male C57BL/6 mice weighing between 18.9-25.5 g. Mice had access to food and water ad libitum throughout the pre- and post-dose sampling period.

On the day of dosing, the formulation of each compound was prepared by dissolving solid compound in phosphate buffer saline (50 mM) using vortexing, creating colourless solutions (pH 6.4-6.5) for each compound.

Compounds were dosed to mice by IP injection (10 mL/kg dose volume via a 27G needle; n=9 mice per compound) and blood samples were collected at 5 and 30 min; 1, 2 and 4 h post-dose (n=3 mice per time point for each compound). A maximum of three blood samples were obtained from each mouse, with plasma samples being taken via submandibular bleed (approximately 120 µL). Once collected, blood samples were centrifuged immediately, supernatant plasma was removed, and stored at −80° C. until analysis by LCMS. In addition, at the 5 and 30 min and 4 h post-dose time points, the whole brain was rapidly removed from the carcass soon after the blood collection. The whole brains were blotted to remove excess blood, placed into pre-weighed polypropylene vials, and weighed. The brains were snap frozen in dry ice and subsequently stored frozen (−80° C.) until analysis.

Bioanalytical Method Summary:

Concentrations of test compound in plasma and tissue samples were determined using an LCMS/MS method validated for linearity, accuracy, precision, matrix factor and recovery (Table 2). Test compound standard solutions were diluted from a concentrated stock solution (32 mM in $H_2O$) using 50% can in $H_2O$ (v/v) and a calibration curve was prepared in a matched matrix to the test samples.

Plasma: The plasma calibration curve was prepared by spiking aliquots of blank mouse plasma (25 µL) with test compound standard solutions (5 µL) and internal standard solution (5 µL of diazepam, 5 µg/mL in 50% acetonitrile in water). Test plasma samples (25 µL) were thawed, mixed, and then spiked with internal standard solution (5 µL). Plasma protein precipitation was performed by addition of acetonitrile (3-fold volume ratio) and thorough vortex mixing. Samples were centrifuged (RCF=9391×g) for 3 minutes and the supernatant (90 µL) was collected for analysis.

Tissue: Pre-weighed tissue samples (brain) were homogenised using a glass rod in buffer containing an EDTA/potassium fluoride solution (0.1 M/4 mg/ml) as a stabilisation cocktail to minimise the potential for ex vivo degradation (3 mL cocktail/g tissue). The tissue homogenate was briefly centrifuged (RCF=79×g) for 10 seconds to separate the foam layer before transferring an aliquot of the tissue homogenate (200 µL) to a fresh Eppendorf tube for sample extraction. Calibration standards were prepared by spiking blank brain homogenate (200 µL) with the solution standards (10 µL) and the internal standard (10 µL). Study samples were similarly prepared, except that acetonitrile (10 µL) was added instead of solution standards to maintain the same volume. Protein precipitation was carried out by the addition of a 3-fold volume of acetonitrile, followed by vortex mixing and centrifugation (RCF=9391×g) for 3 min to recover the supernatant for analysis.

Replicate analysis: Triplicate analytical replicate (ARs) samples were prepared similarly to the standards for each sample type at three concentrations (50, 500 and 2,000 ng/ml) and repeat injections of these ARs were included throughout the analytical run to assess assay performance. The extraction of the test compound from the standards and ARs were conducted as described above.

All test samples were quantified within the calibration range of the assay and the assay performance for ARs were deemed acceptable. The stability of each test compound was confirmed in homogenate during the period of sample processing (15 min; <15% loss).

TABLE 2

Summary of bioanalytical method for a subset of exemplar compounds

| | |
|---|---|
| Instrument | Waters Xevo TQS Micro coupled to a Waters Acquity UPLC |
| Detection | Positive electrospray ionisation multiple-reaction monitoring mode |
| Column | Kinetex 2.6u PFP 100A column (50 × 2.1 mm, 2.6 μm) |
| LC Conditions | Gradient cycle time: 4 min; Injection vol: 1 μL; Flow rate: 0.4 mL/min |
| Mobile Phase | (A) 0.005M ammonium formate in water; (B) 0.05% ammonium formate in methanol |
| Sample Preparation | Plasma: Protein precipitation using acetonitrile (3-fold volume ratio)<br>Tissue: Protein precipitation using acetonitrile (3-fold volume ratio) |

| Analyte | $t_R$* (min) | Transition (m/z) | Cone Voltage (V) | CID# (V) |
|---|---|---|---|---|
| P-8 | 2.31 | 220.17 > 175.03 | 20 | 20 |
| P-5 | 2.18 | 220.11 > 58.00 | 20 | 15 |
| P-3 | 2.18 | 220.11 > 175.10 | 20 | 15 |
| P-1 | 1.91 | 220.11 > 175.03 | 20 | 15 |
| Diazepam (IS) | 1.87/2.41 | 285.15 > 193.10 | 40 | 25 |

The highest abundance product ion with minimum interference with the matrix were selected for quantification. Data acquisition was performed using MassLynx software (V4.2).
IS: Internal standard |
*Retention time |
Collision-Induced Dissociation Maximal plasma concentrations of compounds P-8, P-5, P-3, and P-1 following IP administration at 10 mg/kg are shown in Table 3. Comprehensive pharmacokinetic data including brain penetration information is displayed in FIG. 1 and/or Table 4.

TABLE 3

Exposure parameters for a subset of exemplar compounds: P-8, P-5, P-3, and P-1 in male C57BL/6 mice following IP administration at 10 mg/kg.

| Parameter | P-8 | P-5 | P-3 | P-1 |
|---|---|---|---|---|
| Plasma $C_{max}$ (μM) | 7.66 | 5.38 | 5.80 | 6.53 |
| $T_{max}$ (min) | 5 | 5 | 5 | 5 |
| Plasma $AUC_{0\text{-}last}$ (h*μM) | 1.94 | 1.63 | 1.70 | 1.37 |

TABLE 4

Individual and mean ± SD (n = 3) plasma and brain concentrations, and brain-to-plasma (B:P) ratios, of a subset of exemplar compounds P-8, P-5, P-3, and P-1 in male C57BL/6 mice following IP administration at 10 mg/kg.

| Time (h) | Mouse ID | Plasma Concentration (μM) Individual | Plasma Concentration (μM) Mean ± SD | Brain Parenchyma Concentration (μM) Individual | Brain Parenchyma Concentration (μM) Mean ± SD | B:P Ratio Individual | B:P Ratio Mean ± SD |
|---|---|---|---|---|---|---|---|
| | | | P-8 | | | | |
| 0.083 | 1 | 5.42 | 7.66 ± | 3.60 | 5.41 ± | 0.66 | 0.72 ± |
| | 2 | 6.18 | 3.25 | 5.06 | 2.01 | 0.82 | 0.089 |
| | 3 | 11.4 | | 7.57 | | 0.66 | |
| 0.5 | 4 | 0.846 | 0.744 ± | 5.77 | 6.12 ± | 6.8 | 8.3 ± |
| | 5 | 0.800 | 0.139 | 7.58 | 1.32 | 9.5 | 1.4 |
| | 6 | 0.586 | | 5.01 | | 8.6 | |
| 4 | 7 | ND | 0.0030 | 0.0263 | 0.0326 ± | — | 6.4 |
| | 8 | 0.0030$^a$ | | 0.0192 | 0.0174 | 6.4 | |
| | 9 | ND | | 0.0522 | | — | |
| | | | P-5 | | | | |
| 0.083 | 10 | 5.88 | 5.38 ± | 0.23 | 0.984 ± | 0.21 | 0.19 ± |
| | 11 | 1.97 | 3.18 | 0.365 | 0.540 | 0.19 | 0.022 |
| | 12 | 8.28 | | 1.36 | | 0.16 | |
| 0.5 | 13 | 0.815 | 0.859 ± | 1.61 | 1.97 ± | 2.0 | 2.3 ± |
| | 14 | 0.985 | 0.111 | 2.42 | 0.414 | 2.5 | 0.26 |
| | 15 | 0.776 | | 1.86 | | 2.4 | |
| 4 | 16 | <LLQ | — | <LLQ | — | — | — |
| | 17 | <LLQ | | <LLQ | | | |
| | 18 | <LLQ | | <LLQ | | | |
| | | | P-3 | | | | |
| 0.083 | 1A | 6.70 | 5.80 ± | 9.02 | 6.46 ± | 1.3 | 1.1 ± |
| | 2A | 5.48 | 0.793 | 4.78 | 2.26 | 0.87 | 0.24 |
| | 3A | 5.21 | | 5.57 | | 1.1 | |
| 0.5 | 4A | 0.865 | 0.791 ± | 8.62 | 7.80 ± | 10 | 9.9 ± |
| | 5A | 0.752 | 0.0641 | 7.64 | 0.745 | 10 | 0.36 |
| | 6A | 0.756 | | 7.15 | | 9.5 | |
| 4 | 7A | 0.0071 | 0.0057 ± | 0.0465 | 0.0554 ± | 6.6 | 9.9 ± |
| | 8A | 0.0053 | 0.0012 | 0.0913 | 0.0324 | 17 | 6.2 |
| | 9A | 0.0047 | | 0.0283 | | 6.1 | |

TABLE 4-continued

Individual and mean ± SD (n = 3) plasma and brain concentrations, and brain-to-plasma (B:P) ratios, of a subset of exemplar compounds P-8, P-5, P-3, and P-1 in male C57BL/6 mice following IP administration at 10 mg/kg.

| Time (h) | Mouse ID | Plasma Concentration (µM) | | Brain Parenchyma Concentration (µM) | | B:P Ratio | |
|---|---|---|---|---|---|---|---|
| | | Individual | Mean ± SD | Individual | Mean ± SD | Individual | Mean ± SD |
| P-1 | | | | | | | |
| 0.083 | 10A | 7.66 | 6.53 ± 1.93 | 2.06 | 1.89 ± 0.776 | 0.27 | 0.28 ± 0.048 |
| | 11A | 4.30 | | 1.04 | | 0.24 | |
| | 12A | 7.63 | | 2.56 | | 0.34 | |
| 0.5 | 13A | 1.03 | 0.585 ± 0.387 | 0.307 | 0.482 ± 0.201 | 0.30 | 1.2 ± 1.0 |
| | 14A | 0.307 | | 0.701 | | 2.3 | |
| | 15A | 0.420 | | 0.437 | | 1.0 | |
| 4 | 16A | <LLQ | — | <LLQ | — | — | — |
| | 17A | <LLQ | | ND | | — | |
| | 18A | <LLQ | | <LLQ | | — | |

ND-Not Detected;
<LLQ-Below the analytical lower limit of quantitation

Example 77: Biotelemetry and Head-Twitch Response (HTR) Experiments

Mice (C57BL/6J males) were purchased from the Jackson Laboratory (Bar Harbor, ME, USA) at 5-6 weeks of age and allowed at least 1-2 weeks to acclimate to the NIDA, Intramural Research Program (IRP), animal research facility in Baltimore, MD, USA. The animal facility is fully accredited by the Association for the Assessment and Accreditation of Laboratory Animal Care, and all procedures were approved by the NIDA IRP Animal Care and Use Committee. Mice were initially group housed 3-5 per cage during acclimation and housed in a 12 h light-dark cycle throughout the study, with lights on at 0700 h. Food and water were available ad libitum except during testing. Cohorts of 20-24 mice were used for each test drug. The mice were subjected to experimental testing once every 1-2 weeks for 2-3 months to complete dose-effect curves and antagonist experiments. A minimum of 7 days between treatments was utilized to avoid any tolerance to effects of repeated drug administration. All drug doses represent the weight of the salt dissolved in 0.9% saline vehicle. Mice were tested first in dose-response studies to assess the effects of each compound at doses from 0.03 to 30 mg/kg s.c. and were subsequently tested in antagonist reversal studies utilizing pretreatment with M100907 and WAY100635. All experiments were conducted from 0900 to 1700 local time during the light phase, as sensitivity of rodents to other tryptamine psychedelics is diurnal, with maximal HTR observed in the middle of the light phase. Experiments were run during the light phase also to avoid any potential influence of melatonin receptor activity on HTR as melatonin and related agonists are known to reduce HTR induced by DOI in rats. For each experiment, mice were acclimated to the testing room in their home cage for at least 1 h prior to experimental sessions. Behavioral test sessions were carried out in Tru Scan mouse locomotor arenas equipped with photobeam arrays (Coulbourn Instruments, Holliston, MA, USA), which were modified with cylindrical inserts and transparent floors useful in detecting mouse HTR.

Subcutaneous Temperature Transponder Implants. At least 1 week prior to the start of the experiments, mice received s.c. implanted temperature transponders (14×2 mm, model IPTT-300, Bio Medic Data Systems, Inc., Seaford, DE, USA) under brief isoflurane anesthesia. Mice were single housed post implant for the remainder of the study to protect the transponder from removal by cage mates. Temperature was determined noninvasively using a handheld receiver that is sensitive to signals emitted from the implanted transponders.

Prior to each experiment, mouse body weight and temperature were recorded. Mice were then placed into testing chambers for acclimation. In dose-response studies, after a brief 5 min acclimation, mouse body temperature was recorded for baseline measurement, mice received s.c. injection of test substance or vehicle, and animals were returned to the testing arena for 30 min. During the session, locomotor activity was monitored via photobeam tracking of movements in the horizontal plane to yield distance traveled in centimeter. HTR was monitored by the analysis of GoPro Hero Black 7 video recordings (120 frames per sec and 960p resolution) using a commercially available software package from Clever Sys Inc. (Reston, VA, USA).82 Post-treatment body temperature values were also recorded, and temperature data are represented as change from pretreatment baseline.

In antagonist reversal experiments, mice received a s.c. injection of either receptor antagonists or vehicle and were returned to the testing chamber for 30 min. During this period, locomotor activity was monitored to examine the potential effects of antagonist treatment on general behavior or movement. At 30 min after antagonist administration, mice were given test drug or vehicle and returned to the chambers for an additional 30 min of video recording used for analyses.

All statistical analyses were conducted using GraphPad Prism 9 (La Jolla, CA, USA). Dose-response data from mouse experiments were analyzed using nonlinear regression, and potency values were determined from the rising phase of the curves for HTR measures. For mouse studies, one-way ANOVA with Dunnett's post hoc test was used to compare all conditions to vehicle controls (0 or 0,0) in dose-response and antagonist experiments. Time-course drug effects for all parameters in mouse studies are shown for reference. Mean HTR count, distance traveled, and temperature change for each condition were used for statistical comparisons. Alpha was set at 0.05 for all analyses.

Results of these experiments for P-4, P-3 and P-1 are shown in FIGS. 2, 3, 4 and 5. These data show that compounds of the invention are well-tolerated. These data also show that the compounds are not promoting increased head-twitch response, suggesting they are likely not hallucinogenic.

Head-twitch response results for other compounds may be provided by analogous protocols.

Example 78: Tail Suspension Test Experiments

Male ICR mice (23±3 g) were purchased from BioLASCO (Taipei, Taiwan) at 4-5 weeks of age and allowed 5-7 days to acclimate to the animal research facility at Pharmacology Discovery Services (Taipei, Taiwan). Mice were housed in groups of 10 in a large cage (47×25×15 cm) on a 12-hour light cycle (lights on: 0700) and provided ad libitum food and water except during acute restraint stress and tail-suspension testing. Temperature was maintained at 20-24° C., and all rooms (colony and testing rooms) had similar lighting intensity. All aspects of this work including housing, experimentation, and animal disposal were performed in accordance with the "Guide for the Care and Use of Laboratory Animals: Eighth Edition" (The National Academies Press, Washington, DC, 2011) in a facility accredited by the Association for Assessment and Accreditation of Laboratory Animal Care. All experiments were conducted between 0900 to 1700 local time, during the light phase. Each mouse underwent a single behavioural experiment in which they were randomly allocated to receive a single treatment with vehicle (50 mM phosphate buffered saline, pH=6.5), Ketamine as a positive control (10 mg/kg, diluted in 0.9% saline from 50 mg/ml stock), or one dose of a test drug (n=10 per dose of test drug, n=12 for vehicle, n=12 for ketamine). All drug doses represent the freebase dose in salt form dissolved in vehicle. All solutions were delivered at 5 ml/kg via intraperitoneal injection.

Acute Restraint Stress (ARS) Procedure: Mice were moved from the colony room to the procedure room in which ARS was to be performed. Mice received oral gavage of water (10 ml/kg) to avoid dehydration, and then were individually restrained for 5 hours in a clear plastic cylinder (50 mL centrifuge tube with air holes drilled for ventilation), positioned horizontally on a bench with bench towel to absorb urine. This restraint prevented physical movement, without causing pain. Restrainers were washed with veterinary disinfectant between mice.

Drug Administration: Immediately after the 5-hour ARS procedure, mice were removed from the restrainers, placed in their home cage, and transported to the room in which Tail Suspension Test was to be conducted. Mice then received intraperitoneal injection with vehicle, ketamine (10 mg/kg), P-3·HCl (3, 10 mg/kg) or P-8·2HCl (3, 10, 30 mg/kg), and were then placed back in their home cage. 10 minutes after treatment, animals then underwent the Tail Suspension Test.

Tail Suspension Test (TST) Procedure: Mice were individually suspended on the edge of a shelf, 58 cm above a tabletop, using adhesive tape placed approximately 1 cm from the tip of the tail, for a total duration of 7 minutes. Using a stopwatch, the experimenters blinded to treatment groups recorded the duration of immobility (defined as hanging passively and motionless) during the 5 minutes spanning from 2-7 minutes. The data from 0-2 minutes was not recorded. Mice undergoing TST were never in view of other mice. Following TST, mice were euthanized via carbon dioxide inhalation.

Figure 6:
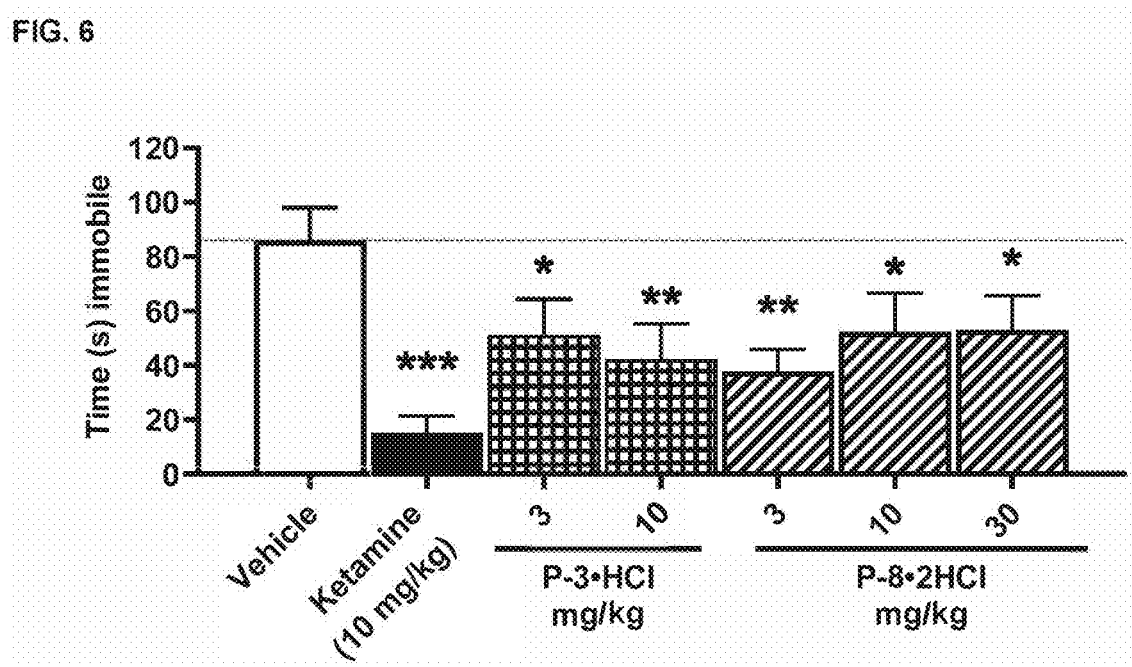
FIG. 6: Time immobilisation results from tail suspension test (TST) experiments described in Example 78 for compounds P-3·2HCl (3 mg/kg; 10 mg/kg) and P-8·2HCl (3 mg/kg; 10 mg/kg; 30 mg/kg) compared with ketamine (10 mg/kg) and vehicle.

Statistical Analysis: Statistical analyses were conducted using GraphPad Prism 9 (La Jolla, CA, USA), using a priori simple effect comparisons within a one-way ANOVA to compare the test compounds to the Vehicle condition, on time spent immobile (in seconds). The datapoints shown in FIG. 6 represent the mean±the standard error of the mean. Significance was set at $\alpha=0.05$. * Signifies $p<0.05$;  $p<0.01$. * $p<0.001$.

Results of this experiment for compounds P-3 and P-8 are shown in FIG. 6. This data indicates the compounds of the invention decrease the immobility time of mice in an Acute Restraining Stressor—Tail Suspension Test mouse model of depression. This indicates that compounds of the invention are likely to be anti-depressant.

Tail Suspension Test results for other compounds may be provided by analogous protocols.

Example 79-IPOne for Receptor Profiling

Briefly, stably transfected cells expressing the receptor of interest (CHO-K1 for human 5-HT2A, mouse 5-HT2A and rat 5-HT2A) grown to mid-log phase in culture media without antibiotics are detached with PBS-EDTA, centrifuged and resuspended in the HTRF IP-One Gq Detection Kit (Revvity, 62IPAPEJ) stimulation buffer.

Test compounds are dissolved in 100% DMSO at a concentration of 10 mM (master solution). Serial dilutions are prepared from master solution in 100% DMSO to obtain intermediate concentrations 200-fold higher than the concentrations to be tested. Each sample is diluted 100-fold in stimulation buffer and dispensed in test plate (5 µl per well)

For agonist testing (384-well, suspension), 5 µl of cell suspension are dispensed in the wells of the 384-well assay plate containing 5 µl of test compound or reference agonist diluted in stimulation buffer. The plate is incubated for 60 min. at 37° C. with 5% CO2. After addition of the lysis buffer containing IP1-d2 and anti-IP1 cryptate detection reagents, plates are incubated 1-hour at room temperature, and fluorescence ratios are measured according to the manufacturer specification, with the HTRF kit.

Example 80—Tissue Binding

Method

Mouse Brain Homogenate Binding:

Stock solutions of test compound(s) and control compound propranolol in DMSO at the concentration of 10 mM are prepared. 2 µL of stock solution (10 mM) is diluted with 98 µL DMSO to obtain working solution (200 µM). 3.5 µL of working solution is removed and is mixed with 697 µL of brain tissue homogenate to achieve final concentration of 1 µM (0.5% DMSO). The resulting mixture is vortexed thoroughly.

Procedure for Equilibrium Dialysis

The assay is run avoiding lights and oxygen after assembling the dialysis set up following the manufacturer's instructions. Cells are loaded with 150 µL of brain tissue homogenate sample and are dialyzed against equal volume of dialysis buffer (PBS). The assay is performed in duplicate. The dialysis plate is sealed and placed in an incubator at 37° C. at approximately 150 rpm for 6 hours. At the end of dialysis, the seal is removed and 50 µL of each post-dialysis samples is pipetted from both buffer and brain tissue homogenate chambers into separate tubes in plate.

Procedure for Sample Analysis

50 µL of blank brain tissue homogenate is added to the buffer samples, and an equal volume of PBS is added to the collected brain tissue homogenate samples. 400 µL of room temperature quench solution (acetonitrile containing internal standards (IS, 200 nM Labetalol, 100 nM Alprazolam and 2 µM Ketoprofen)) is added to precipitate protein. The composition is vortexed for 5 minutes. Samples in plate are centrifuged at 3,220 g for 30 minutes at room temperature. 100 µL of the supernatant is transferred to a new plate. The supernatant may be diluted with 100 µL or 200 µL water according to the LC/MS signal response and peak shape. The composition is mixed well and samples are analysed using LC/MS/MS.

Mouse Plasma Protein Binding:

Preparation of Stock Solutions and Working Solutions

Stock solutions of test compound(s) and control compound warfarin in DMSO are prepared at a concentration of 10 mM. 2 µL of stock solution (10 mM) is diluted with 98 µL DMSO to obtain working solution (200 µM). 3.5 µL of working solution is removed to mix with 697 µL of human, monkey, dog, rat or mouse plasma to achieve final concentration of 1 µM (0.1% DMSO). The composition is vortexed thoroughly.

Procedure for Equilibrium Dialysis

The assay is run avoiding lights and oxygen. The dialysis is assembled and set up following the manufacturer's instructions. Cells are loaded with 150 µL of plasma sample and are dialyzed against equal volume of dialysis buffer (PBS). The assay is performed in duplicate. The dialysis plate is sealed and is placed the plate in an incubator at 37° C. at approximately 150 rpm for 6 hours. At the end of dialysis, the seal removed and 50 µL each of post-dialysis samples from both buffer and plasma chambers are pipetted into separate tubes in plate.

Procedure for Sample Analysis

50 µL of blank plasma is added to the buffer samples, and an equal volume of PBS is added to the collected plasma samples. 400 µL of room temperature quench solution (acetonitrile containing internal standards (IS, 100 nM alprazolam, 200 nM labetalol, 200 nM imipramine and 2 µM ketoprofen)) is added to precipitate protein. The composition is vortexed for 5 minutes. Samples in plate are centrifuged at 3,220 g for 30 minutes at room temperature. 100 µL of the supernatant is transferred to a new plate. The supernatant may be diluted with 100 µL or 200 µL water according to the LC/MS signal response and peak shape. The composition is mixed well and samples are analysed using LC/MS-MS.

Stability Determination in Plasma

50 µL of spiked plasma sample is transferred to a new plate. Samples are incubated at 37° C., 5% $CO_2$ for 0 and 6 hrs. At designated time points, 50 µL of PBS is added to the wells. The compositions are mixed thoroughly and then 400 µL of room temperature quench solution (acetonitrile containing internal standards (IS, 100 nM alprazolam, 200 nM labetalol, 200 nM imipramine and 2 µM ketoprofen)) is added to precipitate protein. Samples are vortexed for 2 minutes and centrifuged for 30 minutes at 3,220 g. The aliquot of 100 µL of the supernatant is diluted by ultra-pure water (100 µL or 200 µL according to the LC/MS signal response and peak shape) and the mixture is used for LC-MS/MS analysis.

Example 81—Pharmacokinetics+Brain Penetration

Method

The study is conducted using established procedures by Pharmaron in vivo pharmacology services and are briefly outlined below.

Dosing Information

The study groups are shown in the following table.

| Group | Treatment | Dose Level (mg/kg) | Dose Volume (mL/kg) | Conc. (mg/mL) | Administration Route | No. of Animals |
|---|---|---|---|---|---|---|
| 1 | Test Article | 3 | 5 | 0.6 | IV | 3 males |
| 2 | | 5 | 5 | 1 | IPA | 3 males |
| 3 | | 5 | 5 | 1 | IPB | 2 males/time point 6 in total |
| 4 | | 10 | 10 | 1 | PO | 3 males |

All animals have free access to food and water.

Pharmacokinetics (PK) Schedule:

| Group | PK time points |
|---|---|
| IV | Plasma: 0.083, 0.25, 0.5, 1, 2, 4, 6, 8 h post dose |
| IP | IPA: Plasma: 0.25, 0.5, 1, 2, 4, 6, 8 h post dose Brain: 8 h post dose IPB: Brain and plasma: 0.25, 1, 4 h post dose |
| PO | Plasma: 0.25, 0.5, 1, 2, 4, 6, 8 h post dose |

| | Blood Sample Collection and Processing |
|---|---|
| Collection Site: | Dorsal metatarsal vein |
| Volume Collected: | ~0.03 mL per time point |
| Anticoagulant: | EDTA-K2 |
| Samples Processing and Storage: | 1) Approximately 0.03 mL blood is collected at each time point. Blood of each sample is transferred into plastic micro centrifuge tubes containing anticoagulant and is mixed well with anticoagulant. Blood samples is centrifuged at 4,000 g for 5 minutes at 4° C. to obtain plasma. 2) The samples are stored in a freezer at −75 ± 15° C. prior to analysis. |
| Tissue Sample Processing and Storage | 1) The mouse is fully exsanguinated prior to tissue collection. Procedure: open chest cavity, cut ventricle and perform a gentle iv saline flush (saline flush volume ~20 ml) with the animal placed head down at a 45 degree angle to facilitate blood removal. 2) Tissue samples are collected at adopted time point, quick frozen in ice box and kept at −75 ± 15° C. 3) All tissue samples are weighted and homogenized with water by tissue weight (g) to water volume (mL) at ratio 1:3 before analysis. The actual concentration is the detected value multiplied by the dilution factor. |

Dose Formulation

Samples are freshly prepared in PBS solution to a maximum concentration of 1 mg/mL.

Bioanalytical Method Qualification

Internal Standard

Verapamil and dexamethasone are normally used as internal standards.

Bioanalytical Criteria

The standard curve is run in duplicate with a minimum of six standards, and a minimum of five standards and the LLOQ should fall within ±20% of the nominal value. The lower limit of quantitation (LLOQ) should have a minimum signal to noise ratio of 5. A minimum of duplicate QC's at three concentrations (low, mid, and high QC) should be incorporated into each run with the low QC no more than 3×LLOQ, the mid QC around the middle of the curve, and the high QC should be near the ULOQ (minimally 80% but less than 100% of the value of the highest standard) for the run and the mean value should be within ±20% of the theoretical value. The results of the QC's provide the basis for accepting or rejecting the run. At least 67% or four of six QC's should be within 20% of their respective nominal values; 33% of the QC's (not replicates of the same concentration) can fall outside 20% of nominal value. The simplest model that adequately describes the concentration-response relationship should be used. Linear or quadratic regression can be used. Weighting should be 1/x, or 1/x2.

PK Samples Analyses

Concentrations of compound in the plasma and brain samples are analyzed using a LC-MS/MS method.

WinNonlin (Phoenix™, version 8.3) or other similar software are used for pharmacokinetic calculations. The following pharmacokinetic parameters are calculated, whenever possible from the plasma and brain concentration versus time data:

IV administration: $T_{1/2}$, C0, $AUC_{last}$, $AUC_{inf}$, $MRT_{inf}$, Cl, $V_{ss}$, $V_z$, Number of Points for Regression.

IP and PO administration: $T_{1/2}$, $C_{max}$, $T_{max}$, $MRT_{inf}$, $AUC_{inf}$, $AUC_{last}$, $AUC_{0-24hr}$, Vz/f, CL/f, Number of Points for Regression.

Brain NCA parameter values post IP doing are analysed using the sparse sample analysis. Brain Kp values are reported at all sampled time points and also based on the Cmax and AUC values.

Additional pharmacokinetic or statistical analysis may be performed at the discretion of the contributing scientist, and will be documented in the data summary.

The invention claimed is:

1. A compound, selected from:

| Compound No. | Structure |
|---|---|
| S1 | |
| S2 | |
| S3 | |
| S4 | 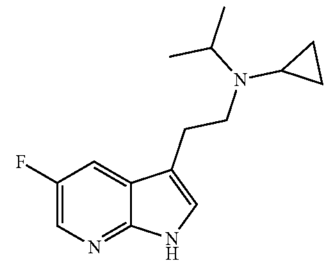 [SMILES: CC(C)N(CCc1c[nH]c2ncc(F)cc12)C1CC1] |
| S5 | 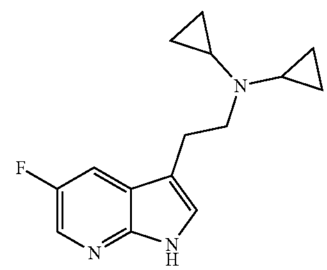 [SMILES: Fc1cnc2[nH]cc(CCN(C3CC3)C3CC3)c2c1] |
| S6 | 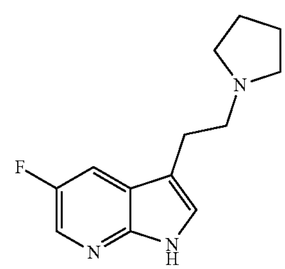 [SMILES: Fc1cnc2[nH]cc(CCN3CCCC3)c2c1] |
| S7 | 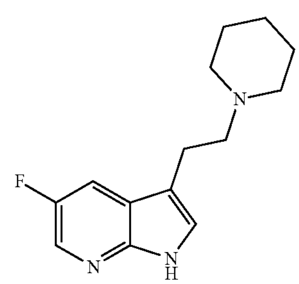 [SMILES: Fc1cnc2[nH]cc(CCN3CCCCC3)c2c1] |
| S8 | 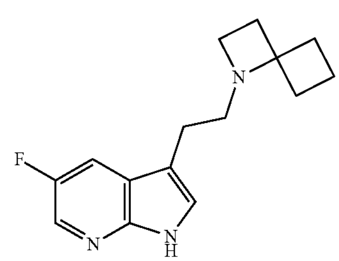 [SMILES: Fc1cnc2[nH]cc(CCN3CCC34CCC4)c2c1] |

| Compound No. | Structure |
|---|---|
| S9 | 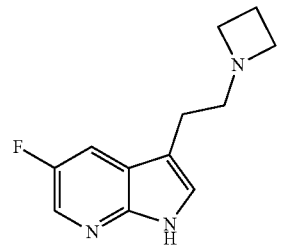 [SMILES: Fc1cnc2[nH]cc(CCN3CCC3)c2c1] |
| S11 | 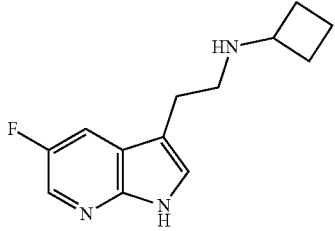 [SMILES: Fc1cnc2[nH]cc(CCNC3CCC3)c2c1] |
| S12 | 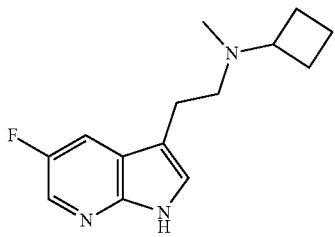 [SMILES: CN(CCc1c[nH]c2ncc(F)cc12)C1CCC1] |
| S13 | 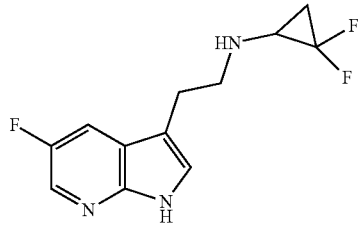 [SMILES: Fc1cnc2[nH]cc(CCNC3CC3(F)F)c2c1] |
| S14 | 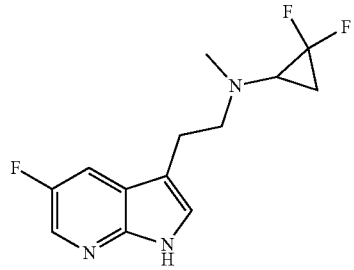 [SMILES: CN(CCc1c[nH]c2ncc(F)cc12)C1CC1(F)F] |
| S15 | 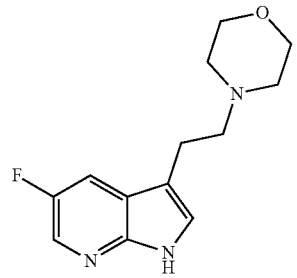 [SMILES: Fc1cnc2[nH]cc(CCN3CCOCC3)c2c1] |
| Compound No. | Structure |
|---|---|
| S16 | 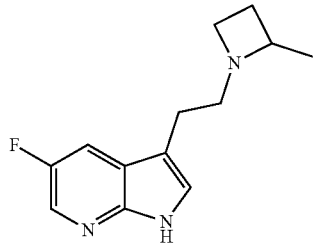 [SMILES: CC1CCN1CCc1c[nH]c2ncc(F)cc12] |
| S17 | 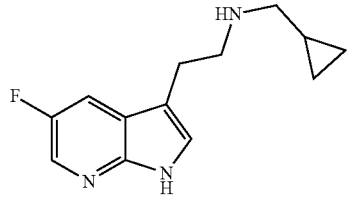 [SMILES: Fc1cnc2[nH]cc(CCNCC3CC3)c2c1] |
| S18 | 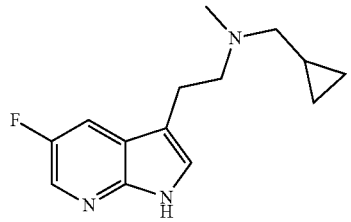 [SMILES: CN(CCc1c[nH]c2ncc(F)cc12)CC1CC1] |
| S19 | 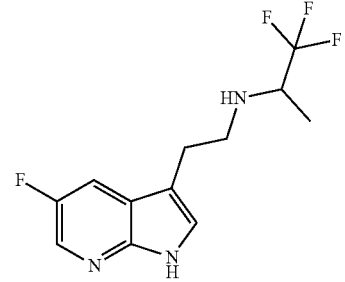 [SMILES: CC(NCCc1c[nH]c2ncc(F)cc12)C(F)(F)F] |
| S20 | 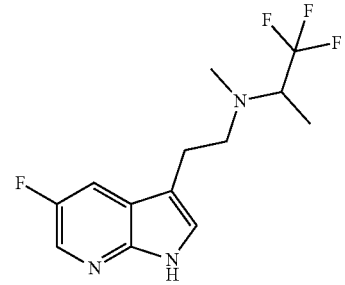 [SMILES: CC(N(C)CCc1c[nH]c2ncc(F)cc12)C(F)(F)F] |
| S21 | 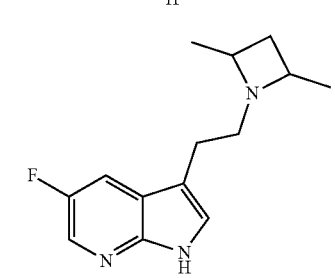 |

| Compound No. | Structure |
|---|---|
| S22 | 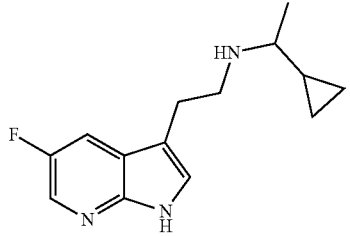 |
| S23 | 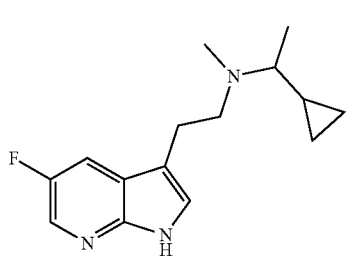 [SMILES: CC(C1CC1)N(C)CCc1c[nH]c2ncc(F)cc12] |
| S24 | 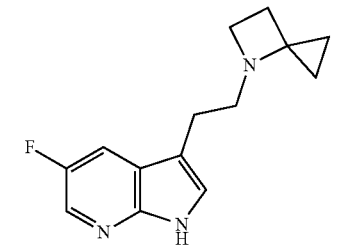 [SMILES: Fc1cnc2[nH]cc(CCN3CCC34CC4)c2c1] |
| S25 | 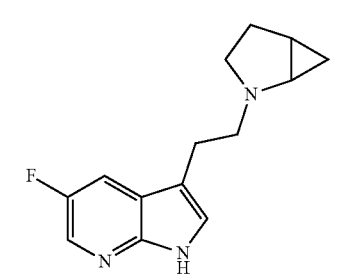 |
| S26 | 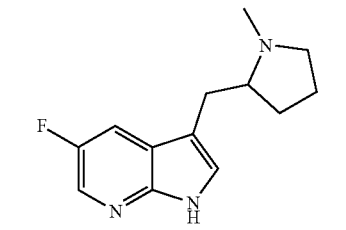 [SMILES: CN1CCCC1Cc1c[nH]c2ncc(F)cc12] |
| S27 | 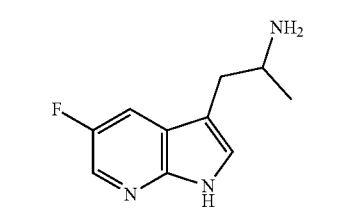 |
| Compound No. | Structure |
|---|---|
| S28 | 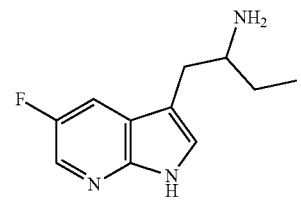 |
| S30 | 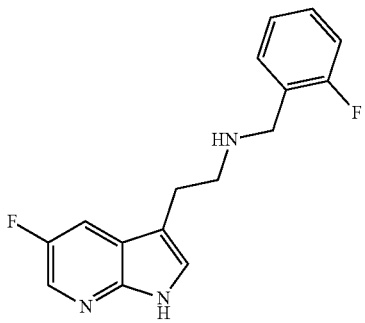 [SMILES: Fc1cnc2[nH]cc(CCNCc3ccccc3F)c2c1] |
| S31 | 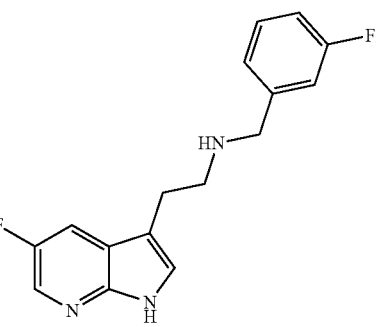 |
| S32 | 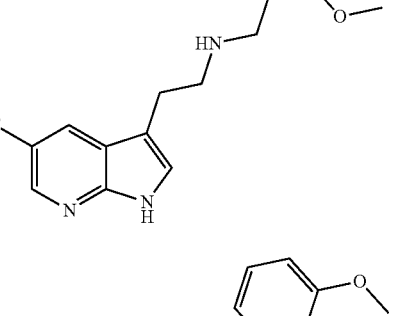 |
| S33 | 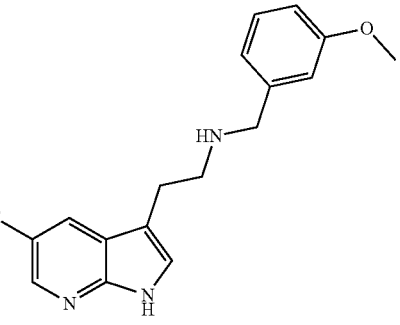 |

| Compound No. | Structure |
|---|---|
| S34 | 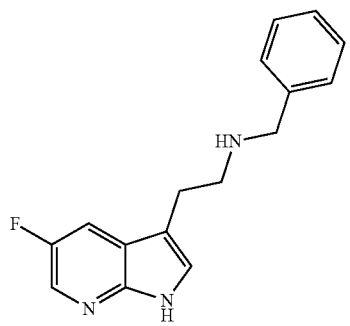 |
| S35 | 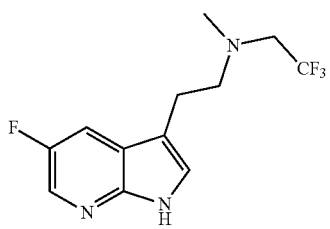 [SMILES: CN(CCc1c[nH]c2ncc(F)cc12)CC(F)(F)F] |
| S36 | 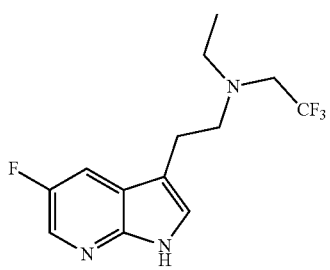 [SMILES: CCN(CCc1c[nH]c2ncc(F)cc12)CC(F)(F)F] |
| S37 | 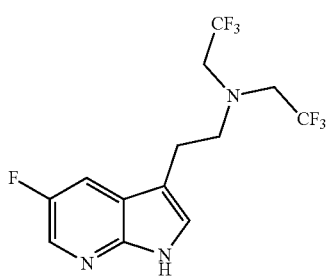 [SMILES: Fc1cnc2[nH]cc(CCN(CC(F)(F)F)CC(F)(F)F)c2c1] |
| S38 | 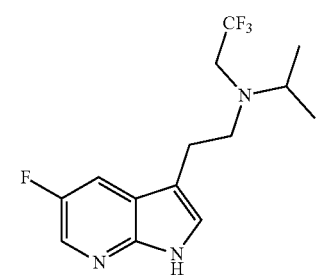 [SMILES: CC(C)N(CCc1c[nH]c2ncc(F)cc12)CC(F)(F)F] |
| Compound No. | Structure |
|---|---|
| S39 | 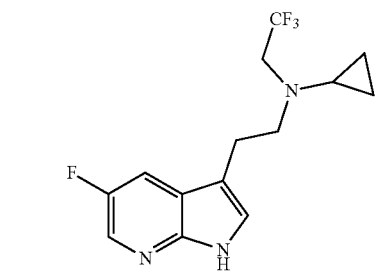 [SMILES: Fc1cnc2[nH]cc(CCN(CC(F)(F)F)C3CC3)c2c1] |
| S40 | 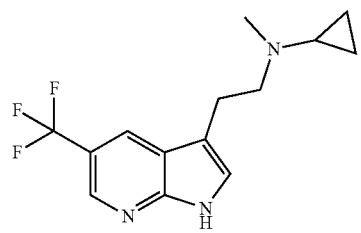 [SMILES: CN(CCc1c[nH]c2ncc(C(F)(F)F)cc12)C1CC1] |
| S41 | 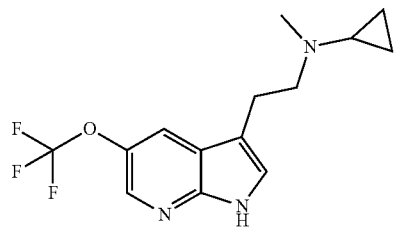 [SMILES: CN(CCc1c[nH]c2ncc(OC(F)(F)F)cc12)C1CC1] |
| S42 | 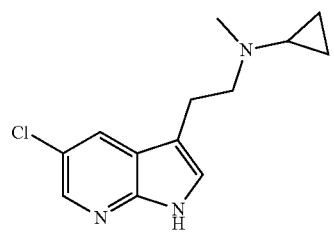 [SMILES: CN(CCc1c[nH]c2ncc(Cl)cc12)C1CC1] |
| S43 | 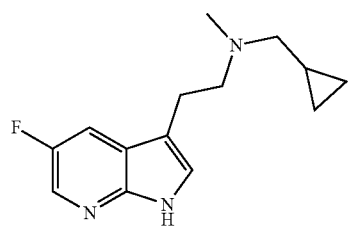 [SMILES: CN(CCc1c[nH]c2ncc(F)cc12)CC1CC1] |
| S44 | 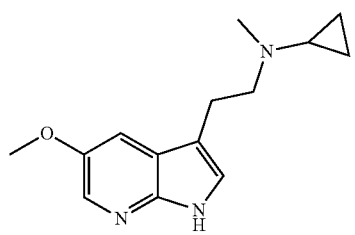 [SMILES: COc1cnc2[nH]cc(CCN(C)C3CC3)c2c1] |

| Compound No. | Structure |
|---|---|
| S45 | 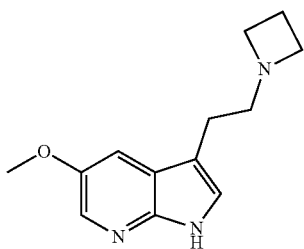 [SMILES: COc1cnc2[nH]cc(CCN3CCC3)c2c1] |
| S46 | 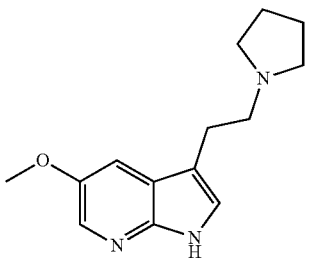 [SMILES: COc1cnc2[nH]cc(CCN3CCCC3)c2c1] |
| S47 | 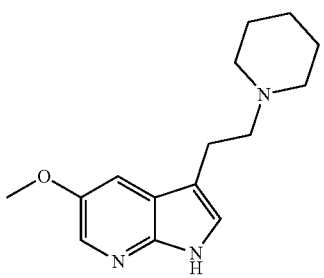 [SMILES: COc1cnc2[nH]cc(CCN3CCCCC3)c2c1] |
| S48 | 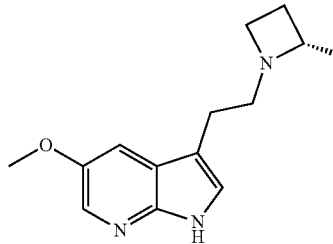 |
| S49 | 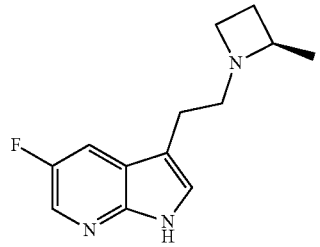 [SMILES: C[C@@H]1CCN1CCc1c[nH]c2ncc(F)cc12] |
| S50 | 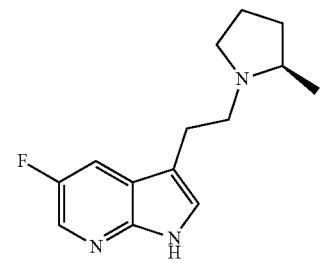 [SMILES: C[C@@H]1CCCN1CCc1c[nH]c2ncc(F)cc12] |
| S51 | 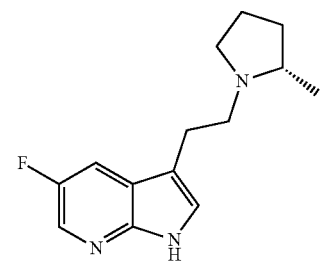 [SMILES: C[C@H]1CCCN1CCc1c[nH]c2ncc(F)cc12] |
| S56 | 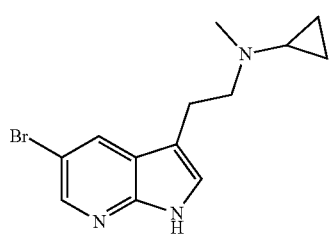 |
| S57 | 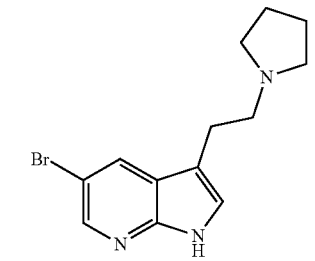 [SMILES: Brc1cnc2[nH]cc(CCN3CCCC3)c2c1] |
| S58 | 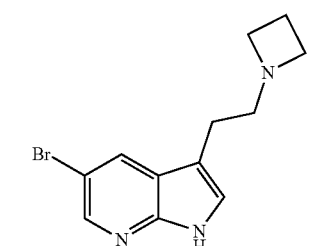 |
| S59 | 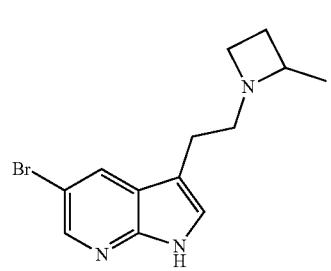 [SMILES: CC1CCN1CCc1c[nH]c2ncc(Br)cc12] |

| Compound No. | Structure |
|---|---|
| S60 | 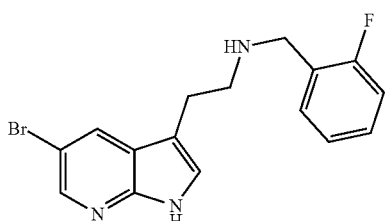 |
| S61 | 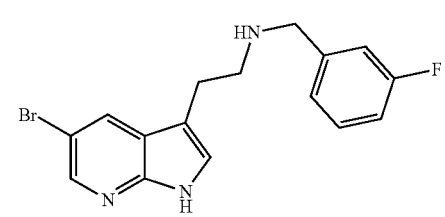 [SMILES: Fc1cccc(CNCCc2c[nH]c3ncc(Br)cc23)c1] |
| S62 | 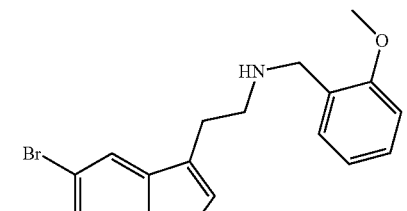 |
| S63 | 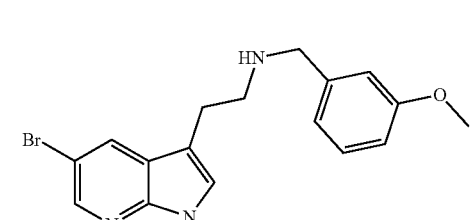 |
| S64 | 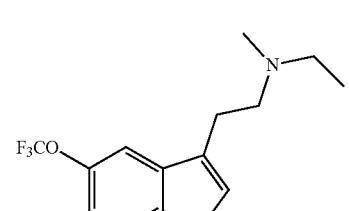 |
| S65 | 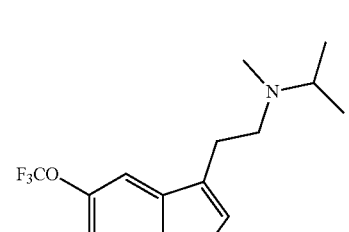 |
| S66 | 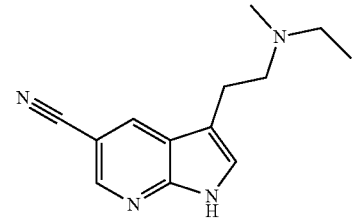 [SMILES: CCN(C)CCc1c[nH]c2ncc(C#N)cc12] |
| S67 | 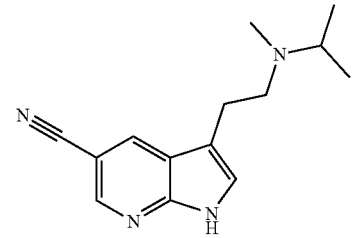 |
| S68 | 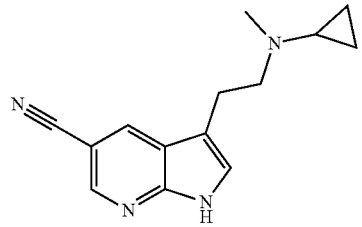 [SMILES: CN(CCc1c[nH]c2ncc(C#N)cc12)C1CC1] |
| S69 | 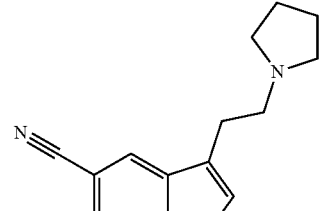 |
| S70 | 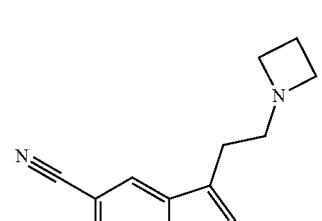 |
| S71 | 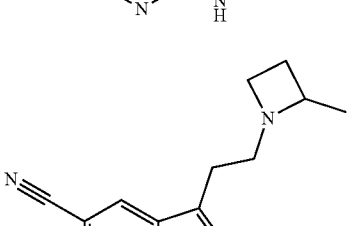 |

| Compound No. | Structure |
|---|---|
| S72 | 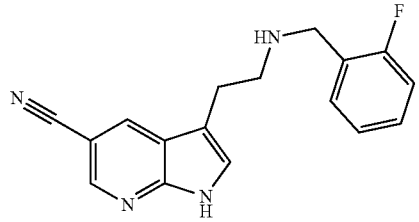 [SMILES: N#Cc1cnc2[nH]cc(CCNCc3ccccc3F)c2c1] |
| S73 | 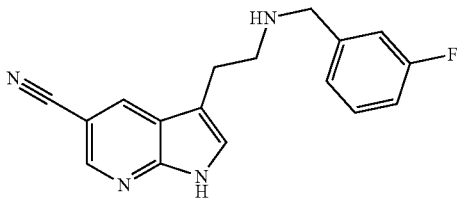 [SMILES: N#Cc1cnc2[nH]cc(CCNCc3cccc(F)c3)c2c1] |
| Compound No. | Structure |
|---|---|
| S74 | 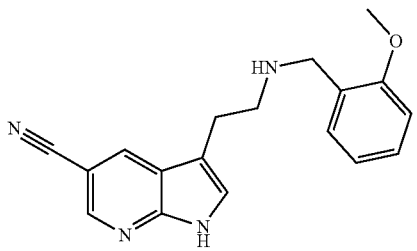 [SMILES: COc1ccccc1CNCCc1c[nH]c2ncc(C#N)cc12] |
| S75 | 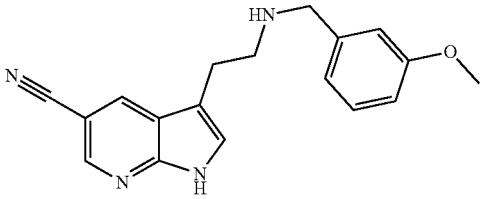 [SMILES: COc1cccc(CNCCc2c[nH]c3ncc(C#N)cc23)c1] |
or a pharmaceutically acceptable salt, solvate, tautomer, N-oxide, or stereoisomer thereof.